United States Patent
Tatani et al.

(10) Patent No.: US 8,815,903 B2
(45) Date of Patent: Aug. 26, 2014

(54) INDOLE DERIVATIVE AND PHARMACOLOGICALLY ACCEPTABLE SALT THEREOF

(75) Inventors: Kazuya Tatani, Nagano (JP); Atsushi Kondo, Nagano (JP); Tatsuhiro Kondo, Niigata (JP); Naohiro Kawamura, Nagano (JP); Shigeki Seto, Nogi (JP); Yasushi Kohno, Nogi (JP)

(73) Assignees: Kissei Pharmaceutical Co., Ltd., Nagano (JP); Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/980,604

(22) PCT Filed: Jan. 24, 2012

(86) PCT No.: PCT/JP2012/051402
§ 371 (c)(1),
(2), (4) Date: Jul. 19, 2013

(87) PCT Pub. No.: WO2012/102255
PCT Pub. Date: Aug. 2, 2012

(65) Prior Publication Data
US 2013/0317065 A1    Nov. 28, 2013

(30) Foreign Application Priority Data
Jan. 25, 2011 (JP) .................. 2011-012955

(51) Int. Cl.
| A61K 31/4439 | (2006.01) |
|---|---|
| A61K 31/404 | (2006.01) |
| A61K 31/41 | (2006.01) |
| A61K 31/4245 | (2006.01) |
| A61K 31/427 | (2006.01) |
| A61K 31/444 | (2006.01) |
| A61K 31/506 | (2006.01) |
| C07D 401/06 | (2006.01) |
| C07D 401/14 | (2006.01) |
| C07D 405/06 | (2006.01) |
| C07D 405/14 | (2006.01) |
| C07D 409/14 | (2006.01) |
| C07D 413/14 | (2006.01) |
| C07D 417/06 | (2006.01) |

(52) U.S. Cl.
USPC ........... 514/313; 514/339; 514/415; 514/414; 514/365; 514/256; 544/333; 546/277.4; 546/268.4; 546/269.4; 546/272.1; 546/256; 548/511; 548/468; 548/200; 548/252

(58) Field of Classification Search
None
See application file for complete search history.

(56) References Cited

U.S. PATENT DOCUMENTS

| 2012/0122931 A1 | 5/2012 | Kondo et al. |
| 2012/0129890 A1 | 5/2012 | Tatani et al. |

FOREIGN PATENT DOCUMENTS

| WO | WO 2008/006790 | 1/2008 |
| WO | WO 2008/006793 | 1/2008 |
| WO | WO 2008/006794 | 1/2008 |
| WO | WO 2008/006795 | 1/2008 |

OTHER PUBLICATIONS

Canadian Patent Application No. 2,825,172, Indole Derivative, and Pharmacologically Acceptable Salt Thereof; National Stage Entry of PCT/JP2012/051401, claiming priority to JP2011-012956, filed Jan. 25, 2011.

Canadian Patent Application No. 2,825,134, Indole Derivative and Pharmacologically Acceptable Salt of Same; National Stage Entry of PCT/JP2012/051402, claiming priority to JP2011-012955, filed Jan. 25, 2011.

(Continued)

*Primary Examiner* — Janet L Andres
*Assistant Examiner* — Timothy R Rozof
(74) *Attorney, Agent, or Firm* — Richard S. Echler

(57) ABSTRACT

The present invention provides a compound represented by the general formula (I) of the present invention, which has $EP_1$ receptor antagonism:

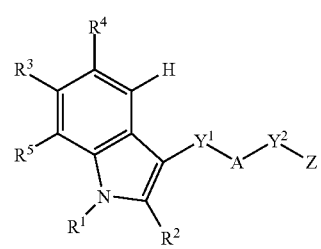

wherein A represents a benzene ring, a pyridine ring, or the like; $Y^1$ represents a $C_{1-6}$ alkylene group or the like; $Y^2$ represents a single bond or the like; Z represents —C(=O)—$NHSO_2R^6$, an acidic 5-membered hetero ring group, or the like; $R^1$ represents a hydrogen atom or the like; $R^2$ represents a phenyl group, a 5-membered aromatic heterocyclic group, or the like; $R^3$ represents a halogen atom, a $C_{1-6}$ alkoxy group, or the like; $R^4$ represents a hydrogen atom, a halogen atom, or the like; $R^5$ represents a hydrogen atom or the like; and $R^6$ represents a $C_{1-6}$ alkyl group or the like], or a pharmaceutically acceptable salt thereof. Furthermore, the compound (I) of the present invention can be used as an agent for treating or preventing LUTS, in particular, various symptoms of OABs.

17 Claims, No Drawings

(56) References Cited

OTHER PUBLICATIONS

European Patent Application No. 12 739 597.8, Indole Derivative, and Pharmacologically Acceptable Salt Thereof; National Stage Entry of PCT/JP2012/051401, claiming priority to JP2011-012956, filed Jan. 25, 2011.

European Patent Application No. 12 739 875.8, Indole Derivative and Pharmacologically Acceptable Salt of Same; National Stage Entry of PCT/JP2012/051402, claiming priority to JP2011-012955, filed Jan. 25, 2011.

Japanese Patent Application No. 2012-554793, Indole Derivative, and Pharmacologically Acceptable Salt Thereof; claiming priority to JP2011-012956, filed Jan. 25, 2011.

Japanese Patent Application No. 2012-554794, Indole Derivative and Pharmacologically Acceptable Salt of Same; National Stage Entry of PCT/JP2012/051402, claiming priority to JP2011-012955, filed Jan. 25, 2011.

Hall, et al., "Discoveery of a novel indole series of EP1 receptor antagonists by scaffold hopping," Bioorganic & Medicinal Chemistry Letters, 18 (2008) 2684-2690.

INDOLE DERIVATIVE AND PHARMACOLOGICALLY ACCEPTABLE SALT THEREOF

CROSS REFERENCE TO RELATED APPLICATIONS

This Application is a National Stage of PCT/JP2012/051402, filed Jan. 24, 2012, which claims priority to Japanese Patent Application Serial No. 2011-012955, filed Jan. 25, 2011, the entirety of which are incorporated herein by reference.

SEQUENCE LISTING

Incorporated by reference in its entirety is a computer-readable sequence listing submitted concurrently herewith and identified as follows: One 5 KB ASCII (Text) file named "03457_P002U1_Sequence_Listing_ST25.txt."

FIELD

The present invention relates to an indole derivative having an $EP_1$ receptor antagonism, which is useful as a pharmaceutical, or a pharmaceutically acceptable salt thereof, a pharmaceutical composition comprising the same, and a pharmaceutical use thereof.

BACKGROUND

With an increasingly aging and stressed society, the number of patients with lower urinary tract dysfunction (LUTD) has increased. LUTD is a generic term for urine collection disorder and dysuria, and the symptoms derived from LUTD are lower urinary tract symptoms (LUTS). One of the LUTS is an overactive bladder syndrome (OABs). OABs may be generally called overactive bladder (OAB) in some cases. In any case, it is a disease defined as "a symptom syndrome which essentially has urinary urgency and which is usually accompanied by urinary frequency and nocturia. Urge urinary incontinence is not necessary". The symptoms associated with OABs interfere with general life such as work, daily life, mental activity, and the like, and thus lower the quality of life (QOL). Currently, a first choice drug as an agent for treating OABs is an anticholinergic agent. However, it is necessary for the anticholinergic agent to be used also in due consideration of an anti-muscarinic effect such as thirst and residual urine, and thus, is not always effective for all patients (see, for example, Non-patent literature 1). Under these circumstances, there is a demand for development of a therapeutic agent which has a different mechanism from that of the anticholinergic agent (see, for example, Non-patent literature 1).

Recently, in LUTS, particularly in OABs, the role of urothelium has attracted attention. For LUTS, it has become clear that various chemical mediators are released in the urothelial cells, which cause a micturition reflex through the receptors of bladder sensory nerve terminals. Among them, one of the chemical mediators, prostaglandin $E_2$ ($PGE_2$), binds with a prostaglandin E receptor 1 ($EP_1$ receptor) in the afferent nerves (especially C fibers) in the urothelium to increase the micturition reflex. In addition, $PGE_2$ binds with the $EP_1$ receptors present in the bladder smooth muscle to contract the bladder. In fact, it has been reported that the $EP_1$ receptor antagonists inhibit both of the increase in the micturition reflex and the increase in the afferent nerve activities by $PGE_2$ (see, for example, Non-patent literature 2 and Non-patent literature 3). From these, it is suggested that $PGE_2$ is involved in contraction of the bladder smooth muscle and increase in the bladder sensory nerves through the $EP_1$ receptors. Furthermore, it is reported that $EP_1$ receptor antagonists do not increase the amount of the residual urine, but increase the bladder capacity (see, for example, Non-patent literature 4).

There exist four subtypes, $EP_2$, $EP_3$, and $EP_4$ as well as $EP_1$, of the $PGE_2$ receptor. The $EP_1$ receptor exists in the lungs as well as the bladder and the urothelium, the skeletal muscle, the renal collecting duct, and the like (see, for example, Non-patent literature 2). Therefore, it is expected that by changing the selectivity of the subtypes of the $PGE_2$ receptor, the target organs of the drugs, or the target tissues, a therapeutic agent for desired diseases can be developed.

Furthermore, as a compound having a substituent containing a sulfonylcarbamoyl group at the 3-position of an indole ring, a compound represented by the general formula (A) has been described as a leukotriene antagonist (see, for example, Patent literature 1).

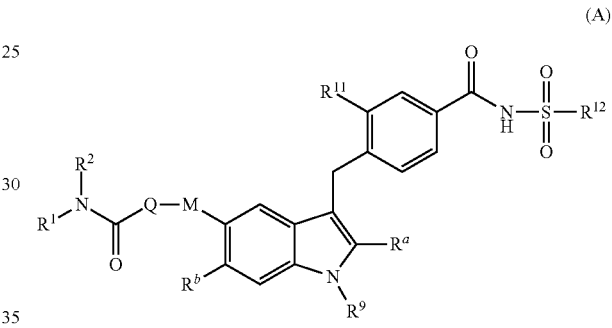

(A)

[in the formula (A), $R^a$, $R^b$, $R^1$, $R^2$, $R^9$, $R^{11}$, $R^{12}$, M, m and Q have the same meanings as defined in Patent literature 1.]

However, the chemical structure of the compound is different from that of the compound of the present invention, and there is no description of $EP_1$ receptor antagonism.

A compound represented by the general formula (B) is disclosed as an indole derivative having an $EP_1$ receptor antagonism (see, for example, Patent literature 2).

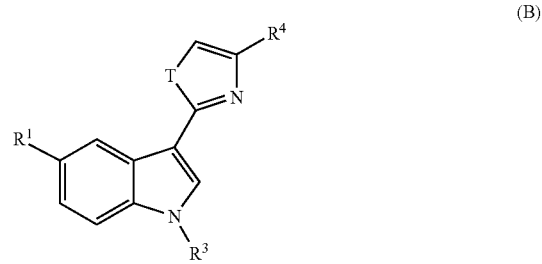

(B)

in the formula (B), T represents an oxygen atom or a sulfur atom, and $R^1$, $R^3$, and $R^4$ have the same meanings as defined in Patent literature 2.

However, the chemical structure of the compound is different from that of the compound of the present invention. Further, there is no description of usefulness thereof as an agent for preventing or treating LUTS, particularly overactive bladder syndromes (OABs).

[Patent literature 1] Japanese Patent No. 2740250
[Patent literature 2] International Publication WO 2008/06794 pamphlet
Narihito Seki, "Folia Pharmacologica Japonica", 2007, Vol. 129, p. 368-373
Xiaojun Wang, et al., "Biomedical Research", 2008, Vol. 29, p. 105-111
Masahito Kawatani, "PAIN RESEARCH", 2004, Vol. 19, p. 185-190
Masanobu Maegawa, "The Journal of The Japan Neurogenic Bladder Society", 2008, Vol. 19, p. 169

SUMMARY

An object of the present invention is to provide a compound having an $EP_1$ receptor antagonism or a pharmaceutically acceptable salt thereof, a pharmaceutical composition comprising the same, and a pharmaceutical use thereof.

The present inventors have conducted extensive studies on a compound having an $EP_1$ receptor antagonism, and as a result, they have found that the compounds (I) of the present invention or a pharmaceutically acceptable salt thereof exhibit a potent $EP_1$ receptor antagonism, thereby completing the present invention.

That is, the means for solving the above-described objects are presented below.

[1] A compound represented by the general formula (I) or a pharmaceutically acceptable salt thereof:

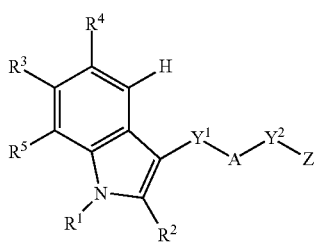

(I)

Wherein A represents a group selected from the group consisting of the following a) to h):

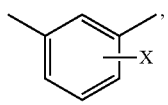  a)

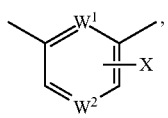  b)

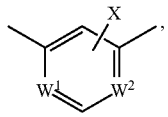  c)

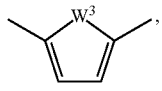  d)

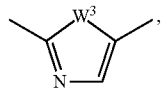  e)

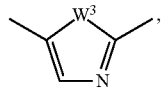  f)

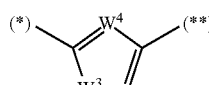  g)

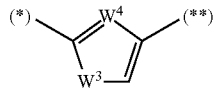  h)

one of $W^1$ and $W^2$ represents a nitrogen atom and the other represents =CH— or a nitrogen atom;
$W^3$ represents an oxygen atom or a sulfur atom;
$W^4$ represents =CH— or a nitrogen atom;
X represents a hydrogen atom or a halogen atom;
$Y^1$ represents a $C_{1-6}$ alkylene group or a halo-$C_{1-6}$ alkylene group;
$Y^2$ represents a single bond, a $C_{1-6}$ alkylene group, a $C_{1-6}$ oxyalkylene group, or a $C_{2-4}$ alkenylene group;
$R^1$ represents a hydrogen atom or a $C_{1-6}$ alkyl group;
$R^2$ represents a group selected from the group consisting of the following i) to m):
  i) a branched $C_{3-6}$ alkyl group,
  j) a $C_{3-6}$ cycloalkyl group, in which the ring is unsubstituted or substituted with one $C_{1-6}$ alkyl group,
  k) a phenyl group, in which the ring is unsubstituted or substituted with one to five groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group,
  l) a 6-membered aromatic heterocyclic group, in which the ring is unsubstituted or substituted with one to four groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group, and
  m) a 5-membered aromatic heterocyclic group, in which the ring is unsubstituted or substituted with one to three groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group;
$R^3$ represents a halogen atom, a $C_{1-6}$ alkyl group, a halo-$C_{1-6}$ alkyl group, a hydroxy-$C_{1-6}$ alkyl group, a $C_{1-6}$ alkoxy group, a halo-$C_{1-6}$ alkoxy group, a $C_{1-6}$ alkylsulfanyl group, a $C_{1-6}$ alkylsulfinyl group, a $C_{1-6}$ alkylsulfonyl group, a $C_{3-6}$ cycloalkyl group, a cyano group, an amino group, or a nitro group;
$R^4$ represents a hydrogen atom, a halogen atom, a $C_{1-6}$ alkyl group, or a $C_{1-6}$ alkoxy group;
$R^5$ represents a hydrogen atom, a halogen atom, a $C_{1-6}$ alkyl group, or a $C_{1-6}$ alkoxy group;
Z represents a group selected from the group consisting of the following n) to s):
  n) —C(=O)—NHSO$_2$R$^6$,
  o) —C(=O)—NHOH,
  p) —C(=O)—NHCN, q) —NH—C(=O)—R⁷,
r) an acidic 5-membered hetero ring group, and
s) a 6-membered ring group substituted with a phenolic hydroxy group; and
R⁶ and R⁷ independently represent a group selected from the group consisting of the following t) to w):
t) a $C_{1-6}$ alkyl group,
u) a halo-$C_{1-6}$ alkyl group,
v) a $C_{3-6}$ cycloalkyl group, and
w) a phenyl group, in which the ring is unsubstituted or substituted with one to five groups independently selected from the group consisting of the following: a halogen atom, a $C_{1-6}$ alkyl group, a halo-$C_{1-6}$ alkyl group, and a $C_{1-6}$ alkoxy group (with the proviso that the bonds with (*) represent binding to $Y^1$; and the bonds with (**) represent binding to $Y^2$)].

[2] The compound as set forth in [1] or a pharmaceutically acceptable salt thereof, wherein A represents a group selected from the group consisting of the following a), b), d), and h):

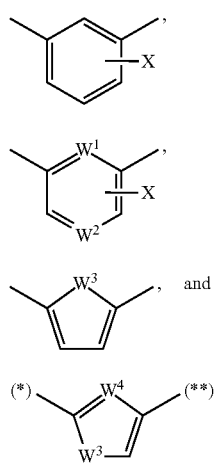

$Y^1$ represents a $C_{1-6}$ alkylene group;
$Y^2$ represents a single bond; and
$R^5$ represents a hydrogen atom (with the proviso that the bond with (*) represents binding to $Y^1$; and the bond with (**) represents binding to $Y^2$).

[3] The compound as set forth in [2] or a pharmaceutically acceptable salt thereof, wherein $R^2$ is a group selected from the group consisting of the following j), x), y) and z):
j) a $C_{3-6}$ cycloalkyl group, in which the ring is unsubstituted or substituted with one $C_{1-6}$ alkyl group,
x) a phenyl group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group,
y) a 6-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group, and
z) a 5-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group.

[4] The compound as set forth in [3] or a pharmaceutically acceptable salt thereof, wherein $R^2$ is a phenyl group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group.

[5] The compound as set forth in [3] or a pharmaceutically acceptable salt thereof, wherein $R^2$ is a 5-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group.

[6] The compound as set forth in [2] or a pharmaceutically acceptable salt thereof, wherein $R^2$ is a branched $C_{3-6}$ alkyl group.

[7] The compound as set forth in any one of [2] to [6] or a pharmaceutically acceptable salt thereof, wherein
Z is —C(=O)—NHSO₂R⁶ or an acidic 5-membered hetero ring group; and
R⁶ is a group selected from the group consisting of the following t) to w):
t) a $C_{1-6}$ alkyl group,
u) a halo-$C_{1-6}$ alkyl group,
v) a $C_{3-6}$ cycloalkyl group, and
w) a phenyl group, in which the ring is unsubstituted or substituted with one to three groups independently selected from a group selected from the group consisting of the following: a halogen atom, a $C_{1-6}$ alkyl group, a halo-$C_{1-6}$ alkyl group, and a $C_{1-6}$ alkoxy group.

[8] The compound as set forth in [7] or a pharmaceutically acceptable salt thereof, wherein Z is —C(=O)—NHSO₂R⁶.

[9] The compound as set forth in [3] or a pharmaceutically acceptable salt thereof, wherein $R^2$ is a $C_{3-6}$ cycloalkyl group, in which the ring is substituted with one $C_{1-6}$ alkyl group.

[10] The compound as set forth in [9] or a pharmaceutically acceptable salt thereof, wherein Z is an acidic 5-membered hetero ring group.

[11] The compound as set forth in [10] or a pharmaceutically acceptable salt thereof, wherein the acidic 5-membered hetero ring group is a group selected from Group D consisting of

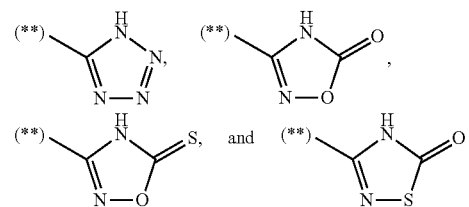

with the proviso that the bonds with (**) represent bonding to $Y^2$ of the compound represented by the general formula (I).

[12] The compound as set forth in [1], which is selected from the following group, or a pharmaceutically acceptable salt thereof.
N-methanesulfonyl-6-(6-methoxy-2-phenyl-1H-indol-3-ylmethyl)pyridine-2-carboxamide,
6-(6-cyclopropyl-2-phenyl-1H-indol-3-ylmethyl)-N-methanesulfonylpyridine-2-carboxamide,
N-methanesulfonyl-6-(6-methyl-2-phenyl-1H-indol-3-ylmethyl)pyridine-2-carboxamide,
6-(5-fluoro-6-methoxy-2-phenyl-1H-indol-3-ylmethyl)-N-methanesulfonylpyridine-2-carboxamide,
N-ethanesulfonyl-6-(6-methoxy-2-thiophen-3-yl-1H-indol-3-ylmethyl)pyridine-2-carboxamide,
6-cyclopropyl-2-phenyl-3-[6-(1H-tetrazol-5-yl)pyridin-2-ylmethyl]-1H-indole, 6-methoxy-2-phenyl-3-[6-(1H-tetrazol-5-yl)pyridin-2-ylmethyl]-1H-indole,
6-methyl-2-phenyl-3-[6-(1H-tetrazol-5-yl)pyridin-2-ylmethyl]-1H-indole,
2-furan-3-yl-6-methoxy-3-[6-(1H-tetrazol-5-yl)pyridin-2-ylmethyl]-1H-indole,
3-[6-(6-methoxy-2-phenyl-1H-indol-3-ylmethyl)pyridin-2-yl]-4,5-dihydro-1,2,4-oxadiazol-5-one,
2-tert-butyl-6-methoxy-3-[6-(1H-tetrazol-5-yl)pyridin-2-ylmethyl]-1H-indole,
6-methoxy-2-(1-methylcyclopropyl)-3-[6-(1H-tetrazol-5-yl)pyridin-2-ylmethyl]-1H-indole,
6-methyl-2-(1-methylcyclopropyl)-3-[6-(1H-tetrazol-5-yl)pyridin-2-ylmethyl]-1H-indole,
6-cyclopropyl-2-(1-methylcyclopropyl)-3-[6-(1H-tetrazol-5-yl)pyridin-2-ylmethyl]-1H-indole,
6-chloro-2-(1-methylcyclopropyl)-3-[6-(1H-tetrazol-5-yl)pyridin-2-ylmethyl]-1H-indole,
6-chloro-5-methoxy-2-(1-methylcyclopropyl)-3-[6-(1H-tetrazol-5-yl)pyridin-2-ylmethyl]-1H-indole,
6-ethyl-2-(1-methylcyclopropyl)-3-[6-(1H-tetrazol-5-yl)pyridin-2-ylmethyl]-1H-indole,
5-chloro-6-methoxy-2-(1-methylcyclopropyl)-3-[6-(1H-tetrazol-5-yl)pyridin-2-ylmethyl]-1H-indole, and
6-methoxy-5-methyl-2-(1-methylcyclopropyl)-3-[6-(1H-tetrazol-5-yl)pyridin-2-ylmethyl]-1H-indole.

[13] A pharmaceutical composition comprising the compound as set forth in any one of [1] to [12] or a pharmaceutically acceptable salt thereof.

[14] The pharmaceutical composition as set forth in [13], comprising a combination of at least one agent selected from the group consisting of the following:

An anticholinergic agent, an $\alpha_1$ antagonist, a $\beta$ agonist, a 5α-reductase inhibitor, a PDE inhibitor, an acetylcholine esterase inhibitor, an anti-androgen, a progesterone-based hormone, an LH-RH analog, a neurokinin inhibitor, an antidiuretic, a calcium channel blocker, a direct smooth muscle agonist, a tricyclic antidepressant, a potassium channel modulator, a sodium channel blocker, an $H_1$ blocker, a serotonin reuptake inhibitor, a norepinephrine reuptake inhibitor, a dopamine reuptake inhibitor, a GABA agonist, a TRPV1 modulator, an endothelin antagonist, a $5\text{-HT}_{1A}$ antagonist, an $\alpha_1$ agonist, an opioid agonist, a $P_2X$ antagonist, a COX inhibitor, a σ agonist, and a muscarinic agonist.

[15] An $EP_1$ receptor antagonist comprising the compound as set forth in any one of [1] to [12] or a pharmaceutically acceptable salt thereof.

[16] An agent for preventing or treating lower urinary tract symptoms, comprising the compound as set forth in any one of [1] to [12] or a pharmaceutically acceptable salt thereof.

[17] A method for preventing or treating lower urinary tract symptoms, comprising administering an effective amount of the compound as set forth in any one of [1] to [12] or a pharmaceutically acceptable salt thereof.

[18] Use of the compound as set forth in any one of [1] to [12] or a pharmaceutically acceptable salt thereof for the manufacture of a pharmaceutical composition for preventing or treating lower urinary tract symptoms.

The compound (I) of the present invention or a pharmaceutically acceptable salt thereof exhibits a potent $EP_1$ receptor antagonism, for example, in a test for confirmation of an $EP_1$ receptor antagonism. Therefore, the compound (I) of the present invention or a pharmaceutically acceptable salt thereof is useful as an agent for treating or preventing lower urinary tract symptoms (LUTS), in particular, overactive bladder syndrome (OABs) or the like, based on its $EP_1$ receptor antagonism.

The terms in the specification are defined.

The "halogen atom" means a fluorine atom, a chlorine atom, a bromine atom, or an iodine atom. It is preferably a fluorine atom or a chlorine atom.

The "$C_{1-6}$ alkyl group" means an alkyl group having 1 to 6 carbon atoms, which may be branched. Examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, a 2-methylbutyl group, a 1,2-dimethylpropyl group, an n-hexyl group, an isohexyl group, and the like. In $R^3$, a methyl group, an ethyl group, or an isopropyl group is preferable, a methyl group or an ethyl group is more preferable, and a methyl group is further preferable. In $R^1$, a methyl group is preferred.

The "branched $C_{3-6}$ alkyl group" means a branched alkyl group having 3 to 6 carbon atoms. Examples thereof include an isopropyl group, an isobutyl group, a sec-butyl group, a tert-butyl group, an isopentyl group, a neopentyl group, a tert-pentyl group, a 1-methylbutyl group, a 2-methylbutyl group, a 1,2-dimethylpropyl group, a 1-ethylpropyl group, an isohexyl group, and the like. It is preferably an isopropyl group, an isobutyl group, a sec-butyl group, a tert-butyl group, or a 1-ethylpropyl group. It is more preferably an isopropyl group, an isobutyl group, a sec-butyl group, or a tert-butyl group. It is further preferably a tert-butyl group.

The "$C_{1-6}$ alkoxy group" means an alkoxy group having 1 to 6 carbon atoms, which may be branched. Examples thereof include a methoxy group, an ethoxy group, a propoxy group, an isopropoxy group, a butoxy group, an isobutoxy group, a sec-butoxy group, a tert-butoxy group, a pentyloxy group, a hexyloxy group, and the like. In $R^3$, a methoxy group or an ethoxy group is preferable, and a methoxy group is more preferable.

The "halo-$C_{1-6}$ alkyl group" means the $C_{1-6}$ alkyl group described above which is substituted with the same or different 1 to 5 halogen atoms described above. Examples thereof include a monofluoromethyl group, a difluoromethyl group, a trifluoromethyl group, a 2-chloroethyl group, a 2-fluoroethyl group, a 2,2-difluoroethyl group, a 1,1-difluoroethyl group, a 1,2-difluoroethyl group, a 2,2,2-trifluoroethyl group, a 1,1,2,2,2-pentafluoroethyl group, a 2,2,2-trichloroethyl group, a 3-fluoropropyl group, a 2-fluoropropyl group, a 1-fluoropropyl group, a 3,3-difluoropropyl group, a 2,2-difluoropropyl group, a 1,1-difluoropropyl group, a 1-fluorobutyl group, a 1-fluoropentyl group, a 1-fluorohexyl group, and the like. It is preferably a monofluoromethyl group, a difluoromethyl group, a trifluoromethyl group, a 2-fluoroethyl group, a 2,2-difluoroethyl group, a 1,1-difluoroethyl group, a 1,2-difluoroethyl group, and a 2,2,2-trifluoroethyl group. It is more preferably a monofluoromethyl group, a trifluoromethyl group, a 2-fluoroethyl group, a 1,1-difluoroethyl group, a 1,2-difluoroethyl group or a 2,2,2-trifluoroethyl group. It is further preferably a monofluoromethyl group and a trifluoromethyl group.

The "hydroxy-$C_{1-6}$ alkyl group" means the $C_{1-6}$ alkyl group described above which is substituted with a hydroxy group. Examples thereof include a hydroxymethyl group, a 1-hydroxyethyl group, a 1-hydroxy-1,1-dimethylmethyl group, a 2-hydroxyethyl group, a 2-hydroxy-2-methylpropyl group, a 3-hydroxypropyl group, and the like.

The "$C_{1-6}$ alkylsulfanyl" means a group represented by ($C_{1-6}$ alkyl)-S—. Examples thereof include a methylsulfanyl group, an ethylsulfanyl group, a propylsulfanyl group, a butylsulfanyl group, a pentylsulfanyl group, a hexylsulfanyl group, and the like.

The "C$_{1-6}$ alkylsulfinyl group" means a group represented by (C$_{1-6}$ alkyl)-S(=O)—. Examples thereof include a methylsulfinyl group, an ethylsulfinyl group, a propylsulfinyl group, a butylsulfinyl group, a pentylsulfinyl group, a hexylsulfinyl group, and the like.

The "C$_{1-6}$ alkylsulfonyl group" means a group represented by (C$_{1-6}$ alkyl)-SO$_2$—. Examples thereof include a methanesulfonyl group, an ethanesulfonyl group, a propanesulfonyl group, a butanesulfonyl group, a pentanesulfonyl group, a hexanesulfonyl group, and the like.

The "C$_{3-6}$ cycloalkyl group" means a monocyclic saturated alicyclic hydrocarbon group having 3 to 6 carbon atoms. Examples thereof include a cyclopropyl group, a cyclobutyl group, a cyclopentyl group, a cyclohexyl group. It is preferably a cyclopropyl group or a cyclopentyl group. In R$^3$, it is more preferably a cyclopropyl group.

The "C$_{3-6}$ cycloalkyl group, in which the ring is substituted with one C$_{1-6}$ alkyl group" means the C$_{3-6}$ cycloalkyl group as described above, which is substituted with the C$_{1-6}$ alkyl group as described above. Examples thereof include a 1-methylcyclopropyl group, a 1-ethylcyclopropyl group, a 1-methylcyclobutyl group, a 2-methylcyclobutyl group, a 1-methylcyclopentyl group, a 2-methylcyclopentyl group, a 1-methylcyclohexyl group, a 2-methylcyclohexyl group, and the like. It is preferably a 1-methylcyclopropyl group or a 1-ethylcyclopropyl group, and more preferably a 1-methylcyclopropyl group.

The "halo-C$_{1-6}$ alkoxy group" means the C$_{1-6}$ alkoxy group described above which is substituted with the same or different 1 to 5 halogen atoms described above. Examples thereof include a monofluoromethoxy group, a difluoromethoxy group, a trifluoromethoxy group, a 2-chloroethoxy group, a 2-fluoroethoxy group, a 2,2-difluoroethoxy group, a 1,1-difluoroethoxy group, a 1,2-difluoroethoxy group, a 2,2,2-trifluoroethoxy group, a 1,1,2,2,2-pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group, a 4-fluorobutoxy group, a 5-fluoropentyloxy group, a 6-fluorohexyloxy group, and the like. It is preferably a monofluoromethoxy group, a difluoromethoxy group, a trifluoromethoxy group, a 2-fluoroethoxy group, a 2,2-difluoroethoxy group, a 1,1-difluoroethoxy group, a 1,2-difluoroethoxy group, or a 2,2,2-trifluoroethoxy group. It is more preferably a monofluoromethoxy group, a difluoromethoxy group, a trifluoromethoxy group, a 2-fluoroethoxy group, a 1,1-difluoroethoxy group, a 1,2-difluoroethoxy group, or a 2,2,2-trifluoroethoxy group. It is further preferably a difluoromethoxy group or a trifluoromethoxy group.

The "C$_{7-10}$ aralkyl group" means an alkyl group having 1 to 4 carbon atoms, which is substituted with an aryl group such as a phenyl group, a naphthyl group, and the like. Examples thereof include a benzyl group, a phenethyl group, a 1-phenylethyl group, a 3-phenylpropyl group, a 4-phenylbutyl group, and the like.

The "5-membered aromatic heterocyclic group" means a 5-membered aromatic group containing 1 to 4 hetero atoms selected from an oxygen atom, a nitrogen atom, and a sulfur atom in the ring. Examples thereof include a furyl group, a pyrrolyl group, a thienyl group, an imidazolyl group, a pyrazolyl group, a 1,2,4-triazolyl group, an isothiazolyl group, an isoxazolyl group, an oxazolyl group, a thiazolyl group, a 1,3,4-oxadiazolyl group, a 1,2,4-oxadiazolyl group, and the like. It is preferably a 2-furyl group, a 3-furyl group, a 2-thienyl group, or a 3-thienyl group. It is more preferably a 3-furyl group or a 3-thienyl group.

The "6-membered aromatic heterocyclic group" means a 6-membered aromatic group containing 1 to 4 nitrogen atoms in the ring. Examples thereof include a pyridyl group, a pyrimidinyl group, a pyrazinyl group, a pyridazinyl group, and the like. It is preferably a pyridyl group, and more preferably a 3-pyridyl group.

The "acidic 5-membered hetero ring group" means a 5-membered ring containing a nitrogen atom bonded to an acidic proton in the ring or a 5-membered nitrogen-containing hetero ring having a phenolic hydroxy group. Examples thereof include the groups of Group A consisting of the formulae:

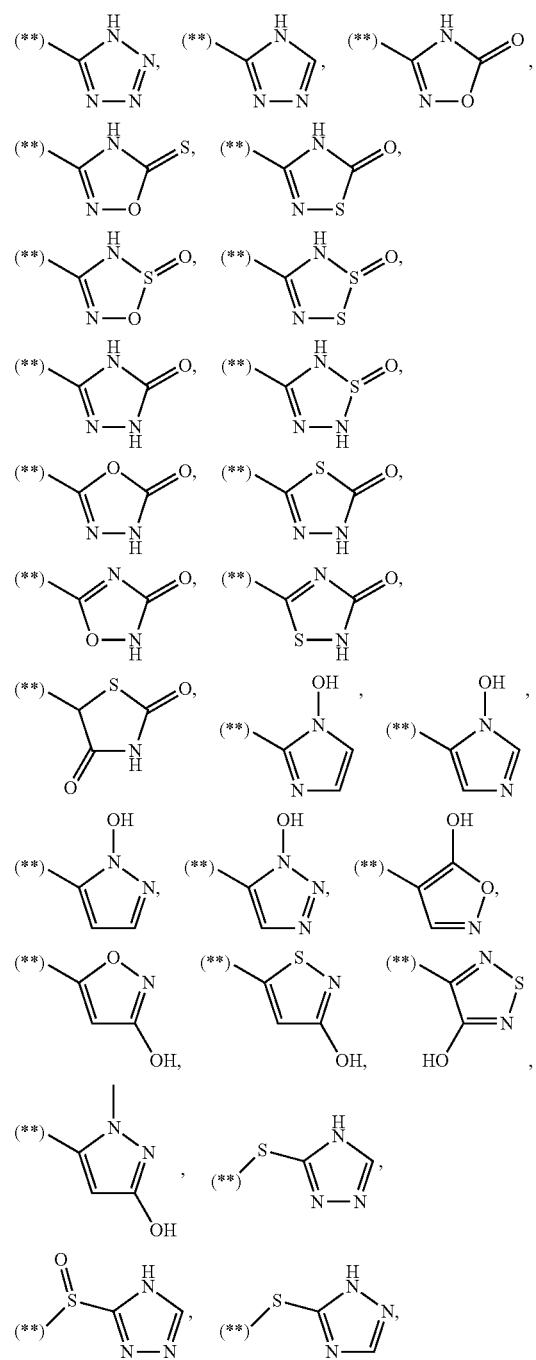

-continued

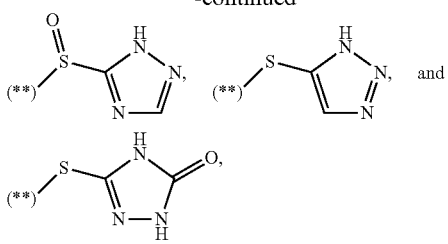

preferably the groups of Group B consisting of the formulae:

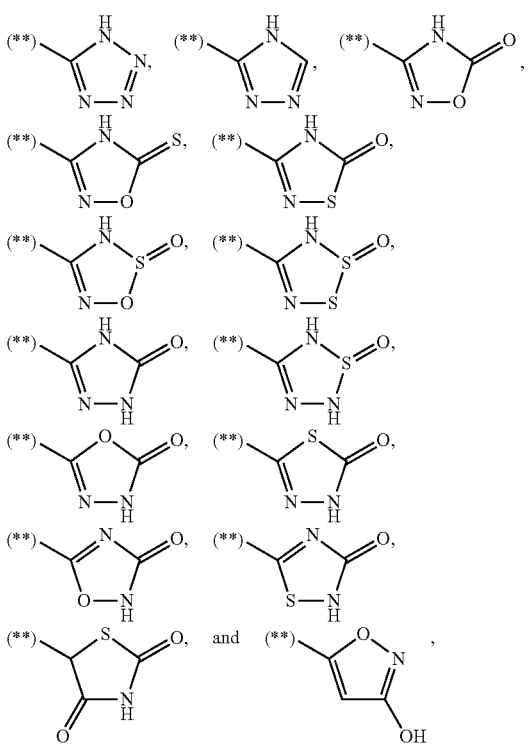

more preferably the groups of Group C consisting of the formulae:

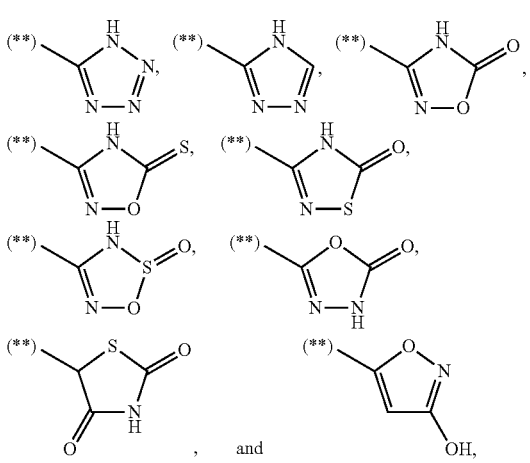

further preferably the groups of Group D consisting of the formulae:

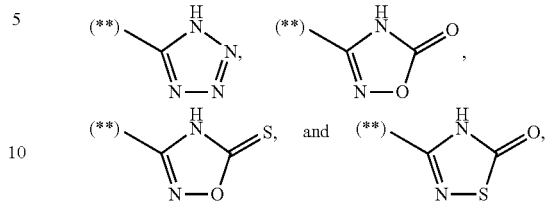

and most preferably a group of the formula:

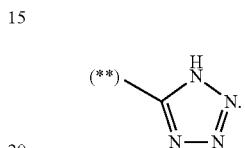

With the proviso that the bonds with (**) represent bonding to $Y^2$ of the compound represented by the general formula (I).

The "6-membered ring group substituted with a phenolic hydroxy group" means a 6-membered hetero ring group or an aromatic ring group which have a phenolic hydroxy group. Examples thereof include groups of the formulae:

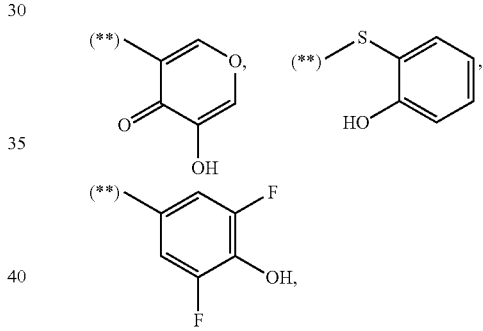

and the like.

With the proviso that the bonds with (**) represent bonding to $Y^2$ of the compound represented by the general formula (I).

The "$C_{1-6}$ alkylene group" means a divalent linear or branched-chained saturated hydrocarbon chain having 1 to 6 carbon atoms. Examples thereof include —CH$_2$—, —CH$_2$CH$_2$—, —CH(CH$_3$)—, —(CH$_2$)$_3$—, —CH(CH$_3$) CH$_2$—, —CH$_2$CH(CH$_3$)—, —CH(CH$_2$CH$_3$)—, —C(CH$_3$)$_2$—, —(CH$_2$)$_4$—, —CH(CH$_3$)—(CH$_2$)$_2$—, —(CH$_2$)$_2$—CH(CH$_3$)—, —CH(CH$_2$CH$_3$)—CH$_2$, —C(CH$_3$)$_2$ CH$_2$—, —CH$_2$—C(CH$_3$)$_2$—, —CH(CH$_3$)—CH (CH$_3$)—, —(CH$_2$)$_5$—, —CH(CH$_3$)—(CH$_2$)$_3$—, —C(CH$_3$)$_2$ CH$_2$CH$_2$—, —(CH$_2$)$_6$—, —C(CH$_3$)$_2$(CH$_2$)$_3$—, and the like.

In addition, in the present specification, —CH$_2$— may be referred to as a methylene group.

The "$C_{1-5}$ alkylene group" means a divalent linear or branched-chained saturated hydrocarbon chain having 1 to 5 carbon atoms. Examples thereof include —CH$_2$—, —(CH$_2$)$_2$—, —CH(CH$_3$)—, —(CH$_2$)$_3$—, —CH$_2$—CH (CH$_3$)—, —C(CH$_3$)$_2$—, —(CH$_2$)$_4$—, —(CH$_2$)$_5$—, and the like.

The "halo-$C_{1-6}$ alkylene group" means a group in which the hydrogen atom(s) of the $C_{1-6}$ alkylene group described above is(are) substituted with 1 to 4 halogen atoms described above. As the halogen atom for substituting the hydrogen atom, a fluorine atom or a chlorine atom is preferable, and more preferably a fluorine atom. Examples of the halo-$C_{1-6}$ alkylene group include —CHF—, —CF$_2$—, —CF$_2$CH$_2$—, —CH$_2$CF$_2$—, —CF$_2$CF$_2$—, —CCl$_2$—, —CCl$_2$CH$_2$—, —CH$_2$CCl$_2$—, —CCl$_2$CCl$_2$—, and the like.

Examples of the "$C_{1-6}$ oxyalkylene group" include —O—CH$_2$—, —CH$_2$—O—, —O—(CH$_2$)$_2$—, —CH$_2$—O—CH$_2$—, —(CH$_2$)$_2$—O—, —O—CH(CH$_3$)—, —CH(CH$_3$)—O—, —O—(CH$_2$)$_3$—, —(CH$_2$)$_3$—O—, —O—CH(CH$_3$)—CH$_2$—, —CH(CH$_3$)—CH$_2$—O—, —O—C(CH$_3$)$_2$—, —C(CH$_3$)$_2$—O—, —O—(CH$_2$)$_4$—, —O—(CH$_2$)$_5$— or —O—(CH$_2$)$_6$—, and the like. It is preferably —O—CH$_2$—, —CH$_2$—O—, —O—(CH$_2$)$_2$—, —O—CH(CH$_3$)—, —O—CH(CH$_3$)—CH$_2$—, or —O—C(CH$_3$)$_2$—. It is more preferably —O—CH$_2$—, —O—CH(CH$_3$)—, or —O—C(CH$_3$)$_2$—.

Examples of the "$C_{2-4}$ alkenylene group" include —CH=CH—, —CCH$_3$=CH—, —CH=CCH$_3$—, —CH=CHCH$_2$—, —CH$_2$CH=CH—, and the like.

Hereinafter, the present invention is described in more detail.

The compounds of the present invention (I) also include stereoisomer such as optical isomers, geometric isomers, and the like thereof.

In the case where the compound (I) of the present invention is an optical isomer having one or more asymmetric carbon atoms, the optical isomer of the compound (I) of the present invention may have any of an R configuration and an S configuration at the respective asymmetric carbon atoms. Also, any of the optical isomers thereof and a mixture of the optical isomers are encompassed by the present invention. Further, in the mixture of the optical active bodies, racemic bodies including equal amounts of the respective optical isomers are also encompassed within the scope of the present invention. In the case where the compound (I) of the present invention is a solid or crystal racemic body, the racemic compound, the racemic mixture, and the racemic solid solution are also encompassed within the scope of the present invention.

In the case where geometric isomers of the compound (I) of the present invention exist, the present invention includes any of the geometric isomers.

Furthermore, in the case where tautomers of the compound (I) of the present invention exist, the present invention includes any of the tautomers.

The compound (I) of the present invention can be converted to a pharmaceutically acceptable salt thereof according to a usual method, as necessary. Such a salt may be presented as an acid addition salt or a salt with a base.

Examples of the acid addition salt include acid addition salts with mineral acids such as hydrochloric acid, hydrobromic acid, hydroiodic acid, sulfuric acid, nitric acid, phosphoric acid and the like, and acid addition salts with organic acids such as formic acid, acetic acid, trifluoroacetic acid, methanesulfonic acid, benzene sulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like.

Examples of the salt with a base include salts with inorganic bases, such as a sodium salt, a potassium salt, a calcium salt, a magnesium salt, and the like, and salts with organic bases such as piperidine, morpholine, pyrrolidine, arginine, lysine, and the like.

In addition, the compound (I) of the present invention or a pharmaceutically acceptable salt thereof also encompasses hydrates, and solvates with pharmaceutically acceptable solvents such as ethanol and the like.

The "EP$_1$ receptor antagonism" as mentioned in the present invention means an action of inhibiting the binding of a prostaglandin E$_2$ (PGE$_2$) to a prostaglandin E receptor 1 (EP$_1$ receptor).

The EP$_1$ receptor antagonism reduces or inhibits the influx amount of calcium into cells and thus decreases the intracellular calcium concentration. As the result, the EP$_1$ receptor antagonism exhibits an action of relaxation of smooth muscles, inhibition of sensory nerve stimulation, or the like. Particularly, the EP$_1$ receptor antagonist acts on the bladder, the urothelium, or the like, whereby it is useful as an agent for treating or preventing LUTS, in particular, the symptoms of OABs or the like.

Furthermore, the EP$_1$ receptor antagonism can be evaluated based on the efficacy of inhibiting the influx amount of calcium into cells by a PGE$_2$. This efficacy can be evaluated by an in vitro test or in vivo test mutatis mutandis in accordance with "Pharmacological Test Examples" described in JP2008-214224A.

Preferable substituents for the compound (I) of the present invention or a pharmaceutically acceptable salt thereof are as follows.

(I-1) A is preferably a benzene ring, a pyridine ring, a furan ring, or a thiazole ring, more preferably a benzene ring or a pyridine ring, and further more preferably a pyridine ring.

(I-2) $Y^1$ is preferably a $C_{1-6}$ alkylene group, more preferably —CH$_2$—, —CH(CH$_3$)—, or —C(CH$_3$)$_2$—, and further preferably a —CH$_2$— group.

(I-3) $Y^2$ is preferably a single bond or a $C_{1-6}$ alkylene group, more preferably a single bond, —CH$_2$—, or —CH(CH$_3$)—, further preferably a single bond or —CH$_2$—, and further more preferably a single bond.

(I-4) $R^1$ is preferably a hydrogen atom or a methyl group, and more preferably a hydrogen atom.

(I-5) $R^2$ is preferably a group selected from the group consisting of the following i1) to m1):

i1) a tert-butyl group, j1) a $C_{3-6}$ cycloalkyl group which is unsubstituted or substituted with one $C_{1-6}$ alkyl group at the 1-position, k1) a phenyl group which is unsubstituted or substituted with one fluorine atom, l1) a 3-pyridyl group, and m1) a 5-membered aromatic heterocyclic group which is unsubstituted or substituted with one methyl group at the 5-position; it is more preferably a tert-butyl group, a phenyl group, a 4-fluorophenyl group, a 3-pyridyl group, a 3-furyl group, a 3-thienyl group, a 5-methyl-furan-3-yl group, a 5-methyl-thiophen-3-yl group, or a 1-methylcyclopropyl group, and further preferably a tert-butyl group, a phenyl group, a 4-fluorophenyl group, a 3-pyridyl group, a 3-furyl group, a 3-thienyl group, a 5-methyl-thiophen-3-yl group, or a 1-methylcyclopropyl group.

(I-6) $R^3$ is preferably a halogen atom, a $C_{1-6}$ alkyl group, a halo-$C_{1-6}$ alkyl group, a $C_{1-6}$ alkoxy group, a halo-$C_{1-6}$ alkoxy group, or a $C_{3-6}$ cycloalkyl group, more preferably a halogen atom, a $C_{1-6}$ alkyl group, a halo-$C_{1-6}$ alkyl group, a $C_{1-6}$ alkoxy group, or a $C_{3-6}$ cycloalkyl group, further preferably a chlorine atom, a fluorine atom, a methyl group, an ethyl group, a trifluoromethyl group, a methoxy group, an ethoxy group, or a cyclopropyl group, further more preferably a chlorine atom, a methyl group, an ethyl group, a methoxy group, or a cyclopropyl group, and most preferably a methoxy group.

(I-7) $R^4$ is preferably a hydrogen atom, a halogen atom, a $C_{1-6}$ alkyl group or a $C_{1-6}$ alkoxy group, and more preferably a hydrogen atom, a fluorine atom, a chlorine atom, a methyl group or a methoxy group.

(I-8) $R^5$ is preferably a hydrogen atom.

(I-9) Z is preferably —C(=O)—NHSO$_2$R$^6$, —C(=O)—NHCN, or an acidic 5-membered hetero ring group, more preferably —C(=O)—NHSO$_2$—CH$_3$, —C(=O)—NHSO$_2$—CH$_2$CH$_3$, —C(=O)—NHSO$_2$—(CH$_2$)$_2$CH$_3$, —C(=O)—NHSO$_2$—CH(CH$_3$)$_2$, —C(=O)—NHSO$_2$-cyclopropyl, —C(=O)—NHSO$_2$-phenyl, or a group selected from Group C, and further preferably —C(=O)—NHSO$_2$—CH$_3$, —C(=O)—NHSO$_2$—CH$_2$CH$_3$, —C(=O)—NHSO$_2$—CH(CH$_3$)$_2$, —C(=O)—NHSO$_2$-cyclopropyl, or a group selected from Group D.

(I-10) $R^6$ is preferably a $C_{1-6}$ alkyl group, a $C_{3-6}$ cycloalkyl group, or a phenyl group, in which the ring is unsubstituted or substituted with one methyl group, and more preferably a methyl group, an ethyl group, an n-propyl group, an isopropyl group, or a cyclopropyl group.

In a preferable embodiment, the compound (I) of the present invention or a pharmaceutically acceptable salt thereof is a compound including a combination of preferable substituents described in (I-1) to (I-10).

EMBODIMENT 1

In a preferable embodiment of the present invention,
A is a benzene ring, a pyridine ring, a furan ring, or a thiazole ring;
$Y^1$ is a $C_{1-6}$ alkylene group;
$Y^2$ is a single bond or a $C_{1-6}$ alkylene group;
$R^1$ is a hydrogen atom or a methyl group;
$R^2$ is a group selected from the group consisting of the following i1) to m1):
i1) a tert-butyl group,
j1) a $C_{3-6}$ cycloalkyl group which is unsubstituted or substituted with one $C_{1-6}$ alkyl group at the 1-position of the ring,
k1) a phenyl group which is unsubstituted or substituted with one fluorine atom,
l1) a 3-pyridyl group, and
m1) a 5-membered aromatic heterocyclic group which is unsubstituted or substituted with one methyl group at the 5-position;
$R^3$ is a halogen atom, a $C_{1-6}$ alkyl group, a halo-$C_{1-6}$ alkyl group, a $C_{1-6}$ alkoxy group, a halo-$C_{1-6}$ alkoxy group, or a $C_{3-6}$ cycloalkyl group;
$R^4$ is a hydrogen atom, a halogen atom, a $C_{1-6}$ alkyl group or a $C_{1-6}$ alkoxy group;
$R^5$ is a hydrogen atom;
Z is —C(=O)—NHSO$_2$R$^6$, —C(=O)—NHCN, or an acidic 5-membered hetero ring group; and
$R^6$ is a $C_{1-6}$ alkyl group, a $C_{3-6}$ cycloalkyl group, or a phenyl group, in which the ring is unsubstituted or substituted with one methyl group.

EMBODIMENT 2

In an embodiment that is preferable to Embodiment 1,
Z is —C(=O)—NHSO$_2$R$^6$, —C(=O)—NHCN, or a group selected from Group C.

EMBODIMENT 3

In an embodiment that is preferable to Embodiment 2,
$Y^1$ is a methylene group;
$Y^2$ is a single bond;
$R^3$ is a halogen atom, a $C_{1-6}$ alkyl group, a halo-$C_{1-6}$ alkyl group, a $C_{1-6}$ alkoxy group, or a $C_{3-6}$ cycloalkyl group; and
$R^6$ is a $C_{1-6}$ alkyl group, a $C_{3-6}$ cycloalkyl group, or a phenyl group.

EMBODIMENT 4

In an embodiment that is preferable to Embodiment 3,
A is a benzene ring or a pyridine ring.

EMBODIMENT 5

In an embodiment that is preferable to Embodiment 4,
$R^1$ is a hydrogen atom.

EMBODIMENT 6

In an embodiment that is preferable to Embodiment 4,
$R^2$ is a phenyl group, a 4-fluorophenyl group, a 3-pyridyl group, a 3-furyl group, a 3-thienyl group, a 5-methylfuran-3-yl group, or a 5-methylthiophen-3-yl group.

EMBODIMENT 7

In an embodiment that is preferable to Embodiment 6,
Z is —C(=O)—NHSO$_2$R$^6$, or a group selected from Group C; and
$R^6$ is a methyl group, an ethyl group, an n-propyl group, an isopropyl group, a cyclopropyl group, or a phenyl group.

EMBODIMENT 8

In an embodiment that is preferable to Embodiment 7,
Z is —C(=O)—NHSO$_2$R$^6$, or a group selected from Group D.

Examples of the concrete compound included in the present embodiment include the following compounds:
N-methanesulfonyl-6-(6-methoxy-2-phenyl-1H-indol-3-ylmethyl)pyridine-2-carboxamide (Example 2-1), 6-(6-cyclopropyl-2-phenyl-1H-indol-3-ylmethyl)-N-methanesulfonylpyridine-2-carboxamide (Example 2-2), N-methanesulfonyl-6-(6-methyl-2-phenyl-1H-indol-3-ylmethyl)pyridine-2-carboxamide (Example 3-1), 6-(5-fluoro-6-methoxy-2-phenyl-1H-indol-3-ylmethyl)-N-methanesulfonylpyridine-2-carboxamide (Example 3-9), N-ethanesulfonyl-6-(6-methoxy-2-thiophen-3-yl-1H-indol-3-ylmethyl)pyridine-2-carboxamide (Example 3-35), 6-cyclopropyl-2-phenyl-3-[6-(1H-tetrazol-5-yl)pyridin-2-ylmethyl]-1H-indole (Example 5-1), 6-methoxy-2-phenyl-3-[6-(1H-tetrazol-5-yl)pyridin-2-ylmethyl]-1H-indole (Example 5-2), 6-methyl-2-phenyl-3-[6-(1H-tetrazol-5-yl)pyridin-2-ylmethyl]-1H-indole (Example 5-3), 2-furan-3-yl-6-methoxy-3-[6-(1H-tetrazol-5-yl)pyridin-2-ylmethyl]-1H-indole (Example 5-11), and 3-[6-(6-methoxy-2-phenyl-1H-indol-3-ylmethyl)pyridin-2-yl]-4,5-dihydro-1,2,4-oxadiazol-5-one (Example 7-1).

EMBODIMENT 9

In an embodiment that is preferable to Embodiment 3,
$R^2$ is a tert-butyl group.

EMBODIMENT 10

In an embodiment that is preferable to Embodiment 9,
$R^3$ is a $C_{1-6}$ alkoxy group;
$R^4$ is a halogen atom;

Z is —C(=O)—NHSO$_2$R$^6$; and
R$^6$ is a methyl group or an ethyl group.

EMBODIMENT 11

In an embodiment that is preferable to Embodiment 9,
R$^3$ is a C$_{1-6}$ alkoxy group;
R$^4$ is a hydrogen atom;
Z is —C(=O)—NHSO$_2$R$^6$; and
R$^6$ is a C$_{3-6}$ cycloalkyl group or a phenyl group.

EMBODIMENT 12

In an embodiment that is preferable to Embodiment 9,
Z is a group selected from Group D.
Examples of the concrete compound included in the present embodiment include the following compound:
2-tert-butyl-6-methoxy-3-[6-(1H-tetrazol-5-yl)pyridin-2-ylmethyl]-1H-indole. (Example 5-7).

EMBODIMENT 13

In an embodiment that is preferable to Embodiment 3,
R$^1$ is a methyl group.

EMBODIMENT 14

In an embodiment that is preferable to Embodiment 13,
Z is —C(=O)—NHSO$_2$R$^6$.

EMBODIMENT 15

In an embodiment that is preferable to Embodiment 2,
Y$^1$ is a methylene group;
Y$^2$ is a single bond;
R$^2$ is a C$_{3-6}$ cycloalkyl group which is substituted with one C$_{1-6}$ alkyl group at the 1-position of the ring; and
R$^3$ is a halogen atom, a C$_{1-6}$ alkyl group, a halo-C$_{1-6}$ alkyl group, a C$_{1-6}$ alkoxy group, or a C$_{3-6}$ cycloalkyl group.

EMBODIMENT 16

In an embodiment that is preferable to Embodiment 15,
A is a benzene ring or a pyridine ring.

EMBODIMENT 17

In an embodiment that is preferable to Embodiment 16,
R$^1$ is a hydrogen atom.

EMBODIMENT 18

In an embodiment that is preferable to Embodiment 16,
R$^2$ is a 1-methylcyclopropyl group; and
R$^6$ is a C$_{1-6}$ alkyl group, a C$_{3-6}$ cycloalkyl group, or a phenyl group.

EMBODIMENT 19

In an embodiment that is preferable to Embodiment 18,
Z is a group selected from Group C.

EMBODIMENT 20

In an embodiment that is preferable to Embodiment 19,
Z is a group selected from Group D.

EMBODIMENT 21

In an embodiment that is preferable to Embodiment 20,
Z is a group of the formula:

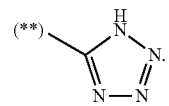

Examples of the concrete compound included in the present embodiment include the following compounds:
6-methoxy-2-(1-methylcyclopropyl)-3-[6-(1H-tetrazol-5-yl)pyridin-2-ylmethyl]-1H-indole (Example 17-11), 6-methyl-2-(1-methylcyclopropyl)-3-[6-(1H-tetrazol-5-yl)pyridin-2-ylmethyl]-1H-indole (Example 17-12), 6-cyclopropyl-2-(1-methylcyclopropyl)-3-[6-(1H-tetrazol-5-yl)pyridin-2-ylmethyl]-1H-indole (Example 17-13), 6-chloro-2-(1-methylcyclopropyl)-3-[6-(1H-tetrazol-5-yl)pyridin-2-ylmethyl]-1H-indole (Example 17-14), 6-chloro-5-methoxy-2-(1-methylcyclopropyl)-3-[6-(1H-tetrazol-5-yl)pyridin-2-ylmethyl]-1H-indole (Example 20-1), 6-ethyl-2-(1-methylcyclopropyl)-3-[6-(1H-tetrazol-5-yl)pyridin-2-ylmethyl]-1H-indole (Example 20-2), 5-chloro-6-methoxy-2-(1-methylcyclopropyl)-3-[6-(1H-tetrazol-5-yl)pyridin-2-ylmethyl]-1H-indole (Example 20-3), and 6-methoxy-5-methyl-2-(1-methylcyclopropyl)-3-[6-(1H-tetrazol-5-yl)pyridin-2-ylmethyl]-1H-indole (Example 20-4).

Production Process of Compound (I) of the Present Invention

The compound (I) of the present invention can be prepared by using a compound (II) as a key intermediate. The compound (II) can be prepared by, for example, the method shown in Scheme 1 or Scheme 2.

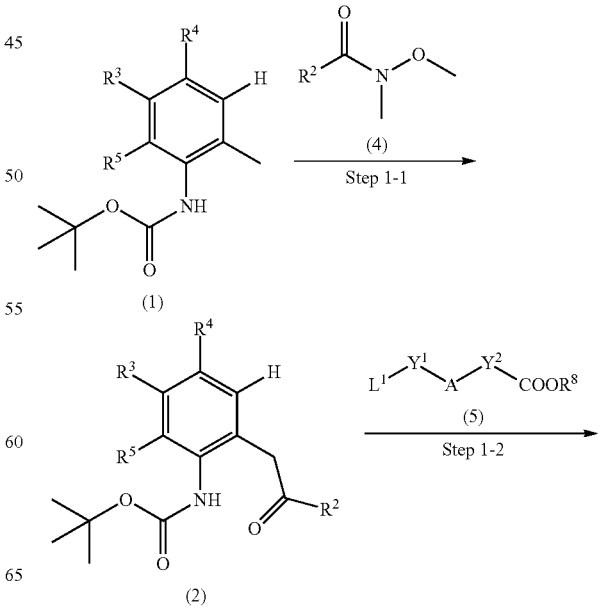

-continued

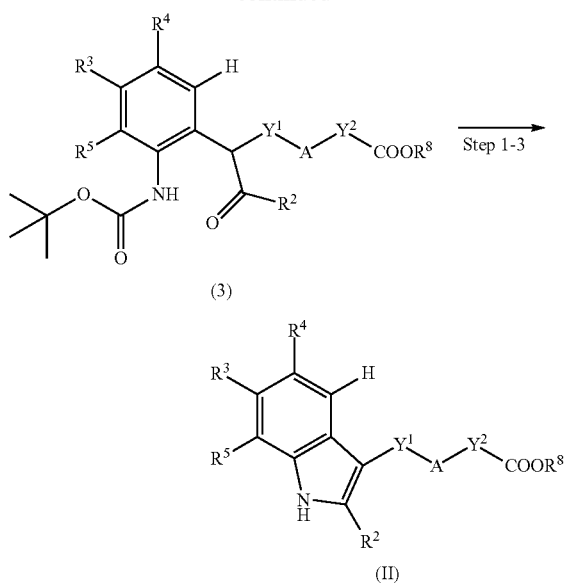

wherein A, $R^2$, $R^3$, $R^4$, $R^5$, $Y^1$, and $Y^2$ have the same meanings as defined above; $R^8$ represents a $C_{1-6}$ alkyl group or a $C_{7-10}$ aralkyl group; and $L^1$ represents a leaving group such as a chlorine atom, a bromine atom, an iodine atom, a methanesulfonyloxy group, and the like.

but it is usually 30 minutes to 1 day. Further, the compounds (1) and (4) used in the present step may be commercially available or can be prepared according to a method described in literature or a similar method thereto.

Step 1-2

A compound (3) can be prepared by reacting the compound (2) that has been treated with a base, with a compound (5) in a solvent. Examples of the solvent to be used include N,N-dimethylformamide, N,N-dimethylacetamide, 1,3-dimethylimidazolidin-2-one, tetrahydrofuran, a mixed solvent thereof, and the like. Examples of the base to be used include sodium hydride, potassium tert-butoxide, cesium carbonate, and the like. The reaction temperature is usually −20° C. to reflux temperature. The reaction time varies depending on a starting material to be used, a solvent to be used, a reaction temperature, or the like, but it is usually 30 minutes to 3 days. Further, the compound (5) used in the present step may be commercially available or can be prepared according to a method described in literature or a similar method thereto.

Step 1-3

The compound (II) can be prepared by treating the compound (3) with an acid in a solvent. Examples of the solvent to be used include dichloromethane, chloroform, methanol, ethanol, tetrahydrofuran, 1,4-dioxane, a mixed solvent thereof, and the like. Examples of the acid to be used include trifluoroacetic acid, methanesulfonic acid, concentrated hydrochloric acid, concentrated sulfuric acid, and the like. The reaction temperature is usually −78° C. to reflux temperature. The reaction time varies depending on a starting material to be used, a solvent to be used, a reaction temperature, or the like, but it is usually 30 minutes to 3 days.

Scheme 2

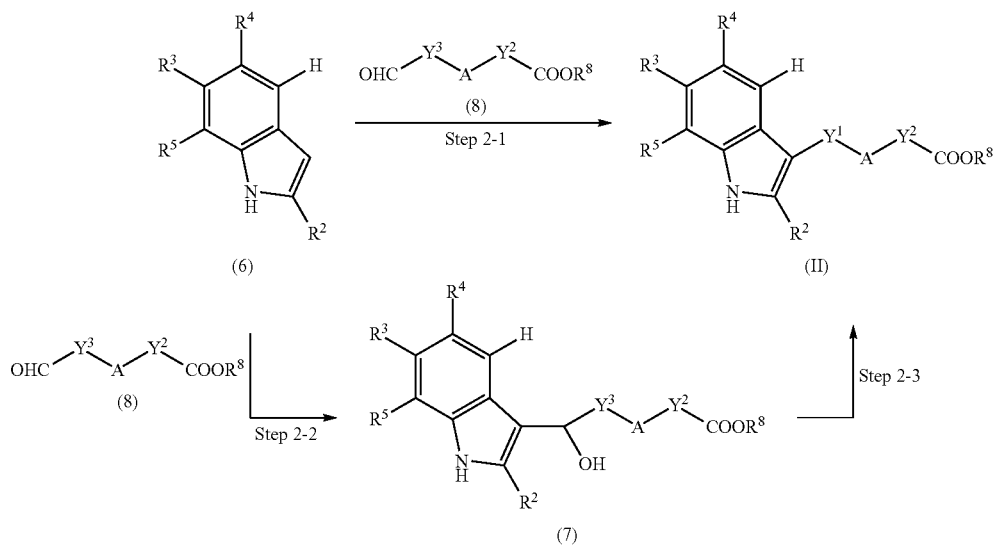

Step 1-1

A compound (2) can be prepared by reacting a compound (1) that has been treated with a base, with a compound (4) in a solvent. Examples of the solvent to be used include tetrahydrofuran, diethyl ether, 1,2-dimethoxyethane, a mixed solvent thereof, and the like. Examples of the base to be used include n-butyllithium, sec-butyllithium, tert-butyllithium, and the like, and sec-butyllithium is preferable. The reaction temperature is usually −78° C. to reflux temperature. The reaction time varies depending on a starting material to be used, a solvent to be used, a reaction temperature, or the like, wherein A, $R^2$, $R^3$, $R^4$, $R^5$, $R^8$, $Y^1$, and $Y^2$ have the same meanings as defined above; and $Y^3$ represents a single bond or a $C_{1-5}$ alkylene group.

Step 2-1

The compound (II) can be prepared by reacting a compound (6) with a compound (8) in the presence of an acid and a reducing agent in a solvent. Examples of the solvent to be used include dichloromethane, chloroform, tetrahydrofuran, a mixed solvent thereof, and the like. Examples of the acid to be used include trifluoroacetic acid, trimethylsilyl trifluoromethanesulfonate, a boron trifluoride diethyl ether complex, and the like. Examples of the reducing agent to be used include triethylsilane. The reaction temperature is usually −78° C. to room temperature. The reaction time varies depending on a starting material to be used, a solvent to be used, a reaction temperature, or the like, but it is usually 30 minutes to 3 days. Further, the compound (8) used in the present step may be commercially available or can be prepared according to a method described in literature or a similar method thereto.

Step 2-2

A compound (7) can be prepared by reacting the compound (6) with the compound (8) in the presence of a base in a solvent. Examples of the solvent to be used include dichloromethane, chloroform, tetrahydrofuran, toluene, methanol, ethanol, a mixed solvent thereof, and the like. Examples of the base to be used include 1,8-diazabicyclo[5,4,0]-7-undecene, 1,5-diazabicyclo[4,3,0]-5-nonene, sodium ethoxide, sodium methoxide, and the like. The reaction temperature is usually −20° C. to 50° C. The reaction time varies depending on a starting material to be used, a solvent to be used, a reaction temperature, or the like, but it is usually 30 minutes to 3 days.

Step 2-3

The compound (II) can be prepared by subjecting a compound (7) to a reduction reaction. Examples of the concrete method include the following methods (a) to (c).

(a) Method for Reacting Compound (7) with the Reagent Prepared from Sodium Iodide and Chlorotrimethylsilane in Solvent The reaction is carried out in a solvent such as acetonitrile and the like. The reaction temperature is usually −30° C. to room temperature. The reaction time varies depending on a starting material to be used, a solvent to be used, a reaction temperature, or the like, but it is usually 10 minutes to 24 hours.

(b) Method for Reacting Compound (7) with Reducing Agent in the Presence of Acid The reaction is carried out in a solvent such as dichloromethane, chloroform, tetrahydrofuran, a mixed solvent thereof, and the like. Examples of the acid to be used include trifluoroacetic acid, trimethylsilyl trifluoromethanesulfonate, a boron trifluoride diethyl ether complex, and the like. Examples of the reducing agent to be used include triethylsilane. The reaction temperature is usually −78° C. to room temperature. The reaction time varies depending on a starting material to be used, a solvent to be used, a reaction temperature, or the like, but it is usually 30 minutes to 3 days.

(c) Method for Treating Compound (7) Under Conditions for Catalytic Hydrogenation The catalytic hydrogenation can be carried out by using a method known to a skilled person in the art. For example, it is carried out using a reduction catalyst such as palladium-carbon, platinum oxide, and the like, in a solvent such as methanol, ethanol, ethyl acetate, tetrahydrofuran, acetic acid, a mixed solvent thereof, and the like, under a hydrogen atmosphere. The reaction time varies depending on a starting material to be used, a solvent to be used, a reaction temperature, or the like, but it is usually 30 minutes to 3 days.

Furthermore, the compound (6) which is used as a starting material in Scheme 2 may be commercially available, or can be prepared from a commercially available reagent according to a method described in other literature or a similar method thereto. Concrete examples of the preparation method are shown in Scheme 3.

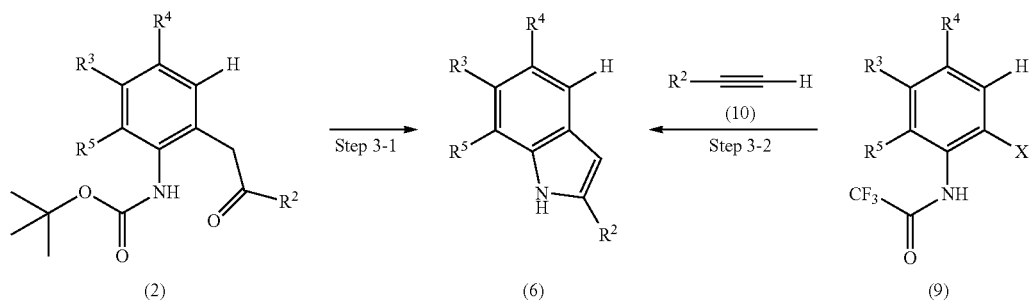

wherein $R^2$, $R^3$, $R^4$, and $R^5$ have the same meanings as defined above; and X represents a bromine atom, an iodine atom, a trifluoromethanesulfonyloxy group, or the like.

Step 3-1

The compound (6) can be prepared by treating the compound (2) with an acid in a solvent. Examples of the solvent to be used include dichloromethane, chloroform, methanol, ethanol, tetrahydrofuran, 1,4-dioxane, a mixed solvent thereof, and the like. Examples of the acid to be used include trifluoroacetic acid, methanesulfonic acid, concentrated hydrochloric acid, concentrated sulfuric acid, and the like. The reaction temperature is usually −78° C. to reflux temperature. The reaction time varies depending on a starting material to be used, a solvent to be used, a reaction temperature, or the like, but it is usually 30 minutes to 3 days.

Step 3-2

The compound (6) can be prepared by reacting a compound (9) with a compound (10) in the presence of a base, a palladium catalyst, and a copper catalyst in a solvent. Examples of the solvent to be used include acetonitrile, tetrahydrofuran, 1,2-dimethoxyethane, N,N-dimethylformamide, toluene, a mixed solvent thereof, and the like. Examples of the base to be used include triethylamine, N,N-diisopropylethylamine, potassium carbonate, tripotassium phosphate, and the like. Examples of the copper catalyst to be used include copper(I) iodide. Examples of the palladium catalyst to be used include bis(triphenylphosphine) palladium (II) dichloride, tetrakis(triphenylphosphine) palladium(0), and the like. The reaction temperature is usually room temperature to 150° C. The reaction time varies depending on a starting material to be used, a solvent to be used, a reaction temperature, or the like, but it is usually 30 minutes to 3 days. Further, the present step can also be carried out in the absence of a palladium catalyst, in which an amino acid derivative such as N,N-dimethylglycine, L-proline, and the like may be preferably used as an additive. Further, the compounds (9) and (10) used in the present step may be commercially available or can be prepared from a commercially available reagent according to a method described in literature or a similar method thereto.

Among the compounds (I) of the present invention, a compound represented by the following general formula (Ia) can be prepared by the method shown in Scheme 4.

Step 4-2
A compound (12) can be prepared by treating the compound (11) by an ordinary method for converting an ester group into a carboxy group. Such a method is well-known to a skilled person in the art, and can be carried out according to the method described in, for example, 'Greene's Protective Groups in Organic Synthesis', fourth edition, Wiley-Interscience, 2006, edited by Greene & Wuts.

Step 4-3
The compound (Ia) of the present invention can be prepared by reacting the compound (12) with a compound (14) in

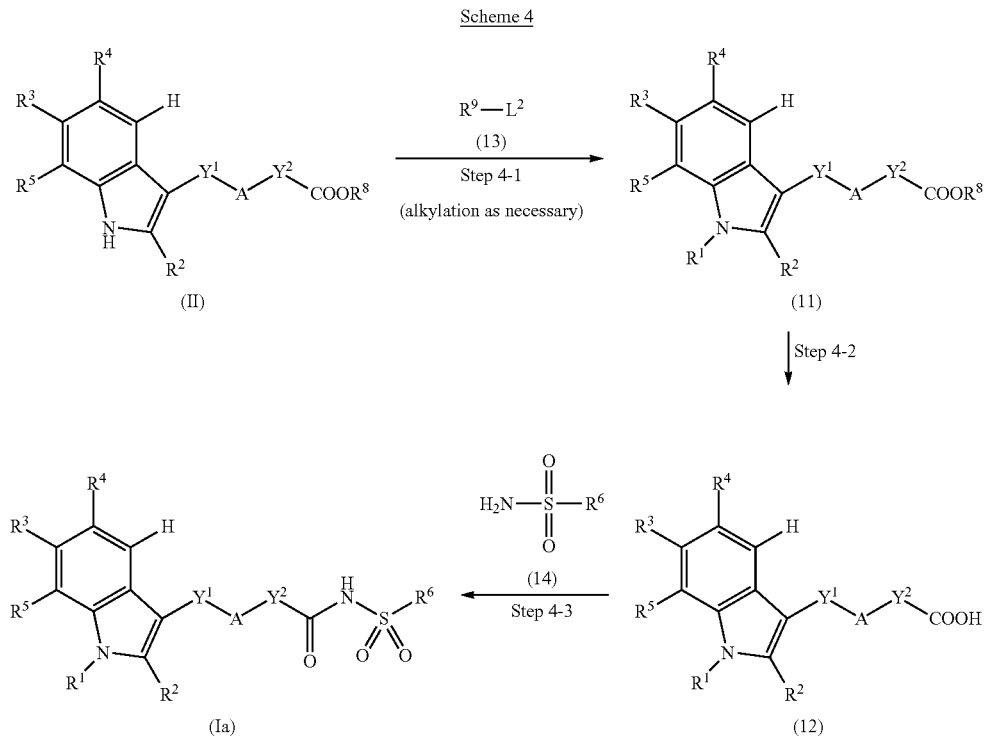

wherein A, $R^1$, $R^2$, $R^3$, $R^4$, $R^5$, $R^6$, $R^8$, $Y^1$, and $Y^2$ have the same meanings as defined above; $R^9$ represents a $C_{1-6}$ alkyl group; and $L^2$ represents a leaving group such as a chlorine atom, a bromine atom, an iodine atom, a methanesulfonyloxy group, and the like.

Step 4-1

The present step is a step for preparing the compound (Ia) of the present invention, in which $R^1$ is a $C_{1-6}$ alkyl group. A compound (11) can be prepared by reacting a compound (II) with a compound (13), as necessary, in the presence of a base in a solvent. Examples of the solvent to be used include N,N-dimethylformamide, N,N-dimethylacetamide, 1,3-dimethylimidazolidin-2-one, N-methyl-2-pyrrolidinone, a mixed solvent thereof, and the like. Examples of the base to be used include sodium hydride, potassium tert-butoxide, cesium carbonate, potassium carbonate, and the like. The reaction temperature is usually –20° C. to 60° C. The reaction time varies depending on a starting material to be used, a solvent to be used, a reaction temperature, or the like, but it is usually 30 minutes to 3 days. Further, the compound (13) used in the present step may be commercially available or can be prepared according to a method described in literature or a similar method thereto.

the presence of a base and a condensing agent in a solvent. Examples of the solvent to be used include dichloromethane, chloroform, N,N-dimethylformamide, N,N-dimethylacetamide, a mixed solvent thereof, and the like. Examples of the base to be used include 4-dimethylaminopyridine, pyridine, triethylamine, N,N-diisopropylethylamine, and the like. Examples of the condensing agent to be used include 1-ethyl-3-(3-dimethylaminopropyl)carbodiimide hydrochloride, 1,1'-carbonyldiimidazole, dicyclohexylcarbodiimide, and the like. The reaction temperature is usually 0° C. to 60° C. The reaction time varies depending on a starting material to be used, a solvent to be used, a reaction temperature, or the like, but it is usually 30 minutes to 3 days. Further, the present step can also be carried out by the addition of a reaction accelerator such as 1-hydroxybenzotriazole and the like. Further, the compound (14) used in the present step may be commercially available or can be prepared according to a method described in literature or a similar method thereto.

Among the compounds (I) of the present invention, a compound represented by the following general formula (Ib) can be prepared by the method shown in Scheme 5.

Scheme 5

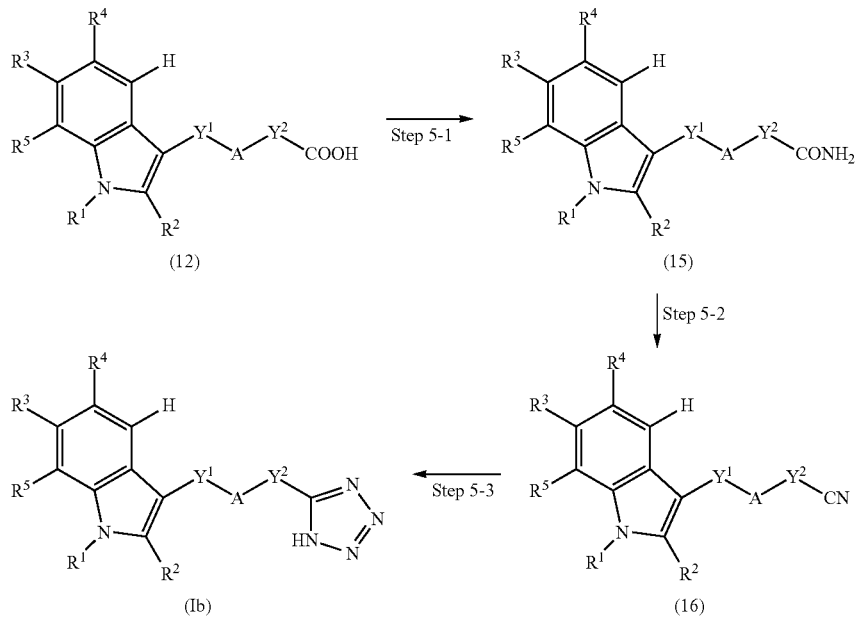

wherein A, $R^1$, $R^2$, $R^3$, $R^4$, $R^5$, $Y^1$, and $Y^2$ have the same meanings as defined above.

Step 5-1

A compound (15) can be prepared by treating the compound (12) by an ordinary method for converting a carboxy group to a carbamoyl group. For example, an example of the method is a method in which a carboxyl group is activated by a condensing agent in the presence or absence of a base in a solvent to undergo a reaction with ammonia or ammonium chloride. Examples of the solvent to be used include tetrahydrofuran, N,N-dimethylformamide, dichloromethane, a mixed solvent thereof, and the like. Examples of the base to be used include 4-dimethylaminopyridine, pyridine, triethylamine, N,N-diisopropylethylamine, and the like. Examples of the condensing agent to be used include 1-ethyl-3-(3-dimethylaminopropyl)carbodiimide hydrochloride, 1,1'-carbonyldiimidazole, diphenylphosphorylazide, dicyclohexylcarbodiimide, and the like. The reaction temperature is usually −20° C. to 60° C. The reaction time varies depending on a starting material to be used, a solvent to be used, a reaction temperature, or the like, but it is usually 30 minutes to 3 days.

Step 5-2

A compound (16) can be prepared by treating the compound (15) with a dehydrating reagent in the presence or absence of a base in a solvent. Examples of the solvent to be used include dichloromethane, chloroform, toluene, N,N-dimethylformamide, a mixed solvent thereof, and the like. Examples of the base to be used, as necessary, include triethylamine, N,N-diisopropylethylamine, pyridine, and the like. Examples of the dehydrating reagent to be used include trifluoroacetic anhydride, phosphoryl chloride, trifluoromethanesulfonic anhydride, phosphorous pentachloride, and the like. The reaction temperature is usually −20° C. to 60° C. The reaction time varies depending on a starting material to be used, a solvent to be used, a reaction temperature, or the like, but it is usually 30 minutes to 3 days.

Step 5-3

The compound (Ib) of the present invention can be prepared by reacting the compound (16) with sodium azide or the like in the presence of an acid in a solvent. Examples of the solvent to be used include tetrahydrofuran, N,N-dimethylformamide, ethanol, 1-propanol, isopropyl alcohol, 1-butanol, water, a mixed solvent thereof, and the like. Examples of the acid to be used include ammonium chloride, zinc chloride, zinc bromide, and the like. The reaction temperature is usually room temperature to reflux temperature. The reaction time varies depending on a starting material to be used, a solvent to be used, a reaction temperature, or the like, but it is usually 30 minutes to 3 days.

Among the compounds (I) of the present invention, a compound represented by the following general formula (Ic) can be prepared by the method shown in Scheme 6.

Scheme 6

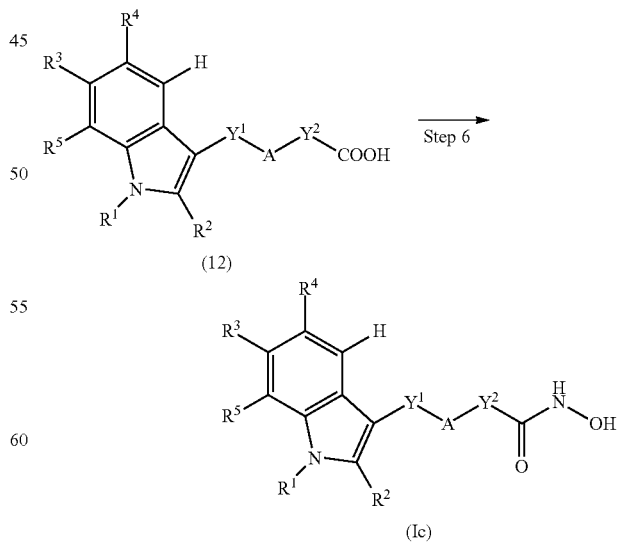

wherein A, $R^1$, $R^2$, $R^3$, $R^4$, $R^5$, $Y^1$, and $Y^2$ have the same meanings as defined above.

Step 6

The compound (Ic) of the present invention can be prepared by subjecting the compound (12) and hydroxylamine to an amidation reaction. Such an amidation reaction is well-known to a skilled person in the art, and examples thereof include the following methods (d) to (f).

(d) Method Using Acid Halide

The reaction can be carried out by reacting an acid halide that has been obtained by reacting the compound (12) with oxalyl chloride, thionyl chloride, or the like in a solvent or without a solvent, with hydroxylamine in the presence of a base in a solvent. Preparation of the acid halide is carried out in a solvent such as methylene chloride, chloroform, diethyl ether, tetrahydrofuran, toluene, a mixed solvent thereof, and the like, or without the solvent. The reaction temperature is usually −20° C. to reflux temperature. This reaction time varies depending on a starting material to be used, a solvent to be used, a reaction temperature, or the like, but it is usually 10 minutes to 24 hours. The reaction of the acid halide with hydroxylamine is carried out in a solvent such as methylene chloride, chloroform, diethyl ether, tetrahydrofuran, toluene, a mixed solvent thereof, and the like. Examples of the base to be used include pyridine, triethylamine, dimethylaniline, 4-dimethylaminopyridine, and the like. The reaction temperature is usually 0 to 50° C. The reaction time varies depending on a starting material to be used, a solvent to be used, a reaction temperature, or the like, but it is usually 30 minutes to 3 days.

(e) Method Using Mixed Acid Anhydride

The reaction can be carried out by reacting a mixed acid anhydride that has been obtained by reacting the compound (12) with pivaloyl chloride, tosyl chloride, mesyl chloride, ethyl chloroformate, isobutyl chloroformate, or the like in a solvent or without a solvent, with hydroxylamine in the presence of a base in a solvent. Preparation of the mixed acid anhydride is carried out, as necessary, in a solvent such as methylene chloride, chloroform, diethyl ether, tetrahydrofuran, a mixed solvent thereof, and the like. The reaction temperature is usually −20° C. to 40° C. The reaction time varies depending on a starting material to be used, a solvent to be used, a reaction temperature, or the like, but it is usually 10 minutes to 24 hours. The reaction of the mixed acid anhydride with hydroxylamine is carried out in a solvent such as methylene chloride, chloroform, diethyl ether, tetrahydrofuran, a mixed solvent thereof, and the like. Examples of the base to be used include pyridine, triethylamine, dimethylaniline, 4-dimethylaminopyridine, and the like. The reaction temperature is usually 0 to 50° C. The reaction time varies depending on a starting material to be used, a solvent to be used, a reaction temperature, or the like, but it is usually 30 minutes to 3 days.

(f) Method Using Condensing Agent

The reaction can be carried out by reacting the compound (12) with a condensing agent such as 1-ethyl-3-(3-dimethylaminopropyl)carbodiimide hydrochloride, 1,1'-carbonyldiimidazole, diphenylphosphorylazide, dicyclohexylcarbodiimide, and the like and hydroxylamine, in the presence of a base in a solvent. Examples of the solvent to be used include methylene chloride, chloroform, N,N-dimethylformamide, a mixed solvent thereof, and the like. The reaction temperature is usually 0° C. to 50° C. The reaction time varies depending on a starting material to be used, a solvent to be used, a reaction temperature, or the like, but it is usually 30 minutes to 3 days.

Among the compounds (I) of the present invention, a compound represented by the following general formula (Id) can be prepared by the method shown in Scheme 7.

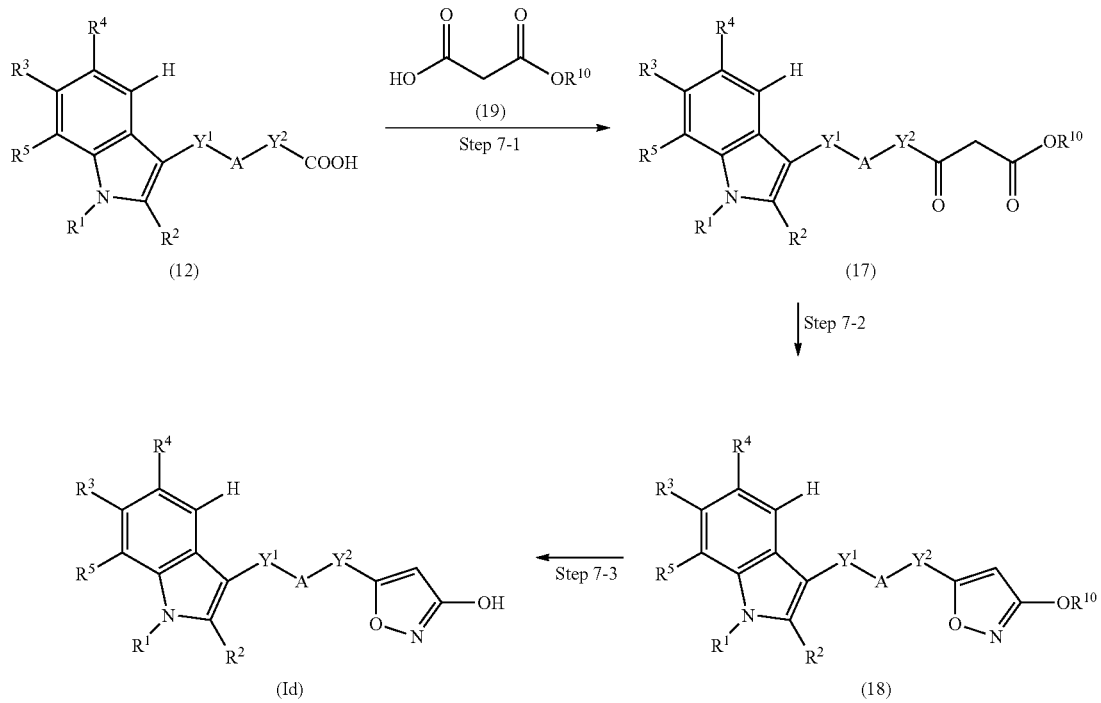

wherein A, $R^1$, $R^2$, $R^3$, $R^4$, $R^5$, $Y^1$, and $Y^2$ have the same meanings as defined above; and $R^{10}$ represents a $C_{1-6}$ alkyl group.

Step 7-1

A compound (17) can be prepared by reacting a reactive derivative of the compound (12) with a compound (19), in the presence of a base such as triethylamine, N,N-diisopropylethylamine, and the like and an inorganic salt such as magnesium chloride and the like in a solvent. Examples of the solvent to be used include acetonitrile, tetrahydrofuran, ethyl acetate, methylene chloride, toluene, a mixed solvent thereof, and the like. The reaction temperature is usually 0° C. to reflux temperature. The reaction time varies depending on a starting material to be used, a solvent to be used, a reaction temperature, or the like, but it is usually 30 minutes to 3 days. The reactive derivative as described above means a carboxylic acid derivative such as an acid halide, an acid anhydride, an active ester, and the like, and can be prepared by an ordinary method. Further, the compound (19) used in the present step may be commercially available or can be prepared according to a method described in literature or a similar method thereto.

Step 7-2

A compound (18) can be prepared by reacting the compound (17) with hydroxylamine in the presence of a base in a solvent. Examples of the solvent to be used include methanol, ethanol, water, a mixed solvent thereof, and the like. Examples of the base to be used include sodium hydroxide, potassium hydroxide, and the like. The reaction temperature is usually −78° C. to room temperature. The reaction time varies depending on a starting material to be used, a solvent to be used, a reaction temperature, or the like, but it is usually 30 minutes to 3 days.

Step 7-3

The compound (Id) of the present invention can be prepared by treating the compound (18) with an acid in a solvent or without a solvent. Examples of the acid to be used include concentrated hydrochloric acid, and the like. Examples of the solvent to be used include methanol, ethanol, water, a mixed solvent thereof, and the like. The reaction temperature is usually room temperature to reflux temperature. The reaction time varies depending on a starting material to be used, a solvent to be used, a reaction temperature, or the like, but it is usually 30 minutes to 24 hours.

Among the compounds (I) of the present invention, a compound represented by the following general formula (Ie) can be prepared by the method shown in Scheme 8.

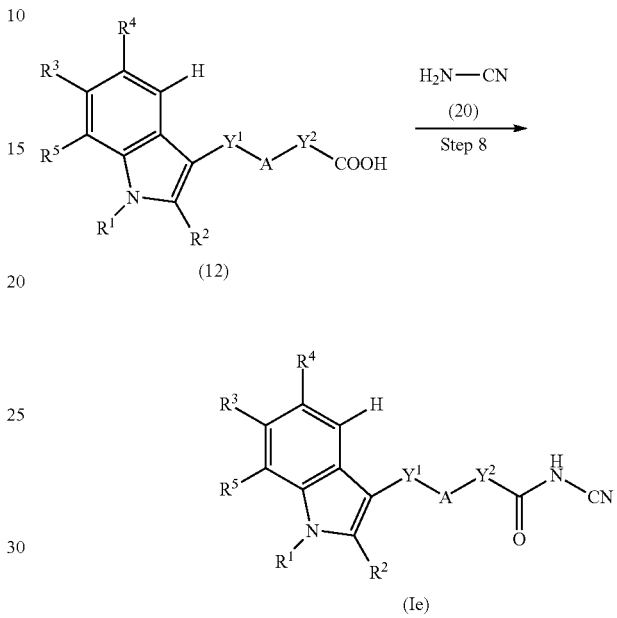

wherein A, $R^1$, $R^2$, $R^3$, $R^4$, $R^5$, $Y^1$, and $Y^2$ have the same meanings as defined above.

Step 8

The compound (Ie) of the present invention can be prepared by the same method as in Step 4-3 except that a compound (20) was used instead of the compound (14).

Among the compounds (I) of the present invention, compounds represented by the following general formulae (If), (Ig), (Ih), and (Ii) can be prepared by the method shown in Scheme 9.

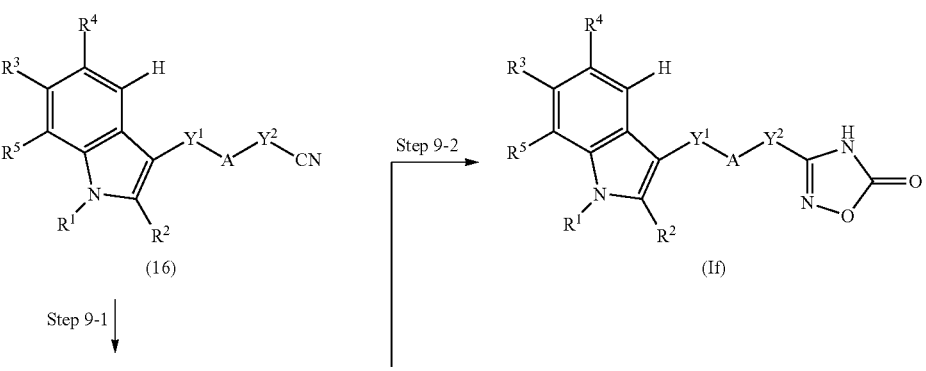

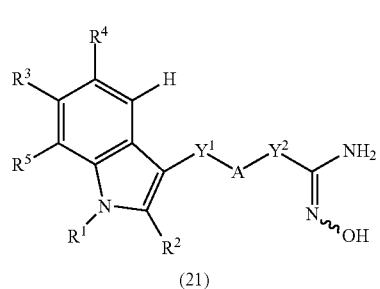

(21)

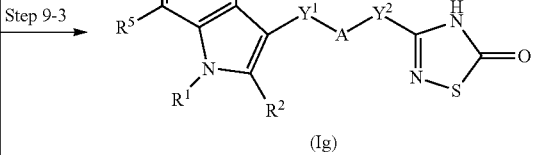

(Ig)

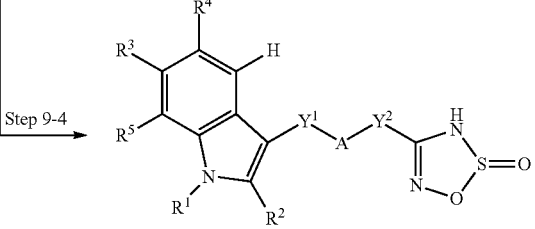

(Ih)

Step 9-6 ↓

Step 9-5

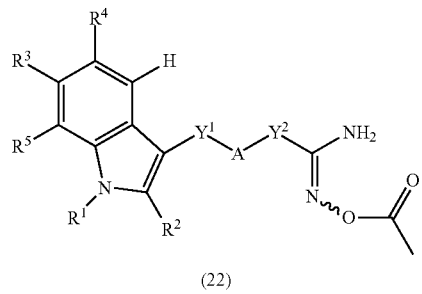

(22)

Step 9-7

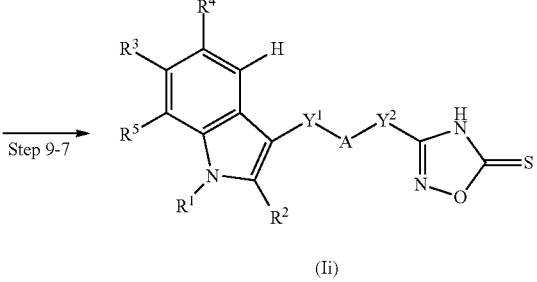

(Ii)

wherein A, $R^1$, $R^2$, $R^3$, $R^4$, $R^5$, $Y^1$ and $Y^2$ have the same meanings as defined above.

Step 9-1

A compound (21) can be prepared by reacting the compound (16) with hydroxylamine in the presence or absence of a base in a solvent. Examples of the solvent to be used include dimethylsulfoxide, methanol, ethanol, water, a mixed solvent thereof, and the like. Examples of the base to be used include potassium carbonate, sodium hydrogen carbonate, triethylamine, and the like. The reaction temperature is usually room temperature to reflux temperature. The reaction time varies depending on a starting material to be used, a solvent to be used, a reaction temperature, or the like, but it is usually 30 minutes to 3 days. Further, hydroxylamine used in the present step may be commercially available or can also be prepared by treating hydroxylamine hydrochloride or the like with a base.

Step 9-2

The compound (If) of the present invention can be prepared by reacting the compound (21) with a carbonylating agent in the presence of a base in a solvent. Examples of the solvent to be used include tetrahydrofuran, acetonitrile, toluene, xylene, a mixed solvent thereof, and the like. Examples of the base to be used include pyridine, 1,8-diazabicyclo[5,4,0]-7-undecene, 1,5-diazabicyclo[4,3,0]-5-nonene, and the like. Examples of the carbonylating agent to be used include 1,1'-carbonyldiimidazole, 2-ethylhexyl chloroformate, and the like. The reaction temperature is usually room temperature to reflux temperature. The reaction time varies depending on a starting material to be used, a solvent to be used, a reaction temperature, or the like, but it is usually 30 minutes to 3 days.

Step 9-3

The compound (Ig) of the present invention can be prepared by reacting the compound (21) with a thiocarbonylating agent and then treating the product with an acid in a solvent. Examples of the solvent to be used include tetrahydrofuran, methanol, chloroform, a mixed solvent thereof, and the like. Examples of the thiocarbonylating agent to be used include 1,1'-thiocarbonyldiimidazole, and the like. Examples of the acid to be used include a Lewis acid such as a boron trifluoride diethyl ether complex and the like, silica gel, and the like. The reaction temperature is usually −20° C. to room temperature. The reaction time varies depending on a starting material to be used, a solvent to be used, a reaction temperature, or the like, but it is usually 30 minutes to 3 days.

Step 9-4

The compound (Ih) of the present invention can be prepared by reacting the compound (21) with thionyl chloride in the presence of a base in a solvent. Examples of the solvent to be used include dichloromethane, chloroform, tetrahydrofuran, a mixed solvent thereof, and the like. Examples of the base to be used include pyridine, 4-dimethylaminopyridine, and the like. The reaction temperature is usually −20° C. to room temperature. The reaction time varies depending on a starting material to be used, a solvent to be used, a reaction temperature, or the like, but it is usually 30 minutes to 3 days.

Step 9-5

The compound (Ii) of the present invention can be prepared by reacting the compound (21) with a thiocarbonylating agent in the presence of a base in a solvent. Examples of the solvent to be used include acetonitrile, tetrahydrofuran, toluene, xylene, a mixed solvent thereof, and the like. Examples of the base to be used include 1,8-diazabicyclo[5,4,0]-7-undecene, 1,5-diazabicyclo[4,3,0]-5-nonene, and the like. Examples of the thiocarbonylating agent to be used include 1,1'-thiocarbonyldiimidazole and the like. The reaction temperature is usually room temperature to reflux temperature. The reaction time varies depending on a starting material to be used, a solvent to be used, a reaction temperature, or the like, but it is usually 30 minutes to 3 days.

Step 9-6

A compound (22) can be prepared by reacting the compound (21) with an acetylating agent in the presence of a base in a solvent. Examples of the solvent to be used include dichloromethane, chloroform, acetonitrile, pyridine, toluene, a mixed solvent thereof, and the like. Examples of the base to be used include triethylamine, N,N-diisopropylethylamine, pyridine, and the like. Examples of the acetylating agent to be used include acetic anhydride and the like. The reaction temperature is usually −20° C. to room temperature. The reaction time varies depending on a starting material to be used, a solvent to be used, a reaction temperature, or the like, but it is usually 30 minutes to 3 days.

Step 9-7

The compound (Ii) of the present invention can be prepared by reacting the compound (22) with carbon disulfide in the presence of a base in a solvent. Examples of the solvent to be used include N,N-dimethylformamide, and the like. Examples of the base to be used include sodium hydride, and the like. The reaction temperature is usually −20° C. to room temperature. The reaction time varies depending on a starting material to be used, a solvent to be used, a reaction temperature, or the like, but it is usually 30 minutes to 3 days.

Among the compounds (I) of the present invention, a compound represented by the following general formula (Ij) can be prepared by the method shown in Scheme 10.

Scheme 10

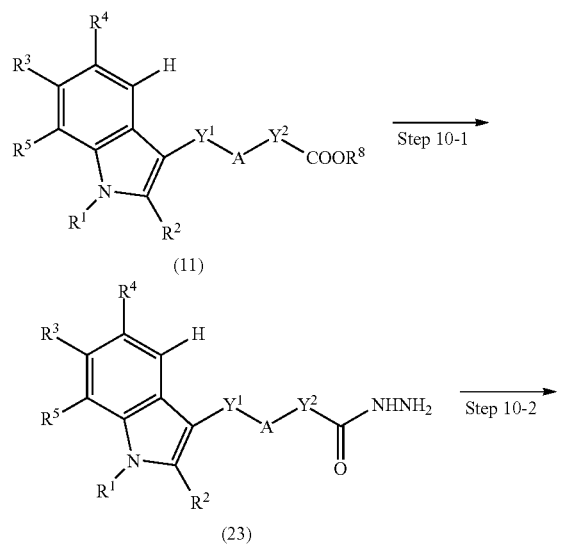

(11)

(23)

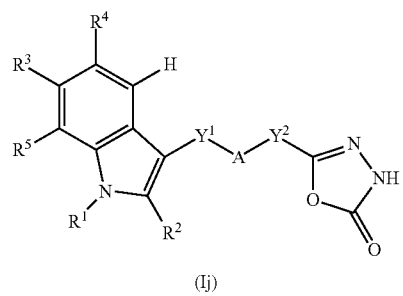

(Ij)

wherein A, $R^1$, $R^2$, $R^3$, $R^4$, $R^5$, $R^8$, $Y^1$, and $Y^2$ have the same meanings as defined above.

Step 10-1

A compound (23) can be prepared by reacting the compound (11) with hydrazine monohydrate in a solvent. Examples of the solvent to be used include water, methanol, ethanol, tetrahydrofuran, 1,4-dioxane, dichloromethane, toluene, a mixed solvent thereof, and the like. The reaction temperature is usually room temperature to reflux temperature. The reaction time varies depending on a starting material to be used, a solvent to be used, a reaction temperature, or the like, but it is usually 30 minutes to 3 days.

Step 10-2

The compound (Ij) of the present invention can be prepared by reacting the compound (23) with a carbonylating agent in a solvent. Examples of the solvent to be used include tetrahydrofuran, 1,4-dioxane, N,N-dimethylformamide, dichloromethane, toluene, water, a mixture solvent thereof, and the like. Examples of the carbonylating agent to be used include 1,1'-carbonyldiimidazole, phosgene, diethyl carbonate, and the like. Further, the present step can be carried in the presence of a base, as necessary. Examples of the base to be used include triethylamine, N,N-diisopropylethylamine, pyridine, potassium carbonate, sodium hydrogen carbonate, and the like. The reaction temperature is usually 0° C. to reflux temperature. The reaction time varies depending on a starting material to be used, a solvent to be used, a reaction temperature, or the like, but it is usually 30 minutes to 1 day.

Among the compounds (I) of the present invention, the compound represented by the following general formula (Ik) can be prepared by the method shown in Scheme 11.

Scheme 11

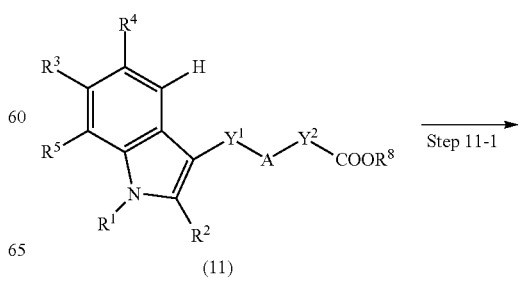

(11)

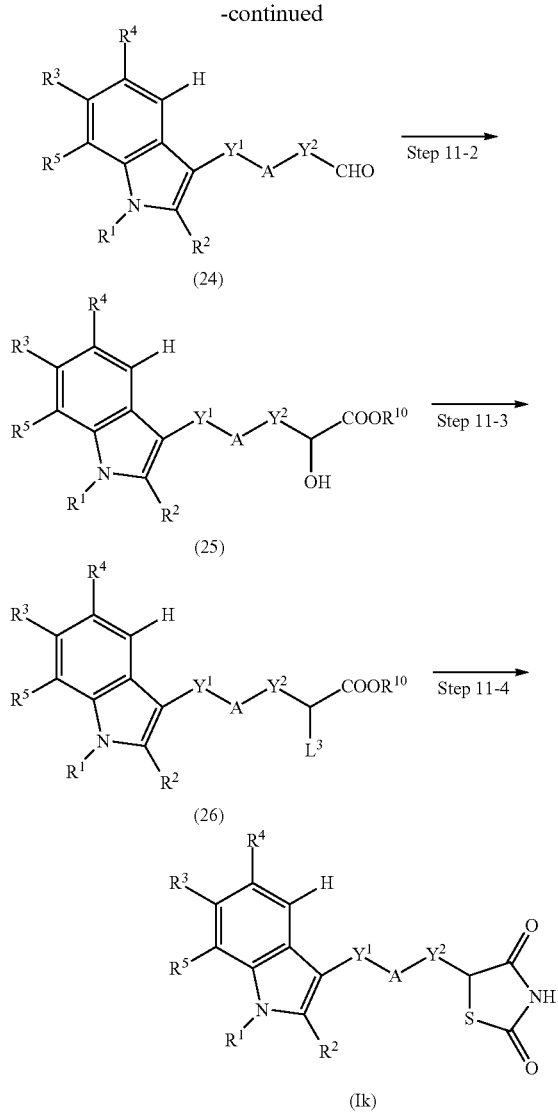

wherein A, $R^1$, $R^2$, $R^3$, $R^4$, $R^5$, $R^8$, $R^{10}$, $Y^1$ and $Y^2$ have the same meanings as defined above; and $L^3$ represents a leaving group such as a chlorine atom, a bromine atom, an iodine atom, a methanesulfonyloxy group, and the like.

Step 11-1

A compound (24) can be prepared by using a known method for converting an ester group into a formyl group. Examples of such a method include the methods described in the following literature: Min Sung Kim, et al., 'Tetrahedron Letters', 2007, Vol. 48, No. 29, p. 5061-5064; Jung In Song, et al., 'Chemistry Letters', 2007, Vol. 36, No. 7, p. 886-887; Min Jung Chae, et al., 'Bulletin of the Korean Chemical Society', 2007, Vol. 28, No. 12, p. 2517-2518, and the like.

Step 11-2

A compound (25) can be prepared by treating cyanohydrin or 1-(trimethylsilyloxy)nitrile prepared from the compound (24) with an acid in a solvent. Examples of the solvent to be used include alcohols such as methanol, ethanol, and the like. Examples of the acid to be used include hydrochloric acid, hydrobromic acid, concentrated sulfuric acid, methanesulfonic acid, p-toluenesulfonic acid, and the like. Further, in the present step, an ester corresponding to the solvent used can be obtained. For example, in the case where methanol is used as a solvent, an ester having a methyl group as $R^{10}$ is prepared. The reaction temperature is usually room temperature to reflux temperature. The reaction time varies depending on a starting material to be used, a solvent to be used, a reaction temperature, or the like, but it is usually 30 minutes to 3 days. The cyanohydrins required in the present step can be prepared by reacting the compound (24) with a cyanating agent in the presence of an acid in a solvent. Examples of the solvent to be used include water, methanol, ethanol, tetrahydrofuran, diethyl ether, dichloromethane, ethyl acetate, a mixed solvent thereof, and the like. Examples of the cyanating agent include sodium cyanide, potassium cyanide, trimethylsilyl cyanide, and the like. Examples of the acid to be used include hydrochloric acid, sulfuric acid, acetic acid, ammonium chloride, Lewis acids such as zinc iodide, and the like. The reaction temperature is usually −78° C. to room temperature. The reaction time varies depending on a starting material to be used, a solvent to be used, a reaction temperature, or the like, but it is usually 30 minutes to 3 days. On the other hand, the 1-(trimethylsilyloxy)nitrile can be prepared by reacting the compound (24) with trimethylsilyl cyanide in the presence of an acid or a base in a solvent. Examples of the solvent to be used include tetrahydrofuran, diethyl ether, dichloromethane, N,N-dimethylformamide, acetonitrile, a mixed solvent thereof, and the like. Examples of the acid to be used include Lewis acids such as zinc cyanide, and the like. Examples of the base to be used include triethylamine, potassium carbonate, and the like. The reaction temperature is usually −78° C. to reflux temperature. The reaction time varies depending on a starting material to be used, a solvent to be used, a reaction temperature, or the like, but it is usually 30 minutes to 3 days.

Step 11-3

A compound (26) can be prepared by treating the compound (25) according to an ordinary method for converting a hydroxy group to a chlorine atom, a bromine atom, an iodine atom, or a methanesulfonyloxy group. For example, the compound (26) in which $L^3$ is a chlorine atom can be prepared by reacting the compound (25) with thionyl chloride in a solvent. Examples of the solvent to be used include tetrahydrofuran, diethyl ether, toluene, dichloromethane, pyridine, a mixed solvent thereof, and the like. Further, the present step can be carried out by the addition of a base, as necessary. Examples of the base to be used include pyridine, triethylamine, N,N-diisopropylethylamine, and the like. The reaction temperature is usually −78° C. to reflux temperature. The reaction time varies depending on a starting material to be used, a solvent to be used, a reaction temperature, or the like, but it is usually 30 minutes to 1 day.

Step 11-4

The compound (Ik) of the present invention can be prepared by reacting the compound (26) with thiourea in the presence of a base in a solvent and then treating the product with an acid. Examples of the solvent to be used include water, methanol, ethanol, isopropyl alcohol, acetone, 1,4-dioxane, a mixed solvent thereof, and the like. Examples of the base to be used include sodium acetate, potassium carbonate, triethylamine, N,N-diisopropylethylamine, pyridine, and the like. Examples of the acid to be used include hydrochloric acid, sulfuric acid, p-toluenesulfonic acid, and the like. The reaction temperature is usually 0° C. to reflux temperature. The reaction time varies depending on a starting material to be used, a solvent to be used, a reaction temperature, or the like, but it is usually 30 minutes to 3 days.

Furthermore, the compound (16) described in each of Schemes 5 and 9 can also be prepared by using the following compound (5b) instead of the compound (5) in Scheme 1 and using the following compound (8b) instead of the compound (8) in Scheme 2. The compounds (5b) and (8b) may be commercially available or can also be prepared according to a method described in literature or a similar method thereto.

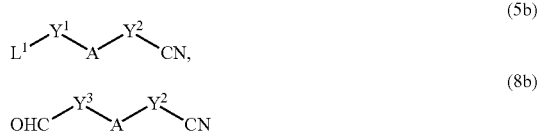

wherein A, $Y^1$, $Y^2$, $Y^3$, and $L^1$ have the same meanings as defined above.

These schemes shown above are exemplification of the method for preparing the compound (I) of the present invention or an intermediate for preparation thereof. These can be modified into the schemes that can be easily understood by a skilled person in the art.

Also, in the case that there is a need of a protective group according to the kind of the functional group, combinations of introduction and cleavage can be appropriately carried out in accordance to a usual methods. The type, introduction, and cleavage of the protective group can be illustrated in reference to the method described in, for example, "Greene's Protective Groups in Organic Synthesis", edited by Theodra W. Greene & Peter G. M. Wuts, fourth edition, Wiley-Interscience, 2006.

The compound (I) of the present invention or a pharmaceutically acceptable salt thereof, and an intermediates for preparing the same can be isolated/purified, as necessary, by solvent extraction, crystallization, recrystallization, chromatography, preparative high performance liquid chromatography, or the like, that is an purification/isolation means known to a skilled person in the art.

Pharmaceutical Composition Comprising Compound (I) of the Present Invention or Pharmaceutically Acceptable Salt Thereof The pharmaceutical composition comprising the compound (I) of the present invention or a pharmaceutically acceptable salt thereof as an active ingredient is used in various dosage forms according to the usages. Examples of the dosage forms include powders, granules, fine granules, dry syrups, tablets, capsules, injections, liquids, ointments, suppositories, plasters, sublinguals, and the like, which are administered orally or parenterally.

These pharmaceutical compositions can be prepared by appropriately mixing or diluting/dissolving with pharmaceutical additives such as an excipient, a disintegrant, a binder, a lubricant, a diluent, a buffering agent, a tonicity agent, a preservative, a wetting agent, an emulsifier, a dispersant, a stabilizer, a solubilizing aid, and the like by a known method according to the dosage forms. In addition, when the compound (I) of the present invention or a pharmaceutically acceptable salt thereof is used in combination with agents other than the $EP_1$ receptor antagonist, the pharmaceutical compositions can be prepared by formulating the respective active ingredients simultaneously or separately as described above.

Pharmaceutical Use of Compound (I) of the Present Invention or Pharmaceutically Acceptable Salt Thereof The compound (I) of the present invention or a pharmaceutically acceptable salt thereof exhibits a potent $EP_1$ receptor antagonism in a test for confirmation of an $EP_1$ receptor antagonism and the like. Therefore, the compound (I) of the present invention can decrease the intracellular calcium concentration. Accordingly, a pharmaceutical composition comprising the compound (I) of the present invention or a pharmaceutically acceptable salt thereof as an active ingredient can be used as an agent for treating or preventing diseases or symptoms caused by activation of the $EP_1$ receptor due to stimulus of a $PGE_2$.

In addition, examples of the diseases with the activation of the $EP_1$ receptor due to the $PGE_2$ stimulus include lower urinary tract symptoms (LUTS), inflammatory diseases, pain diseases, osteoporosis, cancer, and the like. The pharmaceutical composition comprising the compound (I) of the present invention or a pharmaceutically acceptable salt thereof as an active ingredient is preferably used as an agent for treating or preventing LUTS, inflammatory diseases, or pain diseases. It is more preferably LUTS.

Examples of the disease that causes the lower urinary tract symptoms include overactive bladder (OAB), benign prostatic hyperplasia (BPH), cystitis such as interstitial cystitis and the like, prostatitis, and the like.

The "lower urinary tract symptoms" means storage symptoms, voiding symptoms, post micturition symptoms, or the like. The compound (I) of the present invention or a pharmaceutically acceptable salt thereof is preferably used for treatment or prevention of storage symptoms.

Examples of the "storage symptoms" include urinary urgency, increased daytime frequency, nocturia, urinary incontinence (stress urinary incontinence, urge urinary incontinence, mixed urinary incontinence, enuresis, nocturnal enuresis, continuous urinary incontinence, and the like), and bladder sensation (increased bladder sensation, reduced bladder sensation, absent bladder sensation, non-specific bladder sensation, and the like). The compound (I) of the present invention or a pharmaceutically acceptable salt thereof is preferably used for treatment or prevention of urinary urgency, increased daytime frequency, nocturia, urge urinary incontinence, mixed urinary incontinence, enuresis, nocturnal enuresis, increased bladder sensation, or non-specific bladder sensation. It is more preferably urinary urgency, increased daytime frequency, nocturia, urge urinary incontinence, or increased bladder sensation. Further, the compound (I) of the present invention or a pharmaceutically acceptable salt thereof is particularly preferably used for treatment or prevention of OABs.

Combinations or Mixtures of Compound (I) of the Present Invention or Pharmaceutically Acceptable Salt Thereof The compound (I) of the present invention or a pharmaceutically acceptable salt thereof can also be appropriately used in combination with at least one agent other than the $EP_1$ receptor antagonist.

Examples of the agent that can be used in combination with the compound (I) of the present invention or a pharmaceutically acceptable salt thereof include agents for treatment of overactive bladder (OAB), benign prostatic hyperplasia (BPH), cystitis such as interstitial cystitis and the like, prostatitis, and the like, which have different action mechanisms from that of the $EP_1$ receptor antagonist. Examples of the agent include an anticholinergic agent, an $\alpha_1$ antagonist, a β agonist, a 5α-reductase inhibitor, a PDE inhibitor, an acetylcholine esterase inhibitor, an anti-androgen, a progesterone-based hormone, an LH-RH analog, a neurokinin inhibitor, an anti-diuretic, a calcium channel blocker, a direct smooth muscle agonist, a tricyclic antidepressant, a potassium channel modulator, a sodium channel blocker, an $H_1$ blocker, a serotonin reuptake inhibitor, a norepinephrine reuptake inhibitor, a dopamine reuptake inhibitor, a GABA agonist, a TRPV1 modulator, an endothelin antagonist, a $5\text{-HT}_{1A}$ antagonist, an $\alpha_1$ agonist, an opioid agonist, a $P_2X$ antagonist, a COX inhibitor, a σ agonist, a muscarinic agonist, and the like. It is preferably an anticholinergic agent, an $\alpha_1$ antagonist, a $\beta$ agonist, a 5$\alpha$-reductase inhibitor, a PDE inhibitor, a progesterone-based hormone, an anti-diuretic, a direct smooth muscle agonist, or a tricyclic antidepressant. It is more preferably an anticholinergic agent, an $\alpha_1$ antagonist, a $\beta$ agonist, a direct smooth muscle agonist, or a tricyclic antidepressant. Further more preferably, it is an anticholinergic agent, an $\alpha_1$ antagonist, or a tricyclic antidepressant, and most preferably, an anticholinergic agent.

Furthermore, concrete examples of the agent that is used in combination are illustrated as below, but the context of the present invention is not limited thereto. Further, examples of the concrete compound include a free form thereof, and other pharmaceutically acceptable salts.

Examples of the "anticholinergic agents" include oxybutynin, propiverine, solifenacin, tolterodine, imidafenacin, temiverine, darifenacin, fesoterodine, trospium, propantheline, and the like. It is preferably oxybutynin, propiverine, solifenacin, tolterodine, or imidafenacin. It is more preferably solifenacin or imidafenacin.

Examples of the "$\alpha_1$ antagonist" include urapidil, naftopidil, tamsulosin, silodosin, prazosin, terazosin, alfuzosin, doxazosin, CR-2991, fiduxosin, and the like. It is preferably urapidil, naftopidil, tamsulosin, silodosin, prazosin, terazosin, or fiduxosin. It is more preferably tamsulosin, silodosin, or prazosin. It is further preferably tamsulosin or silodosin. Silodosin is the most preferable.

Examples of the "$\beta$ agonist" include mirabegron, KUC-7483, KRP-204, SM-350300, TRK-380, amibegron, clenbuterol, SAR-150640, solabegron, and the like. It is preferably mirabegron or KUC-7483. It is more preferably mirabegron.

Examples of the "5$\alpha$-reductase inhibitor" include dutasteride, TF-505, finasteride, izonsteride, and the like. It is preferably dutasteride or izonsteride.

The "PDE inhibitor" means a phosphodiesterase inhibitor. Examples of the "PDE inhibitor" include tadalafil, vardenafil, sildenafil, avanafil, UK-369003, T-0156, AKP-002, etazolate, and the like. It is preferably tadalafil, vardenafil, sildenafil, or avanafil.

Examples of the "acetylcholine esterase inhibitor" include distigmine, donepezil, Z-338, rivastigmine, ganstigmine, BGC-20-1259, galantamine, itopride, NP-61, SPH-1286, tolserine, ZT-1, and the like.

Examples of the "anti-androgen" include gestonorone, oxendolone, bicalutamide, BMS-641988, CB-03-01, CH-4892789, flutamide, MDV-3100, nilutamide, TAK-700, YM-580, and the like.

Examples of the "progesterone-based hormone" include chlormadinone, allylestrenol, and the like.

The "LH-RH analog" means a gonadotropin-releasing hormone analog. In addition, gonadotropin-releasing hormone is also called "luteinizing hormone-releasing hormone". Examples of the "LH-RH analog" include AEZS-108, buserelin, deslorelin, goserelin, histrelin, leuprorelin, lutropin, nafarelin, triptorelin, AEZS-019, cetrorelix, degarelix, elagolix, ganirelix, ozarelix, PTD-634, TAK-385, teverelix, TAK-448, TAK-683, and the like.

Examples of the "neurokinin inhibitor" include KRP-103, aprepitant, AV-608, casopitant, CP-122721, DNK-333, fosaprepitant, LY-686017, netupitant, orvepitant, rolapitant, TA-5538, T-2328, vestipitant, AZD-2624, Z-501, 1144814, MEN-15596, MEN-11420, SAR-102779, SAR-102279, saredutant, SSR-241586, and the like.

Examples of the "anti-diuretic" include desmopressin, VA-106483, and the like.

Examples of the "calcium channel blocker" include amlodipine, cilnidipine, propiverine, temiverine, PD-299685, aranidipine, azelnidipine, barnidipine, benidipine, bevantolol, clevidipine, CYC-381, diltiazem, efonidipine, fasudil, felodipine, gabapentin, gallopamil, isradipine, lacidipine, lercanidipine, lomerizine, manidipine, MEM-1003, nicardipine, nifedipine, nilvadipine, nimodipine, nisoldipine, SB-751689, verapamil, YM-58483, ziconotide, and the like.

Examples of the "direct smooth muscle agonist" include flavoxate and the like.

Examples of the "tricyclic antidepressant" include imipramine, clomipramine, amitriptyline, and the like. It is preferably imipramine.

Examples of the "potassium channel modulator" include nicorandil, NIP-141, NS-4591, NS-1643, andolast, diazoxide, ICA-105665, minoxidil, pinacidil, tilisolol, VRX-698, and the like.

Examples of the "sodium channel blocker" include bepridil, dronedarone, propafenone, safinamide, SUN-N8075, SMP-986, 1014802, 552-02, A-803467, brivaracetam, cibenzoline, eslicarbazepine, F-15845, flecamide, fosphenyloin, lacosamide, lamotrigine, levobupivacaine, M-58373, mexiletine, moracizine, nerispirdine, NW-3509, oxcarbazepine, pilsicamide, pirmenol, propafenone, NW-1029, ropivacaine, vernakalant, and the like.

Examples of the "$H_1$ blocker" include acrivastine, alcaftadine, bepotastine, bilastine, cetirizine, desloratadine, ebastine, efletirizine, epinastine, fexofenadine, GSK-835726, levocabastine, levocetirizine, loratadine, mequitazine, mizolastine, NBI-75043, ReN-1869, terfenadine, UCB-35440, vapitadine, YM-344484, diphenhydramine, chlorpheniramine, and the like.

Examples of the "serotonin reuptake inhibitor" include UCB-46331, 424887, AD-337, BGC-20-1259, BMS-505130, citalopram, dapoxetine, desvenlafaxine, DOV-102677, DOV-216303, DOV-21947, duloxetine, escitalopram, F-2695, F-98214-TA, fluoxetine, fluvoxamine, IDN-5491, milnacipran, minaprine, NS-2359, NSD-644, paroxetine, PF-184298, SD-726, SEP-225289, SEP-227162, SEP-228425, SEP-228432, sertraline, sibutramine, tesofensine, tramadol, trazodone, UCB-46331, venlafaxine, vilazodone, WAY-426, WF-516, and the like.

Examples of the "norepinephrine reuptake inhibitor" include AD-337, desvenlafaxine, DOV-102677, DOV-216303, DOV-21947, duloxetine, F-2695, F-98214-TA, milnacipran, NS-2359, NSD-644, PF-184298, SD-726, SEP-225289, SEP-227162, SEP-228425, SEP-228432, sibutramine, tesofensine, tramadol, venlafaxine, bupropion, radafaxine, atomoxetine, DDP-225, LY-2216684, neboglamine, NRI-193, reboxetine, tapentadol, WAY-256805, WAY-260022, and the like.

Examples of the "dopamine reuptake inhibitor" include DOV-102677, DOV-216303, DOV-21947, IDN-5491, NS-2359, NSD-644, SEP-225289, SEP-228425, SEP-228432, sibutramine, tesofensine, tramadol, brasofensine, bupropion, NS-27100, radafaxine, safinamide, and the like.

Examples of the "GABA agonist" include retigabine, eszopiclone, indiplon, pagoclone, SEP-225441, acamprosate, baclofen, AZD-7325, BL-1020, brotizolam, DP-VPA, progabide, propofol, topiramate, zopiclone, EVT-201, AZD-3043, ganaxolone, NS-11394, arbaclofen, AZD-3355, GS-39783, ADX-71441, ADX-71943, and the like.

Examples of the "TRPV1 modulator" include capsaicin, resiniferatoxin, DE-096, GRC-6211, AMG-8562, JTS-653, SB-705498, A-425619, A-784168, ABT-102, AMG-628, AZD-1386, JNJ-17203212, NGD-8243, PF-3864086, SAR-115740, SB-782443, and the like.

Examples of the "endothelin antagonist" include SB-234551, ACT-064992, ambrisentan, atrasentan, bosentan, clazosentan, darusentan, fandosentan, S-0139, TA-0201, TBC-3711, zibotentan, BMS-509701, PS-433540, and the like.

Examples of the "5-HT$_{1A}$ antagonist" include espindolol, lecozotan, lurasidone, E-2110, REC-0206, SB-649915, WAY-426, WF-516, and the like.

Examples of the "$\alpha_1$ agonist" include CM-2236, armodafinil, midodrine, modafinil, and the like.

Examples of the "opioid agonist" include morphine, TRK-130, DPI-125, DPI-3290, fentanyl, LIF-301, loperamide, loperamide oxide, remifentanil, tapentadol, WY-16225, oxycodone, PTI-202, PTI-721, ADL-5747, ADL-5859, DPI-221, DPI-353, IPP-102199, SN-11, ADL-10-0101, ADL-10-0116, asimadoline, buprenorphine, CR-665, CR-845, eptazocine, nalbuphine, nalfurafine, pentazocine, XEN-0548, W-212393, ZP-120, nalmefene, and the like.

Examples of the "P$_2$X antagonist" include A-740003, AZ-11657312, AZD-9056, GSK-1482160, GSK-31481A, and the like.

The "COX inhibitor" means a cyclooxygenase inhibitor. Examples of the "COX inhibitor" include aceclofenac, ST-679, aspirin, bromfenac, dexketoprofen, flurbiprofen, FYO-750, ibuprofen, ketoprofen, ketorolac, licofelone, lornoxicam, loxoprofen, LT-NS001, diclofenac, mofezolac, nabumetone, naproxen, oxaprozin, piroxicam, pranoprofen, suprofen, tenoxicam, tiaprofenic acid, tolfenamic acid, zaltoprofen, 644784, ABT-963, ajulemic acid, apricoxib, celecoxib, cimicoxib, etoricoxib, iguratimod, lumiracoxib, meloxicam, nimesulide, parecoxib, RO-26-2198, valdecoxib, and the like.

Examples of the "$\sigma$ agonist" include ANAVEX-27-1041, PRS-013, SA-4503, ANAVEX-2-73, siramesine, ANAVEX-7-1037, ANAVEX-1-41, and the like.

Examples of the "muscarinic agonist" include AC-260584, cevimeline, MCD-386, NGX-267, NGX-292, sabcomeline, pilocarpine, bethanechol, and the like.

When the compound (I) of the present invention or a pharmaceutically acceptable salt thereof is used in combination with one or more of the above-described agents, the pharmaceutical composition of the present invention includes at least one administration method selected from 1) to 5) below:

1) simultaneous administration by a combination preparation,
2) simultaneous administration by the same administration pathway as a separate formulation,
3) simultaneous administration by a different administration pathway as a separate formulation,
4) administration at different times by the same administration pathway as a separate formulation, and
5) administration at different times by a different administration pathway as a separate formulation. Further, in the case of administration at different times as a separate formulation as in 4) or 5), the order of administration of the compound (I) of the present invention and the above-described agents is not particularly limited.

Furthermore, the compound (I) of the present invention or a pharmaceutically acceptable salt thereof can be used appropriately in combination of one or more of the above-described agents to attain an advantageous effect that is equal to or more than an additive effect in prevention or treatment of the above-described diseases. Alternatively, as compared with a case of being used alone, the amount used can be reduced, or the side effects of the agent(s) used together can be avoided or mitigated.

Usage/Dose of Compound (I) of the Present Invention

The pharmaceutical composition of the present invention can be administered systemically or locally, orally or parenterally (nasal, pulmonary, intravenous, rectal, subcutaneous, intramuscular, transdermal routes, and the like).

When the pharmaceutical composition of the present invention is used for practical treatments, the dose of the compound (I) of the present invention or a pharmaceutically acceptable salt thereof that is the active ingredient is appropriately determined by taking the patient's age, gender, weight, medical condition, degree of the treatment, and the like into consideration. For example, in a case of oral administration, administration can be conducted appropriately at a daily dose in the range from about 3 to 1000 mg for an adult (regarded as a body weight of 60 kg) in one portion or in several divided portions. The daily dose as an oral administration agent is preferably from 6 to 540 mg, and more preferably from 18 to 180 mg. In a case of parenteral administration, administration can be conducted appropriately at a daily dose in the range from about 0.01 to 300 mg for an adult in one portion or in several divided portions. The daily dose as a parenteral administration agent is preferably from 1 to 100 mg, and more preferably from 6 to 60 mg. In addition, the dose of the compound (I) of the present invention or a pharmaceutically acceptable salt thereof as the active ingredient can be reduced according to the amount of the agent(s) other than an EP$_1$ receptor antagonist.

Hereinbelow, the present invention is illustrated in detail with reference to Examples, Reference Examples, and Test Examples, but the scope of the present invention is not limited thereto.

EXAMPLES

In the symbols used in each of Reference Examples, Examples, and Tables, Ref No. means Reference Example No., Ex. No. means Example No., Strc means a chemical structural formula, Physical data means physical property values, $^1$H-NMR means a proton nuclear magnetic resonance spectrum, CDCl$_3$ means chloroform-d, and DMSO-d$_6$ means dimethylsulfoxide-d$_6$. Further, ESI-MS means mass spectroscopic spectrum data measured by an electrospray ionization method.

Reference Example 1

Tert-Butyl [5-methoxy-2-(2-oxo-2-thiophen-3-yl-ethyl)phenyl]carbamate

Under an argon atmosphere, to a solution of tert-butyl (5-methoxy-2-methylphenyl)carbamate (2.00 g) in tetrahydrofuran (38 mL) was added dropwise sec-butyllithium (1.00 mol/L hexane-cyclohexane solution, 18.5 mL) at −45° C., and this mixture was stirred for 30 minutes. Then, a solution of N-methoxy-N-methylthiophene-3-carboxamide (1.59 g) in tetrahydrofuran (4.1 mL) was added dropwise thereto, and this mixture was stirred at −45° C. for 30 minutes and at room temperature for additional 1 hour. To the reaction mixture were added a saturated aqueous ammonium chloride solution and water, followed by extraction with ethyl acetate. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (1.87 g). $^1$H-NMR (CDCl$_3$) δ ppm: 1.53 (9H, s), 3.79 (3H, s), 4.08 (2H, s), 6.59 (1H, dd, J=2.8, 8.5 Hz), 7.08 (1H, d, J=8.5 Hz), 7.35 (1H, dd, J=2.8, 5.1 Hz), 7.43-7.56 (1H, br), 7.60 (1H, dd, J=1.3, 5.1 Hz), 7.80-8.10 (1H, br), 8.23 (1H, dd, J=1.3, 2.8 Hz).

Reference Example 2

Methyl 6-[2-(2-tert-butoxycarbonylamino-4-methoxyphenyl)-3-oxo-3-thiophen-3-ylpropyl]pyridine-2-carboxylate Under an argon atmosphere, to a solution of tert-butyl [5-methoxy-2-(2-oxo-2-thiophen-3-ylethyl)phenyl]carbamate (1.87 g) in N,N-dimethylformamide (27 mL) was added sodium hydride (min. 55% in oil, 247 mg) in five divided portions under ice-cooling with stirring. This mixture was stirred for 70 minutes under ice-cooling. Then, methyl 6-chloromethylpyridine-2-carboxylate (999 mg) was added thereto in one portion, followed by stirring at 35° C. for 16 hours. To the reaction mixture were added a saturated aqueous ammonium chloride solution and water, followed by extraction with ethyl acetate. The organic layer was washed with water and saturated brine successively, dried over anhydrous sodium sulfate, and then concentrated under reduced pressure. The residue was purified by silica gel column chromatography (eluting solvent: ethyl acetate-hexane) to obtain the title compound (2.10 g). $^1$H-NMR (CDCl$_3$) δ ppm: 1.60 (9H, s), 3.54 (1H, dd, J=10.2, 15.8 Hz), 3.61-3.75 (4H, m), 4.05 (3H, s), 5.40 (1H, dd, J=4.9, 10.2 Hz), 6.55 (1H, dd, J=2.8, 8.5 Hz), 7.00-7.12 (2H, m), 7.15-7.25 (2H, m), 7.50 (1H, dd, J=1.3, 5.0 Hz), 7.63 (1H, t, J=7.8 Hz), 7.89-7.95 (1H, m), 8.00-8.11 (2H, m).

Reference Example 3

Methyl 6-(6-methoxy-2-thiophen-3-yl-1H-indol-3-ylmethyl)pyridine-2-carboxylate

To a solution of methyl 6-[2-(2-tert-butoxycarbonylamino-4-methoxyphenyl)-3-oxo-3-thiophen-3-ylpropyl]pyridine-2-carboxylate (2.10 g) in dichloromethane (21 mL) was added dropwise trifluoroacetic acid (4.2 mL) under ice-cooling. This mixture was stirred at 30° C. overnight. The reaction mixture was concentrated under reduced pressure. The residue was dissolved in ethyl acetate, and this solution was washed with a saturated aqueous sodium hydrogen carbonate solution. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (938 mg). $^1$H-NMR (CDCl$_3$) δ ppm: 3.86 (3H, s), 4.05 (3H, s), 4.54 (2H, s), 6.76 (1H, dd, J=2.2, 8.5 Hz), 6.90 (1H, d, J=2.2 Hz), 7.19-7.24 (1H, m), 7.28-7.35 (2H, m), 7.41 (1H, dd, J=3.0, 5.0 Hz), 7.52 (1H, dd, J=1.3, 3.0 Hz), 7.62 (1H, t, J=7.8 Hz), 7.93-7.98 (1H, m), 8.07 (1H, br s).

Reference Example 4

6-(6-Methoxy-2-thiophen-3-yl-1H-indol-3-ylmethyl)pyridine-2-carboxylic acid

To a solution of methyl 6-(6-methoxy-2-thiophen-3-yl-1H-indol-3-ylmethyl)pyridine-2-carboxylate (936 mg) in tetrahydrofuran/methanol (14.7 mL/6.3 mL) was added 2 mol/L aqueous sodium hydroxide solution (3.71 mL) at room temperature, and this mixture was stirred at 60° C. for 2 hours. The reaction mixture was left to be cooled and concentrated under reduced pressure. The residue was suspended in water (30 mL) and the resulting mixture was acidified by the addition of 1 mol/L hydrochloric acid (7.8 mL). After stirring at room temperature for 1 hour, the precipitate was collected by filtration, washed with water, and then dried under reduced pressure. The suspension of the solid in ethanol was heated under reflux to give a solution. The solution was left to be cooled. The precipitate was collected by filtration and dried under reduced pressure to obtain the title compound (547 mg). $^1$H-NMR (DMSO-d$_6$) δ ppm: 3.77 (3H, s), 4.37 (2H, s), 6.64 (1H, dd, J=2.3, 8.8 Hz), 6.85 (1H, d, J=2.3 Hz), 7.37 (1H, dd, J=1.5, 7.3 Hz), 7.42 (1H, d, J=8.8 Hz), 7.57 (1H, dd, J=1.3, 5.0 Hz), 7.67 (1H, dd, J=2.8, 5.0 Hz), 7.77-7.88 (2H, m), 8.09 (1H, dd, J=1.3, 2.8 Hz), 11.13 (1H, s), 12.60-13.70 (1H, br).

Reference Example 5

Tert-Butyl [5-methoxy-2-(2-oxo-2-phenylethyl)phenyl]carbamate

In the same method as in Reference Example 1 using the corresponding starting material and reaction agents, the title compound was synthesized. $^1$H-NMR (CDCl$_3$) δ ppm: 1.53 (9H, s), 3.79 (3H, s), 4.20 (2H, s), 6.59 (1H, dd, J=2.6, 8.4 Hz), 7.09 (1H, d, J=8.4 Hz), 7.43-7.55 (3H, m), 7.56-7.96 (2H, m), 8.04-8.10 (2H, m).

Reference Example 6

Methyl 6-[2-(2-tert-butoxycarbonylamino-4-methoxyphenyl)-3-oxo-3-phenylpropyl]pyridine-2-carboxylate In the same method as in Reference Example 2 using the corresponding starting material and reaction agents, the title compound was synthesized. $^1$H-NMR (CDCl$_3$) δ ppm: 1.60 (9H, s), 3.55 (1H, dd, J=9.9, 15.6 Hz), 3.65-3.75 (4H, m), 4.03 (3H, s), 5.54 (1H, dd, J=5.3, 9.9 Hz), 6.52 (1H, dd, J=2.6, 8.7 Hz), 7.02-7.16 (2H, m), 7.18-7.24 (1H, m), 7.30-7.39 (2H, m), 7.41-7.49 (1H, m), 7.64 (1H, t, J=7.8 Hz), 7.88-8.07 (4H, m).

Reference Example 7

Methyl 6-(6-methoxy-2-phenyl-1H-indol-3-ylmethyl)pyridine-2-carboxylate

In the same method as in Reference Example 3 using the corresponding starting material and reaction agents, the title compound was synthesized. $^1$H-NMR (CDCl$_3$) δ ppm: 3.86 (3H, s), 4.05 (3H, s), 4.56 (2H, s), 6.74 (1H, dd, J=2.3, 8.6 Hz), 6.92 (1H, d, J=2.3 Hz), 7.16-7.22 (1H, m), 7.26 (1H, d, J=8.6 Hz), 7.29-7.46 (3H, m), 7.48-7.56 (2H, m), 7.62 (1H, t, J=7.8 Hz), 7.93-8.00 (1H, m), 8.11 (1H, br s).

Reference Example 8

6-(6-Methoxy-2-phenyl-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 3.77 (3H, s), 4.36 (2H, s), 6.62 (1H, dd, J=2.3, 8.5 Hz), 6.88 (1H, d, J=2.3 Hz), 7.26-7.40 (3H, m), 7.42-7.51 (2H, m), 7.71-7.89 (4H, m), 11.17 (1H, s). ESI-MS (m/z): 359 (M+H)$^+$

Reference Example 9

Benzyl 6-(6-methoxy-2-phenyl-1H-indol-3-ylmethyl)pyridine-2-carboxylate

To a solution of 6-(6-methoxy-2-phenyl-1H-indol-3-ylmethyl)pyridine-2-carboxylic acid (3.00 g) in N,N-dimethylformamide (16.8 mL) were added potassium carbonate (1.39 g) and benzyl bromide (0.996 mL) successively, and this mixture was stirred at room temperature for 3 hours. The reaction mixture was diluted with water, followed by extraction with ethyl acetate. The organic layer was washed with water and saturated brine successively, dried over anhydrous sodium sulfate, and then concentrated under reduced pressure. The residue was purified by silica gel column chromatography (eluting solvent: ethyl acetate-hexane) to obtain the title compound (3.06 g). $^1$H-NMR (CDCl$_3$) δ ppm: 3.85 (3H, s), 4.54 (2H, s), 5.48 (2H, s), 6.72 (1H, dd, J=2.2, 8.5 Hz), 6.91 (1H, d, J=2.2 Hz), 7.16-7.23 (1H, m), 7.27-7.44 (7H, m), 7.47-7.57 (4H, m), 7.60 (1H, t, J=7.8 Hz), 7.90-7.97 (1H, m), 8.10 (1H, br s).

Reference Example 10

Benzyl 6-(1-benzenesulfonyl-6-methoxy-2-phenyl-1H-indol-3-ylmethyl)pyridine-2-carboxylate To a solution of benzyl 6-(6-methoxy-2-phenyl-1H-indol-3-ylmethyl)pyridine-2-carboxylate (3.04 g) in N,N-dimethylformamide (34 mL) was added sodium hydride (50 to 72% in oil, 342 mg) in one portion under ice-cooling. This mixture was stirred for 30 minutes under ice-cooling. Then, benzenesulfonyl chloride (1.04 mL) was added dropwise thereto, followed by stirring at room temperature for 4.5 hours. The reaction mixture was poured into a saturated aqueous ammonium chloride solution, followed by extraction with ethyl acetate. The organic layer was washed with water and saturated brine successively, dried over anhydrous sodium sulfate, and then concentrated under reduced pressure. The residue was purified by silica gel column chromatography (eluting solvent: ethyl acetate-hexane) to obtain the title compound (1.10 g). $^1$H-NMR (CDCl$_3$) δ ppm: 3.92 (3H, s), 4.09 (2H, s), 5.44 (2H, s), 6.62-6.68 (1H, m), 6.80 (1H, dd, J=2.4, 8.6 Hz), 7.21 (1H, d, J=8.6 Hz), 7.24-7.53 (16H, m), 7.85-7.93 (2H, m).

Reference Example 11

6-(1-Benzenesulfonyl-6-methoxy-2-phenyl-1H-indol-3-ylmethyl)pyridine-2-carboxylic acid To a solution of benzyl 6-(1-benzenesulfonyl-6-methoxy-2-phenyl-1H-indol-3-ylmethyl)pyridine-2-carboxylate (1.10 g) in ethyl acetate (9.3 mL) was added 10% palladium on carbon (56.5% water included, 253 mg), and this mixture was stirred at room temperature for 100 minutes under a hydrogen atmosphere. The reaction mixture was filtrated through a Celite (registered trademark) pad. The filtrate was concentrated under reduced pressure to obtain the title compound (869 mg). $^1$H-NMR (DMSO-d$_6$) δ ppm: 3.84 (3H, s), 3.97 (2H, s), 6.87 (1H, dd, J=2.3, 8.6 Hz), 6.95-7.02 (1H, m), 7.30 (1H, d, J=8.6 Hz), 7.40-7.51 (7H, m), 7.56-7.68 (4H, m), 7.70-7.85 (2H, m), 12.80-13.60 (1H, br).

Reference Example 12

6-(1-Benzenesulfonyl-6-methoxy-2-phenyl-1H-indol-3-ylmethyl)-N-methanesulfonylpyridine-2-carboxamide To a solution of 6-(1-benzenesulfonyl-6-methoxy-2-phenyl-1H-indol-3-ylmethyl)pyridine-2-carboxylic acid (867 mg) in dichloromethane (17.4 mL) were added methanesulfonamide (199 mg), 4-dimethylaminopyridine (510 mg), and 1-ethyl-3-(3-dimethylaminopropyl)carbodiimide hydrochloride (800 mg) successively, and this mixture was stirred at room temperature for 24 hours. To the reaction mixture was added 1 mol/L hydrochloric acid, followed by extraction with dichloromethane. The organic layer was washed with 1 mol/L hydrochloric acid, dried over anhydrous sodium sulfate, and then concentrated under reduced pressure. The residue was purified by silica gel column chromatography (eluting solvent: methanol-dichloromethane) to obtain the title compound (633 mg). $^1$H-NMR (DMSO-d$_6$) δ ppm: 3.39 (3H, s), 3.86 (3H, s), 4.03 (2H, s), 6.85-6.98 (2H, m), 7.37 (1H, d, J=8.8 Hz), 7.39-7.53 (9H, m), 7.60-7.71 (2H, m), 7.77-7.88 (2H, m), 11.00-11.56 (1H, br). ESI-MS (m/z): 576 (M+H)$^+$

Reference Example 13

5-Cyclopropyl-2-methylaniline

To a mixture of 5-bromo-2-methylaniline (3.51 g), cyclopropylboronic acid monohydrate (2.55 g), tricyclohexylphosphine (about 0.6 mol/L toluene solution, 3.14 mL), tripotassium phosphate monohydrate (15.2 g), toluene (52.4 mL), and water (5.24 mL) was added palladium(II) acetate (212 mg), and this mixture was stirred at 100° C. for 15 hours. The reaction mixture was left to be cooled, and filtrated through a Celite (registered trademark) pad. The pad was washed with ethyl acetate (100 mL). The filtrate and the washing liquid were mixed, and washed with water/saturated brine (1/1). The organic layer was dried over anhydrous sodium sulfate and concentrated under reduced pressure. The residue was purified by silica gel column chromatography (eluting solvent: ethyl acetate-hexane) to obtain the title compound (2.25 g). $^1$H-NMR (CDCl$_3$) δ ppm: 0.58-0.67 (2H, m), 0.83-0.93 (2H, m), 1.73-1.84 (1H, m), 2.12 (3H, s), 3.54 (2H, br s), 6.35-6.50 (2H, m), 6.93 (1H, d, J=7.5 Hz).

Reference Example 14

Tert-Butyl (5-cyclopropyl-2-methylphenyl)carbamate

A solution of 5-cyclopropyl-2-methylaniline (2.25 g) and di-tert-butyl dicarbonate (3.67 g) in tetrahydrofuran (30.6 mL) was heated under reflux for 28 hours. The reaction mixture was left to be cooled and concentrated under reduced pressure. The residue was purified by aminopropylated silica gel column chromatography (eluting solvent: ethyl acetate-hexane) to obtain the title compound (3.67 g). $^1$H-NMR (CDCl$_3$) δ ppm: 0.63-0.71 (2H, m), 0.85-0.95 (2H, m), 1.52 (9H, s), 1.82-1.92 (1H, m), 2.19 (3H, s), 6.06-6.38 (1H, br), 6.69 (1H, dd, J=1.8, 7.8 Hz), 7.01 (1H, d, J=7.8 Hz), 7.42-7.76 (1H, br).

Reference Example 15

Tert-Butyl [5-cyclopropyl-2-(2-oxo-2-phenylethyl)phenyl]carbamate

In the same method as in Reference Example 1 using the corresponding starting material and reaction agents, the title compound was synthesized. $^1$H-NMR (CDCl$_3$) δ ppm: 0.64-0.72 (2H, m), 0.84-0.96 (2H, m), 1.52 (9H, s), 1.82-1.92 (1H, m), 4.22 (2H, s), 6.73 (1H, dd, J=1.8, 7.8 Hz), 7.08 (1H, d, J=7.8 Hz), 7.33-7.95 (5H, m), 8.02-8.11 (2H, m).

Reference Example 16

Methyl 6-[2-(2-tert-butoxycarbonylamino-4-cyclopropylphenyl)-3-oxo-3-phenylpropyl]pyridine-2-carboxylate In the same method as in Reference Example 2 using the corresponding starting material and reaction agents, the title compound was synthesized. $^1$H-NMR (CDCl$_3$) δ ppm: 0.52-0.64 (2H, m), 0.78-0.90 (2H, m), 1.60 (9H, s), 1.68-1.79 (1H, m), 3.55 (1H, dd, J=9.7, 15.7 Hz), 3.70 (1H, dd, J=5.3, 15.7 Hz), 4.03 (3H, s), 5.59 (1H, dd, J=5.3, 9.7 Hz), 6.63 (1H, dd, J=1.9, 8.1 Hz), 7.04 (1H, d, J=8.1 Hz), 7.14-7.49 (5H, m), 7.64 (1H, t, J=7.8 Hz), 7.88-8.10 (4H, m).

Reference Example 17

Methyl 6-(6-cyclopropyl-2-phenyl-1H-indol-3-ylmethyl)pyridine-2-carboxylate

In the same method as in Reference Example 3 using the corresponding starting material and reaction agents, the title compound was synthesized. $^1$H-NMR (CDCl$_3$) δ ppm: 0.69-0.76 (2H, m), 0.92-1.02 (2H, m), 1.96-2.07 (1H, m), 4.04 (3H, s), 4.56 (2H, s), 6.83 (1H, dd, J=1.5, 8.3 Hz), 7.11-7.22 (2H, m), 7.27 (1H, d, J=8.3 Hz), 7.30-7.46 (3H, m), 7.49-7.56 (2H, m), 7.61 (1H, t, J=7.8 Hz), 7.92-7.99 (1H, m), 8.10 (1H, br s).

Reference Example 18

6-(6-Cyclopropyl-2-phenyl-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 0.59-0.68 (2H, m), 0.88-0.98 (2H, m), 1.93-2.04 (1H, m), 4.35 (2H, s), 6.70 (1H, dd, J=1.5, 8.3 Hz), 7.08 (1H, s), 7.25-7.40 (3H, m), 7.43-7.52 (2H, m), 7.72-7.89 (4H, m), 11.18 (1H, s), 12.40-13.80 (1H, br).

Reference Example 19

Benzyl 6-(6-cyclopropyl-2-phenyl-1H-indol-3-ylmethyl)pyridine-2-carboxylate

In the same method as in Reference Example 9 using the corresponding starting material and reaction agents, the title compound was synthesized. $^1$H-NMR (CDCl$_3$) δ ppm: 0.67-0.76 (2H, m), 0.91-1.00 (2H, m), 1.95-2.06 (1H, m), 4.54 (2H, s), 5.48 (2H, s), 6.81 (1H, dd, J=1.4, 8.2 Hz), 7.09-7.22 (2H, m), 7.28-7.44 (7H, m), 7.47-7.63 (5H, m), 7.90-7.96 (1H, m), 8.09 (1H, br s).

Reference Example 20

Benzyl 6-(1-benzenesulfonyl-6-cyclopropyl-2-phenyl-1H-indol-3-ylmethyl)pyridine-2-carboxylate In the same method as in Reference Example 10 using the corresponding starting material and reaction agents, the title compound was synthesized. $^1$H-NMR (CDCl$_3$) δ ppm: 0.73-0.81 (2H, m), 0.99-1.07 (2H, m), 2.00-2.10 (1H, m), 4.09 (2H, s), 5.44 (2H, s), 6.62-6.69 (1H, m), 6.89 (1H, dd, J=1.5, 8.1 Hz), 7.20 (1H, d, J=8.1 Hz), 7.25-7.52 (16H, m), 7.84-7.91 (1H, m), 8.04-8.09 (1H, m).

Reference Example 21

6-(1-Benzenesulfonyl-6-cyclopropyl-2-phenyl-1H-indol-3-ylmethyl)pyridine-2-carboxylic acid In the same method as in Reference Example 11 using the corresponding starting material and reaction agents, the title compound was synthesized. $^1$H-NMR (DMSO-d$_6$) δ ppm: 0.64-0.73 (2H, m), 0.95-1.06 (2H, m), 2.00-2.12 (1H, m), 3.97 (2H, s), 6.91-7.05 (2H, m), 7.26 (1H, d, J=8.0 Hz), 7.32-7.89 (13H, m), 12.60-13.80 (1H, br).

Reference Example 22

6-(1-Benzenesulfonyl-6-cyclopropyl-2-phenyl-1H-indol-3-ylmethyl)-N-methanesulfonylpyridine-2-carboxamide In the same method as in Reference Example 12 using the corresponding starting material and reaction agents, the title compound was synthesized. $^1$H-NMR (DMSO-d$_6$) δ ppm: 0.68-0.75 (2H, m), 0.98-1.06 (2H, m), 2.04-2.14 (1H, m), 3.39 (3H, s), 4.03 (2H, s), 6.91-7.02 (2H, m), 7.34 (1H, d, J=8.0 Hz), 7.37-7.54 (9H, m), 7.60-7.68 (1H, m), 7.77-7.88 (3H, m), 10.95-11.60 (1H, br).

Reference Example 23

Tert-Butyl [5-methyl-2-(2-oxo-2-phenylethyl)phenyl]carbamate

In the same method as in Reference Example 1 using the corresponding starting material and reaction agents, the title compound was synthesized. $^1$H-NMR (CDCl$_3$) δ ppm: 1.52 (9H, s), 2.32 (3H, s), 4.24 (2H, s), 6.82-6.90 (1H, m), 7.09 (1H, d, J=7.8 Hz), 7.45-7.80 (5H, m), 8.02-8.12 (2H, m).

Reference Example 24

Methyl 6-[2-(2-tert-butoxycarbonylamino-4-methylphenyl)-3-oxo-3-phenylpropyl]pyridine-2-carboxylate In the same method as in Reference Example 2 using the corresponding starting material and reaction agents, the title compound was synthesized. $^1$H-NMR (CDCl$_3$) δ ppm: 1.61 (9H, s), 2.19 (3H, s), 3.56 (1H, dd, J=9.9, 15.7 Hz), 3.71 (1H, dd, J=5.3, 15.7 Hz), 4.03 (3H, s), 5.59 (1H, dd, J=5.3, 9.9 Hz), 6.74-6.81 (1H, m), 7.04 (1H, d, J=8.0 Hz), 7.17-7.48 (5H, m), 7.59-7.67 (1H, m), 7.88-7.96 (3H, m), 8.03 (1H, br s).

Reference Example 25

Methyl 6-(6-methyl-2-phenyl-1H-indol-3-ylmethyl)pyridine-2-carboxylate

In the same method as in Reference Example 3 using the corresponding starting material and reaction agents, the title compound was synthesized. $^1$H-NMR (CDCl$_3$) δ ppm: 2.47 (3H, s), 4.05 (3H, s), 4.57 (2H, s), 6.88-6.94 (1H, m), 7.16-7.24 (2H, m), 7.24-7.30 (1H, m), 7.31-7.38 (1H, m), 7.38-7.46 (2H, m), 7.50-7.57 (2H, m), 7.61 (1H, t, J=7.8 Hz), 7.93-7.98 (1H, m), 8.10 (1H, br s).

Reference Example 26

6-(6-Methyl-2-phenyl-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 2.38 (3H, s), 4.36 (2H, s), 6.74-6.83 (1H, m), 7.13-7.52 (6H, m), 7.71-7.89 (4H, m), 11.20 (1H, s), 12.60-13.60 (1H, br).

Reference Example 27

2-tert-Butyl-5-chloro-6-methoxy-1H-indole

A solution of 4-chloro-3-methoxyaniline (4.68 g) in ethanol (4.5 mL) was heated under reflux while stirring. To the solution was added 1-bromo-3,3-dimethyl-2-butanone (0.243 mL×5) in five portions at an interval of 5 minutes, and this mixture was heated under reflux while stirring for 4 hours. The reaction mixture was left to be cooled. To the reaction mixture were added 2 mol/L hydrochloric acid and water successively, followed by extraction with ethyl acetate. The organic layer was washed with water and saturated brine, dried over anhydrous magnesium sulfate, and then concentrated under reduced pressure. The residue was purified by silica gel column chromatography (eluting solvent: ethyl acetate-hexane) to obtain the title compound (893 mg). $^1$H-NMR (CDCl$_3$) δ ppm: 1.37 (9H, s), 3.89 (3H, s), 6.09-6.16 (1H, m), 6.88 (1H, s), 7.50 (1H, s), 7.72-8.12 (1H, br).

Reference Example 28

Methyl 6-(2-tert-butyl-5-chloro-6-methoxy-1H-indol-3-ylmethyl)pyridine-2-carboxylate To a solution of triethylsilane (0.202 mL) and trifluoroacetic acid (0.049 mL) in dichloromethane (2 mL) was added a suspension of 2-tert-butyl-5-chloro-6-methoxy-1H-indole (100 mg) and methyl 6-formylpyridine-2-carboxylate (76.2 mg) in dichloromethane (1.5 mL) under ice-cooling, and this mixture was stirred at room temperature overnight. To the reaction mixture was added water, and then the resulting mixture was alkalified by the addition of sodium hydrogen carbonate. The organic layer was separated and concentrated under reduced pressure. The residue was purified by aminopropylated silica gel column chromatography (eluting solvent: ethyl acetate-hexane) to obtain the title compound (152 mg). $^1$H-NMR (CDCl$_3$) δ ppm: 1.39 (9H, s), 3.90 (3H, s), 4.05 (3H, s), 4.52 (2H, s), 6.91 (1H, s), 6.95-7.05 (1H, m), 7.28 (1H, s), 7.60 (1H, t, J=7.8 Hz), 7.80-8.20 (2H, m).

Reference Example 29

6-(2-tert-Butyl-5-chloro-6-methoxy-1H-indol-3-ylmethyl)pyridine-2-carboxylic acid In the same method as in Reference Example 4 using the corresponding starting material and reaction agents, the title compound was synthesized. $^1$H-NMR (DMSO-d$_6$) δ ppm: 1.35 (9H, s), 3.82 (3H, s), 4.36 (2H, s), 6.98 (1H, s), 7.00-7.10 (1H, m), 7.35 (1H, s), 7.70-7.90 (2H, m), 10.66 (1H, s), 12.80-13.40 (1H, br). ESI-MS (m/z): 373 (M+H)$^+$ Reference Example 30

5-Fluoro-6-methoxy-2-phenyl-1H-indole

In the same method as in Reference Example 27 using the corresponding starting material and reaction agents, the title compound was synthesized. $^1$H-NMR (DMSO-d$_6$) δ ppm: 3.87 (3H, s), 6.78-6.83 (1H, m), 7.02 (1H, d, J=7.5 Hz), 7.24-7.35 (2H, m), 7.39-7.48 (2H, m), 7.75-7.83 (2H, m), 11.47 (1H, s).

Reference Example 31

Methyl 6-[(5-fluoro-6-methoxy-2-phenyl-1H-indol-3-yl)hydroxymethyl]pyridine-2-carboxylate To a suspension of 5-fluoro-6-methoxy-2-phenyl-1H-indole (176 mg) and methyl 6-formylpyridine-2-carboxylate (133 mg) in dichloromethane (3.6 mL) was added 1,8-diazabicyclo[5,4,0]-7-undecene (0.011 mL), and this mixture was stirred at room temperature for 20 hours. The reaction mixture was purified by silica gel column chromatography (eluting solvent: ethyl acetate-hexane) to obtain the title compound (210 mg). $^1$H-NMR (CDCl$_3$) δ ppm: 3.88 (3H, s), 4.05 (3H, s), 5.31 (1H, d, J=2.8 Hz), 6.10-6.16 (1H, m), 6.81 (1H, d, J=11.8 Hz), 6.91 (1H, d, J=7.0 Hz), 7.23-7.29 (1H, m), 7.38-7.54 (3H, m), 7.66-7.75 (3H, m), 8.00-8.06 (1H, m), 8.12 (1H, br s).

Reference Example 32

Methyl 6-(5-fluoro-6-methoxy-2-phenyl-1H-indol-3-ylmethyl)pyridine-2-carboxylate Under an argon atmosphere, to a solution of sodium iodide (308 mg) in acetonitrile (3.1 mL) was added chlorotrimethylsilane (0.260 mL) under ice-cooling, and this mixture was stirred for 15 minutes. Then, a solution of methyl 6-[(5-fluoro-6-methoxy-2-phenyl-1H-indol-3-ylmethyl)hydroxymethyl]pyridine-2-carboxylate (209 mg) in acetonitrile (2 mL) was added dropwise thereto, followed by stirring for 2 hours under ice-cooling. To the reaction mixture was added a saturated aqueous sodium hydrogen carbonate solution, followed by extraction with ethyl acetate. The organic layer was washed with 1 mol/L aqueous sodium thiosulfate solution and saturated brine, dried over anhydrous sodium sulfate, and then concentrated under reduced pressure. The residue was purified by silica gel column chromatography (eluting solvent: ethyl acetate-hexane) to obtain the title compound (186 mg). $^1$H-NMR (CDCl$_3$) δ ppm: 3.93 (3H, s), 4.04 (3H, s), 4.50 (2H, s), 6.97 (1H, d, J=7.0 Hz), 7.10 (1H, d, J=11.6

Hz), 7.15-7.20 (1H, m), 7.30-7.47 (3H, m), 7.49-7.56 (2H, m), 7.64 (1H, t, J=7.8 Hz), 7.94-8.00 (1H, m), 8.10 (1H, br s).

Reference Example 33

6-(5-Fluoro-6-methoxy-2-phenyl-1H-indol-3-ylmethyl)pyridine-2-carboxylic acid

In the same method as in Reference Example 4 using the corresponding starting material and reaction agents, the title compound was synthesized. $^1$H-NMR (DMSO-$d_6$) δ ppm: 3.85 (3H, s), 4.33 (2H, s), 7.02 (1H, d, J=7.5 Hz), 7.28 (1H, d, J=12.0 Hz), 7.31-7.40 (2H, m), 7.42-7.51 (2H, m), 7.71-7.89 (4H, m), 11.28 (1H, s), 12.60-13.60 (1H, br). ESI-MS (m/z): 377 (M+H)$^+$

Reference Example 34

Methyl 6-(2-tert-butyl-6-methoxy-1H-indol-3-ylmethyl)pyridine-2-carboxylate

In the same method as in Reference Example 28 using the corresponding starting material and reaction agents, the title compound was synthesized. $^1$H-NMR (CDCl$_3$) δ ppm: 1.39 (9H, s), 3.83 (3H, s), 4.04 (3H, s), 4.57 (2H, s), 6.69 (1H, dd, J=2.3, 8.8 Hz), 6.86 (1H, d, J=2.3 Hz), 7.01-7.08 (1H, m), 7.13 (1H, d, J=8.8 Hz), 7.57 (1H, t, J=7.8 Hz), 7.84-8.01 (2H, m).

Reference Example 35

6-(2-tert-Butyl-6-methoxy-1H-indol-3-ylmethyl)pyridine-2-carboxylic acid

In the same method as in Reference Example 4 using the corresponding starting material and reaction agents, the title compound was synthesized. $^1$H-NMR (DMSO-$d_6$) δ ppm: 1.36 (9H, s), 3.73 (3H, s), 4.37 (2H, s), 6.55 (1H, dd, J=2.3, 8.7 Hz), 6.84 (1H, d, J=2.3 Hz), 7.02-7.10 (1H, m), 7.15 (1H, d, J=8.7 Hz), 7.73-7.86 (2H, m), 10.45 (1H, s). ESI-MS (m/z): 339 (M+H)$^+$

Reference Example 36

Tert-Butyl [5-methyl-2-(2-oxo-2-thiophen-3-ylethyl)phenyl]carbamate

In the same method as in Reference Example 1 using the corresponding starting material and reaction agents, the title compound was synthesized. $^1$H-NMR (CDCl$_3$) δ ppm: 1.53 (9H, s), 2.32 (3H, s), 4.12 (2H, s), 6.81-6.90 (1H, m), 7.08 (1H, d, J=7.8 Hz), 7.35 (1H, dd, J=2.9, 5.1 Hz), 7.55-8.19 (3H, m), 8.23 (1H, dd, J=1.3, 2.9 Hz).

Reference Example 37

Methyl 6-[2-(2-tert-butoxycarbonylamino-4-methylphenyl)-3-oxo-3-thiophen-3-ylpropyl]pyridine-2-carboxylate In the same method as in Reference Example 2 using the corresponding starting material and reaction agents, the title compound was synthesized. $^1$H-NMR (CDCl$_3$) δ ppm: 1.59 (9H, s), 2.21 (3H, s), 3.56 (1H, dd, J=10.2, 15.8 Hz), 3.69 (1H, dd, J=5.0, 15.8 Hz), 4.05 (3H, s), 5.46 (1H, dd, J=5.0, 10.2 Hz), 6.78-6.84 (1H, m), 7.08 (1H, d, J=7.8 Hz), 7.18 (1H, dd, J=2.9, 5.2 Hz), 7.19-7.24 (1H, m), 7.50 (1H, dd, J=1.2, 5.2 Hz), 7.63 (1H, t, J=7.8 Hz), 7.88-7.94 (1H, m), 8.04 (1H, br s), 8.09 (1H, dd, J=1.2, 2.9 Hz).

Reference Example 38

Methyl 6-(6-methyl-2-thiophen-3-yl-1H-indol-3-ylmethyl)pyridine-2-carboxylate

In the same method as in Reference Example 3 using the corresponding starting material and reaction agents, the title compound was synthesized. $^1$H-NMR (CDCl$_3$) δ ppm: 2.47 (3H, s), 4.05 (3H, s), 4.56 (2H, s), 6.89-6.96 (1H, m), 7.17-7.24 (2H, m), 7.29-7.37 (2H, m), 7.41 (1H, dd, J=2.8, 5.0 Hz), 7.55 (1H, dd, J=1.4, 2.8 Hz), 7.61 (1H, t, J=7.8 Hz), 7.92-7.98 (1H, m), 8.06 (1H, br s).

Reference Example 39

6-(6-Methyl-2-thiophen-3-yl-1H-indol-3-ylmethyl)pyridine-2-carboxylic acid

In the same method as in Reference Example 4 using the corresponding starting material and reaction agents, the title compound was synthesized. $^1$H-NMR (DMSO-$d_6$) δ ppm: 2.39 (3H, s), 4.38 (2H, s), 6.78-6.85 (1H, m), 7.12-7.40 (2H, m), 7.42 (1H, d, J=8.0 Hz), 7.59 (1H, dd, J=1.3, 5.0 Hz), 7.68 (1H, dd, J=3.0, 5.0 Hz), 7.77-7.88 (2H, m), 8.14 (1H, dd, J=1.3, 3.0 Hz), 11.14 (1H, s), 12.50-13.70 (1H, br). ESI-MS (m/z): 349 (M+H)$^+$

Reference Example 40

Tert-Butyl {2-[2-(4-fluorophenyl)-2-oxoethyl]-5-methoxyphenyl}carbamate

In the same method as in Reference Example 1 using the corresponding starting material and reaction agents, the title compound was synthesized. $^1$H-NMR (CDCl$_3$) δ ppm: 1.52 (9H, s), 3.79 (3H, s), 4.16 (2H, s), 6.60 (1H, dd, J=2.7, 8.5 Hz), 7.07 (1H, d, J=8.5 Hz), 7.10-7.20 (2H, m), 7.40-7.55 (1H, m), 7.60-7.80 (1H, m), 8.00-8.15 (2H, m).

Reference Example 41

Methyl 6-[2-(2-tert-butoxycarbonylamino-4-methoxyphenyl)-3-(4-fluorophenyl)-3-oxopropyl]pyridine-2-carboxylate In the same method as in Reference Example 2 using the corresponding starting material and reaction agents, the title compound was synthesized. $^1$H-NMR (CDCl$_3$) δ ppm: 1.55-1.65 (9H, m), 3.54 (1H, dd, J=10.1, 15.9 Hz), 3.60-3.75 (4H, m), 4.03 (3H, s), 5.51 (1H, dd, J=5.3, 10.1 Hz), 6.53 (1H, dd, J=2.7, 8.7 Hz), 6.80-8.25 (10H, m). ESI-MS (m/z): 509 (M+H)$^+$

Reference Example 42

Methyl 6-[2-(4-fluorophenyl)-6-methoxy-1H-indol-3-ylmethyl]pyridine-2-carboxylate In the same method as in Reference Example 3 using the corresponding starting material and reaction agents, the title compound was synthesized. $^1$H-NMR (CDCl$_3$) δ ppm: 3.86 (3H, s), 4.04 (3H, s), 4.50 (2H, s), 6.75 (1H, dd, J=2.2, 8.7

Hz), 6.91 (1H, d, J=2.2 Hz), 7.05-7.35 (4H, m), 7.45-7.70 (3H, m), 7.90-8.00 (1H, m), 8.03 (1H, br s).

Reference Example 43

6-[2-(4-Fluorophenyl)-6-methoxy-1H-indol-3-ylmethyl]pyridine-2-carboxylic acid

In the same method as in Reference Example 4 using the corresponding starting material and reaction agents, the title compound was synthesized. $^1$H-NMR (DMSO-d$_6$) δ ppm: 3.76 (3H, s), 4.31 (2H, s), 6.62 (1H, dd, J=2.2, 8.7 Hz), 6.86 (1H, d, J=2.2 Hz), 7.25-7.40 (4H, m), 7.75-7.90 (4H, m), 11.18 (1H, s). ESI-MS (m/z): 377 (M+H)$^+$.

Reference Example 44

Methyl 6-(6-methoxy-1-methyl-2-phenyl-1H-indol-3-ylmethyl)pyridine-2-carboxylate To a solution of methyl 6-(6-methoxy-2-phenyl-1H-indol-3-ylmethyl)pyridine-2-carboxylate (500 mg) in N,N-dimethylformamide (5.4 mL) were added cesium carbonate (1.09 g) and methyl iodide (0.168 mL), and this mixture was stirred at room temperature for 67 hours. The reaction mixture was diluted with water, followed by extraction with ethyl acetate. The organic layer was washed with water and saturated brine, dried over anhydrous sodium sulfate, and then concentrated under reduced pressure. The residue was purified by silica gel column chromatography (eluting solvent: ethyl acetate-hexane) to obtain the title compound (508 mg). $^1$H-NMR (CDCl$_3$) δ ppm: 3.61 (3H, s), 3.89 (3H, s), 4.02 (3H, s), 4.35 (2H, s), 6.74 (1H, dd, J=2.3, 8.5 Hz), 6.84 (1H, d, J=2.3 Hz), 7.12-7.18 (1H, m), 7.28 (1H, d, J=8.5 Hz), 7.33-7.49 (5H, m), 7.59 (1H, t, J=7.8 Hz), 7.88-7.94 (1H, m).

Reference Example 45

6-(6-Methoxy-1-methyl-2-phenyl-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 3.58 (3H, s), 3.80 (3H, s), 4.13 (2H, s), 6.65 (1H, dd, J=2.3, 8.5 Hz), 7.02 (1H, d, J=2.3 Hz), 7.24-7.33 (2H, m), 7.41-7.65 (5H, m), 7.75-7.85 (2H, m), 12.50-13.70 (1H, br). ESI-MS (m/z): 373 (M+H)$^+$ Reference Example 46

Methyl 3-(6-methoxy-2-phenyl-1H-indol-3-ylmethyl)benzoate

In the same method as in Reference Example 28 using the corresponding starting material and reaction agents, the title compound was synthesized. $^1$H-NMR (CDCl$_3$) δ ppm: 3.85 (3H, s), 3.88 (3H, s), 4.28 (2H, s), 6.72 (1H, dd, J=2.2, 8.7 Hz), 6.90 (1H, d, J=2.2 Hz), 7.15-7.55 (8H, m), 7.80-8.05 (3H, m).

Reference Example 47

3-(6-Methoxy-2-phenyl-1H-indol-3-ylmethyl)benzoic acid

In the same method as in Reference Example 4 using the corresponding starting material and reaction agents, the title compound was synthesized. $^1$H-NMR (DMSO-d$_6$) δ ppm: 3.78 (3H, s), 4.26 (2H, s), 6.62 (1H, dd, J=2.2, 8.7 Hz), 6.89 (1H, d, J=2.2 Hz), 7.21 (1H, d, J=8.7 Hz), 7.25-7.60 (7H, m), 7.70-7.80 (2H, m), 11.19 (1H, s), 12.70-13.00 (1H, br).

Reference Example 48

Trimethyl(5-methylthiophen-3-ylethynyl)silane

A mixture of 4-bromo-2-methylthiophene (1.00 g), trimethylsilyl acetylene (1.17 mL), bis(triphenylphosphine) palladium(II) dichloride (119 mg), copper(I) iodide (65 mg), triethylamine (1.57 mL), and acetonitrile (15 mL) was stirred at 80° C. for 4 hours under an argon atmosphere. The reaction mixture was left to be cooled and filtrated through a Celite (registered trademark) pad. To the filtrate was added saturated brine, followed by extraction with ethyl acetate. The organic layer was dried over anhydrous magnesium sulfate and concentrated under reduced pressure. The residue was purified by silica gel column chromatography (eluting solvent: ethyl acetate-hexane) to obtain the title compound (605 mg). $^1$H-NMR (CDCl$_3$) δ ppm: 0.23 (9H, s), 2.44 (3H, d, J=1.0 Hz), 6.75-6.80 (1H, m), 7.21-7.25 (1H, m).

Reference Example 49

6-Methoxy-2-(5-methylthiophen-3-yl)-1H-indole

To a mixture of 2,2,2-trifluoro-N-(2-iodo-5-methoxyphenyl)acetamide (1.00 g), trimethyl(5-methylthiophen-3-ylethynyl)silane (845 mg), bis(triphenylphosphine) palladium (II) dichloride (61 mg), copper(I) iodide (33 mg), triethylamine (0.81 mL), and acetonitrile (15 mL) was added tetrabutylammonium fluoride in tetrahydrofuran solution (1 mol/L, 4.4 mL) at 50° C. This mixture was stirred at 50° C. for 1 hour. Then, potassium carbonate (801 mg) was added thereto, followed by stirring at 50° C. overnight. To the reaction mixture was added saturated brine, followed by extraction with ethyl acetate. The organic layer was dried over anhydrous magnesium sulfate and concentrated under reduced pressure. The residue was purified by silica gel column chromatography (eluting solvent: ethyl acetate-hexane) to obtain the title compound (449 mg). $^1$H-NMR (CDCl$_3$) δ ppm: 2.53 (3H, d, J=1.0 Hz), 3.86 (3H, s), 6.53-6.59 (1H, m), 6.77 (1H, dd, J=2.3, 8.6 Hz), 6.84-6.89 (1H, m), 7.01-7.11 (2H, m), 7.46 (1H, d, J=8.6 Hz), 7.94-8.16 (1H, br).

Reference Example 50

Methyl 6-{hydroxy-[6-methoxy-2-(5-methylthiophen-3-yl)-1H-indol-3-yl]methyl}pyridine-2-carboxylate In the same method as in Reference Example 31 using the corresponding starting material and reaction agents, the title compound was synthesized. $^1$H-NMR (CDCl$_3$) δ ppm: 2.54 (3H, d, J=0.8 Hz), 3.79 (3H, s), 4.04 (3H, s), 5.11 (1H, d, J=2.8 Hz), 6.21-6.25 (1H, m), 6.59 (1H, dd, J=2.3, 8.9 Hz), 6.82 (1H, d, J=2.3 Hz), 6.98 (1H, d, J=8.9 Hz), 7.09-7.14 (1H, m), 7.33-7.39 (1H, m), 7.43-7.46 (1H, m), 7.70 (1H, t, J=7.8 Hz), 7.97-8.05 (2H, m).

Reference Example 51

Methyl 6-[6-methoxy-2-(5-methylthiophen-3-yl)-1H-indol-3-ylmethyl]pyridine-2-carboxylate To a solution of methyl 6-{hydroxy-[6-methoxy-2-(5-methylthiophen-3-yl)-1H-indol-3-yl]methyl}pyridine-2-carboxylate (335 mg) and a boran-2-picoline complex (92.1 mg) in methanol (1.7 mL) was added acetic acid (1.7 mL), and this mixture was stirred at room temperature for 8 hours. The reaction mixture was diluted with ethyl acetate, washed with 5% aqueous sodium hydrogen carbonate solution and saturated brine successively, dried over anhydrous magnesium sulfate, and then concentrated under reduced pressure. The residue was purified by silica gel column chromatography (eluting solvent: ethyl acetate-hexane) to obtain the title compound (255 mg). $^1$H-NMR (CDCl$_3$) δ ppm: 2.48-2.53 (3H, m), 3.85 (3H, s), 4.05 (3H, s), 4.54 (2H, s), 6.74 (1H, dd, J=2.2, 8.6 Hz), 6.88 (1H, d, J=2.2 Hz), 6.96-7.01 (1H, m), 7.17-7.22 (2H, m), 7.29 (1H, d, J=8.6 Hz), 7.62 (1H, t, J=7.8 Hz), 7.93-7.98 (1H, m), 8.01 (1H, br s).

Reference Example 52

6-[6-Methoxy-2-(5-methylthiophen-3-yl)-1H-indol-3-ylmethyl]pyridine-2-carboxylic acid In the same method as in Reference Example 4 using the corresponding starting material and reaction agents, the title compound was synthesized. $^1$H-NMR (DMSO-d$_6$) δ ppm: 3.76 (3H, s), 4.35 (2H, s), 6.64 (1H, dd, J=2.3, 8.7 Hz), 6.82 (1H, d, J=2.3 Hz), 7.32-7.45 (3H, m), 7.72-7.88 (3H, m), 11.06 (1H, s), 12.70-13.60 (1H, br). ESI-MS (m/z): 379 (M+H)$^+$ Reference Example 53

2-Furan-3-yl-6-methoxy-1H-indole

To a mixture of 2,2,2-trifluoro-N-(2-iodo-5-methoxyphenyl)acetamide (1.00 g), furan-3-ylethynyltrimethylsilane (714 mg), bis(triphenylphosphine) palladium(II) dichloride (61 mg), copper(I) iodide (33 mg), triethylamine (0.81 mL), and acetonitrile (15 mL) was added tetrabutylammonium fluoride in tetrahydrofuran solution (1 mol/L, 4.4 mL) at 50° C. This mixture was stirred at 50° C. for 1 hour. Then, potassium carbonate (801 mg) was added thereto, followed by stirring at 50° C. overnight. To the reaction mixture was added saturated brine, followed by extraction with ethyl acetate. The organic layer was dried over anhydrous magnesium sulfate and concentrated under reduced pressure. The residue was purified by silica gel column chromatography (eluting solvent: ethyl acetate-hexane) to obtain the title compound (422 mg). $^1$H-NMR (CDCl$_3$) δ ppm: 3.86 (3H, s), 6.51-6.56 (1H, m), 6.64-6.69 (1H, m), 6.78 (1H, dd, J=2.3, 8.5 Hz), 6.84-6.90 (1H, m), 7.42-7.51 (2H, m), 7.67-7.73 (1H, m), 7.78-8.13 (1H, br).

Reference Example 54

Methyl 6-[(2-furan-3-yl-6-methoxy-1H-indol-3-yl)hydroxymethyl]pyridine-2-carboxylate In the same method as in Reference Example 31 using the corresponding starting material and reaction agents, the title compound was synthesized. $^1$H-NMR (CDCl$_3$) δ ppm: 3.80 (3H, s), 4.04 (3H, s), 4.96 (1H, d, J=2.8 Hz), 6.14-6.20 (1H, m), 6.61 (1H, d, J=2.3, 8.7 Hz), 6.72-6.77 (1H, m), 6.82 (1H, d, J=2.3 Hz), 7.06 (1H, d, J=8.7 Hz), 7.37-7.44 (1H, m), 7.52-7.57 (1H, m), 7.72 (1H, t, J=7.8 Hz), 7.90-8.05 (3H, m).

Reference Example 55

Methyl 6-(2-furan-3-yl-6-methoxy-1H-indol-3-ylmethyl)pyridine-2-carboxylate

To a solution of methyl 6-[(2-furan-3-yl-6-methoxy-1H-indol-3-yl)hydroxymethyl]pyridine-2-carboxylate (590 mg) and a boran-2-picoline complex (175 mg) in methanol (3 mL) was added acetic acid (3 mL), and this mixture was stirred at room temperature for 8 hours. The reaction mixture was diluted with ethyl acetate, washed with 5% aqueous sodium hydrogen carbonate solution and saturated brine successively, dried over anhydrous magnesium sulfate, and then concentrated under reduced pressure. The residue was purified by silica gel column chromatography (eluting solvent: ethyl acetate-hexane) to obtain the title compound (386 mg). $^1$H-NMR (CDCl$_3$) δ ppm: 3.85 (3H, s), 4.05 (3H, s), 4.48 (2H, s), 6.62-6.67 (1H, m), 6.76 (1H, dd, J=2.3, 8.5 Hz), 6.87-6.91 (1H, m), 7.17-7.23 (1H, m), 7.34 (1H, d, J=8.5 Hz), 7.47-7.52 (1H, m), 7.62 (1H, t, J=7.8 Hz), 7.78-7.84 (1H, m), 7.90-8.06 (2H, m).

Reference Example 56

6-(2-Furan-3-yl-6-methoxy-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 3.77 (3H, s), 4.32 (2H, s), 6.65 (1H, dd, J=2.2, 8.7 Hz), 6.83 (1H, d, J=2.2 Hz), 6.90-7.00 (1H, m), 7.39 (1H, dd, J=1.6, 7.3 Hz), 7.45 (1H, d, J=8.7 Hz), 7.70-7.90 (3H, m), 8.35-8.45 (1H, m), 11.04 (1H, s), 12.80-13.70 (1H, br). ESI-MS (m/z): 349 (M+H)$^+$ Reference Example 57

Methyl 6-(6-chloro-2-phenyl-1H-indol-3-ylmethyl)pyridine-2-carboxylate

In the same method as in Reference Example 28 using the corresponding starting material and reaction agents, the title compound was synthesized. $^1$H-NMR (CDCl$_3$) δ ppm: 4.04 (3H, s), 4.55 (2H, s), 7.03 (1H, dd, J=1.9, 8.5 Hz), 7.11-7.17 (1H, m), 7.30 (1H, d, J=8.5 Hz), 7.33-7.59 (6H, m), 7.63 (1H, t, J=7.8 Hz), 7.93-8.00 (1H, m), 8.27 (1H, br s).

Reference Example 58

6-(6-Chloro-2-phenyl-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 4.38 (2H, s), 6.98 (1H, dd, J=2.0, 8.5 Hz), 7.30-7.55 (6H, m), 7.75-7.90 (4H, m), 11.56 (1H, s), 12.60-13.70 (1H, br).

Reference Example 59

Methyl 6-(2-phenyl-6-trifluoromethyl-1H-indol-3-ylmethyl)pyridine-2-carboxylate

In the same method as in Reference Example 28 using the corresponding starting material and reaction agents, the title compound was synthesized. $^1$H-NMR (CDCl$_3$) δ ppm: 4.04

(3H, s), 4.58 (2H, s), 7.11-7.18 (1H, m), 7.27-7.34 (1H, m), 7.37-7.52 (4H, m), 7.54-7.73 (4H, m), 7.94-8.01 (1H, m), 8.53 (1H, br s).

Reference Example 60

6-(2-Phenyl-6-trifluoromethyl-1H-indol-3-ylmethyl)pyridine-2-carboxylic acid

In the same method as in Reference Example 4 using the corresponding starting material and reaction agents, the title compound was synthesized. $^1$H-NMR (DMSO-d$^6$) δ ppm: 4.42 (2H, s), 7.23-7.30 (1H, m), 7.34-7.40 (1H, m), 7.41-7.57 (3H, m), 7.62-7.71 (2H, m), 7.78-7.90 (4H, m), 11.88 (1H, s), 12.70-13.60 (1H, br).

Reference Example 61

6-Methoxy-2-pyridin-3-yl-1H-indole

A mixture of 2,2,2-trifluoro-N-(2-iodo-5-methoxyphenyl)acetamide (1.00 g), 3-ethynylpyridine (359 mg), bis(triphenylphosphine)palladium(II) dichloride (61.3 mg), copper(I) iodide (33.1 mg), triethylamine (0.81 mL), and acetonitrile (15 mL) was stirred at 50° C. for 1 hour. Then, potassium carbonate (801 mg) was added thereto, followed by stirring at 50° C. overnight. To the reaction mixture was added saturated brine, followed by extraction with ethyl acetate. The organic layer was dried over anhydrous magnesium sulfate and concentrated under reduced pressure. The residue was purified by silica gel column chromatography (eluting solvent: ethyl acetate-hexane) to obtain the title compound (353 mg). $^1$H-NMR (CDCl$_3$) δ ppm: 3.87 (3H, s), 6.78-6.86 (2H, m), 6.89-6.94 (1H, m), 7.29-7.43 (1H, m), 7.52 (1H, d, J=8.5 Hz), 7.85-7.94 (1H, m), 8.20-9.10 (3H, m).

Reference Example 62

Methyl 6-[hydroxy(6-methoxy-2-pyridin-3-yl-1H-indol-3-yl)methyl]pyridine-2-carboxylate In the same method as in Reference Example 31 using the corresponding starting material and reaction agents, the title compound was synthesized. $^1$H-NMR (CDCl$_3$) δ ppm: 3.80 (3H, s), 4.04 (3H, s), 5.25 (1H, d, J=2.5 Hz), 6.06-6.11 (1H, m), 6.63 (1H, dd, J=2.2, 8.8 Hz), 6.86 (1H, d, J=2.2 Hz), 7.02 (1H, d, J=8.8 Hz), 7.32-7.43 (2H, m), 7.71 (1H, t, J=7.8 Hz), 7.99-8.05 (1H, m), 8.10-8.16 (1H, m), 8.27 (1H, br s), 8.58-8.64 (1H, m), 8.89-8.94 (1H, m).

Reference Example 63

Methyl 6-(6-methoxy-2-pyridin-3-yl-1H-indol-3-ylmethyl)pyridine-2-carboxylate

In the same method as in Reference Example 51 using the corresponding starting material and reaction agents, the title compound was synthesized. $^1$H-NMR (CDCl$_3$) δ ppm: 3.86 (3H, s), 4.04 (3H, s), 4.51 (2H, s), 6.77 (1H, dd, J=2.2, 8.5 Hz), 6.93 (1H, d, J=2.2 Hz), 7.18-7.24 (1H, m), 7.30-7.38 (2H, m), 7.64 (1H, t, J=7.8 Hz), 7.90-7.99 (2H, m), 8.19 (1H, br s), 8.54-8.60 (1H, m), 8.78-8.84 (1H, m).

Reference Example 64

6-(6-Methoxy-2-pyridin-3-yl-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 3.78 (3H, s), 4.35 (2H, s), 6.65 (1H, dd, J=2.2, 8.7 Hz), 6.88 (1H, d, J=2.2 Hz), 7.35-7.55 (3H, m), 7.80-7.90 (2H, m), 8.25-8.35 (1H, m), 8.50-8.60 (1H, m), 8.90-9.00 (1H, m), 11.34 (1H, s), 12.80-13.40 (1H, br). ESI-MS (m/z): 360 (M+H)$^+$ Reference Example 65

Ethyl 6-[(5,6-dimethyl-2-phenyl-1H-indol-3-yl)hydroxymethyl]pyridine-2-carboxylate In the same method as in Reference Example 31 using the corresponding starting material and reaction agents, the title compound was synthesized. $^1$H-NMR (CDCl$_3$) δ ppm: 1.48 (3H, t, J=7.2 Hz), 2.17 (3H, s), 2.30 (3H, s), 4.51 (2H, q, J=7.2 Hz), 5.20-5.35 (1H, br), 6.15 (1H, s), 6.91 (1H, s), 7.14 (1H, s), 7.25-7.35 (1H, m), 7.35-7.55 (3H, m), 7.60-7.80 (3H, m), 7.95-8.10 (2H, m).

Reference Example 66

Ethyl 6-(5,6-dimethyl-2-phenyl-1H-indol-3-ylmethyl)pyridine-2-carboxylate

In the same method as in Reference Example 32 using the corresponding starting material and reaction agents, the title compound was synthesized. $^1$H-NMR (CDCl$_3$) δ ppm: 1.47 (3H, t, J=7.2 Hz), 2.29 (3H, s), 2.37 (3H, s), 4.52 (2H, q, J=7.2 Hz), 4.55 (2H, s), 7.10-7.65 (9H, m), 7.90-8.00 (1H, m), 8.01 (1H, s).

Reference Example 67

6-(5,6-Dimethyl-2-phenyl-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 2.23 (3H, s), 2.29 (3H, s), 4.35 (2H, s), 7.16 (1H, s), 7.20 (1H, s), 7.25-7.50 (4H, m), 7.65-7.90 (4H, m), 11.08 (1H, s), 12.60-13.50 (1H, br). ESI-MS (m/z): 357 (M+H)$^+$ Reference Example 68

Methyl 6-(1,6-dimethyl-2-phenyl-1H-indol-3-ylmethyl)pyridine-2-carboxylate

To a solution of methyl 6-(6-methyl-2-phenyl-1H-indol-3-ylmethyl)pyridine-2-carboxylate (100 mg) in N,N-dimethylformamide (2 mL) was added sodium hydride (min. 55% in oil, 13 mg) under ice-cooling, and this mixture was stirred at room temperature for 30 minutes. Then, methyl iodide (0.026 mL) was added thereto, followed by stirring at room temperature overnight. To the reaction mixture were added ethyl acetate and water, and the organic layer was separated. The organic layer was washed with water and saturated brine successively, dried over anhydrous magnesium sulfate, and then concentrated under reduced pressure. The residue was purified by aminopropylated silica gel column chromatography (eluting solvent: ethyl acetate-hexane) to obtain the title compound (35.3 mg). $^1$H-NMR (CDCl$_3$) δ ppm: 2.51 (3H, s), 3.62 (3H, s), 4.02 (3H, s), 4.36 (2H, s), 6.88-6.95 (1H, m), 7.12-7.20 (2H, m), 7.29 (1H, d, J=8.0 Hz), 7.33-7.49 (5H, m), 7.58 (1H, t, J=7.8 Hz), 7.88-7.95 (1H, m).

Reference Example 69

6-(1,6-Dimethyl-2-phenyl-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 2.42 (3H, s), 3.58 (3H, s), 4.14 (2H, s), 6.80-6.87 (1H, m), 7.21-7.36 (3H, m), 7.43-7.66 (5H, m), 7.74-7.85 (2H, m). ESI-MS (m/z): 357 (M+H)$^+$

Reference Example 70

Methyl 5-(6-methoxy-2-phenyl-1H-indol-3-ylmethyl)furan-2-carboxylate

In the same method as in Reference Example 28 using the corresponding starting material and reaction agents, the title compound was synthesized. $^1$H-NMR (CDCl$_3$) δ ppm: 3.86 (3H, s), 3.89 (3H, s), 4.24 (2H, s), 5.95-6.05 (1H, m), 6.79 (1H, dd, J=2.2, 8.7 Hz), 6.91 (1H, d, J=2.2 Hz), 7.07 (1H, d, J=3.5 Hz), 7.30-7.55 (6H, m), 8.08 (1H, br s).

Reference Example 71

5-(6-Methoxy-2-phenyl-1H-indol-3-ylmethyl)furan-2-carboxylic acid

In the same method as in Reference Example 4 using the corresponding starting material and reaction agents, the title compound was synthesized. $^1$H-NMR (CDCl$_3$) δ ppm: 3.87 (3H, s), 4.27 (2H, s), 6.05 (1H, d, J=3.5 Hz), 6.80 (1H, dd, J=2.2, 8.7 Hz), 6.91 (1H, d, J=2.2 Hz), 7.21 (1H, d, J=3.5 Hz), 7.30-7.55 (6H, m), 8.08 (1H, br s). ESI-MS (m/z): 348 (M+H)$^+$

Reference Example 72

Tert-Butyl [5-methoxy-2-(4-methyl-2-oxopentyl)phenyl]carbamate

In the same method as in Reference Example 1 using the corresponding starting material and reaction agents, the title compound was synthesized. $^1$H-NMR (CDCl$_3$) δ ppm: 0.88 (6H, d, J=6.6 Hz), 1.52 (9H, s), 2.05-2.25 (1H, m), 2.41 (2H, d, J=6.9 Hz), 3.58 (2H, s), 3.80 (3H, s), 6.60 (1H, dd, J=2.7, 8.4 Hz), 7.02 (1H, d, J=8.4 Hz), 7.50-7.65 (2H, m).

Reference Example 73

Methyl 6-[2-(2-tert-butoxycarbonylamino-4-methoxyphenyl)-5-methyl-3-oxohexyl]pyridine-2-carboxylate In the same method as in Reference Example 2 using the corresponding starting material and reaction agents, the title compound was synthesized. $^1$H-NMR (CDCl$_3$) δ ppm: 0.71 (3H, d, J=6.7 Hz), 0.83 (3H, d, J=6.7 Hz), 1.56 (9H, s), 2.00-2.15 (1H, m), 2.21 (1H, dd, J=7.3, 16.5 Hz), 2.32 (1H, dd, J=6.5, 16.5 Hz), 3.35 (1H, dd, J=10.4, 16.4 Hz), 3.61 (1H, dd, J=5.0, 16.4 Hz), 3.74 (3H, s), 4.06 (3H, s), 4.70-4.85 (1H, m), 6.60 (1H, dd, J=2.7, 8.7 Hz), 6.96 (1H, d, J=8.7 Hz), 7.06 (1H, s), 7.15-7.25 (1H, m), 7.55-7.70 (1H, m), 7.80-7.95 (2H, m).

Reference Example 74

Methyl 6-(2-isobutyl-6-methoxy-1H-indol-3-ylmethyl)pyridine-2-carboxylate

In the same method as in Reference Example 3 using the corresponding starting material and reaction agents, the title compound was synthesized. $^1$H-NMR (CDCl$_3$) δ ppm: 0.90 (6H, d, J=6.6 Hz), 1.80-2.00 (1H, m), 2.59 (2H, d, J=7.4 Hz), 3.82 (3H, s), 4.04 (3H, s), 4.35 (2H, s), 6.69 (1H, dd, J=2.2, 8.6 Hz), 6.84 (1H, d, J=2.2 Hz), 7.05-7.15 (1H, m), 7.18 (1H, d, J=8.6 Hz), 7.50-7.65 (1H, m), 7.80 (1H, s), 7.90-8.00 (1H, m).

Reference Example 75

6-(2-Isobutyl-6-methoxy-1H-indol-3-ylmethyl)pyridine-2-carboxylic acid

In the same method as in Reference Example 4 using the corresponding starting material and reaction agents, the title compound was synthesized. $^1$H-NMR (DMSO-d$_6$) δ ppm: 0.84 (6H, d, J=6.6 Hz), 1.85-2.05 (1H, m), 2.59 (2H, d, J=7.3 Hz), 3.73 (3H, s), 4.18 (2H, s), 6.54 (1H, dd, J=2.2, 8.6 Hz), 6.77 (1H, d, J=2.2 Hz), 7.18 (1H, d, J=8.6 Hz), 7.20-7.30 (1H, m), 7.75-7.90 (2H, m), 10.62 (1H, s). ESI-MS (m/z): 339 (M+H)$^+$

Reference Example 76

Tert-Butyl [2-(2-cyclopentyl-2-oxoethyl)-5-methoxyphenyl]carbamate

In the same method as in Reference Example 1 using the corresponding starting material and reaction agents, the title compound was synthesized. $^1$H-NMR (CDCl$_3$) δ ppm: 1.40-2.00 (17H, m), 2.95-3.15 (1H, m), 3.66 (2H, s), 3.80 (3H, s), 6.58 (1H, dd, J=2.6, 8.5 Hz), 7.02 (1H, d, J=8.5 Hz), 7.40-7.55 (1H, br), 7.65-7.90 (1H, br).

Reference Example 77

Methyl 6-[2-(2-tert-butoxycarbonylamino-4-methoxyphenyl)-3-cyclopentyl-3-oxopropyl]pyridine-2-carboxylate In the same method as in Reference Example 2 using the corresponding starting material and reaction agents, the title compound was synthesized. $^1$H-NMR (CDCl$_3$) δ ppm: 1.30-2.00 (17H, m), 2.75-2.95 (1H, m), 3.36 (1H, dd, J=10.6, 16.2 Hz), 3.60 (1H, dd, J=4.8, 16.2 Hz), 3.74 (3H, s), 4.06 (3H, s), 4.90 (1H, dd, J=4.8, 10.6 Hz), 6.60 (1H, dd, J=2.7, 8.7 Hz), 6.95 (1H, d, J=8.7 Hz), 7.04 (1H, s), 7.15-7.25 (1H, m), 7.55-7.70 (1H, m), 7.75-8.00 (2H, m).

Reference Example 78

Methyl 6-(2-cyclopentyl-6-methoxy-1H-indol-3-ylmethyl)pyridine-2-carboxylate In the same method as in Reference Example 3 using the corresponding starting material and reaction agents, the title compound was synthesized. $^1$H-NMR (CDCl$_3$) δ ppm: 1.50-2.10 (8H, m), 3.20-3.40 (1H, m), 3.82 (3H, s), 4.04 (3H, s), 4.37 (2H, s), 6.70 (1H, dd, J=2.2, 8.6 Hz), 6.84 (1H, d, J=2.2

Hz), 7.05-7.20 (1H, m), 7.22 (1H, d, J=8.6 Hz), 7.50-7.65 (1H, m), 7.85 (1H, s), 7.90-8.00 (1H, m).

Reference Example 79

6-(2-Cyclopentyl-6-methoxy-1H-indol-3-ylmethyl)pyridine-2-carboxylic acid

In the same method as in Reference Example 4 using the corresponding starting material and reaction agents, the title compound was synthesized. $^1$H-NMR (DMSO-$d_6$) δ ppm: 1.55-2.05 (8H, s), 3.72 (3H, s), 4.17 (2H, s), 6.54 (1H, dd, J=2.2, 8.6 Hz), 6.77 (1H, d, J=2.2 Hz), 7.15-7.30 (2H, m), 7.70-7.90 (2H, m), 10.57 (1H, s). ESI-MS (m/z): 351 (M+H)$^+$ Reference Example 80

Ethyl 2-[hydroxy(6-methoxy-2-phenyl-1H-indol-3-yl)methyl]thiazole-4-carboxylate

In the same method as in Reference Example 31 using the corresponding starting material and reaction agents, the title compound was synthesized. $^1$H-NMR (CDCl$_3$) δ ppm: 1.39 (3H, t, J=7.2 Hz), 3.41 (1H, d, J=2.9 Hz), 3.83 (3H, s), 4.40 (2H, q, J=7.2 Hz), 6.34 (1H, d, J=2.9 Hz), 6.72 (1H, dd, J=2.3, 8.7 Hz), 6.86 (1H, d, J=2.3 Hz), 7.35-7.55 (4H, m), 7.60-7.70 (2H, m), 8.13 (1H, s), 8.18 (1H, br s).

Reference Example 81

Ethyl 2-(6-methoxy-2-phenyl-1H-indol-3-ylmethyl)thiazole-4-carboxylate

Under an argon atmosphere, to an ice-cooled solution of ethyl 2-[hydroxy(6-methoxy-2-phenyl-1H-indol-3-yl)methyl]thiazole-4-carboxylate (69.0 mg) and triethylsilane (0.135 mL) in methylene chloride (1.7 mL) was slowly added dropwise a boron trifluoride diethyl ether complex (0.107 mL). After stirring for 10 minutes, the mixture was stirred at room temperature for additional 15 minutes. To the reaction mixture was added a saturated aqueous sodium hydrogen carbonate solution. The organic layer was separated, dried over anhydrous sodium sulfate, and then concentrated under reduced pressure. The residue was purified by aminopropylated silica gel column chromatography (eluting solvent: ethyl acetate-hexane) to obtain the title compound (17.0 mg). $^1$H-NMR (CDCl$_3$) δ ppm: 1.43 (3H, t, J=7.2 Hz), 3.87 (3H, s), 4.45 (2H, q, J=7.2 Hz), 4.61 (2H, s), 6.79 (1H, dd, J=2.1, 8.7 Hz), 6.93 (1H, d, J=2.1 Hz), 7.30-7.60 (6H, m), 7.99 (1H, s), 8.13 (1H, br s).

Reference Example 82

2-(6-Methoxy-2-phenyl-1H-indol-3-ylmethyl)thiazole-4-carboxylic acid

In the same method as in Reference Example 4 using the corresponding starting material and reaction agents, the title compound was synthesized. $^1$H-NMR (DMSO-$d_6$) δ ppm: 3.79 (3H, s), 4.51 (2H, s), 6.68 (1H, dd, J=2.2, 8.8 Hz), 6.90 (1H, d, J=2.2 Hz), 7.30-7.40 (2H, m), 7.45-7.55 (2H, m), 7.55-7.65 (2H, m), 8.16 (1H, s), 11.32 (1H, s), 12.80-13.20 (1H, br). ESI-MS (m/z): 365 (M+H)$^+$ Reference Example 83

Methyl 3-[2-(2-tert-butoxycarbonylamino-4-methoxyphenyl)-3-oxo-3-phenylpropyl]-2-fluorobenzoate In the same method as in Reference Example 2 using the corresponding starting material and reaction agents, the title compound was synthesized. ESI-MS (m/z): 506 (M–H)$^-$ Reference Example 84

Methyl 2-fluoro-3-(6-methoxy-2-phenyl-1H-indol-3-ylmethyl)benzoate

In the same method as in Reference Example 3 using the corresponding starting material and reaction agents, the title compound was synthesized. $^1$H-NMR (CDCl$_3$) δ ppm: 3.86 (3H, s), 3.95 (3H, s), 4.27 (2H, s), 6.75 (1H, dd, J=2.2, 8.7 Hz), 6.92 (1H, d, J=2.2 Hz), 6.90-7.05 (1H, m), 7.10-7.20 (1H, m), 7.23 (1H, d, J=8.7 Hz), 7.30-7.50 (5H, m), 7.70-7.80 (1H, m), 8.08 (1H, s).

Reference Example 85

2-Fluoro-3-(6-methoxy-2-phenyl-1H-indol-3-ylmethyl)benzoic acid

In the same method as in Reference Example 4 using the corresponding starting material and reaction agents, the title compound was synthesized. $^1$H-NMR (DMSO-$d_6$) δ ppm: 3.77 (3H, s), 4.17 (2H, s), 6.62 (1H, dd, J=2.3, 8.6 Hz), 6.85-7.00 (3H, m), 7.19 (1H, d, J=8.6 Hz), 7.25-7.60 (6H, m), 11.19 (1H, s). ESI-MS (m/z): 376 (M+H)$^+$ Reference Example 86

6-(6-Cyclopropyl-2-phenyl-1H-indol-3-ylmethyl)pyridine-2-carboxamide

Benzyl 6-(6-cyclopropyl-2-phenyl-1H-indol-3-ylmethyl)pyridine-2-carboxylate (200 mg) was dissolved in a solution of ammonia in methanol (about 7 mol/L, 3.3 mL). This solution was stirred at room temperature for 17 hours. The reaction mixture was concentrated under reduced pressure. The residue was purified by silica gel column chromatography (eluting solvent: ethyl acetate-hexane) to obtain the title compound (138 mg). $^1$H-NMR (CDCl$_3$) δ ppm: 0.69-0.77 (2H, m), 0.92-1.02 (2H, m), 1.97-2.06 (1H, m), 4.42 (2H, s), 5.38-5.59 (1H, br), 6.86 (1H, dd, J=1.4, 8.2 Hz), 7.11-7.15 (1H, m), 7.24-7.29 (1H, m), 7.32-7.48 (4H, m), 7.51-7.58 (2H, m), 7.63-7.71 (1H, m), 7.76-7.96 (1H, br), 7.97-8.03 (1H, m), 8.08 (1H, br).

Reference Example 87

6-(6-Cyclopropyl-2-phenyl-1H-indol-3-ylmethyl)pyridine-2-carbonitrile

To a solution of 6-(6-cyclopropyl-2-phenyl-1H-indol-3-ylmethyl)pyridine-2-carboxamide (137 mg) in N,N-dimethylformamide (1.5 mL) was added dropwise phosphoryl chloride (0.051 mL) under ice-cooling. This mixture was stirred for 50 minutes under ice-cooling. To the reaction mixture was added a saturated aqueous sodium hydrogen carbonate solution, followed by extraction with ethyl acetate. The organic layer was washed with saturated brine, dried over anhydrous sodium sulfate, and then concentrated under reduced pressure. The residue was purified by silica gel column chromatography (eluting solvent: ethyl acetate-hexane) to obtain the title compound (94.4 mg). $^1$H-NMR (CDCl$_3$) δ ppm: 0.69-0.77 (2H, m), 0.92-1.03 (2H, m), 1.97-2.07 (1H, m), 4.46 (2H, s), 6.86 (1H, dd, J=1.5, 8.3 Hz), 7.11-7.17 (1H, m), 7.21-7.32 (2H, m), 7.33-7.64 (7H, m), 8.09 (1H, br s).

Reference Example 88

6-(6-Methoxy-2-phenyl-1H-indol-3-ylmethyl)pyridine-2-carboxamide

A mixture of methyl 6-(6-methoxy-2-phenyl-1H-indol-3-ylmethyl)pyridine-2-carboxylate (500 mg), a solution (about 7 mol/L, 20.1 mL) of ammonia in methanol, and tetrahydrofuran (6.7 mL) was stirred at room temperature for 61 hours. The reaction mixture was concentrated under reduced pressure to obtain the title compound (490 mg). $^1$H-NMR (CDCl$_3$) δ ppm: 3.86 (3H, s), 4.42 (2H, s), 5.37-5.60 (1H, br), 6.77 (1H, dd, J=2.3, 8.8 Hz), 6.92 (1H, d, J=2.3 Hz), 7.24-7.29 (1H, m), 7.31-7.39 (2H, m), 7.40-7.49 (2H, m), 7.50-7.58 (2H, m), 7.69 (1H, t, J=7.8 Hz), 7.75-7.95 (1H, br), 7.97-8.03 (1H, m), 8.09 (1H, br s).

Reference Example 89

6-(6-Methoxy-2-phenyl-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 3.86 (3H, s), 4.46 (2H, s), 6.77 (1H, dd, J=2.2, 8.5 Hz), 6.92 (1H, d, J=2.2 Hz), 7.21-7.57 (8H, m), 7.61 (1H, t, J=7.8 Hz), 8.10 (1H, br s).

Reference Example 90

6-(6-Methyl-2-phenyl-1H-indol-3-ylmethyl)pyridine-2-carboxamide

In the same method as in Reference Example 88 using the corresponding starting material and reaction agents, the title compound was synthesized. $^1$H-NMR (CDCl$_3$) δ ppm: 2.47 (3H, s), 4.43 (2H, s), 5.32-5.64 (1H, br), 6.91-6.97 (1H, m), 7.20-7.24 (1H, m), 7.24-7.29 (1H, m), 7.33-7.40 (2H, m), 7.41-7.50 (2H, m), 7.52-7.60 (2H, m), 7.63-7.72 (1H, m), 7.74-7.98 (1H, br), 7.97-8.04 (1H, m), 8.08 (1H, br s).

Reference Example 91

6-(6-Methyl-2-phenyl-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 2.47 (3H, s), 4.46 (2H, s), 6.90-6.97 (1H, m), 7.19-7.32 (3H, m), 7.33-7.64 (7H, m), 8.11 (1H, br s).

Reference Example 92

6-(6-Methoxy-2-thiophen-3-yl-1H-indol-3-ylmethyl)pyridine-2-carboxamide

In the same method as in Reference Example 88 using the corresponding starting material and reaction agents, the title compound was synthesized. $^1$H-NMR (CDCl$_3$) δ ppm: 3.86 (3H, s), 4.42 (2H, s), 5.34-5.66 (1H, br), 6.78 (1H, dd, J=2.3, 8.5 Hz), 6.90 (1H, d, J=2.3 Hz), 7.24-7.31 (1H, m), 7.33 (1H, dd, J=1.4, 4.8 Hz), 7.37 (1H, d, J=8.5 Hz), 7.40 (1H, dd, J=1.4, 3.0 Hz), 7.44 (1H, dd, J=3.0, 4.8 Hz), 7.68 (1H, t, J=7.8 Hz), 7.74-7.98 (1H, br), 7.98-8.04 (1H, m), 8.07 (1H, br s).

Reference Example 93

6-(6-Methoxy-2-thiophen-3-yl-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 3.86 (3H, s), 4.45 (2H, s), 6.78 (1H, dd, J=2.3, 8.5 Hz), 6.90 (1H, d, J=2.3 Hz), 7.25-7.36 (3H, m), 7.41-7.54 (3H, m), 7.61 (1H, t, J=7.8 Hz), 8.09 (1H, br s).

Reference Example 94

6-(2-tert-Butyl-5-chloro-6-methoxy-1H-indol-3-ylmethyl)pyridine-2-carboxamide

In the same method as in Reference Example 88 using the corresponding starting material and reaction agents, the title compound was synthesized. $^1$H-NMR (CDCl$_3$) δ ppm: 1.41 (9H, s), 3.92 (3H, s), 4.39 (2H, s), 5.35-5.75 (1H, br), 6.91 (1H, s), 7.07-7.14 (1H, m), 7.37 (1H, s), 7.62-7.69 (1H, m), 7.76-8.04 (3H, m).

Reference Example 95

6-(2-tert-Butyl-5-chloro-6-methoxy-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 1.39 (9H, s), 3.91 (3H, s), 4.43 (2H, s), 6.92 (1H, s), 7.07-7.15 (1H, m), 7.27 (1H, s), 7.47-7.55 (1H, m), 7.60 (1H, t, J=7.8 Hz), 8.01 (1H, br s).

Reference Example 96

Tert-Butyl {2-[1-(3-cyanobenzyl)-2-oxo-2-phenylethyl]-5-methoxyphenyl}carbamate

In the same method as in Reference Example 2 using the corresponding starting material and reaction agents, the title compound was synthesized. $^1$H-NMR (CDCl$_3$) δ ppm: 1.56 (9H, s), 3.13 (1H, dd, J=7.2, 13.6 Hz), 3.53 (1H, dd, J=7.2, 13.6 Hz), 3.76 (3H, s), 4.77 (1H, t, J=7.2 Hz), 6.40-6.58 (1H, br), 6.61 (1H, dd, J=2.6, 8.6 Hz), 7.02 (1H, d, J=8.6 Hz), 7.13-7.58 (8H, m), 7.81-7.95 (2H, m).

Reference Example 97

3-(6-Methoxy-2-phenyl-1H-indol-3-ylmethyl)benzonitrile

In the same method as in Reference Example 3 using the corresponding starting material and reaction agents, the title compound was synthesized. $^1$H-NMR (CDCl$_3$) δ ppm: 3.87 (3H, s), 4.26 (2H, s), 6.75 (1H, dd, J=2.3, 8.7 Hz), 6.92 (1H, d, J=2.3 Hz), 7.19 (1H, d, J=8.7 Hz), 7.30-7.56 (9H, m), 8.08 (1H, br s).

Reference Example 98

6-(2-tert-Butyl-6-methoxy-1H-indol-3-ylmethyl) pyridine-2-carboxamide

In the same method as in Reference Example 88 using the corresponding starting material and reaction agents, the title compound was synthesized. $^1$H-NMR (CDCl$_3$) δ ppm: 1.41 (9H, s), 3.84 (3H, s), 4.43 (2H, s), 5.38-5.70 (1H, br), 6.71 (1H, dd, J=2.3, 8.8 Hz), 6.86 (1H, d, J=2.3 Hz), 7.08-7.16 (1H, m), 7.21 (1H, d, J=8.8 Hz), 7.58-7.67 (1H, m), 7.72-8.07 (3H, m).

Reference Example 99

6-(2-tert-Butyl-6-methoxy-1H-indol-3-ylmethyl) pyridine-2-carbonitrile

In the same method as in Reference Example 87 using the corresponding starting material and reaction agents, the title compound was synthesized. $^1$H-NMR (CDCl$_3$) δ ppm: 1.40 (9H, s), 3.83 (3H, s), 4.47 (2H, s), 6.71 (1H, dd, J=2.2, 8.5 Hz), 6.87 (1H, d, J=2.2 Hz), 7.11-7.19 (2H, m), 7.46-7.52 (1H, m), 7.57 (1H, t, J=7.8 Hz), 7.93 (1H, br s).

Reference Example 100

6-(5-Fluoro-6-methoxy-2-phenyl-1H-indol-3-ylmethyl)pyridine-2-carboxamide

To a solution of 6-(5-fluoro-6-methoxy-2-phenyl-1H-indol-3-ylmethyl)pyridine-2-carboxylic acid (105 mg) in tetrahydrofuran (2.8 mL) was added 1,1'-carbonyldiimidazole (90.5 mg), and this mixture was stirred at room temperature for 9 hours. Then, 28% aqueous ammonia (0.56 mL) was added thereto, followed by stirring at room temperature for 14 hours. To the reaction mixture was added water, followed by extraction with ethyl acetate. The organic layer was washed with 10% aqueous citric acid solution, a saturated aqueous sodium hydrogen carbonate solution, and saturated brine successively, dried over anhydrous sodium sulfate, and then concentrated under reduced pressure to obtain the title compound (103 mg). $^1$H-NMR (CDCl$_3$) δ ppm: 3.94 (3H, s), 4.37 (2H, s), 5.30-5.60 (1H, br), 6.97 (1H, d, J=7.0 Hz), 7.16 (1H, d, J=11.5 Hz), 7.23-7.28 (1H, m), 7.34-7.41 (1H, m), 7.41-7.49 (2H, m), 7.49-7.57 (2H, m), 7.66-7.94 (2H, m), 7.98-8.13 (2H, m).

Reference Example 101

6-(5-Fluoro-6-methoxy-2-phenyl-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 3.93 (3H, s), 4.40 (2H, s), 6.97 (1H, d, J=7.0 Hz), 7.06 (1H, d, J=11.6 Hz), 7.20-7.30 (1H, m), 7.33-7.58 (6H, m), 7.59-7.67 (1H, m), 8.10 (1H, br s).

Reference Example 102

6-[2-(4-Fluorophenyl)-6-methoxy-1H-indol-3-ylmethyl]pyridine-2-carboxamide

In the same method as in Reference Example 88 using the corresponding starting material and reaction agents, the title compound was synthesized. $^1$H-NMR (DMSO-d$_6$) δ ppm: 3.77 (3H, s), 4.36 (2H, s), 6.64 (1H, dd, J=2.3, 8.7 Hz), 6.86 (1H, d, J=2.3 Hz), 7.24-7.41 (4H, m), 7.58-7.94 (6H, m), 11.20 (1H, s).

Reference Example 103

6-[2-(4-Fluorophenyl)-6-methoxy-1H-indol-3-ylmethyl]pyridine-2-carbonitrile

In the same method as in Reference Example 87 using the corresponding starting material and reaction agents, the title compound was synthesized. $^1$H-NMR (CDCl$_3$) δ ppm: 3.86 (3H, s), 4.40 (2H, s), 6.77 (1H, dd, J=2.2, 8.8 Hz), 6.91 (1H, d, J=2.2 Hz), 7.11-7.19 (2H, m), 7.23-7.32 (2H, m), 7.47-7.55 (3H, m), 7.62 (1H, t, J=7.8 Hz), 8.04 (1H, br s).

Reference Example 104

6-(6-Methoxy-2-pyridin-3-yl-1H-indol-3-ylmethyl) pyridine-2-carboxamide

In the same method as in Reference Example 88 using the corresponding starting material and reaction agents, the title compound was synthesized. $^1$H-NMR (DMSO-d$_6$) δ ppm: 3.78 (3H, s), 4.40 (2H, s), 6.67 (1H, dd, J=2.3, 8.5 Hz), 6.88 (1H, d, J=2.3 Hz), 7.28-7.36 (1H, m), 7.44 (1H, d, J=8.5 Hz), 7.46-7.53 (1H, m), 7.60-7.86 (4H, m), 8.04-8.11 (1H, m), 8.49-8.56 (1H, m), 8.87-8.93 (1H, m), 11.33 (1H, s).

Reference Example 105

6-(6-Methoxy-2-pyridin-3-yl-1H-indol-3-ylmethyl) pyridine-2-carbonitrile

In the same method as in Reference Example 87 using the corresponding starting material and reaction agents, the title compound was synthesized. $^1$H-NMR (CDCl$_3$) δ ppm: 3.87 (3H, s), 4.42 (2H, s), 6.80 (1H, dd, J=2.1, 8.7 Hz), 6.93 (1H, d, J=2.1 Hz), 7.25-7.43 (3H, m), 7.49-7.54 (1H, m), 7.64 (1H, t, J=7.8 Hz), 7.88-7.95 (1H, m), 8.18 (1H, br s), 8.57-8.63 (1H, m), 8.77-8.84 (1H, m).

Reference Example 106

6-(2-Furan-3-yl-6-methoxy-1H-indol-3-ylmethyl) pyridine-2-carboxamide

In the same method as in Reference Example 88 using the corresponding starting material and reaction agents, the title compound was synthesized. $^1$H-NMR (CDCl$_3$) δ ppm: 3.86 (3H, s), 4.37 (2H, s), 5.38-5.66 (1H, br), 6.63-6.68 (1H, m), 6.78 (1H, dd, J=2.2, 8.7 Hz), 6.89 (1H, d, J=2.2 Hz), 7.22-7.29 (1H, m), 7.37 (1H, d, J=8.7 Hz), 7.49-7.54 (1H, m), 7.64-7.72 (2H, m), 7.75-8.08 (3H, m).

Reference Example 107

6-(2-Furan-3-yl-6-methoxy-1H-indol-3-ylmethyl) pyridine-2-carbonitrile

In the same method as in Reference Example 87 using the corresponding starting material and reaction agents, the title compound was synthesized. $^1$H-NMR (CDCl$_3$) δ ppm: 3.86 (3H, s), 4.39 (2H, s), 6.63-6.68 (1H, m), 6.78 (1H, dd, J=2.2, 8.8 Hz), 6.89 (1H, d, J=2.2 Hz), 7.24-7.30 (1H, m), 7.34 (1H, d, J=8.8 Hz), 7.47-7.55 (2H, m), 7.57-7.66 (1H, m), 7.72-7.79 (1H, m), 7.89-8.05 (1H, br).

Reference Example 108

6-[6-Methoxy-2-(5-methylthiophen-3-yl)-1H-indol-3-ylmethyl]pyridine-2-carboxamide In the same method as in Reference Example 88 using the corresponding starting material and reaction agents, the title compound was synthesized. $^1$H-NMR (CDCl$_3$) δ ppm: 2.52 (3H, d, J=1.0 Hz), 3.85 (3H, s), 4.41 (2H, s), 5.40-5.60 (1H, br), 6.76 (1H, dd, J=2.3, 8.5 Hz), 6.88 (1H, d, J=2.3 Hz), 6.97-7.04 (1H, m), 7.13 (1H, d, J=1.5 Hz), 7.23-7.29 (1H, m), 7.34 (1H, d, J=8.5 Hz), 7.68 (1H, t, J=7.8 Hz), 7.75-8.10 (3H, m).

Reference Example 109

6-[6-Methoxy-2-(5-methylthiophen-3-yl)-1H-indol-3-ylmethyl]pyridine-2-carbonitrile In the same method as in Reference Example 87 using the corresponding starting material and reaction agents, the title compound was synthesized. $^1$H-NMR (CDCl$_3$) δ ppm: 2.53 (3H, d, J=1.0 Hz), 3.85 (3H, s), 4.44 (2H, s), 6.76 (1H, dd, J=2.3, 8.5 Hz), 6.88 (1H, d, J=2.3 Hz), 6.96-7.00 (1H, m), 7.17 (1H, d, J=1.5 Hz), 7.23-7.33 (2H, m), 7.47-7.54 (1H, m), 7.61 (1H, t, J=7.8 Hz), 8.02 (1H, br s).

Reference Example 110

6-(6-Methyl-2-thiophen-3-yl-1H-indol-3-ylmethyl)pyridine-2-carboxamide

In the same method as in Reference Example 88 using the corresponding starting material and reaction agents, the title compound was synthesized. $^1$H-NMR (CDCl$_3$) δ ppm: 2.47 (3H, s), 4.44 (2H, s), 5.34-5.64 (1H, br), 6.91-6.98 (1H, m), 7.20 (1H, s), 7.23-7.30 (1H, m), 7.35 (1H, dd, J=1.9, 4.4 Hz), 7.38 (1H, d, J=8.0 Hz), 7.41-7.46 (2H, m), 7.64-7.71 (1H, m), 7.75-8.14 (3H, m).

Reference Example 111

6-(6-Methyl-2-thiophen-3-yl-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 2.47 (3H, s), 4.46 (2H, s), 6.92-6.98 (1H, m), 7.17-7.22 (1H, m), 7.24-7.37 (3H, m), 7.45 (1H, dd, J=3.0, 5.0 Hz), 7.46-7.54 (2H, m), 7.56-7.64 (1H, m), 8.06 (1H, br s).

Reference Example 112

6-(6-Methoxy-1-methyl-2-phenyl-1H-indol-3-ylmethyl)pyridine-2-carboxamide

In the same method as in Reference Example 88 using the corresponding starting material and reaction agents, the title compound was synthesized. $^1$H-NMR (CDCl$_3$) δ ppm: 3.60 (3H, s), 3.90 (3H, s), 4.22 (2H, s), 5.35-5.60 (1H, br), 6.78 (1H, dd, J=2.3, 8.5 Hz), 6.83 (1H, d, J=2.3 Hz), 7.14-7.21 (1H, m), 7.32-7.52 (6H, m), 7.64 (1H, t, J=7.8 Hz), 7.71-8.00 (2H, m).

Reference Example 113

6-(6-Methoxy-1-methyl-2-phenyl-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 3.60 (3H, s), 3.90 (3H, s), 4.25 (2H, s), 6.77 (1H, d, J=2.2, 8.8 Hz), 6.83 (1H, d, J=2.2 Hz), 7.16-7.21 (1H, m), 7.31 (1H, d, J=8.8 Hz), 7.34-7.51 (6H, m), 7.57 (1H, t, J=7.8 Hz).

Reference Example 114

6-(6-Methoxy-2-phenyl-1H-indol-3-ylmethyl)pyridine-2-carbohydrazide

A mixture of methyl 6-(6-methoxy-2-phenyl-1H-indol-3-ylmethyl)pyridine-2-carboxylate (300 mg), hydrazine monohydrate (0.4 mL), methanol (6 mL), and tetrahydrofuran (2 mL) was stirred at room temperature overnight. The precipitate was collected by filtration, washed with methanol, and then dried under reduced pressure to obtain the title compound (258 mg). $^1$H-NMR (DMSO-d$_6$) δ ppm: 3.77 (3H, s), 4.38 (2H, s), 4.58 (2H, d, J=4.8 Hz), 6.63 (1H, dd, J=2.3, 8.7 Hz), 6.87 (1H, d, J=2.3 Hz), 7.21 (1H, dd, J=1.8, 7.0 Hz), 7.30-7.39 (2H, m), 7.43-7.53 (2H, m), 7.61-7.70 (2H, m), 7.73-7.83 (2H, m), 9.47-9.58 (1H, m), 11.20 (1H, s).

Reference Example 115

6-(6-Methoxy-2-phenyl-1H-indol-3-ylmethyl)pyridine-2-carboxamidoxime

To a solution of hydroxylammonium chloride (891 mg) in dimethylsulfoxide (5 mL) was added sodium hydrogen carbonate (1.29 g), and this mixture was stirred at 50° C. for 75 minutes. Then, a solution of 6-(6-methoxy-2-phenyl-1H-indol-3-ylmethyl)pyridine-2-carbonitrile (435 mg) in dimethylsulfoxide (1.4 mL) was added dropwise thereto, followed by stirring at 50° C. for 24 hours. The reaction mixture was left to be cooled and diluted with water, followed by extraction with ethyl acetate. The organic layer was washed with water and saturated brine, dried over anhydrous sodium sulfate, and then concentrated under reduced pressure to obtain the title compound (504 mg). $^1$H-NMR (CDCl$_3$) δ ppm: 3.86 (3H, s), 4.40 (2H, s), 5.63 (2H, br s), 6.43-6.69 (1H, br), 6.77 (1H, dd, J=2.2, 8.8 Hz), 6.91 (1H, d, J=2.2 Hz), 7.09-7.15 (1H, m), 7.31-7.40 (2H, m), 7.40-7.49 (2H, m), 7.49-7.60 (3H, m), 7.66-7.74 (1H, m), 8.06 (1H, br s).

Reference Example 116

6-(6-Methyl-2-phenyl-1H-indol-3-ylmethyl)pyridine-2-carboxamidoxime

To a suspension of hydroxylammonium chloride (27.6 mg) in ethanol (1 mL) was added sodium hydrogen carbonate (33.4 mg), and this mixture was heated under reflux for 45 minutes. Then, a solution of 6-(6-methyl-2-phenyl-1H-indol-3-ylmethyl)pyridine-2-carbonitrile (61 mg) in ethanol (1.3 mL) was added dropwise thereto under ice-cooling, and the mixture was heated under reflux for additional 3.5 hours. The reaction mixture was left to be cooled and concentrated under reduced pressure. To the residue was added water, followed by extraction with ethyl acetate. The organic layer was washed with saturated brine, dried over anhydrous magnesium sulfate, and then concentrated under reduced pressure. The residue was purified by silica gel column chromatography (eluting solvent: ethyl acetate-hexane) to obtain the title compound (60.8 mg). $^1$H-NMR (CDCl$_3$) δ ppm: 2.47 (3H, s), 4.42 (2H, s), 5.64 (2H, br s), 6.48-6.84 (1H, br), 6.90-6.97 (1H, m), 7.08-7.14 (1H, m), 7.18-7.23 (1H, m), 7.32-7.49 (4H, m), 7.52 (1H, t, J=7.8 Hz), 7.54-7.61 (2H, m), 7.66-7.74 (1H, m), 8.06 (1H, br s). ESI-MS (m/z): 357 (M+H)$^+$ Example 1

N-Methanesulfonyl-6-(6-methoxy-2-thiophen-3-yl-1H-indol-3-ylmethyl)pyridine-2-carboxamide

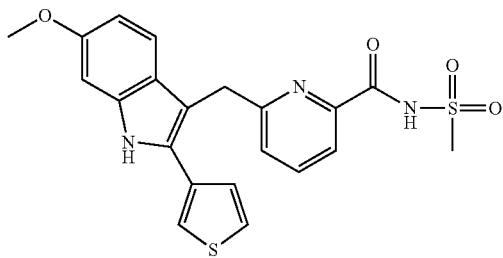 [SMILES: COc1ccc2c(Cc3cccc(C(=O)NS(C)(=O)=O)n3)c(-c3ccsc3)[nH]c2c1]

Under an argon atmosphere, to a suspension of 6-(6-methoxy-2-thiophen-3-yl-1H-indol-3-ylmethyl)pyridine-2-carboxylic acid (45.5 mg) in dichloromethane (0.6 mL) were added methane sulfonamide (11.9 mg), 1-ethyl-3-(3-dimethylaminopropyl)carbodiimide hydrochloride (23.9 mg), and 4-dimethylaminopyridine (15.3 mg), and this mixture was stirred at room temperature for 2 days. The reaction mixture was concentrated under reduced pressure. To the residue was added 10% aqueous citric acid solution, followed by extraction with ethyl acetate. The organic layer was washed with a saturated aqueous sodium hydrogen carbonate solution and saturated brine successively, dried over anhydrous sodium sulfate, and then concentrated under reduced pressure. To the residue was added ethanol, and this suspension was heated to reflux for 45 minutes to give a solution. This solution was left to be cooled. The precipitate was collected by filtration and dried under reduced pressure to obtain the title compound (21.9 mg). $^1$H-NMR (DMSO-d$_6$) δ ppm: 3.38 (3H, s), 3.77 (3H, s), 4.47 (2H, s), 6.65 (1H, dd, J=2.3, 8.6 Hz), 6.85 (1H, d, J=2.3 Hz), 7.27-7.35 (1H, m), 7.42 (1H, d, J=8.6 Hz), 7.56 (1H, dd, J=1.3, 5.0 Hz), 7.67 (1H, dd, J=3.0, 5.0 Hz), 7.81-7.91 (3H, m), 11.17 (1H, s), 11.42-11.66 (1H, br).

Example 2-1

N-Methanesulfonyl-6-(6-methoxy-2-phenyl-1H-indol-3-ylmethyl)pyridine-2-carboxamide To a solution of 6-(1-benzenesulfonyl-6-methoxy-2-phenyl-1H-indol-3-ylmethyl)-N-methanesulfonylpyridine-2-carboxamide (632 mg) in tetrahydrofuran/methanol (7.4 mL/3.7 mL) was added cesium carbonate (1.43 g), and this mixture was stirred at 50° C. for 29 hours. Cesium carbonate (1.43 g) was added thereto, and further stirred for additional 45.5 hours. The reaction mixture was left to be cooled. To the reaction mixture was added 1 mol/L hydrochloric acid (20 mL), followed by extraction with ethyl acetate. The organic layer was washed with water, dried over anhydrous sodium sulfate, and then concentrated under reduced pressure. The residue was purified by silica gel column chromatography (eluting solvent: methanol-dichloromethane) to obtain the title compound (375 mg).

Further, the structural formula and spectrum data of the title compound are shown in Table 1.

Example 2-2

6-(6-Cyclopropyl-2-phenyl-1H-indol-3-ylmethyl)-N-methanesulfonylpyridine-2-carboxamide In the same method as in Example 2-1 using the corresponding starting material, the title compound was synthesized.

Further, the structural formula and spectrum data of the title compound are shown in Table 1.

Example 3-1

N-Methanesulfonyl-6-(6-methyl-2-phenyl-1H-indol-3-ylmethyl)pyridine-2-carboxamide Under an argon atmosphere, to a solution of 6-(6-methyl-2-phenyl-1H-indol-3-ylmethyl)pyridine-2-carboxylic acid (838 mg) in dichloromethane (17.4 mL) were added methane sulfonamide (279 mg), 4-dimethylaminopyridine (718 mg), and 1-ethyl-3-(3-dimethylaminopropyl)carbodiimide hydrochloride (1.13 g) successively, and this mixture was stirred at room temperature for 24 hours. To the reaction mixture was added 1 mol/L hydrochloric acid, followed by extraction with dichloromethane. The organic layer was washed with 1 mol/L hydrochloric acid, dried over anhydrous sodium sulfate, and then concentrated under reduced pressure. The residue was purified by silica gel column chromatography (eluting solvent: methanol-dichloromethane) to obtain the title compound (740 mg).

Further, the structural formula and spectrum data of the title compound are shown in Table 2.

Examples 3-2 to 3-43

In the same method as in Example 3-1 using the corresponding starting material, the compounds shown in Tables 2 to 11 were synthesized.

Example 4

N-Methanesulfonyl-6-(1,6-dimethyl-2-phenyl-1H-indol-3-ylmethyl)pyridine-2-carboxamide

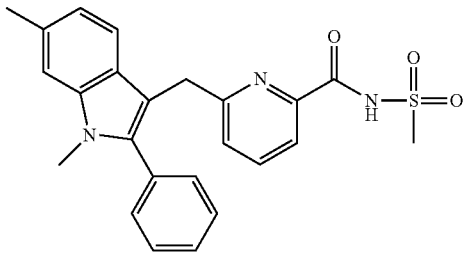 [SMILES: Cc1ccc2c(Cc3cccc(C(=O)NS(C)(=O)=O)n3)c(-c3ccccc3)n(C)c2c1]

To a solution of N-methanesulfonyl-6-(6-methyl-2-phenyl-1H-indol-3-ylmethyl)pyridine-2-carboxamide (100 mg) in N,N-dimethylformamide (1.2 mL) were added cesium carbonate (155 mg) and methyl iodide (0.023 mL), and this mixture was stirred at room temperature for 17 hours. The reaction mixture was diluted with water, followed by extraction with ethyl acetate. The organic layer was washed with water and saturated brine, dried over anhydrous sodium sulfate, and then concentrated under reduced pressure. The residue was purified by silica gel column chromatography (eluting solvent: ethyl acetate-hexane) to obtain the title compound (38.3 mg). $^1$H-NMR (DMSO-$d_6$) δ ppm: 2.43 (3H, s), 3.38 (3H, s), 3.57 (3H, s), 4.21 (2H, s), 6.82-6.89 (1H, m), 7.24-7.33 (2H, m), 7.37 (1H, d, J=8.0 Hz), 7.43-7.58 (5H, m), 7.81-7.90 (2H, m), 10.90-11.55 (1H, br). ESI-MS (m/z): 434 (M+H)$^+$.

Example 5-1

6-Cyclopropyl-2-phenyl-3-[6-(1H-tetrazol-5-yl)pyridin-2-ylmethyl]-1H-indole

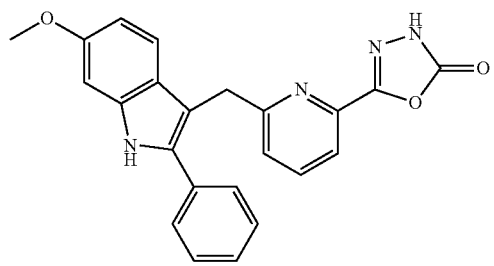 [SMILES: COc1ccc2c(Cc3cccc(-c4n[nH]c(=O)o4)n3)c(-c3ccccc3)[nH]c2c1]

To a mixture of 6-(6-cyclopropyl-2-phenyl-1H-indol-3-ylmethyl)pyridine-2-carbonitrile (93 mg), sodium azide (86.5 mg), isopropyl alcohol (3.2 mL), and water (2.1 mL) was added zinc bromide (74.9 mg), and this mixture was heated under reflux for 23 hours while stirring. The reaction mixture was left to be cooled. To the reaction mixture was added 1 mol/L hydrochloric acid, followed by extraction with ethyl acetate. The organic layer was washed with saturated brine, dried over anhydrous sodium sulfate, and then concentrated under reduced pressure. The residue was purified by silica gel column chromatography (eluting solvent: methanol-dichloromethane) to obtain the title compound (89.2 mg).

Further, the structural formula and spectrum data of the title compound are shown in Table 12.

Examples 5-2 to 5-14

In the same method as in Example 5-1 using the corresponding starting material, the compounds shown in Tables 12 to 15 were synthesized.

Example 6

5-[6-(6-Methoxy-2-phenyl-1H-indol-3-ylmethyl)pyridin-2-yl]-2,3-dihydro-1,3,4-oxadiazol-2-one

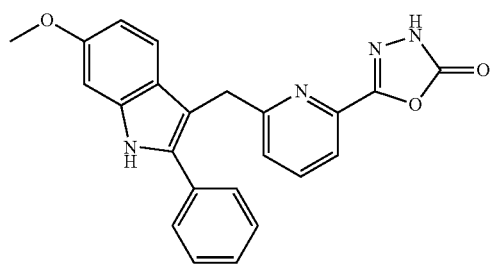 [SMILES: COc1ccc2c(Cc3cccc(-c4n[nH]c(=O)o4)n3)c(-c3ccccc3)[nH]c2c1]

To a suspension of 6-(6-methoxy-2-phenyl-1H-indol-3-ylmethyl)pyridine-2-carbohydrazide (258 mg) in tetrahydrofuran (3.5 mL) was added 1,1'-carbonyldiimidazole (135 mg), and this mixture was stirred at room temperature for 3 hours. To the reaction mixture was added 1 mol/L hydrochloric acid, followed by extraction with ethyl acetate. The organic layer was washed with water, dried over anhydrous magnesium sulfate, and then concentrated under reduced pressure. The residue was purified by silica gel column chromatography (eluting solvent: ethyl acetate-hexane) to obtain the title compound (270 mg). $^1$H-NMR (DMSO-$d_6$) δ ppm: 3.77 (3H, s), 4.34 (2H, s), 6.63 (1H, dd, J=2.3, 8.5 Hz), 6.87 (1H, d, J=2.3 Hz), 7.27-7.40 (3H, m), 7.42-7.53 (2H, m), 7.68-7.90 (4H, m), 11.20 (1H, s), 12.76 (1H, br s). ESI-MS (m/z): 399 (M+H)$^+$.

Example 7-1

3-[6-(6-Methoxy-2-phenyl-1H-indol-3-ylmethyl)pyridin-2-yl]-4,5-dihydro-1,2,4-oxadiazol-5-one

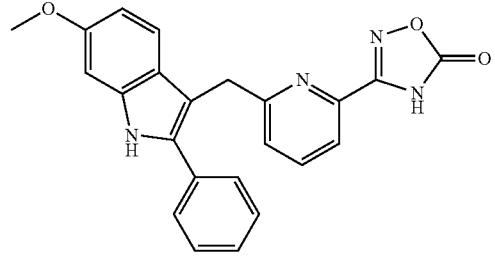 [SMILES: COc1ccc2c(Cc3cccc(-c4noc(=O)[nH]4)n3)c(-c3ccccc3)[nH]c2c1]

Under an argon atmosphere, to a solution of 6-(6-methoxy-2-phenyl-1H-indol-3-ylmethyl)pyridine-2-carboxamidoxime (46.9 mg) in tetrahydrofuran (0.63 mL) were added 1,1'-carbonyldiimidazole (24.5 mg) and 1,8-diazabicyclo[5,4,0]-7-undecene (0.019 mL), and this mixture was stirred at room temperature for 3 hours. 1,1'-Carbonyldiimidazole (16.3 mg) was added thereto, followed by stirring for 80 minutes. Then, 1,8-diazabicyclo[5,4,0]-7-undecene (0.019 mL) was added thereto, followed by stirring for additional 1 hour. To the reaction mixture was added 1 mol/L hydrochloric acid, followed by extraction with ethyl acetate. The organic layer was washed with 1 mol/L hydrochloric acid, a saturated aqueous sodium hydrogen carbonate solution, and saturated brine successively, dried over anhydrous sodium sulfate, and then concentrated under reduced pressure. The residue was purified by silica gel column chromatography (eluting solvent: methanol-dichloromethane) to obtain the title compound (43.2 mg).

Further, the structural formula and spectrum data of the title compound are shown in Table 16.

Example 7-2

In the same method as in Example 7-1 using the corresponding starting material, the compound shown in Table 16 was synthesized.

Example 8

N-Hydroxy-6-(6-methoxy-2-phenyl-1H-indol-3-ylmethyl)pyridine-2-carboxamide

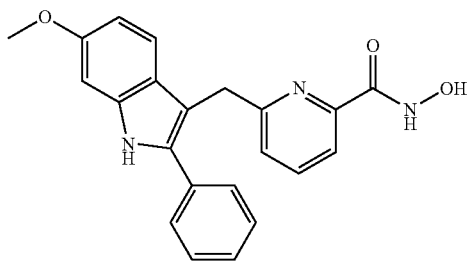 [SMILES: COc1ccc2c(Cc3cccc(C(=O)NO)n3)c(-c3ccccc3)[nH]c2c1]

To a solution of hydroxylammonium chloride (373 mg) in dimethylsulfoxide (2.7 mL) was added sodium hydrogen carbonate (541 mg), and this mixture was stirred at 50° C. for 70 minutes. Then, methyl 6-(6-methoxy-2-phenyl-1H-indol-3-ylmethyl)pyridine-2-carboxylate (200 mg) was added thereto, followed by stirring at 50° C. for 3 days. The reaction mixture was left to be cooled and diluted with water, followed by extraction with ethyl acetate. The organic layer was washed with water and saturated brine, dried over anhydrous sodium sulfate, and then concentrated under reduced pressure. The residue was purified by silica gel column chromatography (eluting solvent: methanol-dichloromethane) to obtain the title compound (186 mg). $^1$H-NMR (DMSO-$d_6$) δ ppm: 3.77 (3H, s), 4.38 (2H, s), 6.63 (1H, dd, J=2.3, 8.5 Hz), 6.87 (1H, d, J=2.3 Hz), 7.15 (1H, dd, J=1.5, 7.3 Hz), 7.29-7.39 (2H, m), 7.42-7.53 (2H, m), 7.59-7.70 (2H, m), 7.70-7.81 (2H, m), 9.13 (1H, s), 11.10 (1H, s), 11.18 (1H, s). ESI-MS (m/z): 374 (M+H)$^+$

Example 9

3-[6-(6-Methoxy-2-phenyl-1H-indol-3-ylmethyl)pyridin-2-yl]-4,5-dihydro-1,2,4-oxadiazole-5-thione

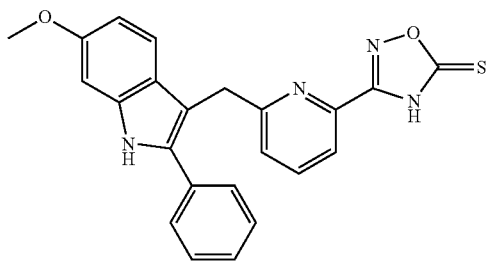 [SMILES: COc1ccc2c(Cc3cccc(-c4noc(=S)[nH]4)n3)c(-c3ccccc3)[nH]c2c1]

Under an argon atmosphere, to a solution of 6-(6-methoxy-2-phenyl-1H-indol-3-ylmethyl)pyridine-2-carboxamidoxime (174 mg) in acetonitrile (3.7 mL) were added 1,1'-thiocarbonyldiimidazole (125 mg) and 1,8-diazabicyclo[5,4,0]-7-undecene (0.278 mL), and this mixture was stirred at room temperature for 22 hours. The reaction mixture was concentrated under reduced pressure. To the residue was added 10% aqueous citric acid solution, followed by extraction with ethyl acetate. The organic layer was washed with a saturated aqueous sodium hydrogen carbonate solution and saturated brine, dried over anhydrous sodium sulfate, and then concentrated under reduced pressure. The residue was purified by silica gel column chromatography (eluting solvent: methanol-ethyl acetate) to obtain the title compound (196 mg). $^1$H-NMR (DMSO-$d_6$) δ ppm: 3.77 (3H, s), 4.33 (2H, s), 6.63 (1H, dd, J=2.3, 8.7 Hz), 6.88 (1H, d, J=2.3 Hz), 7.12 (1H, dd, J=2.3, 6.5 Hz), 7.28-7.39 (2H, m), 7.41-7.52 (2H, m), 7.68-7.79 (4H, m), 11.16 (1H, s). ESI-MS (m/z): 415 (M+H)$^+$

Example 10

N-Cyano-6-(6-methoxy-2-phenyl-1H-indol-3-ylmethyl)pyridine-2-carboxamide

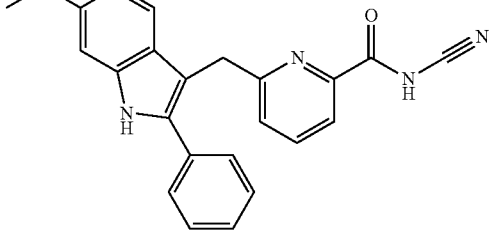

Under an argon atmosphere, to a suspension of 6-(6-methoxy-2-phenyl-1H-indol-3-ylmethyl)pyridine-2-carboxylic acid (100 mg) in dichloromethane (2.8 mL) were added cyanamide (12.9 mg), 4-dimethylaminopyridine (75 mg), and 1-ethyl-3-(3-dimethylaminopropyl)carbodiimide hydrochloride (118 mg) successively, and this mixture was stirred at room temperature for 60 hours. To the reaction mixture was added 1 mol/L hydrochloric acid, followed by extraction with ethyl acetate. The organic layer was washed with 1 mol/L hydrochloric acid, water, and saturated brine successively, dried over anhydrous sodium sulfate, and then concentrated under reduced pressure. The residue was purified by silica gel column chromatography (eluting solvent: methanol-dichloromethane) to obtain the title compound (73.1 mg). $^1$H-NMR (DMSO-$d_6$) δ ppm: 3.78 (3H, s), 4.47 (2H, s), 6.64 (1H, dd, J=2.3, 8.8 Hz), 6.89 (1H, d, J=2.3 Hz), 7.18-7.39 (3H, m), 7.42-7.52 (2H, m), 7.56-7.68 (2H, m), 7.84-7.99 (2H, m), 11.24 (1H, s). ESI-MS (m/z): 383 (M+H)$^+$

Example 11

4-[6-(6-Methoxy-2-phenyl-1H-indol-3-ylmethyl)pyridin-2-yl]-3H-[1,2,3,5]-oxathiadiazole-2-oxide

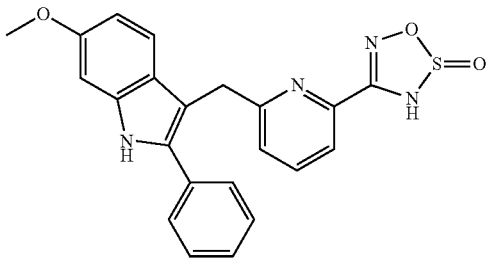 [SMILES: COc1ccc2c(Cc3cccc(C4=NOS(=O)N4)n3)c(-c3ccccc3)[nH]c2c1]

Under an argon atmosphere, a solution of 6-(6-methoxy-2-phenyl-1H-indol-3-ylmethyl)pyridine-2-carboxamidoxime (277 mg) and pyridine (0.121 mL) in tetrahydrofuran (3.1 mL) was ice-cooled. A solution of thionyl chloride (0.055 mL) in methylene chloride (0.62 mL) was added dropwise thereto, and this mixture was stirred at the same temperature for 2 hours. To the reaction mixture was added water, followed by extraction with dichloromethane. The organic layer was dried over anhydrous sodium sulfate and concentrated under reduced pressure. The residue was purified by silica gel column chromatography (eluting solvent: methanol-dichloromethane) to obtain the title compound (60.9 mg). $^1$H-NMR (DMSO-$d_6$) δ ppm: 3.78 (3H, s), 4.44 (2H, s), 6.64 (1H, dd, J=2.3, 8.5 Hz), 6.89 (1H, d, J=2.3 Hz), 7.18 (1H, dd, J=1.8, 7.3 Hz), 7.26-7.38 (2H, m), 7.41-7.54 (2H, m), 7.59-7.66 (2H, m), 7.79-7.90 (2H, m), 11.23 (1H, s), 11.80-12.20 (1H, br). ESI-MS (m/z): 419 (M+H)$^+$

TABLE 1

| Ex. No. | Struc | Physical Data |
| --- | --- | --- |
| 2-1 | | $^1$H-NMR (DMSO-$d_6$) δ ppm: 3.40 (3H, s), 3.77 (3H, s), 4.44 (2H, s), 6.64 (1H, dd, J = 2.3, 8.7 Hz), 6.88 (1H, d, J = 2.3 Hz), 7.24-7.54 (5H, m), 7.60-7.74 (2H, m), 7.83-7.96 (2H, m), 11.22 (1H, s), 11.00-11.90 (1H, br). ESI-MS (m/z): 436 (M + H)$^+$ |
| 2-2 | | $^1$H-NMR (DMSO-$d_6$) δ ppm: 0.60-0.68 (2H, m), 0.88-0.97 (2H, m), 1.93-2.05 (1H, m), 3.41 (3H, s), 4.44 (2H, s), 6.72 (1H, dd, J = 1.5, 8.3 Hz), 7.06-7.12 (1H, m), 7.31-7.40 (3H, m), 7.44-7.54 (2H, m), 7.64-7.73 (2H, m), 7.85-7.92 (2H, m), 11.21 (1H, s), 11.00-11.80 (1H, br). ESI-MS (m/z): 446 (M + H)$^+$ |

TABLE 2

| Ex. No. | Strc | Physical Data |
| --- | --- | --- |
| 3-1 | | $^1$H-NMR (DMSO-$d_6$) δ ppm: 2.39 (3H, s), 3.41 (3H, s), 4.45 (2H, s), 6.77-6.86 (1H, m), 7.18 (1H, s), 7.31-7.41 (3H, m), 7.44-7.53 (2H, m), 7.66-7.75 (2H, m), 7.84-7.94 (2H, m), 11.23 (1H, s), 11.00-11.85 (1H, br). ESI-MS (m/z): 420 (M + H)$^+$ |
| 3-2 | | $^1$H-NMR (DMSO-$d_6$) δ ppm: 1.37 (9H, s), 3.83 (3H, s), 4.44 (2H, s), 6.99 (1H, s), 7.06-7.15 (1H, m), 7.36 (1H, s), 7.61-7.86 (5H, m), 8.03-8.11 (2H, m), 10.68 (1H, s), 11.75-12.55 (1H, br). ESI-MS (m/z): 512. 514 (M + H)$^+$ |

TABLE 3

| Ex. No. | Strc | Physical Data |
|---|---|---|
| 3-3 | | ¹H-NMR (DMSO-d₆) δ ppm: 3.78 (3H, s), 4.45 (2H, s), 6.65 (1H, dd, J = 2.3, 8.8 Hz), 6.88 (1H, d, J = 2.3 Hz), 7.23-7.42 (3H, m), 7.42-7.53 (2H, m), 7.59-7.88 (7H, m), 8.00-8.10 (2H, m), 11.22 (1H, s), 11.50-12.70 (1H, br). ESI-MS (m/z): 498 (M + H)⁺ |
| 3-4 | | ¹H-NMR (DMSO-d₆) δ ppm: 1.00 (3H, t, J = 7.4 Hz), 1.69-1.83 (2H, m), 3.47-3.57 (2H, m), 3.77 (3H, s), 4.44 (2H, s), 6.64 (1H, dd, J = 2.3, 8.8 Hz), 6.88 (1H, d, J = 2.3 Hz), 7.29-7.53 (5H, m), 7.63-7.73 (2H, m), 7.83-7.93 (2H, m), 11.20 (1H, s), 11.15-11.61 (1H, br). ESI-MS (m/z): 464 (M + H)⁺ |
| 3-5 | | ¹H-NMR (DMSO-d₆) δ ppm: 1.00 (3H, t, J = 7.4 Hz), 1.37 (9H, s), 1.69-1.83 (2H, m), 3.47-3.58 (2H, m), 3.82 (3H, s), 4.43 (2H, s), 6.98 (1H, s), 7.14-7.22 (1H, m), 7.35 (1H, s), 7.82-7.91 (2H, m), 10.65 (1H, s), 11.15-11.69 (1H, br). ESI-MS (m/z): 478, 480 (M + H)⁺ |
| 3-6 | | ¹H-NMR (DMSO-d₆) δ ppm: 1.28 (3H, t, J = 7.4 Hz), 3.54 (2H, q, J = 7.4 Hz), 3.77 (3H, s), 4.44 (2H, s), 6.64 (1H, d, J = 2.3, 8.5 Hz), 6.88 (1H, d, J = 2.3 Hz), 7.29-7.53 (5H, m), 7.63-7.74 (2H, m), 7.82-7.93 (2H, m), 11.20 (1H, s), 11.16-11.58 (1H, br). ESI-MS (m/z): 450 (M + H)⁺ |
| 3-7 | | ¹H-NMR (DMSO-d₆) δ ppm: 1.28 (3H, t, J = 7.4 Hz), 1.37 (9H, s), 3.54 (q, 2H, J = 7.4 Hz), 3.82 (3H, s), 4.43 (2H, s), 6.98 (1H, s), 7.12-7.22 (1H, m), 7.36 (1H, s), 7.82-7.91 (2H, m), 10.65 (1H s), 11.10-11.70 (1H, br). ESI-MS (m/z): 464, 466 (M + H)⁺ |

TABLE 4

| Ex. No. | Strc | Physical Data |
|---|---|---|
| 3-8 | | $^1$H-NMR (DMSO-d$_6$) δ ppm: 1.08-1.27 (4H, m), 1.37 (9H, s), 3.08-3.17 (1H, m), 3.82 (3H, s), 4.43 (2H, s), 6.99 (1H, s), 7.12-7.20 (1H, m), 7.35 (1H, s), 7.83-7.91 (2H, m), 10.66 (1H, s), 11.20-11.75 (1H, br). ESI-MS (m/z): 476, 478 (M + H)$^+$ |
| 3-9 | | $^1$H-NMR (DMSO-d$_6$) δ ppm: 3.40 (3H, s), 3.86 (3H, s), 4.41 (2H, s), 7.02 (1H, d, J = 7.5 Hz), 7.24-7.55 (5H, m), 7.60-7.75 (2H m), 7.82-7.96 (2H, m), 11.31 (1H, s), 11.06-11.74 (1H, br). ESI-MS (m/z): 454 (M + H)$^+$ |
| 3-10 | | $^1$H-NMR (DMSO-d$_6$) δ ppm: 1.06-1.27 (4H, m), 3.06-3.17 (1H, m), 3.77 (3H, s), 4.44 (2H, s), 6.65 (1H, dd, J = 2.3, 8.5 Hz), 6.88 (1H, d, J = 2.3 Hz), 7.30-7.41 (3H, m), 7.43-7.52 (2H, m), 7.64-7.72 (2H, m), 7.84-7.93 (2H, m), 11.20 (1H, s), 11.24-11.64 (1H, br). ESI-MS (m/z): 462 (M + H)$^+$ |
| 3-11 | | $^1$H-NMR (DMSO-d$_6$) δ ppm: 1.37 (9H, s), 3.73 (3H, s), 4.44 (2H, s), 6.56 (1H, dd, J = 2.3, 8.7 Hz), 6.84 (1H, d, J = 2.3 Hz), 7.09-7.20 (2H, m), 7.61-7.85 (5H, m), 8.02-8.09 (2H, m), 10.46 (1H, s), 11.60-12.60 (1H, br). ESI-MS (m/z): 478 (M + H)$^+$ |
| 3-12 | | $^1$H-NMR (DMSO-d$_6$) δ ppm: 2.39 (3H, s), 3.40 (3H, s), 4.49 (2H, s), 6.78-6.86 (1H, m), 7.16 (1H, s), 7.28-7.35 (1H, m), 7.42 (1H, d, J = 8.3 Hz), 7.58 (1H, dd, J = 1.4, 5.1 Hz), 7.67 (1H, dd, J = 3.0, 5.1 Hz), 7.82-7.92 (3H, m), 11.18 (1H, s), 11.30-11.74 (1H, br). ESI-MS (m/z): 426 (M + H)$^+$ |

TABLE 5

| Ex. No. | Strc | Physical Data |
|---|---|---|
| 3-13 | 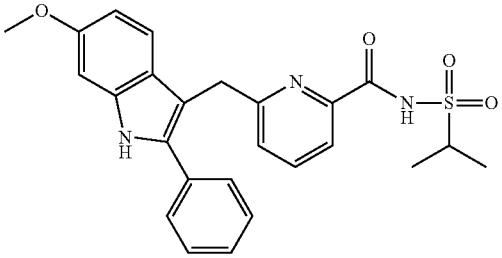 [SMILES: COc1ccc2c(Cc3cccc(C(=O)NS(=O)(=O)C(C)C)n3)c(-c3ccccc3)[nH]c2c1] | $^1$H-NMR (DMSO-d$_6$) δ ppm:<br>1.34 (6H, d, J = 7.0 Hz), 3.71-3.86 (4H, m), 4.45 (2H, s), 6.64 (1H, d, J = 2.3, 8.8 Hz), 6.87 (1H, d, J = 2.3 Hz), 7.30-7.52 (5H, m), 7.65-7.73 (2H, m), 7.82-7.94 (2H, m), 11.21 (1H, s), 11.10-11.60 (1H, br).<br>ESI-MS (m/z): 464 (M + H)$^+$ |
| 3-14 | 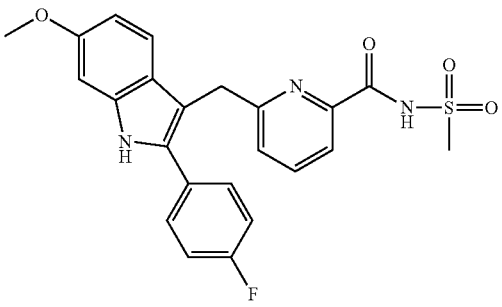 [SMILES: COc1ccc2c(Cc3cccc(C(=O)NS(C)(=O)=O)n3)c(-c3ccc(F)cc3)[nH]c2c1] | $^1$H-NMR (DMSO-d$_6$) δ ppm:<br>3.41 (3H, s), 3.77 (3H, s), 4.41 (2H, s), 6.65 (1H, dd, J = 2.3, 8.8 Hz), 6.87 (1H, d, J = 2.3 Hz), 7.25-7.50 (4H, m), 7.70-7.80 (2H, m), 7.85-7.95 (2H, m), 11.23 (1H, s), 11.30-11.70 (1H, br).<br>ESI-MS (m/z): 454 (M + H)$^+$ |
| 3-15 | 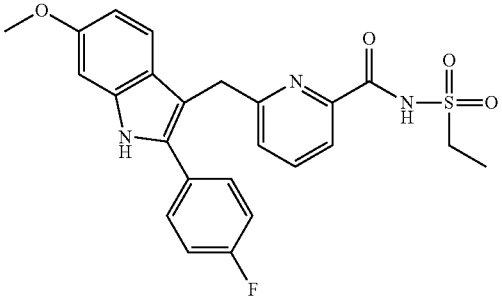 [SMILES: CCS(=O)(=O)NC(=O)c1cccc(Cc2c(-c3ccc(F)cc3)[nH]c3cc(OC)ccc23)n1] | $^1$H-NMR (DMSO-d$_6$) δ ppm:<br>1.28 (3H, t, J = 7.4 Hz), 3.54 (2H, q, J = 7.4 Hz), 3.77 (3H, s), 4.41 (2H, s), 6.65 (1H, dd, J = 2.2, 8.8 Hz), 6.86 (1H, d, J = 2.2 Hz), 7.25-7.50 (4H, m), 7.70-7.95 (4H, m), 11.23 (1H, s), 11.30-11.70 (1H, br).<br>ESI-MS (m/z): 468 (M + H)$^+$ |
| 3-16 | 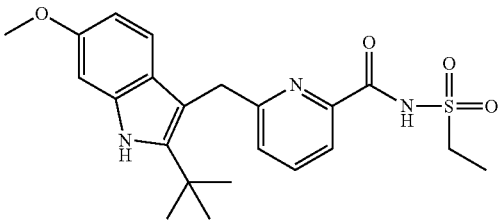 [SMILES: CCS(=O)(=O)NC(=O)c1cccc(Cc2c(C(C)(C)C)[nH]c3cc(OC)ccc23)n1] | $^1$H-NMR (DMSO-d$_6$) δ ppm:<br>1.28 (3H, t, J = 7.3 Hz), 1.37 (9H, s), 3.53 (2H, q, J = 7.3 Hz), 3.73 (3H, s), 4.43 (2H, s), 6.55 (1H, dd, J = 2.2, 8.5 Hz), 6.83 (1H, d, J = 2.2 Hz), 7.12-7.23 (2H, m), 7.80-7.88 (2H, m), 10.47 (1H, s), 11.20-11.65 (1H, br).<br>ESI-MS (m/z): 430 (M + H)$^+$ |
| 3-17 | 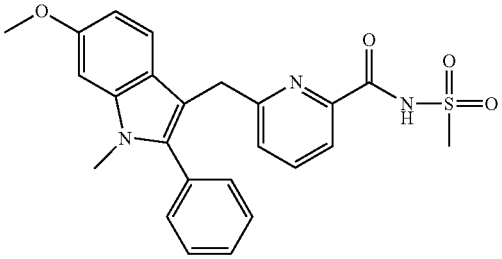 [SMILES: COc1ccc2c(Cc3cccc(C(=O)NS(C)(=O)=O)n3)c(-c3ccccc3)n(C)c2c1] | $^1$H-NMR (DMSO-d$_6$) δ ppm:<br>3.39 (3H, s), 3.57 (3H, s), 3.81 (3H, s), 4.20 (2H, s), 6.67 (1H, d, J = 2.2, 8.5 Hz), 7.03 (1H, d, J = 2.2 Hz), 7.26-7.41 (2H, m), 7.42-7.59 (5H, m), 7.82-7.90 (2H, m), 11.00-11.56 (1H, br).<br>ESI-MS (m/z): 450 (M + H)$^+$ |

TABLE 6

| Ex. No. | Strc | Physical Data |
|---|---|---|
| 3-18 | | $^1$H-NMR (DMSO-d$_6$) δ ppm:<br>1.27 (3H, t, J = 7.3 Hz), 3.46-3.62 (5H, m), 3.81 (3H, s), 4.21 (2H, s), 6.67 (1H, dd, J = 2.2, 8.8 Hz), 7.02 (1H, d, J = 2.2 Hz), 7.25-7.35 (1H, m), 7.40 (1H, d, J = 8.8 Hz), 7.43-7.58 (5H, m), 7.79-7.90 (2H, m), 11.00-11.56 (1H, br).<br>ESI-MS (m/z): 464 (M + H)$^+$ |
| 3-19 | | $^1$H-NMR (DMSO-d$_6$) δ ppm:<br>3.32 (3H, s), 3.77 (3H, s), 4.26 (2H, s), 6.61 (1H, d, J = 2.3, 8.6 Hz), 6.88 (1H, d, J = 2.3 Hz), 7.19 (1H, d, J = 8.6 Hz), 7.29-7.60 (7H, m), 7.70-7.79 (2H, m), 11.20 (1H, s), 12.11 (1H, br s).<br>ESI-MS (m/z): 435 (M + H)$^+$ |
| 3-20 | | $^1$H-NMR (DMSO-d$_6$) δ ppm;<br>3.27 (3H, br s), 3.77 (3H, s), 4.42 (2H, s), 6.57-6.70 (1H, m), 6.83 (1H, d, J = 2.0 Hz), 7.17-7.48 (3H, s), 7.61 (1H, br s), 7.75-7.95 (2H, m), 11.09 (1H, s), 11.15-11.95 (1H, br).<br>ESI-MS (m/z): 456 (M + H)$^+$ |
| 3-21 | | $^1$H-NMR (DMSO-d$_6$) δ ppm:<br>1.28 (3H, t, J = 7.4 Hz), 3.54 (2H, q, J = 7.4 Hz), 3.77 (3H, s), 4.46 (2H, s), 6.64 (1H, dd, J = 2.3, 8.6 Hz), 6.83 (1H, d, J = 2.3 Hz), 7.27-7.38 (2H, m), 7.45 (1H, d, J = 8.6 Hz), 7.55-7.59 (1H, m), 7.83-7.90 (2H, m), 11.10 (1H, s), 11.30-11.80 (1H, br).<br>ESI-MS (m/z): 470 (M + H)$^+$ |
| 3-22 | | $^1$H-NMR (DMSO-d$_6$) δ ppm:<br>3.41 (3H, s), 3.77 (3H, s), 4.42 (2H, s), 6.65 (1H, dd, J = 2.1, 8.6 Hz), 6.84 (1H, d, J = 2.1 Hz), 6.95-7.05 (1H, m), 7.25-7.35 (1H, m), 7.44 (1H, d, J = 8.6 Hz), 7.70-7.90 (3H, m), 8.10-8.20 (1H, m), 11.10 (1H, s), 11.40-11.80 (1H, br).<br>ESI-MS (m/z): 426 (M + H)$^+$ |

TABLE 7

| Ex. No. | Strc | Physical Data |
| --- | --- | --- |
| 3-23 | | $^1$H-NMR (DMSO-$d_6$) δ ppm:<br>1.28 (3H, t, J = 7.4 Hz), 3.54 (2H, q, J = 7.4 Hz), 3.77 (3H, s), 4.43 (2H, s), 6.65 (1H, dd, J = 2.1 (8.6 Hz), 6.84 (1H, d, J = 2.1 Hz), 6.95-7.05 (1H, m), 7.25-7.40 (1H, m), 7.47 (1H, d, J = 8.6 Hz), 7.70-7.90 (3H, m), 8.15-8.25 (1H, m), 11.09 (1H, s), 11.40-11.80 (1H, br).<br>ESI-MS (m/z): 440 (M + H)$^+$ |
| 3-24 | | $^1$H-NMR (DMSO-$d_6$) δ ppm:<br>1.27 (3H, t, J = 7.4 Hz), 3.52 (2H, q, J = 7.4 Hz), 4.47 (2H, s), 7.00 (1H, dd, J = 1.9, 8.4 Hz), 7.32-7.45 (3H, m), 7.47-7.58 (3H, m), 7.70-7.77 (2H, m), 7.83-7.94 (2H, m), 11.25-11 55 (1H, br), 11.59 (1H, s).<br>ESI-MS (m/z): 454. 456 (M + H)$^+$ |
| 3-25 | | $^1$H-NMR (DMSO-$d_6$) δ ppm:<br>3.40 (3H, s), 4.46 (2H, s), 7.00 (1H, dd, J = 1.8, 8.5 Hz), 7.32-7.45 (3H, m), 7.47-7.56 (3H, m), 7.68-7.75 (2H, m), 7.86-7.94 (2H, m), 11.00-11.80 (1H, br), 11.59 (1H, s).<br>ESI-MS (m/z): 440, 442 (M + H)$^+$ |
| 3-26 | | $^1$H-NMR (DMSO-$d_6$) δ ppm:<br>1.26 (3H, t, J = 7.4 Hz), 3.53 (2H, q, J = 7.4 Hz), 4.52 (2H, s), 7.25-7.32 (1H, m), 7.35-7.60 (4H, m), 7.66-7.81 (4H, m), 7.84-7.94 (2H, m), 11.00-11.75 (1H, br), 11.90 (1H, s).<br>ESI-MS (m/z): 488 (M + H)$^+$ |
| 3-27 | | $^1$H-NMR (DMSO-$d_6$) δ ppm:<br>3.40 (3H, s), 4.51 (2H, s), 7.25-7.32 (1H, m), 7.34-7.59 (4H, m), 7.64-7.80 (4H, m), 7.86-7.94 (2H, m), 11.00-11.80 (1H, br), 11.91 (1H, s).<br>ESI-MS (m/z): 474 (M + H)$^+$ |

TABLE 8

| Ex. No. | Strc | Physical Data |
|---|---|---|
| 3-28 | | $^1$H-NMR (DMSO-d$_6$) δ ppm: 3.40 (3H, s), 3.78 (3H, s), 4.45 (2H, s), 6.67 (1H, dd, J = 2.2, 8.8 Hz), 6.89 (1H, d, J = 2.2 Hz), 7.30-7.40 (1H, m), 7.42 (1H, d, J = 8.8 Hz), 7.45-7.55 (1H, m), 7.80-7.95 (2H, m), 8.10-8.20 (1H, m), 8.53 (1H, dd, J = 1.5, 4.8 Hz), 8.80-8.85 (1H, m), 11.38 (1H, s). ESI-MS (m/z): 437 (M + H)$^+$ |
| 3-29 | | $^1$H-NMR (DMSO-d$_6$) δ ppm: 1.28 (3H, t, J = 7.4 Hz), 3.54 (2H, q, J = 7.4 Hz), 3.78 (3H, s), 4.46 (2H, s), 6.67 (1H, dd, J = 2.2, 8.8 Hz), 6.89 (1H, d, J = 2.2 Hz), 7.38 (1H, dd, J = 1.8, 7.0 Hz), 7.40-7.55 (2H, m), 7.80-7.95 (2H, m), 8.10-8.20 (1H, m), 8.53 (1H, dd, J = 1.5, 4.8 Hz), 8.80-8.90 (1H, m), 11.38 (1H, s). ESI-MS (m/z): 451 (M + H)$^+$ |
| 3-30 | | $^1$H-NMR (DMSO-d$_6$) δ ppm: 2.24 (3H, s), 2.30 (3H, s), 3.41 (3H, s), 4.43 (2H, s), 7.17 (1H, s), 7.25 (1H, s), 7.30-7.55 (4H, m), 7.60-7.70 (2H, m), 7.85-7.95 (2H, m), 11.13 (1H, s), 11.20-11.80 (1H, br). ESI-MS (m/z): 434 (M + H)$^+$ |
| 3-31 | | $^1$H-NMR (DMSO-d$_6$) δ ppm: 1.28 (3H, t, J = 7.3 Hz), 2.24 (3H, s), 2.30 (3H, s) (3.55 (2H, q, J = 7.3 Hz), 4.44 (2H, s), 7.17 (1H, s), 7.27 (1H, s), 7.30-7.55 (4H, m), 7.60-7.75 (2H, m), 7.80-7.95 (2H, m), 11.12 (1H, s), 11.20-11.70 (1H, br). ESI-MS (m/z) : 448 (M + H)$^+$ |
| 3-32 | | $^1$H-NMR (DMSO-d$_6$) δ ppm: 1.28 (3H, t, J = 7.3 Hz), 3.54 (2H, q, J = 7.3 Hz), 3.85 (3H, s), 4.42 (2H, s), 7.02 (1H, d, J = 7.5 Hz), 7.32-7.42 (3H, m), 7.44-7.53 (2H, m), 7.66-7.74 (2H, m), 7.84-7.93 (2H, m), 11.20-11.68 (1H, br) 11.33 (1H, s). ESI-MS (m/z): 468 (M + H)$^+$ |

TABLE 9

| Ex. No. | Strc | Physical Data |
|---|---|---|
| 3-33 | | ¹H-NMR (DMSO-d₆) δ ppm:<br>0.60-0.69 (2H, m), 0.88-0.98 (2H, m), 1.28 (3H, t, J = 7.4 Hz), 1.94-2.04 (1H, m), 3.54 (2H, q, J = 7.4 Hz), 4.44 (2H, s), 6.72 (1H, dd, J = 1.5, 8.3 Hz), 7.09 (1H, s), 7.31-7.41 (3H, m), 7.44-7.53 (2H, m), 7.65-7.74 (2H, m), 7.83-7.93 (2H, m), 11.10-11.70 (1H, br), 11.21 (1H, s).<br>ESI-MS (m/z): 460 (M + H)⁺ |
| 3-34 | | ¹H-NMR (DMSO-d₆) δ ppm:<br>1 28 (3H, t, J = 7.3 Hz), 2.39 (3H, s), 3.55 (2H, q, J = 7.3 Hz), 4.45 (2H, s), 6.77-6.84 (1H, m), 7.18 (1H, s), 7.31-7.41 (3H, m), 7.44-7.53 (2H, m), 7.65-7.75 (2H, m), 7.82-7.93 (2H, m), 11.16-11.70 (1H, br), 11.24 (1H, s).<br>ESI-MS (m/z): 434 (M + H)⁺ |
| 3-35 | | ¹H-NMR (DMSO-d₆) δ ppm:<br>1.29 (3H, t, J = 7.4 Hz), 3.54 (2H, q, J = 7.4 Hz), 3.78 (3H, s), 4.48 (2H, s), 6.66 (1H, dd, J = 2.3, 8.5 Hz), 6.85 (1H, d, J = 2.3 Hz), 7.31-7.38 (1H, m), 7.46 (1H, d, J = 8.5 Hz), 7.57 (1H, dd, J = 1.3, 5.0 Hz), 7.66 (1H, dd, J = 2.8, 5.0 Hz), 7.82-7.92 (3H, m), 11.18 (1H, s), 11.33-11.73 (1H, br).<br>ESI-MS (m/z): 456 (M + H)⁺ |
| 3-36 | | ¹H-NMR (DMSO-d₆) δ ppm:<br>1.27 (3H, t, J = 7.4 Hz), 2.43 (3H, s), 3.53 (2H, q, J = 7.4 Hz), 3.57 (3H, s), 4.22 (2H, s), 6.81-6.90 (1H, m), 7.24-7.33 (2H, m), 7.40 (1H, d, J = 8.0 Hz), 7.43-7.59 (5H, m), 7.78-7.90 (2H, m), 10.80-11.75 (1H, br).<br>ESI-MS (m/z): 448 (M + H)⁺ |
| 3-37 | | ¹H-NMR (DMSO-d₆) δ ppm:<br>1.22 (3H, t, J = 7.4 Hz), 3.45 (2H, q, J = 7.4 Hz), 3.78 (3H, s), 4 22 (2H, s), 6.26 (1H, d, J = 3.5 Hz), 6.66 (1H, dd, J = 2.3, 8.5 Hz), 6.87 (1H, d, J = 2.3 Hz), 7.32-7.41 (2H, m), 7 45-7.55 (3H, m), 7.58-7.66 (2H, m), 11.22 (1H s), 11.89 (1H, s).<br>ESI-MS (m/z) : 439 (M + H)⁺ |

TABLE 10

| Ex. No. | Strc | Physical Data |
| --- | --- | --- |
| 3-38 | | ¹H-NMR (DMSO-d₆) δ ppm:<br>3.32 (3H, s), 3.78 (3H, s), 4.22 (2H, s), 6.26 (1H, d, J = 3.5 Hz), 6.66 (1H, dd, J = 2.3, 8.8 Hz), 6.87 (1H, d, J = 2.3 Hz), 7.31-7.42 (2H, m), 7.44-7.55 (3H, m), 7.57-7.66 (2H, m), 11.23 (1H, s), 12.00 (1H, br s).<br>ESI-MS (m/z): 425 (M + H)⁺ |
| 3-39 | | ¹H-NMR (DMSO-d₆) δ ppm:<br>0.85 (6H, d, J = 6.5 Hz), 1.28 (3H, t, J = 7.3 Hz), 1.88-2.03 (1H, m), 2.62 (1H, d, J = 7.3 Hz), 3.54 (2H, q, J = 7.3 Hz), 3.72 (3H, s), 4.22 (2H, s), 6.55 (1H, dd, J = 2.3, 8.7 Hz), 6.77 (1H, d, J = 2.3 Hz), 7.27 (1H, d, J = 8.7 Hz), 7.35 (1H, dd, J = 2.1, 6.7 Hz), 7.81-7.91 (2H, m), 10.64 (1H, s), 11.05-11.75 (1H, br).<br>ESI-MS (m/z): 430 (M + H)⁺ |
| 3-40 | | ¹H-NMR (DMSO-d₆) δ ppm:<br>1.28 (3H, t, J = 7.4 Hz), 1.56-2.00 (8H, m), 3.54 (2H, q, J = 7.4 Hz), 3.72 (3H, s), 4.23 (2H, s), 6.55 (1H, dd, J = 2.3, 8.5 Hz), 6.76 (1H, d, J = 2.3 Hz), 7.35 (1H, d, J = 8.5 Hz), 7.37-7.42 (1H, m), 7.81-7.92 (2H, m), 10.60 (1H, s), 11.10-11.70 (1H, br).<br>ESI-MS (m/z): 442 (M + H)⁺ |
| 3-41 | | ¹H-NMR (DMSO-d₆) δ ppm:<br>1.26 (3H, t, J = 7.4 Hz), 3.49 (2H, q, J = 7.4 Hz), 3.79 (3H, s), 4.55 (2H, s), 6.69 (1H, dd, J = 2.3, 8.7 Hz), 6.90 (1H, d, J = 2.3 Hz), 7.33-7.42 (2H, m), 7.44-7.54 (2H, m), 7.56-7.66 (2H, m), 8.40 (1H, s), 11.37 (1H, s), 11.64-11.96 (1H, br).<br>ESI-MS (m/z): 456 (M + H)⁺ |

TABLE 11

| Ex. No. | Strc | Physical Data |
| --- | --- | --- |
| 3-42 | | ¹H-NMR (DMSO-d₆) δ ppm:<br>3.26 (3H, s), 3.78 (3H, s), 4.20 (2H, s), 6.62 (1H, dd, J = 2.3, 8.6 Hz), 6.89 (1H, d, J = 2.3 Hz), 6.98-7.12 (2H, m), 7.18 (1H, d, J = 8.6 Hz), 7.30-7.38 (1H, m), 7.40-7.56 (5H, m), 11.24 (1H, s), 12.29 (1H, s).<br>ESI-MS (m/z): 451 (M − H)⁻ |

TABLE 11-continued

| Ex. No. | Strc | Physical Data |
|---|---|---|
| 3-43 | | $^1$H-NMR (DMSO-d$_6$) δ ppm:<br>1.28 (3H, t, J = 7.4 Hz), 3.50 (2H, q, J = 7.4 Hz), 3.78 (3H, s), 4.22 (2H, s), 6.63 (1H, dd, J = 2.3, 8.8 Hz), 6.89 (1H, d, J = 2.3 Hz), 7.05-7.16 (2H, m), 7.18 (1H, d, J = 8.8 Hz), 7.30-7.38 (1H, m), 7.39-7.58 (5H, m), 11.25 (1H, s), 12.21 (1H, s).<br>ESI-MS (m/z): 465 (M − H)$^-$ |

TABLE 12

| Ex. No. | Strc | Physical Data |
|---|---|---|
| 5-1 | | $^1$H-NMR (DMSO-d$_6$) δ ppm:<br>0.60-0.69 (2H, m), 0.88-0.97 (2H, m), 1.94-2.05 (1H, m), 4.46 (2H, s), 6.66-6.75 (1H, m), 7.06-7.18 (2H, m), 7.29 (1H, d, J = 8.0 Hz), 7.31-7.39 (1H, m), 7.42-7.52 (2H, m), 7.60-7.69 (2H, m), 7.86 (1H, t, J = 7.8 Hz), 7.98-8.06 (1H, m), 11.24 (1H, s).<br>ESI-MS (m/z): 393 (M + H)$^+$ |
| 5-2 | | $^1$H-NMR (DMSO-d$_6$) δ ppm:<br>3.78 (3H, s), 4.47 (2H, s), 6.63 (1H, dd, J = 2.3, 8.7 Hz), 6.89 (1H, d, J = 2.3 Hz), 7.12-7.19 (1H, m), 7.26-7.39 (2H, m), 7.42-7.52 (2H, m), 7.58-7.68 (2H, m), 7.88 (1H, t, J = 7.8 Hz), 7.99-8.07 (1H, m), 11.25 (1H, s).<br>ESI-MS (m/z): 383 (M + H)$^+$ |

TABLE 13

| Ex. No. | Strc | Physical Data |
|---|---|---|
| 5-3 | | $^1$H-NMR (DMSO-d$_6$) δ ppm:<br>2.39 (3H, s), 4.48 (2H, s), 6.76-6.84 (1H, m), 7.11-7.22 (2H, m), 7.26-7.40 (2H, m), 7.42-7.53 (2H, m), 7.61-7.70 (2H, m), 7.87 (1H, t, J = 7.8 Hz), 7.99-8.07 (1H, m), 11.26 (1H, s).<br>ESI-MS (m/z): 367 (M+H)$^+$ |
| 5-4 | | $^1$H-NMR (DMSO-d$_6$) δ ppm :<br>3.78 (3H, s), 4.45 (2H, s), 6.65 (1H, dd, J = 2.3, 8.8 Hz), 6.86 (1H, d, J = 2.3 Hz), 7.11-7.18 (1H, m), 7.42 (1H, d, J = 8.8 Hz), 7.53 (1H, dd, J = 1.3, 5.0 Hz), 7.66 (1H, dd, J = 3.0, 5.1 Hz), 7.81 (1H, t, J = 7.8 Hz), 7.90-8.00 (2H, m), 11.18 (1H, s).<br>ESI-MS (m/z): 389 (M + H)$^+$ |

TABLE 13-continued

| Ex. No. | Strc | Physical Data |
|---|---|---|
| 5-5 | | $^1$H-NMR (DMSO-$d_6$) δ ppm: 1.35 (9H, s), 3.83 (3H, s), 4.45 (2H, s), 6.92-7.02 (2H, m), 7.38 (1H, s), 7.86 (1H, t, J = 7.8 Hz), 7.97-8.04 (1H, m), 10.71 (1H, s). ESI-MS (m/z): 397, 399 (M + H)$^+$ |
| 5-6 | | $^1$H-NMR (DMSO-$d_6$) δ ppm : 3.77 (3H, s), 4.30 (2H, s), 6.61 (1H, dd, J = 2.3, 8.5 Hz), 6.89 (1H, d, J = 2.3 Hz), 7.22 (1H, d, J = 8.5 Hz), 7.29-7.38 (2H, m), 7.42-7.51 (3H, m), 7.53-7.62 (2H, m), 7.78-7.85 (1H, m), 7.86-7.92 (1H, m), 11.21 (1H, s). ESI-MS (m/z): 382 (M+H)$^+$ |
| 5-7 | | $^1$H-NMR (DMSO-$d_6$) δ ppm: 1.36 (9H s), 3.74 (3H, s), 4.46 (2H, s), 6.56 (1H, dd, J = 2.3, 8.7 Hz), 6.85 (1H, d, J = 2.3 Hz), 6.94-7.02 (1H, m), 7.17 (1H, d, J = 8.7 Hz), 7.79-7.88 (1H, m), 7.96-8.03 (1H, m), 10.49 (1H, s). ESI-MS (m/z): 363 (M + H)$^+$ |

TABLE 14

| Ex. No. | Strc | Physical Data |
|---|---|---|
| 5-8 | | $^1$H-NMR (DMSO-$d_6$) δ ppm: 3.86 C3H, s), 4.44 (2H, s), 7.04 (1H, d, J = 7.3 Hz), 7.11-7.20 (1H, m), 7.23-7.39 (2H, m), 7.40-7.52 (2H, m), 7.55-7.70 (2H, m), 7.89 (1H, t, J = 7.8 Hz), 7.98-8.08 (1H, m), 11.37 (1H, s). ESI-MS (m/z): 401 (M + H)$^+$ |
| 5-9 | | $^1$H-NMR (DMSO-$d_6$) δ ppm: 3.77 (3H, s), 4.43 (2H, s), 6.63 (1H, dd, J = 2.2, 8.7 Hz), 6.88 (1H, d, J = 2.2 Hz), 7.18 (1H, d, J = 7.7 Hz), 7.25-7.40 (3H, m), 7.60-7.75 (2H, m), 7.88 (1H, t, J = 7.7 Hz), 8.00-8.10 (1H, m), 11.25 (1H, s), ESI-MS (m/z): 401 (M + H)$^+$ |

TABLE 14-continued

| Ex. No. | Strc | Physical Data |
|---|---|---|
| 5-10 | | ¹H-NMR (DMSO-d₆) δ ppm : 3.78 (3H, s), 4.47 (2H, s), 6.66 (1H, dd, J = 2.2, 8.7 Hz), 6.90 (1H, d, J = 2.2 Hz), 7.15-7.25 (1H, m), 7.37 (1H, d, J = 8.7 Hz), 7.45-7.55 (1H, m), 7.89 (1H, t, J = 7.9 Hz), 7.95-8.15 (2H, m), 8.52 (1H, dd, J = 1.5, 4.7 Hz), 8.80-8.90 (1H, m), 11.40 (1H, s). ESI-MS (m/z): 384 (M + H)⁺ |
| 5-11 | | ¹H-NMR (DMSO-d₆) δ ppm: 3.77 (3H, s), 4.42 (2H, s), 6.65 (1H, dd, J = 2.2, 8.6 Hz), 6.85 (1H, d, J = 2.2 Hz), 6.90-7.00 (1H, m), 7.10-7.25 (1H, m), 7.43 (1H, d, J = 8.6 Hz), 7.75-7.80 (1H, m), 7.86 (1H, t, J = 7.9 Hz), 7.95-8.05 (1H, m), 8.15-8.20 (1H, m), 11.10 (1H, s). ESI-MS (m/z): 373 (M + H)⁺ |
| 5-12 | | ¹H-NMR (DMSO-d₆) δ ppm: 2.46 (3H, d, J = 0.7 Hz), 3.77 (3H, s), 4.47 (2H, s), 6.64 (1H, dd, J = 2.3, 8.8 Hz), 6.84 (1H, d, J = 2.3 Hz), 7.18 (1H, d, J = 7.8 Hz), 7.20-7.30 (1H, m), 7.39 (1H, d, J = 8.8 Hz), 7.54 (1H, s), 7.87 (1H, t, J = 7.8 Hz), 8.02 (1H, d, J = 7.8 Hz), 11.12 (1H, s). ESI-MS (m/z): 403 (M + H)⁺ |

TABLE 15

| Ex. No. | Strc | Physical Data |
|---|---|---|
| 5-13 | | ¹H-NMR (DMSO-d₆) δ ppm: 2.39 (3H, s), 4.46 (2H, s), 6.78-6.86 (1H, m), 7.08-7.19 (2H, m), 7.42 (1H, d. J = 8.0 Hz), 7.55 (1H, dd, J = 1.3, 5.0 Hz), 7.67 (1H, dd, J = 3.0, 5.0 Hz), 7.75-7.84 (1H, m), 7.92-8.02 (2H, m), 11.19 (1H, s). ESI-MS (m/z): 373 (M + H)⁺ |
| 5-14 | | ¹H-NMR (DMSO-d₆) δ ppm: 3.59 (3H, s), 3.81 (3H, s), 4.23 (2H, s), 6.65 (1H, dd, J = 2.1, 8.6 Hz), 7.04 (1H, d, J = 2.1 Hz), 7.08-7.15 (1H, m), 7.31 (1H, d, J = 8.6 Hz), 7.40-7.57 (5H, m), 7.85 (1H, t, J = 7.8 Hz), 7.95-8.02 (1H, m). ESI-MS (m/z): 397 (M + H)⁺ |

TABLE 16

| Ex. No. | Strc | Physical Data |
|---|---|---|
| 7-1 | | ¹H-NMR (DMSO-d₆) δ ppm:<br>3.77 (3H, s), 4.42 (2H, s), 6.63 (1H, dd, J = 2.3, 8.5 Hz), 6.88 (1H, d, J = 2.3 Hz), 7.15-7.22 (1H, m), 7.26-7.39 (2H, m), 7.41-7.52 (2H, m), 7.56-7.68 (2H, m), 7.75-7.81 (1H, m), 7.85 (1H, t, J = 7.8 Hz), 11.24 (1H, s), 13.11 (1H, br s).<br>ESI-MS (m/z): 399 (M + H)⁺ |
| 7-2 | | ¹H-NMR (DMSO-d₆) δ ppm:<br>2.39 (3H, s), 4.43 (2H, s), 6.76-6.84 (1H, m), 7.14-7.22 (2H, m), 7.29 (1H, d, J = 8.0 Hz), 7.31-7.40 (1H, m), 7.43-7.52 (2H, m), 7.60-7.70 (2H, m), 7.74-7.80 (1H, m), 7.83 (1H, t, J = 7.8 Hz), 11.22 (1H, s), 13.07 (1H, br s).<br>ESI-MS (m/z): 383 (M + H)⁺ |

Reference Examples 117-1 to 117-13

In the same method as in Reference Example 118-1 using the corresponding starting materials and reaction agents, the title compounds were synthesized.

Reference Example 117-1

6-(2-Furan-3-yl-6-methoxy-1H-indol-3-ylmethyl)-pyridine-2-carboxamidoxime ¹H-NMR (DMSO-d₆) δ ppm: 3.77 (3H, s), 4.32 (2H, s), 5.80 (2H, br s), 6.64 (1H, dd, J=2.3, 8.5 Hz), 6.83 (1H, d, J=2.3 Hz), 6.95-7.01 (1H, m), 7.10-7.18 (1H, m), 7.42 (1H, d, J=8.5 Hz), 7.59-7.68 (2H, m), 7.75-7.80 (1H, m), 8.10-8.15 (1H, m), 9.85 (1H, s), 11.01 (1H, s). ESI-MS (m/z): 363 (M+H)⁺

Reference Example 117-2

6-(2-tert-Butyl-6-methoxy-1H-indol-3-ylmethyl)-pyridine-2-carboxamidoxime ¹H-NMR (CDCl₃) δ ppm: 1.41 (9H, s), 3.84 (3H, s), 4.43 (2H, s), 5.69 (2H, br s), 6.47 (1H, br s), 6.71 (1H, dd, J=2.3, 8.5 Hz), 6.86 (1H, d, J=2.3 Hz), 6.92-6.99 (1H, m), 7.22 (1H, d, J=8.5 Hz), 7.47 (1H, t, J=7.8 Hz), 7.65-7.71 (1H, m), 7.87 (1H, br s). ESI-MS (m/z): 353 (M+H)⁺

Reference Example 117-3

6-(2-tert-Butyl-5-chloro-6-methoxy-1H-indol-3-ylmethyl)-pyridine-2-carboxamidoxime ¹H-NMR (DMSO-d₆) δ ppm: 1.37 (9H, s), 3.82 (3H, s), 4.32 (2H, s), 5.79 (2H, br s), 6.91-7.02 (2H, m), 7.36 (1H, s), 7.58-7.66 (2H, m), 9.86 (1H, s), 10.60 (1H, s).

Reference Example 117-4

5-(6-Methoxy-2-phenyl-1H-indol-3-ylmethyl)furan-2-carboxamidoxime ¹H-NMR (DMSO-d₆) δ ppm: 3.78 (3H, s), 4.13 (2H, s), 5.57 (2H, br s), 6.04 (1H, d, J=3.3 Hz), 6.60-6.68 (2H, m), 6.86 (1H, d, J=2.3 Hz), 7.32-7.40 (2H, m), 7.45-7.54 (2H, m), 7.58-7.66 (2H, m), 9.51 (1H, s), 11.14 (1H, s). ESI-MS (m/z): 362 (M+H)⁺

Reference Example 117-5

6-(5-Fluoro-6-methoxy-2-phenyl-1H-indol-3-ylmethyl)-pyridine-2-carboxamidoxime ¹H-NMR (DMSO-d₆) δ ppm: 3.85 (3H, s), 4.31 (2H, s), 5.74 (2H, br s), 7.01 (1H, d, J=7.3 Hz), 7.19 (1H, dd, J=2.0, 6.5 Hz), 7.30 (1H, d, J=12.1 Hz), 7.32-7.40 (1H, m), 7.43-7.54 (2H, m), 7.61-7.75 (4H, m), 9.87 (1H, s), 11.25 (1H, s).

Reference Example 117-6

6-(6-Cyclopropyl-2-phenyl-1H-indol-3-ylmethyl)-pyridine-2-carboxamidoxime ¹H-NMR (DMSO-d₆) δ ppm: 0.60-0.68 (2H, m), 0.88-0.98 (2H, m), 1.93-2.04 (1H, m), 4.33 (2H, s), 5.75 (2H, br s), 6.71 (1H, dd, J=1.5, 8.3 Hz), 7.05-7.20 (2H, m), 7.32-7.41 (2H, m), 7.43-7.53 (2H, m), 7.60-7.77 (4H, m), 9.87 (1H, s), 11.13 (1H, s).

Reference Example 117-7

6-(5,6-Dimethyl-2-phenyl-1H-indol-3-ylmethyl)-pyridine-2-carboxamidoxime ¹H-NMR (DMSO-d₆) δ ppm: 2.24 (3H, s), 2.30 (3H, s), 4.33 (2H, s), 5.77 (2H, br s), 7.09-7.19 (2H, m), 7.26 (1H, s), 7.30-7.38 (1H, m), 7.42-7.51 (2H, m), 7.60-7.73 (4H, m), 9.87 (1H, s), 11.04 (1H, s). ESI-MS (m/z): 371 (M+H)⁺

Reference Example 117-8

6-[2-(4-Fluorophenyl)-6-methoxy-1H-indol-3-ylmethyl]-pyridine-2-carboxamidoxime ¹H-NMR (DMSO-d₆) δ ppm: 3.77 (3H, s), 4.31 (2H, s), 5.74 (2H, br s), 6.64 (1H, dd, J=2.3, 8.5 Hz), 6.86 (1H, d, J=2.3 Hz), 7.13-7.23 (1H, m), 7.27-7.41 (3H, m), 7.60-7.81 (4H, m), 9.87 (1H, s), 11.16 (1H, s). ESI-MS (m/z): 391 (M+H)⁺

Reference Example 117-9

6-(6-Methyl-2-thiophen-3-yl-1H-indol-3-ylmethyl)pyridine-2-carboxamidoxime ¹H-NMR (CDCl₃) δ ppm: 2.47

(3H, s), 4.42 (2H, s), 5.64 (2H, br s), 6.40-6.90 (1H, br), 6.91-6.97 (1H, m), 7.08-7.21 (2H, m), 7.33-7.48 (4H, m), 7.51 (1H, t, J=7.8 Hz), 7.67-7.74 (1H, m), 8.02 (1H, br s).

Reference Example 117-10

6-(6-Methoxy-1-methyl-2-phenyl-1H-indol-3-ylmethyl) pyridine-2-carboxamidoxime $^1$H-NMR (CDCl$_3$) δ ppm: 3.59 (3H, s), 3.89 (3H, s), 4.20 (2H, s), 5.59 (2H, br s), 6.20-6.64 (1H, br), 6.77 (1H, dd, J=2.3, 8.5 Hz), 6.80-6.85 (1H, m), 7.01-7.06 (1H, m), 7.34-7.54 (7H, m), 7.63-7.70 (1H, m).

Reference Example 117-11

6-(2-Furan-3-yl-6-methyl-1H-indol-3-ylmethyl)-pyridine-2-carboxamidoxime $^1$H-NMR (CDCl$_3$) δ ppm: 2.46 (3H, s), 4.37 (2H, s), 5.65 (2H, br s), 6.65-6.71 (1H, m), 6.91-6.99 (1H, m), 7.06-7.12 (1H, m), 7.15-7.20 (1H, m), 7.40 (1H, d, J=8.0 Hz), 7.47-7.55 (2H, m), 7.67-7.76 (2H, m), 7.92 (1H, br s). ESI-MS (m/z): 347 (M+H)$^+$

Reference Example 117-12

6-(2-Cyclohexyl-6-methoxy-1H-indol-3-ylmethyl)-pyridine-2-carboxamidoxime $^1$H-NMR (CDCl$_3$) δ ppm: 1.16-1.94 (10H, m), 2.83-2.97 (1H, m), 3.82 (3H, s), 4.23 (2H, s), 5.69 (2H, br s), 6.71 (1H, dd, J=2.3, 8.5 Hz), 6.83 (1H, d, J=2.3 Hz), 7.01-7.07 (1H, m), 7.28 (1H, d, J=8.5 Hz), 7.49 (1H, t, J=7.8 Hz), 7.65-7.72 (1H, m), 7.75 (1H, br s). ESI-MS (m/z): 379 (M+H)$^+$

Reference Example 117-13

6-(6-Cyclopropyl-2-furan-3-yl-1H-indol-3-ylmethyl)-pyridine-2-carboxamidoxime $^1$H-NMR (CDCl$_3$) δ ppm: 0.68-0.76 (2H, m), 0.91-1.01 (2H, m), 1.96-2.06 (1H, m), 4.36 (2H, s), 5.65 (2H, br s), 6.64-6.71 (1H, m), 6.83-6.92 (1H, m), 7.06-7.15 (2H, m), 7.39 (1H, d, J=8.3 Hz), 7.47-7.56 (2H, m), 7.67-7.77 (2H, m), 7.92 (1H, br s). ESI-MS (m/z): 373 (M+H)$^+$

Reference Example 118-1

6-[6-Methoxy-2-(1-methylcyclopropyl)-1H-indol-3-ylmethyl]pyridine-2-carboxamidoxime To a solution of hydroxylammonium chloride (117 mg) in dimethylsulfoxide (1.7 mL) was added sodium hydrogen carbonate (170 mg), and the mixture was stirred at 50° C. for 1 hour. Then, a solution of 6-[6-methoxy-2-(1-methylcyclopropyl)-1H-indol-3-ylmethyl]pyridine-2-carbonitrile (53.6 mg) in dimethylsulfoxide (1.7 mL) was added dropwise thereto, followed by stirring at 80° C. for 2.5 hours. The reaction mixture was left to be cooled and diluted with water, followed by extraction with ethyl acetate. The organic layer was washed with water and saturated brine, dried over anhydrous sodium sulfate, and then concentrated under reduced pressure to obtain the title compound (62.9 mg). $^1$H-NMR (CDCl$_3$) δ ppm: 0.68-0.76 (2H, m), 0.84-0.92 (2H, m), 1.34 (3H, s), 3.82 (3H, s), 4.35 (2H, s), 5.68 (2H, br s), 6.69 (1H, dd, J=2.3, 8.8 Hz), 6.82 (1H, d, J=2.3 Hz), 6.98-7.05 (1H, m), 7.23 (1H, d, J=8.8 Hz), 7.50 (1H, t, J=7.8 Hz), 7.66-7.73 (1H, m), 7.82 (1H, br s). ESI-MS (m/z): 351 (M+H)$^+$

Reference Examples 118-2 to 118-4

In the same method as in Reference Example 118-1 using the corresponding starting materials and reaction agents, the title compounds were synthesized.

Reference Example 118-2

6-[6-methyl-2-(1-methylcyclopropyl)-1H-indol-3-ylmethyl]pyridine-2-carboxamidoxime $^1$H-NMR (CDCl$_3$) δ ppm: 0.65-0.78 (2H, m), 0.80-0.95 (2H, m), 1.34 (3H, s), 2.43 (3H, s), 4.36 (2H, s), 5.69 (2H, br s), 6.50-7.14 (4H, m), 7.24 (1H, d, J=8.0 Hz), 7.48 (1H, t, J=7.8 Hz), 7.64-7.72 (1H, m), 7.81 (1H, br s).

Reference Example 118-3

6-[6-Cyclopropyl-2-(1-methylcyclopropyl)-1H-indol-3-ylmethyl]-pyridine-2-carboxamidoxime $^1$H-NMR (CDCl$_3$) δ ppm: 0.63-0.76 (4H, m), 0.83-0.96 (4H, m), 1.33 (3H, s), 1.93-2.02 (1H, m), 4.35 (2H, s), 5.68 (2H, br s), 6.38-6.70 (1H, br), 6.79 (1H, dd, J=1.5, 8.2 Hz), 6.98-7.04 (2H, m), 7.23 (1H, d, J=8.2 Hz), 7.48 (1H, t, J=7.8 Hz), 7.65-7.71 (1H, m), 7.80 (1H, br s). ESI-MS (m/z): 361 (M+H)$^+$

Reference Example 118-4

6-[6-Chloro-2-(1-methylcyclopropyl)-1H-indol-3-ylmethyl]-pyridine-2-carboxamidoxime: $^1$H-NMR (CDCl$_3$) δ ppm: 0.71-0.78 (2H, m), 0.86-0.94 (2H, m), 1.35 (3H, s), 4.35 (2H, s), 5.64 (2H, br s), 6.95-7.04 (2H, m), 7.24-7.30 (2H, m), 7.51 (1H, t, J=7.8 Hz), 7.67-7.73 (1H, m), 7.94 (1H, br s). ESI-MS (m/z): 355 (M+H)$^+$

Reference Example 119

(6-Bromopyridin-2-yl)(6-methoxy-2-phenyl-1H-indol-3-yl)methanol

To a suspension of 6-methoxy-2-phenyl-1H-indole (893 mg) and 6-bromopyridine-2-carboaldehyde (744 mg) in dichloromethane (13.3 mL) was added 1,8-diazabicyclo[5,4,0]-7-undecene (0.060 mL), and the mixture was stirred at room temperature for 13 hours under an argon atmosphere. The reaction mixture was purified by aminopropylated silica gel column chromatography (eluting solvent: ethyl acetate-hexane) to obtain the title compound (1.43 g). $^1$H-NMR (CDCl$_3$) δ ppm: 3.81 (3H, s), 4.71 (1H, d, J=2.6 Hz), 6.09 (1H, d, J=2.6 Hz), 6.65 (1H, dd, J=2.3, 8.7 Hz), 6.86 (1H, d, J=2.3 Hz), 7.02-7.13 (2H, m), 7.33-7.54 (5H, m), 7.64-7.72 (2H, m), 8.10 (1H, br s).

Reference Example 120

3-(6-Bromopyridin-2-ylmethyl)-6-methoxy-2-phenyl-1H-indole

In the same method as in Reference Example 32 using the corresponding starting material and reaction agents, the title compound was synthesized. $^1$H-NMR (CDCl$_3$) δ ppm: 3.86 (3H, s), 4.41 (2H, s), 6.76 (1H, dd, J=2.3, 8.8 Hz), 6.89-6.99 (2H, m), 7.24-7.55 (8H, m), 8.09 (1H, br s).

Reference Example 121

Tert-Butyl 3-(6-bromopyridin-2-ylmethyl)-6-methoxy-2-phenylindole-1-carboxylate

To a solution of 3-(6-bromopyridin-2-ylmethyl)-6-methoxy-2-phenyl-1H-indole (1.34 g) in acetonitrile (11 mL) were added di-tert-butyl dicarbonate (890 mg) and 4-dimethylaminopyridine (8.3 mg), and the mixture was stirred at room temperature overnight under an argon atmosphere. To the reaction mixture was added water, followed by extraction with ethyl acetate. The organic layer was washed with saturated brine, dried over anhydrous magnesium sulfate, and then concentrated under reduced pressure. The residue was purified by aminopropylated silica gel column chromatography (eluting solvent: ethyl acetate-hexane) to obtain the title compound (1.36 g). $^1$H-NMR (CDCl$_3$) δ ppm: 1.23 (9H, s), 3.90 (3H, s), 4.05 (2H, s), 6.81-6.92 (2H, m), 7.22-7.43 (8H, m), 7.86 (1H, d, J=2.3 Hz).

Reference Example 122

Tert-Butyl 3-[6-(3-hydroxyprop-1-yl)-1-yl)pyridin-2-ylmethyl]-6-methoxy-2-phenylindole-1-carboxylate To a solution of tert-butyl 3-(6-bromopyridin-2-ylmethyl)-6-methoxy-2-phenylindole-1-carboxylate (1.36 g), prop-2-yl)-1-ol (0.24 mL), bis(triphenylphosphine) palladium(II) dichloride (58 mg), and copper(I) iodide (31.5 mg) in acetonitrile (12 mL) was added triethylamine (0.96 mL) at room temperature. The mixture was stirred at 80° C. overnight. The reaction mixture was left to be cooled and concentrated under reduced pressure. To the residue was added ethyl acetate, and the mixture was filtered through Celite (registered trademark). The filtrate was concentrated under reduced pressure. The residue was purified by aminopropylated silica gel column chromatography (eluting solvent: ethyl acetate-hexane) to obtain the title compound (644 mg). $^1$H-NMR (CDCl$_3$) δ ppm: 1.23 (9H, s), 3.89 (3H, s), 4.07 (2H, s), 4.53 (2H, d, J=6.3 Hz), 6.82 (1H, dd, J=2.3, 8.5 Hz), 6.86-6.95 (1H, m), 7.16-7.51 (8H, m) 7.85 (1H, d, J=2.3 Hz). ESI-MS (m/z): 469 (M+H)$^+$ Reference Example 123

Tert-Butyl 6-methoxy-3-[6-(3-oxoprop-1-yl)-1-yl)pyridin-2-ylmethyl]-2-phenylindole-1-carboxylate To a solution of tert-butyl 3-[6-(3-hydroxyprop-1-yl)-1-yl)pyridin-2-ylmethyl]-6-methoxy-2-phenylindole-1-carboxylate (641 mg) in acetonitrile (14 mL) was added Dess-Martin periodinane (679 mg), followed by light shielding, and the mixture was stirred at room temperature for 4.5 hours. The reaction mixture was diluted with ethyl acetate and filtered through Celite (registered trademark). The filtrate was concentrated under reduced pressure. To the residue was added ethyl acetate, and the mixture was filtered through Celite (registered trademark). The residue was purified by silica gel column chromatography (eluting solvent: ethyl acetate-hexane) to obtain the title compound (496 mg). $^1$H-NMR (CDCl$_3$) δ ppm: 1.23 (9H, s), 3.89 (3H, s), 4.11 (2H, s), 6.84 (1H, dd, J=2.3, 8.5 Hz), 6.99-7.06 (1H, m), 7.23 (1H, d, J=8.5 Hz), 7.28-7.45 (6H, m), 7.53 (1H, d, J=7.8 Hz), 7.86 (1H, d, J=2.3 Hz), 9.47 (1H, s).

Reference Example 124

Tert-Butyl 6-methoxy-3-(6-methoxycarbonylethynylpyridin-2-ylmethyl)-2-phenylindole-1-carboxylate To a solution of tert-butyl 6-methoxy-3-[6-(3-oxoprop-1-yl)-1-yl)pyridin-2-ylmethyl]-2-phenylindole-1-carboxylate (494 mg) in dichloromethane/tert-butyl alcohol (17 mL/4 mL) was added 2-methyl-2-butene (0.56 mL). Then, a solution of sodium dihydrogen phosphate dihydrate (813 mg) and sodium chlorite (80%, 1.2 g) in water (8.8 mL) was added thereto in 2 minutes, and the mixture was stirred at room temperature for 2 hours. To the reaction mixture were added ethyl acetate, water, sodium hydrogen carbonate, and sodium hydroxide successively. The organic layer was separated, dried over anhydrous magnesium sulfate, and then concentrated under reduced pressure. To a suspension of the residue and potassium carbonate (381 mg) in N,N-dimethylformamide (20 mL) was added methyl iodide (0.198 mL), and the mixture was stirred at room temperature for 6.5 hours. Methyl iodide (0.198 mL) and potassium carbonate (381 mg) were added thereto, and the mixture was stirred at room temperature overnight. To the reaction mixture were added ethyl acetate and water, followed by stirring for additional 5 minutes. The mixture was filtered through Celite (registered trademark). The organic layer was separated. The organic layer was washed with saturated brine, dried over anhydrous magnesium sulfate, and then concentrated under reduced pressure. The residue was purified by silica gel column chromatography (eluting solvent: ethyl acetate-hexane) to obtain the title compound (218 mg). $^1$H-NMR (CDCl$_3$) δ ppm: 1.23 (9H, s), 3.85 (3H, s), 3.89 (3H, s), 4.09 (2H, s), 6.83 (1H, dd, J=2.4, 8.6 Hz), 6.96-7.02 (1H, m), 7.23 (1H, d, J=8.6 Hz), 7.28-7.43 (6H, m), 7.50 (1H, t, J=7.8 Hz), 7.85 (1H, d, J=2.3 Hz). ESI-MS (m/z): 497 (M+H)$^+$ Reference Example 125

Methyl [6-(6-methoxy-2-phenyl-1H-indol-3-ylmethyl)pyridin-2-yl]propynoate

To a solution of tert-butyl 6-methoxy-3-(6-methoxycarbonylethynylpyridin-2-ylmethyl)-2-phenylindole-1-carboxylate (100 mg) in dichloromethane (1 mL) was added trifluoroacetic acid (0.3 mL), and the mixture was stirred at room temperature for 3 hours. To the reaction mixture were added dichloromethane and an aqueous sodium hydrogen carbonate solution, and the organic layer was separated and concentrated under reduced pressure. The residue was purified by silica gel column chromatography (eluting solvent: ethyl acetate-hexane) to obtain the title compound (75.1 mg). $^1$H-NMR (CDCl$_3$) δ ppm: 3.84-3.89 (6H, m), 4.45 (2H, s), 6.75 (1H, dd, J=2.3, 8.8 Hz), 6.92 (1H, d, J=2.3 Hz), 7.04-7.10 (1H, m), 7.31-7.55 (7H, m), 8.09 (1H, br s). ESI-MS (m/z): 397 (M+H)$^+$ Reference Example 126

6-(2-tert-Butyl-6-methoxy-1H-indol-3-ylmethyl)pyridine-2-carbohydrazide

In the same method as in Reference Example 114 using the corresponding starting material and reaction agents, the title compound was synthesized. $^1$H-NMR (CDCl$_3$) δ ppm: 1.41 (9H, s), 3.83 (3H, s), 4.08 (2H, d, J=4.8 Hz), 4.41 (2H, s), 6.71 (1H, dd, J=2.3, 8.8 Hz), 6.83-6.89 (1H, m), 7.07-7.15 (1H, m), 7.19 (1H, d, J=8.8 Hz), 7.57-7.67 (1H, m), 7.74-8.04 (2H, m), 8.92-9.15 (1H, m).

Reference Example 127

5-(6-Methoxy-2-phenyl-1H-indol-3-ylmethyl)furan-2-carboxamide

In the same method as in Reference Example 100 using the corresponding starting material and reaction agents, the title compound was synthesized. $^1$H-NMR (DMSO-d$_6$) δ ppm: 3.78 (3H, s), 4.18 (2H, s), 6.08 (1H, d, J=3.3 Hz), 6.65 (1H, dd, J=2.3, 8.5 Hz), 6.87 (1H, d, J=2.3 Hz), 6.98 (1H, d, J=3.3 Hz), 7.12-7.67 (8H, m), 11.18 (1H, s). ESI-MS (m/z): 347 (M+H)$^+$ Reference Example 128

5-(6-Methoxy-2-phenyl-1H-indol-3-ylmethyl)furan-2-carbonitrile

In the same method as in Reference Example 87 using the corresponding starting material and reaction agents, the title compound was synthesized. $^1$H-NMR (CDCl$_3$) δ ppm: 3.87 (3H, s), 4.20 (2H, s), 6.07 (1H, d, J=3.5 Hz), 6.81 (1H, dd, J=2.3, 8.5 Hz), 6.89-6.94 (1H, m), 6.98 (1H, d, J=3.5 Hz), 7.32-7.54 (6H, m), 8.06 (1H, br s).

Reference Example 129-1

Tert-Butyl (5-chloro-4-methoxy-2-methylphenyl)carbamate

A solution of 5-chloro-4-methoxy-2-methylaniline (2.21 g) and di-tert-butyl dicarbonate (3.09 g) in tetrahydrofuran (26 mL) was heated under reflux for 9 hours. The reaction mixture was left to be cooled and concentrated under reduced pressure. The residue was purified by silica gel column chromatography (eluting solvent: ethyl acetate-hexane) to obtain the title compound (3.44 g). $^1$H-NMR (CDCl$_3$) δ ppm: 1.51 (9H, s), 2.23 (3H, s), 3.86 (3H, s), 5.80-6.34 (1H, br), 6.72 (1H, s), 7.54-7.94 (1H, br).

Reference Example 129-2

Tert-Butyl (5-chloro-2-methylphenyl)carbamate

In the same method as in Reference Example 14 using the corresponding starting material and reaction agents, the title compound was synthesized. $^1$H-NMR (CDCl$_3$) δ ppm: 1.53 (9H, s), 2.20 (3H, s), 6.27 (1H, br s), 6.95 (1H, dd, J=2.3, 8.0 Hz), 7.01-7.08 (1H, m), 7.96 (1H, br s).

Reference Examples 130-1 to 130-3

In the same method as in Reference Example 1 using the corresponding starting materials and reaction agents, the title compounds were synthesized.

Reference Example 130-1 tert-Butyl [5-chloro-4-methoxy-2-(2-oxo-2-pyridin-3-ylethyl)phenyl]carbamate $^1$H-NMR (CDCl$_3$) δ ppm: 1.47 (9H, s), 3.85 (3H, s), 4.29 (2H, s), 6.58-7.10 (2H, m), 7.43-7.51 (1H, m), 7.64 (1H, br s), 8.26-8.35 (1H, m), 8.79-8.88 (1H, m), 9.25-9.33 (1H, m).

Reference Example 130-2 tert-Butyl [2-(2-furan-3-yl-2-oxoethyl)-5-methylphenyl]carbamate: $^1$H-NMR (CDCl$_3$) δ ppm: 1.52 (9H, s), 2.32 (3H, s), 3.97 (2H, s), 6.76-6.90 (2H, m), 7.04 (1H, d, J=7.5 Hz), 7.43-7.49 (1H, m), 7.58-8.02 (2H, m), 8.14-8.20 (1H, m).

Reference Example 130-3 tert-Butyl [5-cyclopropyl-2-(2-furan-3-yl-2-oxoethyl)phenyl]carbamate $^1$H-NMR (CDCl$_3$) δ ppm: 0.63-0.74 (2H, m), 0.87-0.99 (2H, m), 1.52 (9H, s), 1.82-1.93 (1H, m), 3.96 (2H, s), 6.68-6.84 (2H, m), 7.03 (1H, d, J=7.8 Hz), 7.42-8.09 (3H, m), 8.14-8.21 (1H, m).

Reference Example 131-1

Tert-Butyl {5-methoxy-2-[2-(1-methylcyclopropyl)-2-oxoethyl]phenyl}carbamate

Under an argon atmosphere, to a solution of tert-butyl (5-methoxy-2-methylphenyl)carbamate (2.00 g) in tetrahydrofuran (42 mL) was slowly added dropwise sec-butyllithium (1.08 mol/L hexane-cyclohexane solution, 22 mL) at −45° C., and the mixture was stirred for 45 minutes. Then, a solution of N-methoxy-N,1-dimethylcyclopropane carboxamide (1.33 g) in tetrahydrofuran (4.2 mL) was added dropwise thereto, and the mixture was stirred at −45° C. for 45 minutes, and then stirred at room temperature for 3 hours. To the reaction mixture were added a saturated aqueous ammonium chloride solution and water, followed by extraction with ethyl acetate. The organic layer was washed with saturated brine, dried over anhydrous magnesium sulfate, and then concentrated under reduced pressure. The residue was purified by silica gel column chromatography (eluting solvent: ethyl acetate-hexane) to obtain the title compound (1.77 g). $^1$H-NMR (CDCl$_3$) δ ppm: 0.80-0.89 (2H, m), 1.35-1.44 (5H, m), 1.52 (9H, s), 3.55 (2H, s), 3.80 (3H, s), 6.57 (1H, dd, J=2.8, 8.3 Hz), 6.97 (1H, d, J=8.3 Hz), 7.46 (1H, br s), 7.90-8.28 (1H, br).

Reference Examples 131-2 to 131-4

In the same method as in Reference Example 131-1 using the corresponding starting materials and reaction agents, the title compounds were synthesized.

Reference Example 131-2 tert-Butyl {5-methyl-2-[2-(1-methylcyclopropyl)-2-oxoethyl]phenyl}carbamate $^1$H-NMR (CDCl$_3$) δ ppm: 0.80-0.89 (2H, m), 1.35-1.45 (5H, m), 1.52 (9H, s), 2.32 (3H, s), 3.58 (2H, s), 6.80-6.88 (1H, m), 6.96 (1H, d, J=7.8 Hz), 7.62 (1H, br s), 7.78-8.18 (1H, br).

Reference Example 131-3 tert-Butyl {5-cyclopropyl-2-[2-(1-methylcyclopropyl)-2-oxoethyl]phenyl}-carbamate: $^1$H-NMR (CDCl$_3$) δ ppm: 0.64-0.72 (2H, m), 0.79-0.97 (4H, m), 1.34-1.43 (5H, m), 1.52 (9H, s), 1.83-1.92 (1H, m), 3.57 (2H, s), 6.67-6.74 (1H, m), 6.95 (1H, d, J=8.0 Hz), 7.54 (1H, br s), 7.80-8.12 (1H, br).

Reference Example 131-4 tert-Butyl {5-chloro-2-[2-(1-methylcyclopropyl)-2-oxoethyl]phenyl}carbamate $^1$H-NMR (CDCl$_3$) δ ppm: 0.83-0.92 (2H, m), 1.34-1.44 (5H, m), 1.52 (9H, s), 3.59 (2H, s), 6.96-7.03 (2H, m), 7.82-8.32 (2H, m).

Reference Example 132

6-Chloro-5-methoxy-2-pyridin-3-yl-1H-indole

To a solution of tert-butyl [5-chloro-4-methoxy-2-(2-oxo-2-pyridin-3-ylethyl)phenyl]carbamate (1.28 g) in dichloromethane (17 mL) was added trifluoroacetic acid (3.4 mL) under ice-cooling, and the mixture was stirred at room temperature for 24 hours. The reaction mixture was concentrated under reduced pressure. The residue was dissolved in ethyl acetate, and the resulting mixture was washed with a saturated aqueous sodium hydrogen carbonate solution and saturated brine successively. The organic layer was dried over anhydrous sodium sulfate, and then concentrated under reduced pressure to obtain the title compound (812 mg). $^1$H-NMR (CDCl$_3$) δ ppm: 3.95 (3H, s), 6.77-6.85 (1H, m), 7.14 (1H, s), 7.38 (1H, dd, J=4.8, 8.0 Hz), 7.45 (1H, s), 7.86-7.96 (1H, m), 8.36 (1H, br s), 8.53-8.60 (1H, m), 8.90-8.97 (1H, m).

Reference Example 133

Methyl 6-[(6-chloro-5-methoxy-2-pyridin-3-yl-1H-indol-3-yl)hydroxymethyl]-pyridine-2-carboxylate In the same method as in Reference Example 31 using the corresponding starting material and reaction agents, the title compound was synthesized. $^1$H-NMR (DMSO-d$_6$) δ ppm: 3.73 (3H, s), 3.83 (3H, s), 6.01 (1H, d, J=3.8 Hz), 6.14 (1H, d, J=3.8 Hz), 7.13 (1H, s), 7.38 (1H, s), 7.54-7.61 (1H, m), 7.87-7.93 (1H, m), 8.07 (1H, t, J=7.8 Hz), 8.18-8.25 (1H, m), 8.58-8.69 (2H, m), 9.14-9.19 (1H, m), 11.47 (1H, s).

Reference Example 134

Methyl 6-(6-chloro-5-methoxy-2-pyridin-3-yl-1H-indol-3-ylmethyl)pyridine-2-carboxylate In the same method as in Reference Example 51 using the corresponding starting material and reaction agents, the title compound was synthesized. $^1$H-NMR (CDCl$_3$) δ ppm: 3.84 (3H, s), 4.03 (3H, s), 4.50 (2H, s), 6.98 (1H, s), 7.14-7.20 (1H, m), 7.34-7.41 (1H, m), 7.44 (1H, s), 7.67 (1H, t, J=7.8 Hz), 7.87-8.01 (2H, m), 8.26 (1H, br s), 8.61 (1H, dd, J=1.5, 4.8 Hz), 8.79-8.85 (1H, m). ESI-MS (m/z): 408 (M+H)$^+$ Reference Example 135

6-(6-Chloro-5-methoxy-2-pyridin-3-yl-1H-indol-3-ylmethyl)pyridine-2-carboxylic acid In the same method as in Reference Example 4 using the corresponding starting material and reaction agents, the title compound was synthesized. $^1$H-NMR (DMSO-d$_6$) δ ppm: 3.81 (3H, s), 4.38 (2H, s), 7.30 (1H, s), 7.38-7.58 (3H, m), 7.80-7.89 (2H, m), 8.28-8.36 (1H, m), 8.59 (1H, dd, J=1.5, 4.8 Hz), 8.93-9.01 (1H, m), 11.52 (1H, s), 12.75-13.65 (1H, br). ESI-MS (m/z): 394 (M+H)$^+$ Reference Example 136

[6-(6-Methoxy-2-phenyl-1H-indol-3-ylmethyl)pyridin-2-yl]methanol

To a solution of methyl 6-(6-methoxy-2-phenyl-1H-indol-3-ylmethyl)pyridine-2-carboxylate (1.2 g) in methanol/tetrahydrofuran (6 mL/6 mL) was added sodium borohydride (305 mg) at room temperature. The mixture was stirred at room temperature for 3.5 hours. To the reaction mixture was added a saturated aqueous ammonium chloride solution. The organic layer was separated, washed with a saturated aqueous ammonium chloride solution and saturated brine successively, dried over anhydrous magnesium sulfate, and then concentrated under reduced pressure to obtain the title compound (1.16 g). $^1$H-NMR (CDCl$_3$) δ ppm: 3.86 (3H, s), 4.00-4.10 (1H, m), 4.41 (2H, s), 4.70-4.78 (2H, m), 6.76 (1H, dd, J=2.3, 8.8 Hz), 6.91 (1H, d, J=2.3 Hz), 6.96-7.04 (2H, m), 7.31-7.38 (2H, m), 7.39-7.59 (5H, m), 8.05 (1H, br s).

Reference Example 137

3-[6-(Bromomethyl)pyridin-2-ylmethyl]-6-methoxy-2-phenyl-1H-indole

[6-(6-Methoxy-2-phenyl-1H-indol-3-ylmethyl)pyridin-2-yl]methanol (1.16 g) and triethylamine (0.751 mL) were dissolved in ethyl acetate (9 mL), and to the solution was added mesyl chloride (0.391 mL). The mixture was stirred at room temperature for 1.5 hours. The precipitate was separated by filtration through Celite (registered trademark) and washed with ethyl acetate. To the filtrate was added lithium bromide monohydrate (1.06 g), and the mixture was stirred at 60° C. for 1.5 hours. The reaction mixture was left to be cooled, and washed with water and saturated brine successively. The organic layer was dried over anhydrous magnesium sulfate and concentrated under reduced pressure to obtain the title compound (1.49 g). $^1$H-NMR (CDCl$_3$) δ ppm: 3.86 (3H, s), 4.41 (2H, s), 4.59 (2H, s), 6.72-6.79 (1H, m), 6.88-7.00 (2H, m), 7.30-7.38 (2H, m), 7.39-7.60 (5H, m), 8.05 (1H, br s).

Reference Example 138

[6-(6-Methoxy-2-phenyl-1H-indol-3-ylmethyl)pyridin-2-yl]acetonitrile

To a solution of 3-[6-(bromomethyl)pyridin-2-ylmethyl]-6-methoxy-2-phenyl-1H-indole (1.37 g) in water/ethanol/tetrahydrofuran (4 mL/16 mL/4 mL) was added potassium cyanide (263 mg), and the mixture was stirred at 80° C. for 13.5 hours. The reaction mixture was left to be cooled and concentrated under reduced pressure. To the residue was added water, followed by extraction with dichloromethane. The organic layer was concentrated under reduced pressure. The residue was purified by silica gel column chromatography (eluting solvent: ethyl acetate-hexane) to obtain the title compound (1.05 g). $^1$H-NMR (CDCl$_3$) δ ppm: 3.86 (3H, s), 3.95 (2H, s), 4.39 (2H, s), 6.76 (1H, dd, J=2.3, 8.5 Hz), 6.91 (1H, d, J=2.3 Hz), 7.04 (1H, d, J=7.8 Hz), 7.23 (1H, d, J=7.5 Hz), 7.30-7.39 (2H, m), 7.39-7.49 (2H, m), 7.50-7.61 (3H, m), 8.05 (1H, br s).

Reference Example 139

Methyl 6-(5,6-dimethyl-2-phenyl-1H-indol-3-ylmethyl)pyridine-2-carboxylate

In the same method as in Reference Example 28 using the corresponding starting material and reaction agents, the title compound was synthesized. $^1$H-NMR (CDCl$_3$) δ ppm: 2.28 (3H, s), 2.37 (3H, s), 4.05 (3H, s), 4.56 (2H, s), 7.12-7.24 (3H, m), 7.29-7.45 (3H, m), 7.47-7.55 (2H, m), 7.62 (1H, t, J=7.8 Hz), 7.93-8.09 (2H, m). ESI-MS (m/z): 371 (M+H)$^+$ Reference Example 140

6-(5,6-Dimethyl-2-phenyl-1H-indol-3-ylmethyl)pyridine-2-carboxamide

In the same method as in Reference Example 88 using the corresponding starting material and reaction agents, the title compound was synthesized. $^1$H-NMR (DMSO-d$_6$) δ ppm: 2.24 (3H, s), 2.30 (3H, s), 4.38 (2H, s), 7.16 (1H, s), 7.21-7.38

(3H, m), 7.41-7.51 (2H, m), 7.58-7.72 (3H, m), 7.77-7.92 (3H, m), 11.07 (1H, s). ESI-MS (m/z): 356 (M+H)$^+$

Reference Example 141

6-(5,6-Dimethyl-2-phenyl-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 2.31 (3H, s), 2.37 (3H, s), 4.45 (2H, s), 7.16 (1H, s), 7.20 (1H, s), 7.21-7.28 (1H, m), 7.32-7.55 (6H, m), 7.55-7.63 (1H, m), 8.02 (1H, br s). ESI-MS (m/z): 338 (M+H)$^+$ Reference Example 142

5-Chloro-2-isopropyl-6-methoxy-1H-indole

In the same method as in Reference Example 27 using the corresponding starting material and reaction agents, the title compound was synthesized. $^1$H-NMR (CDCl$_3$) δ ppm: 1.34 (6H, d, J=7.0 Hz), 2.96-3.10 (1H, m), 3.90 (3H, s), 6.08-6.14 (1H, m), 6.87 (1H, s), 7.50 (1H, s), 7.65-7.97 (1H, br).

Reference Example 143

Methyl 6-(5-chloro-2-isopropyl-6-methoxy-1H-indol-3-ylmethyl)pyridine-2-carboxylate In the same method as in Reference Example 28 using the corresponding starting material and reaction agents, the title compound was synthesized. $^1$H-NMR (CDCl$_3$) δ ppm: 1.27 (6H, d, J=7.0 Hz), 3.19-3.34 (1H, m), 3.90 (3H, s), 4.04 (3H, s), 4.32 (2H, s), 6.90 (1H, s), 7.08-7.14 (1H, m), 7.39 (1H, s), 7.62 (1H, t, J=7.8 Hz), 7.86 (1H, br s), 7.91-7.98 (1H, m).

Reference Example 144

6-(5-Chloro-2-isopropyl-6-methoxy-1H-indol-3-ylmethyl)pyridine-2-carboxylic acid In the same method as in Reference Example 4 using the corresponding starting material and reaction agents, the title compound was synthesized. $^1$H-NMR (DMSO-d$_6$) δ ppm: 1.23 (6H, d, J=7.0 Hz), 3.81 (3H, s), 4.16 (2H, s), 6.92 (1H, s), 7.29 (1H, dd, J=2.5, 6.5 Hz), 7.45 (1H, s), 7.76-7.85 (2H, m), 10.80 (1H, s), 12.60-13.45 (1H, br).
ESI-MS (m/z): 359 (M+H)$^+$ Reference Example 145

6-(5-Chloro-2-isopropyl-6-methoxy-1H-indol-3-ylmethyl)pyridine-2-carboxamide

In the same method as in Reference Example 100 using the corresponding starting material and reaction agents, the title compound was synthesized. $^1$H-NMR (CDCl$_3$) δ ppm: 1.28 (6H, d, J=7.0 Hz), 3.21-3.36 (1H, m), 3.91 (3H, s), 4.20 (2H, s), 5.32-5.72 (1H, br), 6.90 (1H, s), 7.15-7.22 (1H, m), 7.45 (1H, s), 7.64-7.72 (1H, m), 7.75-8.04 (3H, m).

Reference Example 146

6-(5-Chloro-2-isopropyl-6-methoxy-1H-indol-3-ylmethyl)pyridine-2-carbonitrile

In the same method as in Reference Example 87 using the corresponding starting material and reaction agents, the title compound was synthesized. $^1$H-NMR (CDCl$_3$) δ ppm: 1.28 (6H, d, J=7.0 Hz), 3.21-3.35 (1H, m), 3.91 (3H, s), 4.22 (2H, s), 6.91 (1H, s), 7.19-7.25 (1H, m), 7.35 (1H, s), 7.47-7.54 (1H, m), 7.63 (1H, t, J=7.8 Hz), 7.84 (1H, br s).

Reference Example 147-1

Tert-Butyl [2-(2-hydroxy-3-methylbutyl)-5-methoxyphenyl]carbamate

Under an argon atmosphere, to a solution of tert-butyl (5-methoxy-2-methylphenyl)carbamate (1.42 g) in tetrahydrofuran (30 mL) was slowly added dropwise sec-butyllithium (1.06 mol/L hexane-cyclohexane solution, 12.5 mL) at −40° C., and the mixture was stirred for 15 minutes. Then, a solution of 2-methylpropionaldehyde (476 mg) in tetrahydrofuran (3 mL) was added dropwise thereto, and the mixture was stirred at −40° C. for 15 minutes, and then stirred at room temperature for additional 40 minutes. To the reaction mixture was added a saturated aqueous ammonium chloride solution, followed by extraction with ethyl acetate. The organic layer was washed with saturated brine, dried over anhydrous magnesium sulfate, and then concentrated under reduced pressure. The residue was purified by silica gel column chromatography (eluting solvent: ethyl acetate-hexane) to obtain the title compound (929 mg). $^1$H-NMR (CDCl$_3$) δ ppm: 0.96-1.06 (6H, m), 1.52 (9H, s), 1.70-1.83 (1H, m), 1.90 (1H, d, J=3.8 Hz), 2.57-2.75 (2H, m), 3.48-3.59 (1H, m), 3.80 (3H, s), 6.59 (1H, dd, J=2.8, 8.5 Hz), 7.00 (1H, d, J=8.5 Hz), 7.43 (1H, br s), 7.91 (1H, br s).

Reference Examples 147-2 to 147-4

In the same method as in Reference Example 147-1 using the corresponding starting materials and reaction agents, the title compounds were synthesized.

Reference Example 147-2 tert-Butyl [2-(2-cyclopropyl-2-hydroxyethyl)-5-methoxyphenyl]carbamate $^1$H-NMR (CDCl$_3$) δ ppm: 0.22-0.35 (2H, m), 0.48-0.66 (2H, m), 0.90-1.02 (1H, m), 1.52 (9H, s), 1.93-1.99 (1H, m), 2.79 (1H, dd, J=7.2, 14.4 Hz), 2.91 (1H, dd, J=2.9, 14.4 Hz), 3.02-3.11 (1H, m), 3.80 (3H, s), 6.57 (1H, dd, J=2.6, 8.4 Hz), 7.02 (1H, d, J=8.4 Hz), 7.46 (1H, br s), 8.12 (1H, br s).

Reference Example 147-3 tert-Butyl [2-(2-cyclohexyl-2-hydroxyethyl)-5-methoxyphenyl]carbamate $^1$H-NMR (CDCl$_3$) δ ppm: 0.98-1.58 (15H, m), 1.62-1.96 (6H, m), 2.61-2.75 (2H, m), 3.48-3.58 (1H, m), 3.80 (3H, s), 6.59 (1H, dd, J=2.6, 8.5 Hz), 6.99 (1H, d, J=8.5 Hz), 7.43 (1H, br s), 7.93 (1H, br s).

Reference Example 147-4 tert-Butyl [2-(2-hydroxy-3-methylpentyl)-5-methoxyphenyl]carbamate; $^1$H-NMR (CDCl$_3$) δ ppm: 0.90-1.90 (19H, m), 2.52-2.79 (2H, m), 3.58-3.74 (1H, m), 3.80 (3H, s), 6.55-6.64 (1H, m), 6.96-7.05 (1H, m), 7.43 (1H, br s), 7.87 (1H, br s).

Reference Example 148-1

Tert-Butyl [5-methoxy-2-(3-methyl-2-oxobutyl)phenyl]carbamate

To a solution of tert-butyl [2-(2-hydroxy-3-methylbutyl)-5-methoxyphenyl]-carbamate (100 mg) in dichloromethane (1.5 mL) was added Dess-Martin periodinane (164 mg), and the mixture was stirred at room temperature for 2 hours. The reaction mixture was filtrated through Celite (registered trademark), and the filtrate was concentrated under reduced pressure. The residue was purified by silica gel column chromatography (eluting solvent: ethyl acetate-hexane) to obtain the title compound (94 mg). $^1$H-NMR (CDCl$_3$) δ ppm: 1.13 (6H, d, J=7.0 Hz), 1.52 (9H, s), 2.72-2.86 (1H, m), 3.66 (2H, s), 3.80 (3H, s), 6.59 (1H, dd, J=2.6, 8.5 Hz), 7.02 (1H, d, J=8.5 Hz), 7.47 (1H, br s), 7.60-7.90 (1H, br).

Reference Examples 148-2 to 148-4

In the same method as in Reference Example 148-1 using the corresponding starting materials and reaction agents, the title compounds were synthesized.

Reference Example 148-2 tert-Butyl [2-(2-cyclopropyl-2-oxoethyl)-5-methoxyphenyl]carbamate: $^1$H-NMR (CDCl$_3$) δ ppm: 0.87-0.97 (2H, m), 1.02-1.11 (2H, m), 1.52 (9H, s), 1.98-2.09 (1H, m), 3.73 (2H, s), 3.80 (3H, s), 6.61 (1H, dd, J=2.8, 8.4 Hz), 7.08 (1H, d, J=8.4 Hz), 7.37-7.63 (2H, m).

Reference Example 148-3 tert-Butyl [2-(2-cyclohexyl-2-oxoethyl)-5-methoxyphenyl]carbamate $^1$H-NMR (CDCl$_3$) δ ppm: 1.12-1.44 (5H, m), 1.52 (9H, s), 1.62-1.93 (5H, m), 2.44-2.58 (1H, m), 3.64 (2H, s), 3.80 (3H, s), 6.58 (1H, dd, J=2.8, 8.5 Hz), 7.01 (1H, d, J=8.5 Hz), 7.38-7.55 (1H, m), 7.60-7.88 (1H, br).

Reference Example 148-4 tert-Butyl [5-methoxy-2-(3-methyl-2-oxopentyl)phenyl]carbamate $^1$H-NMR (CDCl$_3$) δ ppm: 0.77-0.87 (3H, m), 1.09 (3H, d, J=7.0 Hz), 1.35-1.50 (1H, m), 1.52 (9H, s), 1.63-1.79 (1H, m), 2.58-2.70 (1H, m), 3.64 (2H, s), 3.80 (3H, s), 6.55-6.63 (1H, m), 7.01 (1H, d, J=8.5 Hz), 7.38-7.57 (1H, m), 7.68 (1H, br s).

Reference Example 149-1

Tert-Butyl {2-[1-(6-cyanopyridin-2-ylmethyl)-3-methyl-2-oxobutyl]-5-methoxyphenyl}carbamate Under an argon atmosphere, to a solution of tert-butyl [5-methoxy-2-(3-methyl-2-oxobutyl)phenyl]carbamate (337 mg) in N,N-dimethylformamide (4 mL) was added sodium hydride (50-72% in oil, 56 mg) under ice-cooling, and the mixture was stirred for 30 minutes. 6-(Chloromethyl)pyridine-2-carbonitrile (167 mg) was added thereto, followed by stirring for 1 hour. To the reaction mixture was added a saturated aqueous ammonium chloride solution, followed by extraction with ethyl acetate. The organic layer was washed with water and saturated brine successively, dried over anhydrous magnesium sulfate, and then concentrated under reduced pressure. The residue was purified by silica gel column chromatography (eluting solvent: ethyl acetate-hexane) to obtain the title compound (271 mg). $^1$H-NMR (CDCl$_3$) δ ppm: 0.91 (3H, d, J=6.5 Hz), 1.07 (3H, d, J=7.3 Hz), 1.57 (9H, s), 2.56-2.72 (1H, m), 3.18 (1H, dd, J=8.2, 15.9 Hz), 3.61 (1H, dd, J=6.8, 15.9 Hz), 3.77 (3H, s), 4.65-4.74 (1H, m), 6.58 (1H, dd, J=2.8, 8.7 Hz), 6.92 (1H, d, J=8.7 Hz), 7.22-7.29 (1H, m), 7.35 (1H, d, J=2.8 Hz), 7.46-7.60 (2H, m), 7.65 (1H, t, J=7.8 Hz).

Reference Examples 149-2 to 149-6

In the same method as in Reference Example 149-1 using the corresponding starting materials and reaction agents, the title compounds were synthesized.

Reference Example 149-2 tert-Butyl {2-[1-(6-cyanopyridin-2-ylmethyl)-2-cyclopropyl-2-oxoethyl]-5-methoxyphenyl}carbamate $^1$H-NMR (CDCl$_3$) δ ppm: 0.71-1.05 (4H, m), 1.57 (9H, s), 1.80-1.90 (1H, m), 3.15 (1H, dd, J=8.5, 15.8 Hz), 3.67 (1H, dd, J=6.0, 15.8 Hz), 3.78 (3H, s), 4.63-4.71 (1H, m), 6.59 (1H, dd, J=2.8, 8.5 Hz), 6.92 (1H, d, J=8.5 Hz), 7.21-7.29 (1H, m), 7.42 (1H, d, J=2.8 Hz), 7.48-7.62 (2H, m), 7.64 (1H, t, J=7.8 Hz).

Reference Example 149-3 tert-Butyl {2-[1-(6-cyanopyridin-2-ylmethyl)-2-cyclohexyl-2-oxoethyl]-5-methoxyphenyl}carbamate: $^1$H-NMR (CDCl$_3$) δ ppm: 1.03-1.96 (19H, m), 2.32-2.46 (1H, m), 3.16 (1H, dd, J=7.8, 15.8 Hz), 3.59 (1H, dd, J=6.8, 15.8 Hz), 3.78 (3H, s), 4.62-4.72 (1H, m), 6.58 (1H, dd, J=2.8, 8.5 Hz), 6.92 (1H, d, J=8.5 Hz), 7.31-7.39 (1H, m), 7.45-7.60 (2H, m), 7.64 (1H, t, J=7.8 Hz).

Reference Example 149-4 tert-Butyl {2-[1-(6-cyanopyridin-2-ylmethyl)-2-furan-3-yl-2-oxoethyl]-5-methylphenyl}carbamate $^1$H-NMR (CDCl$_3$) δ ppm: 1.60 (9H, s), 2.26 (3H, s), 3.31-3.41 (1H, m), 3.69-3.79 (1H, m), 5.05-5.12 (1H, m), 6.64-6.70 (1H, m), 6.79-6.86 (1H, m), 7.00 (1H, d, J=8.0 Hz), 7.30-7.37 (2H, m), 7.46-7.56 (2H, m), 7.66 (1H, t, J=7.8 Hz), 7.74 (1H, br s), 7.92-7.97 (1H, m).

Reference Example 149-5 tert-Butyl {2-[1-(6-cyanopyridin-2-ylmethyl)-2-furan-3-yl-2-oxoethyl]-5-cyclopropylphenyl}carbamate $^1$H-NMR (CDCl$_3$) δ ppm: 0.58-0.70 (2H, m), 0.84-0.96 (2H, m), 1.60 (9H, s), 1.75-1.86 (1H, m), 3.34 (1H, dd, J=8.5, 15.8 Hz), 3.73 (1H, dd, J=6.0, 15.8 Hz), 5.03-5.12 (1H, m), 6.63-6.75 (2H, m), 6.99 (1H, d, J=8.0 Hz), 7.29-7.44 (3H, m), 7.48-7.55 (1H, m), 7.61-7.77 (2H, m), 7.92-7.98 (1H, m).

Reference Example 149-6 tert-Butyl {2-[1-(6-cyanopyridin-2-ylmethyl)-3-methyl-2-oxopentyl]-5-methoxyphenyl}carbamate $^1$H-NMR (CDCl$_3$) δ ppm: 0.53-1.09 (6H, m), 1.15-1.70 (11H, m), 2.40-2.55 (1H, m), 3.14-3.25 (1H, m), 3.54-3.66 (1H, m), 3.77 (3H, s), 4.62-4.74 (1H, m), 6.55-6.63 (1H, m), 6.89-6.97 (1H, m), 7.24-7.40 (2H, m), 7.47-7.69 (3H, m).

Reference Example 150-1

Tert-Butyl {2-[1-(6-cyanopyridin-2-ylmethyl)-2-(1-methylcyclopropyl)-2-oxoethyl]-5-methoxyphenyl}carbamate Under an argon atmosphere, to a solution of tert-butyl {5-methoxy-2-[2-(1-methylcyclopropyl)-2-oxoethyl]phenyl}carbamate (300 mg) in N,N-dimethylformamide (3.1 mL) was added sodium hydride (50-72% in oil, 50 mg) under ice-cooling, and the mixture was stirred for 1 hour. 6-(Chloromethyl)pyridine-2-carbonitrile (158 mg) was added thereto in one portion, and the mixture was gradually warmed to room temperature. 13 Hours later, to the reaction mixture were added a saturated aqueous ammonium chloride solution and water, followed by extraction with ethyl acetate. The organic layer was washed with water and saturated brine successively, dried over anhydrous magnesium sulfate, and then concentrated under reduced pressure. The residue was purified by silica gel column chromatography (eluting solvent: ethyl acetate-hexane) to obtain the title compound (271 mg). $^1$H-NMR (CDCl$_3$) δ ppm: 0.62-0.73 (2H, m), 1.22-1.30 (5H, m), 1.57 (9H, s), 3.21 (1H, dd, J=8.2, 15.7 Hz), 3.54 (1H, dd, J=6.7, 15.7 Hz), 3.78 (3H, s), 4.68-4.78 (1H, m), 6.54-6.61 (1H, m), 6.95 (1H, d, J=8.5 Hz), 7.18-7.25 (1H, m), 7.33-7.40 (1H, m), 7.48-7.55 (1H, m), 7.64 (1H, t, J=7.8 Hz), 7.82 (1H, br s).

Reference Examples 150-2 to 150-4

In the same method as in Reference Example 150-1 using the corresponding starting materials and reaction agents, the title compounds were synthesized.

Reference Example 150-2 tert-Butyl {2-[1-(6-cyanopyridin-2-ylmethyl)-2-(1-methylcyclopropyl)-2-oxoethyl]-5-methylphenyl}carbamate: $^1$H-NMR (CDCl$_3$) δ ppm: 0.59-0.74 (2H, m), 1.18-1.32 (5H, m), 1.56 (9H, s), 2.29 (3H, s), 3.22 (1H, dd, J=8.0, 15.7 Hz), 3.56 (1H, dd, J=6.6, 15.7 Hz), 4.73-4.84 (1H, m), 6.80-6.88 (1H, m), 6.95 (1H, d, J=8.0 Hz), 7.19-7.25 (1H, m), 7.47-7.59 (2H, m), 7.64 (1H, t, J=7.8 Hz), 7.72 (1H, br s).

Reference Example 150-3 tert-Butyl {2-[1-(6-cyanopyridin-2-ylmethyl)-2-(1-methylcyclopropyl)-2-oxoethyl]-5-cyclopropylphenyl}carbamate: $^1$H-NMR (CDCl$_3$) δ ppm: 0.59-0.75 (4H, m), 0.84-0.97 (2H, m), 1.18-1.33 (5H, m), 1.56 (9H, s), 1.79-1.89 (1H, m), 3.20 (1H, dd, J=7.8, 15.8 Hz), 3.55 (1H, dd, J=6.5, 15.8 Hz), 4.73-4.81 (1H, m), 6.70 (1H, dd, J=2.0, 8.0 Hz), 6.94 (1H, d, J=8.0 Hz), 7.20-7.25 (1H, m), 7.40-7.55 (2H, m), 7.64 (1H, t, J=7.8 Hz), 7.72 (1H, br s).

Reference Example 150-4 tert-Butyl {5-chloro-2-[1-(6-cyanopyridin-2-ylmethyl)-2-(1-methylcyclopropyl)-2-oxoethyl]phenyl}carbamate
$^1$H-NMR (CDCl$_3$) δ ppm: 0.65-0.75 (2H, m), 1.22-1.30 (5H, m), 1.57 (9H, s), 3.22 (1H, dd, J=8.3, 16.0 Hz), 3.57 (1H, dd, J=6.4, 16.0 Hz), 4.75-4.83 (1H, m), 6.95-7.04 (2H, m), 7.50-7.57 (1H, m), 7.67 (1H, t, J=7.8 Hz), 7.81-7.86 (1H, m), 7.95 (1H, br s).

Reference Example 151

6-(2-Isopropyl-6-methoxy-1H-indol-3-ylmethyl)pyridine-2-carbonitrile

To a solution of tert-butyl {2-[1-(6-cyanopyridin-2-ylmethyl)-3-methyl-2-oxobutyl]-5-methoxyphenyl}carbamate (269 mg) in dichloromethane (13 mL) was added trifluoroacetic acid (2.6 mL) under ice-cooling, and the mixture was stirred at room temperature for 2.75 hours. To the reaction mixture was added a saturated aqueous sodium hydrogen carbonate solution. The organic layer was separated, washed with saturated brine, dried over anhydrous magnesium sulfate, and then concentrated under reduced pressure. The residue was purified by silica gel column chromatography (eluting solvent: ethyl acetate-hexane) to obtain the title compound (181 mg). $^1$H-NMR (CDCl$_3$) δ ppm: 1.28 (6H, d, J=7.0 Hz), 3.21-3.35 (1H, m), 3.83 (3H, s), 4.26 (2H, s), 6.73 (1H, dd, J=2.3, 8.8 Hz), 6.86 (1H, d, J=2.3 Hz), 7.19-7.29 (2H, m), 7.45-7.52 (1H, m), 7.55-7.64 (1H, m), 7.80 (1H, br s).

Reference Example 152-1

6-(2-Cyclopropyl-6-methoxy-1H-indol-3-ylmethyl)pyridine-2-carbonitrile

To a solution of tert-butyl {2-[1-(6-cyanopyridin-2-ylmethyl)-2-cyclopropyl-2-oxoethyl]-5-methoxyphenyl}carbamate (290 mg) in acetonitrile/dichloromethane (2.3 mL/2.3 mL) was added trifluoroacetic acid (2.3 mL) under ice-cooling, and the mixture was stirred at room temperature for 2 days. The reaction mixture was concentrated under reduced pressure. The residue was dissolved in ethyl acetate and the resulting mixture was washed with a saturated aqueous sodium hydrogen carbonate solution. The organic layer was separated, washed with water and saturated brine successively, dried over anhydrous magnesium sulfate, and then concentrated under reduced pressure. The residue was purified by silica gel column chromatography (eluting solvent: ethyl acetate-hexane) to obtain the title compound (189 mg). $^1$H-NMR (CDCl$_3$) δ ppm: 0.67-0.76 (2H, m), 0.92-1.02 (2H, m), 1.95-2.08 (1H, m), 3.82 (3H, s), 4.35 (2H, s), 6.71 (1H, dd, J=2.3, 8.5 Hz), 6.80 (1H, d, J=2.3 Hz), 7.18-7.29 (2H, m), 7.46-7.52 (1H, m), 7.55-7.68 (2H, m).

Reference Examples 152-2 to 152-5

In the same method as in Reference Example 152-1 using the corresponding starting materials and reaction agents, the title compounds were synthesized.

Reference Example 152-2

6-(2-Cyclohexyl-6-methoxy-1H-indol-3-ylmethyl)pyridine-2-carbonitrile: $^1$H-NMR (CDCl$_3$) δ ppm: 1.16-1.60 (5H, m), 1.71-1.95 (5H, m), 2.80-2.97 (1H, m), 3.83 (3H, s), 4.26 (2H, s), 6.72 (1H, dd, J=2.3, 8.5 Hz), 6.82-6.89 (1H, m), 7.18-7.28 (2H, m), 7.45-7.52 (1H, m), 7.55-7.63 (1H, m), 7.80 (1H, br s).

Reference Example 152-3

6-(2-Furan-3-yl-6-methyl-1H-indol-3-ylmethyl)pyridine-2-carbonitrile: $^1$H-NMR (CDCl$_3$) δ ppm: 2.46 (3H, s), 4.40 (2H, s), 6.64-6.71 (1H, m), 6.92-7.01 (1H, m), 7.15-7.21 (1H, m), 7.24-7.31 (1H, m), 7.35 (1H, d, J=8.0 Hz), 7.45-7.65 (3H, m), 7.75-7.82 (1H, m), 7.96 (1H, br s).

Reference Example 152-4

6-(6-Cyclopropyl-2-furan-3-yl-1H-indol-3-ylmethyl)pyridine-2-carbonitrile: $^1$H-NMR (CDCl$_3$) δ ppm: 0.67-0.76 (2H, m), 0.92-1.02 (2H, m), 1.96-2.07 (1H, m), 4.39 (2H, s), 6.63-6.70 (1H, m), 6.84-6.92 (1H, m), 7.08-7.13 (1H, m), 7.35 (1H, d, J=8.0 Hz), 7.46-7.55 (2H, m), 7.59 (1H, t, J=7.8 Hz), 7.74-7.80 (1H, m), 7.95 (1H, br s).

Reference Example 152-5

6-[6-Methoxy-2-(1-methylpropyl)-1H-indol-3-ylmethyl]pyridine-2-carbonitrile $^1$H-NMR (CDCl$_3$) δ ppm: 0.76-0.85

(3H, m), 1.26 (3H, d, J=7.0 Hz), 1.48-1.72 (2H, m), 2.94-3.06 (1H, m), 3.83 (3H, s), 4.26 (2H, s), 6.73 (1H, dd, J=2.3, 8.5 Hz), 6.86 (1H, d, J=2.3 Hz), 7.45-7.51 (1H, m), 7.55-7.62 (1H, m), 7.74 (1H, br s).

Reference Example 153-1

6-[6-Methoxy-2-(1-methylcyclopropyl)-1H-indol-3-ylmethyl]pyridine-2-carbonitrile To a solution of tert-butyl {2-[1-(6-cyanopyridin-2-ylmethyl)-2-(1-methylcyclopropyl)-2-oxoethyl]-5-methoxyphenyl}carbamate (270 mg) in acetonitrile/dichloromethane (2.1 mL/2.1 mL) was added trifluoroacetic acid (2.1 mL) under ice-cooling, and the mixture was stirred at room temperature for 44.5 hours. The reaction mixture was concentrated under reduced pressure. The residue was dissolved in ethyl acetate and the resulting mixture was washed with a saturated aqueous sodium hydrogen carbonate solution. The organic layer was dried over anhydrous sodium sulfate, and then concentrated under reduced pressure. The residue was purified by silica gel column chromatography (eluting solvent: ethyl acetate-hexane), and then purified by aminopropylated silica gel column chromatography to obtain the title compound (163 mg). $^1$H-NMR (CDCl$_3$) δ ppm: 0.70-0.78 (2H, m), 0.81-0.89 (2H, m), 1.33 (3H, s), 3.82 (3H, s), 4.39 (2H, s), 6.70 (1H, dd, J=2.3, 8.5 Hz), 6.80-6.85 (1H, m), 7.12-7.22 (2H, m), 7.47-7.53 (1H, m), 7.59 (1H, t, J=7.8 Hz), 7.87 (1H, br s).

Reference Examples 153-2 to 153-4

In the same method as in Reference Example 153-1 using the corresponding starting materials and reaction agents, the title compounds were synthesized.

Reference Example 153-2

6-[6-Methyl-2-(1-methylcyclopropyl)-1H-indol-3-ylmethyl]pyridine-2-carbonitrile $^1$H-NMR (CDCl$_3$) δ ppm: 0.70-0.77 (2H, m), 0.82-0.89 (2H, m), 1.33 (3H, s), 2.43 (3H, s), 4.41 (2H, s), 6.83-6.90 (1H, m), 7.08-7.21 (3H, m), 7.46-7.52 (1H, m), 7.58 (1H, t, J=7.8 Hz), 7.86 (1H, br s).

Reference Example 153-3

6-[6-Cyclopropyl-2-(1-methylcyclopropyl)-1H-indol-3-ylmethyl]pyridine-2-carbonitrile: $^1$H-NMR (CDCl$_3$) δ ppm: 0.63-0.78 (4H, m), 0.80-0.98 (4H, m), 1.33 (3H, s), 1.93-2.03 (1H, m), 4.40 (2H, s), 6.80 (1H, dd, J=1.5, 8.3 Hz), 7.00-7.05 (1H, m), 7.13-7.21 (2H, m), 7.46-7.52 (1H, m), 7.58 (1H, t, J=7.8 Hz), 7.85 (1H, br s).

Reference Example 153-4

6-[6-Chloro-2-(1-methylcyclopropyl)-1H-indol-3-ylmethyl]pyridine-2-carbonitrile $^1$H-NMR (CDCl$_3$) δ ppm: 0.73-0.81 (2H, m), 0.84-0.92 (2H, m), 1.35 (3H, s), 4.40 (2H, s), 6.99 (1H, dd, J=1.8, 8.5 Hz), 7.12-7.24 (2H, m), 7.27-7.32 (1H, m), 7.48-7.55 (1H, m), 7.61 (1H, t, J=7.8 Hz), 7.99 (1H, br s).

Examples 12-1 to 12-17

In the same method as in Example 7-1 using the corresponding starting materials, the compounds shown in Tables 17 to 20 were synthesized.

Example 13

5-[6-(6-Methoxy-2-phenyl-1H-indol-3-ylmethyl)pyridin-2-yl]isoxazol-3-ol

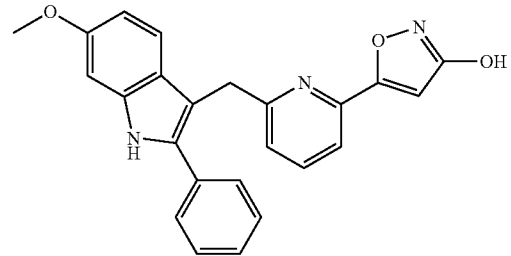 [SMILES: COc1ccc2c(Cc3cccc(-c4cc(O)no4)n3)c(-c3ccccc3)[nH]c2c1]

To a solution of methyl [6-(6-methoxy-2-phenyl-1H-indol-3-ylmethyl)pyridin-2-yl]propynoate (73 mg) and hydroxylamine (50% aqueous solution, 18.2 mg) in methanol (1 mL) was added 2 mol/L aqueous sodium hydroxide solution (0.166 mL), and this mixture was stirred at room temperature for 64 hours. To the reaction mixture were added water, ethyl acetate, and 2 mol/L hydrochloric acid (0.230 mL). The organic layer was separated. This organic layer was washed with water and saturated brine successively, dried over anhydrous magnesium sulfate, and then concentrated under reduced pressure. The residue was purified by silica gel column chromatography (eluting solvent: ethyl acetate-hexane) to obtain the title compound (33 mg). $^1$H-NMR (DMSO-d$_6$) δ ppm: 3.77 (3H, s), 4.34 (2H, s), 6.51 (1H, s), 6.60-6.68 (1H, m), 6.87 (1H, d, J=2.3 Hz), 7.24-7.43 (3H, m), 7.44-7.54 (2H, m), 7.64-7.73 (1H, m), 7.76-7.87 (3H, m), 11.16 (1H, s), 11.47 (1H, s).
ESI-MS (m/z): 398 (M+H)$^+$ Examples 14-1 to 14-6

In the same method as in Example 9 using the corresponding starting materials, the compounds shown in Table 21 were synthesized.

Example 15

5-[6-(2-tert-butyl-6-methoxy-1H-indol-3-ylmethyl)pyridin-2-yl]-2,3-dihydro-1,3,4-oxadiazol-2-one

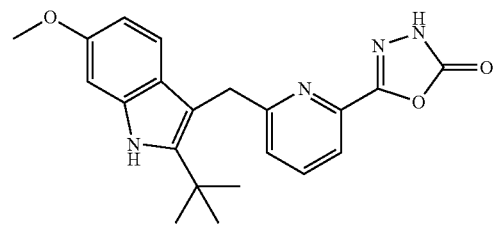 [SMILES: COc1ccc2c(Cc3cccc(-c4n[nH]c(=O)o4)n3)c(C(C)(C)C)[nH]c2c1]

In the same method as in Example 6 using the corresponding starting material, the title compound was synthesized.
¹H-NMR (DMSO-d₆) δ ppm: 1.37 (9H, s), 3.73 (3H, s), 4.36 (2H, s), 6.55 (1H, dd, J=2.3, 8.5 Hz), 6.83 (1H, d, J=2.3 Hz), 7.01-7.08 (1H, m), 7.16 (1H, d, J=8.5 Hz), 7.65-7.72 (1H, m), 7.77 (1H, t, J=7.8 Hz), 10.45 (1H, s), 12.72 (1H, s). ESI-MS (m/z): 379 (M+H)⁺

Examples 16-1 to 16-6

In the same method as in Example 10 using the corresponding starting materials, the compounds shown in Table 22 were synthesized.

Examples 17-1 to 17-14

In the same method as in Example 5-1 using the corresponding starting materials, the compounds shown in Tables 23 to 25 were synthesized.

Examples 18-1 to 18-14

In the same method as in Example 3-1 using the corresponding starting materials, the compounds shown in Tables 26 to 28 were synthesized.

TABLE 17

| Ex. No. | Strc | Physical data |
|---|---|---|
| 12-1 | | ¹H-NMR (DMSO-d₆) δ ppm: 3.77 (3H, s), 4.38 (2H, s), 6.66 (1H, dd, J = 2.3, 8.6 Hz), 6.84 (1H, d, J = 2.3 Hz), 6.92-6.98 (1H, m), 7.19-7.27 (1H, m), 7.43 (1H, d, J = 8.6 Hz), 7.73-7.80 (2H, m), 7.83 (1H, t, J = 7.8 Hz), 8.14-8.20 (1H, m), 11.08 (1H, s), 13.13 (1H, br s). ESI-MS (m/z): 387 (M − H)⁻ |
| 12-2 | | ¹H-NMR (DMSO-d₆) δ ppm: 1.35 (9H, s), 3.74 (3H, s), 4.41 (2H, s), 6.56 (1H, dd, J = 2.3, 8.6 Hz), 6.84 (1H, d, J = 2.3 Hz), 6.96-7.05 (1H, m), 7.15 (1H, d, J = 8.6 Hz), 7.68-7.86 (2H, m), 10.50 (1H, s), 13.08 (1H, br s). ESI-MS (m/z): 379 (M + H)⁺ |
| 12-3 | | ¹H-NMR (DMSO-d₆) δ ppm: 1.35 (9H, s), 3.83 (3H, s), 4.40 (2H, s), 6.96-7.04 (2H, m), 7.35 (1H, s), 7.73-8.86 (2H, m), 10.68 (1H, s), 13.07 (1H, br s). ESI-MS (m/z): 411 (M − H)⁻ |
| 12-4 | | ¹H-NMR (DMSO-d₆) δ ppm: 3.78 (3H, s), 4.23 (2H, s), 6.30 (1H, d, J = 3.5 Hz), 6.66 (1H, dd, J = 2.3, 8.8 Hz), 6.87 (1H, d, J = 2.3 Hz), 7.06 (1H, d, J = 3.5 Hz), 7.32-7.42 (2H, m), 7.45-7.55 (2H, m), 7.58-7.65 (2H, m), 11.20 (1H, s), 12.94 (1H, br s). ESI-MS (m/z): 386 (M − H)⁻ |

TABLE 17-continued

| Ex. No. | Strc | Physical data |
|---|---|---|
| 12-5 | | $^1$H-NMR (DMSO-$d_6$) δ ppm:<br>3.86 (3H, s), 4.36 (2H, s), 7.03 (1H, d, J = 7.3 Hz), 7.14-7.21 (1H, m), 7.26 (1H, d, J = 11.8 Hz), 7.32-7.40 (1H, m), 7.42-7.53 (2H, m), 7.62-7.70 (2H, m), 7.71-7.85 (2H, m), 11.32 (1H, s), 13.08 (1H, br s).<br>ESI-MS (m/z): 415 (M − H)$^-$ |

TABLE 18

| Ex. No. | Strc | Physical data |
|---|---|---|
| 12-6 | | $^1$H-NMR (DMSO-$d_6$) δ ppm:<br>0.59-0.69 (2H, m), 0.88-0.98 (2H, m), 1.94-2.05 (1H, m), 4.42 (2H, s), 6.67-6.74 (1H, m), 7.07-7.12 (1H, m), 7.15-7.21 (1H, m), 7.28 (1H, d, J = 8.0 Hz), 7.32-7.40 (1H, m), 7.43-7.52 (2H, m), 7.60-7.69 (2H, m), 7.75-7.81 (1H, m), 7.84 (1H, t, J = 7.8 Hz), 11.21 (1H, s), 13.08 (1H, br s).<br>ESI-MS (m/z): 407 (M − H)$^-$ |
| 12-7 | | $^1$H-NMR (DMSO-$d_6$) δ ppm:<br>2.23 (3H, s), 2.30 (3H, s), 4.41 (2H, s), 7.11-7.23 (3H, m), 7.30-7.38 (1H, m), 7.40-7.50 (2H, m), 7.57-7.65 (2H, m), 7.74-7.81 (1H, m), 7.84 (1H, t, J = 7.8 Hz), 11.12 (1H, s), 13.08 (1H, br s).<br>ESI-MS (m/z): 397 (M + H)$^+$ |
| 12-8 | | $^1$H-NMR (DMSO-$d_6$) δ ppm:<br>3.77 (3H, s), 4.38 (2H, s), 6.64 (1H, dd, J = 2.3, 8.8 Hz), 6.87 (1H, d, J = 2.3 Hz), 7.19-7.25 (1H, m), 7.26-7.37 (3H, m), 7.62-7.73 (2H, m), 7.74-7.80 (1H, m), 7.85 (1H t, J = 7.8 Hz), 11.22 (1H, s), 13.07 (1H, br s).<br>ESI-MS (m/z): 417 (M + H)$^+$ |
| 12-9 | | $^1$H-NMR (DMSO-$d_6$) δ ppm:<br>2.39 (3H, s), 4.45 (2H, s), 6.79-6.86 (1H, m), 7.13-7.18 (1H, m), 7.18-7.25 (1H, m), 7.41 (1H, d, J = 8.0 Hz), 7.53 (1H, dd, J = 1.5, 5.0 Hz), 7.67 (1H, dd, J = 2.8, 5.0 Hz), 7.74-7.80 (1H, m), 7.83 (1H, t J = 7.8 Hz), 7.85-7.91 (1H, m), 11.17 (1H, s), 13.12 (1H, br s).<br>ESI-MS (m/z): 387 (M − H)$^-$ |

TABLE 18-continued

| Ex. No. | Strc | Physical data |
| --- | --- | --- |
| 12-10 | | $^1$H-NMR (DMSO-d$_6$) δ ppm:<br>3.58 (3H, s), 3.81 (3H, s), 4.19 (2H, s), 6.66 (1H, dd, J = 2.3, 8.5 Hz), 7.03 (1H, d, J = 2.3Hz), 7.11-7.19 (1H, m), 7.30 (1H, d, J = 8.5 Hz), 7.40-7.59 (5H, m), 7.71-7.77 (1H, m), 7.82 (1H, t, J = 7.8 Hz), 13.00 (1H, br s).<br>ESI-MS (m/z): 413 (M + H)$^+$ |

TABLE 19

| Ex. No. | Strc | Physical data |
| --- | --- | --- |
| 12-11 | | $^1$H-NMR(DMSO-d$_6$) δ ppm:<br>2.39 (3H, s), 4.39 (2H, s), 6.79-6.86 (1H, m), 6.95-7.01 (1H, m), 7.11-7.25 (2H, m), 7.43 (1H, d, J = 8.0 Hz), 7.73-7.89 (3H, m), 8.17-8.23 (1H, m), 11.08 (1H, s), 13.12 (1H, br s).<br>ESI-MS (m/z): 371 (M − H)$^-$ |
| 12-12 | | $^1$H-NMR(DMSO-d$_6$) δ ppm:<br>1.10-1.88 (10H, m), 2.86-3.00 (1H, m), 3.72 (3H, s), 4.21 (2H, s), 6.55 (1H, dd, J = 2.3, 8.5 Hz), 6.74-6.80 (1H, m), 7.16-7.23 (1H, m), 7.26 (1H, d, J = 8.5 Hz), 7.71-7.78 (1H, m), 7.82 (1H, t, J = 7.8 Hz), 10.60 (1H, s), 13.05 (1H, br s).<br>ESI-MS(m/z): 405 (M + H)$^+$ |
| 12-13 | | $^1$H-NMR (DMSO-d$_6$) δ ppm:<br>0.60-0.69 (2H, m), 0.89-0.98 (2H, m), 1.93-2.06 (1H, m), 4.38 (2H, s), 6.69-6.76 (1H, m), 6.94-7.00 (1H, m), 7.03-7.08 (1H, m), 7.18-7.25 (1H, m), 7.42 (1H, d, J = 8.3 Hz), 7.73-7.88 (3H, m), 8.17-8.23 (1H, m), 11.07 (1H, s), 13.13 (1H, br s).<br>ESI-MS (m/z): 397 (M − H)$^-$ |
| 12-14 | | 1H-NMR (DMSO-d6) δ ppm:<br>0.63-0.92 (4H, m), 1.30 (3H, s), 3.72 (3H, s) 4.32 (2H, s), 6.53 (1H, dd, J = 2.3, 8.5 Hz), 6.73-6.79 (1H, m), 7.08-7.17 (2H, m), 7.73-7.80 (1H, m), 7.83 (1H, t, J = 7.8 Hz), 10.75 (1H, s), 13.05 (1H, br s).<br>ESI-MS (m/z): 377 (M + H)$^+$ |

TABLE 19-continued

| Ex. No. | Strc | Physical data |
| --- | --- | --- |
| 12-15 | | $^1$H-NMR (DMSO-d$_6$) δ ppm:<br>0.67-0.75 (2H, m), 0.80-0.88 (2H, m), 1.30 (3H, s), 2.33 (3H, s), 4.34 (2H, s), 6.66-6.73 (1H, m), 7.02 -7.15 (3H, m), 7.73-7.79 (1H, m), 7.82 (1H, t, J = 7.8 Hz), 10.76 (1H, s), 13.04 (1H, br s).<br>ESI-MS (m/z): 361 (M + H)$^+$ |

TABLE 20

| Ex. No. | Strc | Physical data |
| --- | --- | --- |
| 12-16 | | $^1$H-NMR (DMSO-d$_6$) δ ppm:<br>0.53-0.62 (2H, m), 0.67-0.76 (2H, m), 0.79-0.93 (4H, m), 1.30 (3H, s), 1.88-1.99 (1H, m), 4.33 (2H, s), 6.58-6.65 (1H, m), 6.92-6.98 (1H, m), 7.07-7.15 (2H, m), 7.72-7.79 (1H, m), 7.82 (1H, t, J = 7.8 Hz), 10.74 (1H, s), 13.04 (1H, br s).<br>ESI-MS (m/z): 387(M + H)$^+$ |
| 12-17 | | $^1$H-NMR (DMSO-d$_6$) δ ppm:<br>0.70-0.77 (2H, m), 0.83-0.90 (2H, m), 1.31 (3H, s), 4.35 (2H, s), 6.85-6.92 (1H, m), 7.11-7.17 (1H, m), 7.24-7.32 (2H, m), 7.74-7.80 (1H, m), 7.84 (1H, t, J = 7.8 Hz), 11.13 (1H, s), 13.04 (1H, br s).<br>ESI-MS (m/z): 379 (M − H)$^-$ |

TABLE 21

| Ex. No. | Strc | Physical data |
| --- | --- | --- |
| 14-1 | | $^1$H-NMR (DMSO-d$_6$) δ ppm:<br>1.35 (9H, s), 3.63 (3H, s), 4.39 (2H, s), 6.91-7.06 (2H, s), 7.36 (1H, s), 7.71-7.89 (2H, m), 10.67 (1H, s).<br>ESI-MS (m/z): 427 (M − H)$^-$ |
| 14-2 | | $^1$H-NMR (DMSO-d$_6$) δ ppm:<br>1.36 (9H, s), 3.73 (3H, s), 4.34 (2H, s), 6.55 (1H, dd, J = 2.3, 8.5 Hz), 6.80-6.90 (2H, m), 7.16 (1H, d, J = 8.5Hz), 7.63-7.70 (2H, m), 10.43 (1H, s).<br>ESI-MS (m/z): 395 (M + H)$^+$ |

TABLE 21-continued

| Ex. No. | Strc | Physical data |
|---|---|---|
| 14-3 | | ¹H-NMR (DMSO-d₆) δ ppm:<br>2.39 (3H, s), 4.34 (2H, s), 6.74-6.85 (1H, m), 7.06-7.22 (2H, m), 7.25-7.55 (4H, m), 7.62-7.85 (4H, m), 11.17 (1H, s).<br>ESI-MS (m/z): 399 (M + H)⁺ |
| 14-4 | | ¹H-NMR (DMSO-d₆) δ ppm:<br>3.65 (3H, s), 4.30 (2H, s), 7.02 (1H, d, J = 7.5 Hz), 7.12-7.18 (1H, m), 7.27 (1H, d, J = 12.1 Hz), 7.31-7.39 (1H, m), 7.42- 7.52 (2H, m), 7.67-7.80 (4H, m), 11.27 (1H, s).<br>ESI-MS (m/z): 431 (M − H)⁻ |
| 14-5 | | ¹H-NMR (DMSO-d₆) δ ppm:<br>0.60-0.68 (2H, m), 0.88-0.97 (2H, m), 1.93-2.05 (1H, m), 4.40 (2H, s), 6.67-6.75 (1H, m), 7.06-7.13 (1H, m), 7.17-7.25 (1H, m), 7.30 (1H, d, J = 8.3 Hz), 7.32-7.40 (1H, m), 7.43-7.53 (2H, m), 7.63-7.73 (2H, m), 7.77-7.89 (2H, m), 11.20 (1H, s).<br>ESI-MS (m/z): 423 (M − H)⁻ |
| 14-6 | | ¹H-NMR (DMSO-d₆) δ ppm:<br>2.39 (3H, s), 4.44 (2H, s), 6.79-6.87 (1H, m), 7.12-7.30 (2H, m), 7.42 (1H, d, J = 8.0 Hz), 7.55 (1H, dd, J = 1.3, 5.0 Hz), 7.67 (1H, dd, J = 3.0, 5.0 Hz), 7.77-7.89 (2H, m), 7.92-7.99 (1H, m), 11.17 (1H, s).<br>ESI-MS (m/z): 403 (M − H)⁻ |

TABLE 22

| Ex. No. | Strc | Physical data |
|---|---|---|
| 16-1 | | ¹H-NMR (DMSO-d₆) δ ppm:<br>2.39 (3H, s), 4.46 (2H, s), 6.76-6.84 (1H, m), 7.15-7.52 (6H, m), 7.58-7.68 (2H, m), 7.80-7.95 (2H, m), 11.25 (1H, s).<br>ESI-MS (m/z): 367 (M + H)⁺ |

TABLE 22-continued

| Ex. No. | Strc | Physical data |
| --- | --- | --- |
| 16-2 | | ¹H-NMR (DMSO-d₆) δ ppm:<br>1.34 (9H, s), 3.74 (3H, s), 4.44 (2H, s), 6.56 (1H, dd, J = 2.3, 8.5 Hz), 6.85 (1H, d, J = 2.3 Hz), 6.97-7.17 (2H, m), 7.76-7.95 (2H, m), 10.49 (1H, s).<br>ESI-MS (m/z): 363 (M + H)⁺ |
| 16-3 | | ¹H-NMR (DMSO-d6) δ ppm:<br>3.85 (3H, s), 4.28 (2H, br s), 6.98-7.94 (10H, m), 11.28 (1H, br s).<br>ESI-MS (m/z): 399 (M − H)⁻ |
| 16-4 | | ¹H-NMR (DMSO-d6) δ ppm:<br>0.58-0.69 (2H, m), 0.87-0.98 (2H, m), 1.93-2.05 (1H, m), 4.32 (2H, br s), 6.62-6.75 (1H, m), 6.93-8.10 (10H, m), 11.17 (1H, br s).<br>ESI-MS (m/z): 393 (M + H)⁺ |
| 16-5 | | ¹H-NMR (DMSO-d6) δ ppm:<br>1.33 (9H, s), 3.83 (3H, s), 4.48 (2H, s), 7.00 (1H, s), 7.05-7.18 (1H, m), 7.38 (1H, s), 7.88-8.04 (2H, m), 10.71 (1H, s).<br>ESI-MS (m/z): 395 (M − H)⁻ |
| 16-6 | | ¹H-NMR (DMSO-d6) δ ppm:<br>2.39 (3H, s), 4.53 (2H, s), 6.79-6.87 (1H, m), 7.14-7.29 (2H, m), 7.37 (1H, d, J = 8.0 Hz), 7.51 (1H, dd, J = 1.3, 5.0 Hz), 7.67 (1H, dd, J = 3.0, 5.0 Hz), 7.76-7.82 (1H, m), 7.87-8.00 (2H, m), 11.22 (1H, s).<br>ESI-MS (m/z): 371 (M − H)⁻ |

TABLE 23

| Ex. No. | Strc | Physical data |
|---|---|---|
| 17-1 | 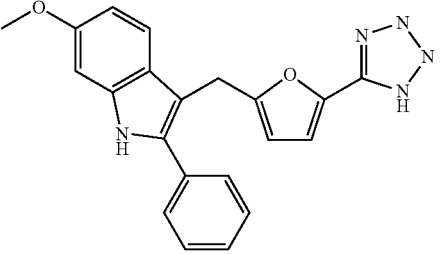 | ¹H-NMR (DMSO-d₆) δ ppm:<br>3.78 (3H, s), 4.27 (2H, s), 6.23-6.31 (1H, m), 6.61-6.70 (1H, m), 6.88 (1H, d, J = 2.3 Hz), 7.12 (1H, d, J = 3.5 Hz), 7.30-7.69 (6H, m), 11.20 (1H, s).<br>ESI-MS (m/z): 370 (M − H)⁻ |
| 17-2 | 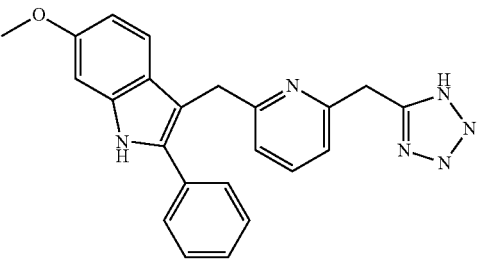 [SMILES: COc1ccc2c(Cc3cccc(CC4=NNNN4)n3)c(-c3ccccc3)[nH]c2c1] | ¹H-NMR (DMSO-d₆) δ ppm:<br>3.77 (3H, s), 4.20 (2H, s), 4.46 (2H, s), 6.60 (1H, dd, J = 2.3, 8.8 Hz), 6.65 (1H, d J = 2.3 Hz), 7.01-7.08 (1H, m), 7.17-7.45 (5H, m), 7.58-7.68 (3H, m), 11.10 (1H s).<br>ESI-MS (m/z): 397 (M + H)⁺ |
| 17-3 | 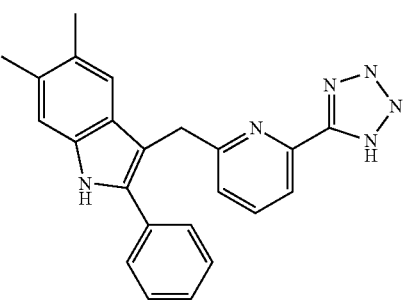 [SMILES: Cc1cc2[nH]c(-c3ccccc3)c(Cc3cccc(C4=NNNN4)n3)c2cc1C] | ¹H-NMR (DMSO-d₆) δ ppm:<br>2.22 (3H, s), 2.30 (3H, s), 4.46 (2H, s), 7.09-7.23 (3H, m), 7.28-7.37 (1H, m), 7.40-7.50 (2H, m), 7.57-7.66 (2H, m), 7.87 (1H, t, J = 7.8 Hz), 7.99-8.06 (1H, m), 11.13 (1H, s).<br>ESI-MS (m/z): 381 (M + H)⁺ |
| 17-4 | 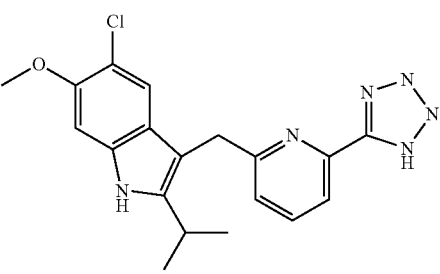 [SMILES: COc1cc2[nH]c(C(C)C)c(Cc3cccc(C4=NNNN4)n3)c2cc1Cl] | ¹H-NMR (DMSO-d₆) δ ppm:<br>1.22 (6H, d, J = 7.0 Hz), 3.26-3.42 (1H, m), 3.81 (3H, s), 4.25 (2H, s), 6.93 (1H, s), 7.15-7.23 (1H, m), 7.49 (1H, s), 7.84-7.92 (1H, m), 7.96-8.03 (1H, m), 10.85 (1H, s).<br>ESI-MS (m/z): 383 (M + H)⁺ |
| 17-5 | 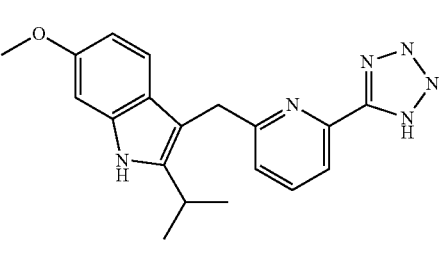 [SMILES: COc1ccc2c(Cc3cccc(C4=NNNN4)n3)c(C(C)C)[nH]c2c1] | ¹H-NMR (DMSO-d₆) δ ppm:<br>1.23 (6H, d, J = 6.8 Hz), 3.72 (3H, s), 4.25 (2H, s), 6.55 (1H, dd, J = 2.3, 8.6 Hz), 6.78 (1H, d, J = 2.3 Hz), 7.13-7.20 (1H, m), 7.28 (1H, d, J = 8.6 Hz), 7.86 (1H, t, J = 7.8 Hz), 7.96-8.04 (1H, m), 10.64 (1H, s).<br>ESI-MS (m/z): 349 (M + H)⁺ |
| 17-6 | 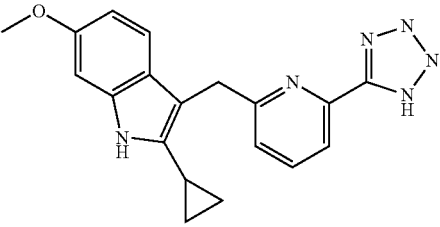 [SMILES: COc1ccc2c(Cc3cccc(C4=NNNN4)n3)c(C3CC3)[nH]c2c1] | ¹H-NMR (DMSO-d₆) δ ppm:<br>0.77-0.86 (2H, m), 0.88-0.98 (2H, m), 2.14-2.25 (1H, m), 3.70 (3H, s), 4.33 (2H, s), 6.50-6.57 (1H, m), 6.69-6.75 (1H, m), 7.17-7.27 (2H, m), 7.87 (1H, t, J = 7.8 Hz), 7.94-8.02 (1H, m), 10.33 (1H, s).<br>ESI-MS (m/z): 347 (M + H)⁺ |

TABLE 24

| Ex. No. | Strc | Physical data |
|---|---|---|
| 17-7 | | ¹H-NMR (DMSO-d₆) δ ppm :<br>1.13-1.83 (10H, m), 2.86-3.00 (1H, m), 3.72 (3H, s), 4.25 (2H, s), 6.54 (1H, dd, J = 2.3, 8.5 Hz), 6.74-6.82 (1H, m), 7.10-7.18 (1H, m), 7.27 (1H, d, J = 8.5 Hz), 7.84 (1H, t, J = 7.8 Hz), 7.94-8.01 (1H, m), 10.59 (1H, s).<br>ESI-MS (m/z): 389 (M + H)⁺ |
| 17-8 | | ¹H-NMR (DMSO-d₆) δ ppm:<br>2.39 (3H, s), 4.43 (2H, s), 6.77-6.86 (1H, m), 6.94-7.03 (1H, m), 7.11-7.22 (2H, m), 7.42 (1H, d, J = 8.0 Hz), 7.74-7.81 (1H, m), 7.84 (1H, d, J = 7.8 Hz), 7.96-8.04 (1H, m), 8.18-8.25 (1H, m), 11.09 (1H, s).<br>ESI-MS (m/z): 357 (M + H)⁺ |
| 17-9 | | ¹H-NMR (DMSO-d₆) δ ppm:<br>0.60-0.69 (2H, m), 0.88-0.98 (2H, m), 1.94-2.04 (1H, m), 4.42 (2H, s), 6.68-6.77 (1H, m), 6.94-7.00 (1H, m), 7.03-7.09 (1H, m), 7.13-7.20 (1H, m), 7.41 (1H, d, J = 8.3 Hz), 7.75-7.80 (1H, m), 7.84 (1H, t, J = 7.8 Hz), 7.95-8.02 (1H, m), 8.18-8.25 (1H, m), 11.08 (1H, s).<br>ESI-MS (m/z): 383 (M + H)⁺ |
| 17-10 | | ¹H-NMR (DMSO-d₆) δ ppm:<br>0.70 (3H, t, J = 7.4 Hz), 1.22 (3H, d, J = 7.0 Hz), 1.52-1.70 (2H, m), 2.97-3.10 (1H, m), 3.73 (3H, s), 4.18-4.32 (2H, m), 6.55 (1H, dd, J = 2.3, 8.5 Hz), 6.75-6.83 (1H, m), 7.11-7.19 (1H, m), 7.28 (1H, d, J = 8.5 Hz), 7.84 (1H, t, J = 7.8 Hz), 7.94-8.02 (1H, m), 10.59 (1H, s).<br>ESI-MS (m/z): 363 (M + H)⁺ |
| 17-11 | | ¹H-NMR (DMSO-d₆) δ ppm:<br>0.66-0.75 (2H, m), 0.80-0.89 (2H, m), 1.31 (3H, s), 3.72 (3H, s), 4.36 (2H, s), 6.53 (1H, dd, J = 2.3, 8.5 Hz), 6.73-6.82 (1H, m), 7.02-7.10 (1H, m), 7.14 (1H, d, J = 8.5 Hz), 7.83 (1H, t, J = 7.8 Hz), 7.95-8.03 (1H, m), 10.76 (1H, s).<br>ESI-MS (m/z): 361 (M + H)⁺ |

TABLE 25

| Ex. No. | Strc | Physical data |
|---|---|---|
| 17-12 | | $^1$H-NMR (DMSO-d$_6$) δ ppm :<br>0.67-0.75 (2H, m), 0.80-0.88 (2H, m), 1.31 (3H, s), 2.33 (3H, s), 4.39 (2H, s), 6.66-6.73 (1H, m), 7.02-7.10 (2H, m), 7.14 (1H, d, J = 8.0 Hz), 7.85 (1H, t, J = 7.8 Hz), 7.97-8.04 (1H, m), 10.78 (1H, s).<br>ESI-MS (m/z): 345 (M + H)$^+$ |
| 17-13 | | $^1$H-NMR (DMSO-d$_6$) δ ppm:<br>0.54-0.61 (2H, m), 0.67-0.75 (2H, m), 0.80-0.92 (4H, m), 1.31 (3H, s), 1.88-1.99 (1H, m), 4.38 (2H, s), 6.58-6.65 (1H, m), 6.94-6.98 (1H, m), 7.04-7.10 (1H, m), 7.13 (1H, d, J = 8.3 Hz), 7.81-7.89 (1H, m), 7.97-8.03 (1H, m), 10.75 (1H, s).<br>ESI-MS (m/z): 371 (M + H)$^+$ |
| 17-14 | | $^1$H-NMR (DMSO-d$_6$) δ ppm:<br>0.70-0.78 (2H, m), 0.83-0.92 (2H, m), 1.31 (3H, s), 4.40 (2H, s), 6.85-6.92 (1H, m), 7.05-7.12 (1H, m), 7.24-7.35 (2H, m), 7.86 (1H, t, J = 7.8 Hz), 7.97-8.04 (1H, m), 11.14 (1H, s).<br>ESI-MS (m/z): 365 (M + H)$^+$ |

TABLE 26

| Ex. No. | Strc | Physical data |
|---|---|---|
| 18-1 | | $^1$H-NMR (DMSO-d$_6$) δ ppm:<br>1.27 (3H, t, J = 7.3 Hz), 3.54 (2H, q, J = 7.3 Hz), 3.81 (3H, s), 4.50 (2H, s), 7.30 (1H, s), 7.38 (1H, dd, J = 2.3, 6.5 Hz), 7.43 (1H, s), 7.47-7.56 (1H, m), 7.83-7.94 (2H, m), 8.13-8.21 (1H, m), 8.53-8.61 (1H, m), 8.81-8.88 (1H, m), 11.00-12.00 (1H, br), 11.51 (1H, s).<br>ESI-MS (m/z): 485 (M + H)$^+$ |
| 18-2 | | $^1$H-NMR (DMSO-d$_6$) δ ppm:<br>2.41 (3H, s), 3.78 (3H, s), 4.44 (2H, s), 6.65 (1H, dd, J = 2.3, 8.8 Hz), 6.85-6.90 (1H, m), 7.27-7.42 (3H, m), 7.42-7.59 (4H, m), 7.64-7.90 (6H, m), 11.20 (1H, s), 11.80-12.12 (1H br),<br>ESI-MS (m/z): 512 (M + H)$^+$ |

TABLE 26-continued

| Ex. No. | Strc | Physical data |
|---|---|---|
| 18-3 | | ¹H-NMR (DMSO-d₆) δ ppm:<br>1.34 (6H, d, J = 6.8 Hz), 3.72-3.89 (4H, m), 4.42 (2H, s), 7.02 (1H, d, J = 7.5 Hz), 7.31-7.42 (3H, m), 7.43-7.53 (2H, m), 7.65-7.73 (2H, m), 7.81-7.94 (2H, m), 11.12-11.52 (1H, br), 11.30 (1H, s).<br>ESI-MS (m/z): 482 (M + H)⁺ |
| 18-4 | | ¹H-NMR (DMSO-d₆) δ ppm:<br>1.07-1.31 (4H, m), 3.07-3.18 (1H, m), 3.86 (3H, s), 4.42 (2H, s), 7.02 (1H, d, J = 7.3 Hz), 7.31-7.41 (3H, m), 7.43-7.53 (2H, m), 7.64-7.73 (2H, m), 7.84-7.94 (2H, m), 11.31 (1H, s), 11.34-11.58 (1H, br).<br>ESI-MS (m/z): 480 (M + H)⁺ |
| 18-5 | | ¹H-NMR (DMSO-d₆) δ ppm:<br>1.00 (3H, t, J = 7.4 Hz), 1.69-1.82 (2H, m), 3.46-3.56 (2H, m), 3.85 (3H, s), 4.42 (2H, s), 7.02 (1H, d, J = 7.5 Hz), 7.31-7.41 (3H, m), 7.43-7.53 (2H, m), 7.65-7.72 (2H, m), 7.83-7.93 (2H, m), 11.23-11.57 (1H, br), 11.80 (1H, s).<br>ESI-MS (m/s): 482 (M + H)⁺ |

TABLE 27

| Ex. No. | Strc | Physical data |
|---|---|---|
| 18-6 | | ¹H-NMR (DMSO-d₆) δ ppm:<br>1.34 (6H, d, J = 6.8 Hz), 1.37 (9H, s), 3.74-3.87 (4H, m), 4.43 (2H, s), 6.98 (1H, s) 7.19 (1H, dd, J = 2.0, 6.8 Hz), 7.36 (1H, s), 7.81-7.91 (2H, m), 10.65 (1H, s), 11.10-11.58 (1H, br).<br>ESI-MS (m/z): 473 (M + H)⁺ |
| 18-7 | | ¹H-NMR (DMSO-d₆) δ ppm:<br>3.78 (3H, s), 4.47 (2H, s), 6.65 (1H, dd, J = 2.3, 8.5 Hz), 6.85-6.91 (1H, m), 7.27-7.40 (3H, m), 7.43-7.52 (2H, m), 7.62-7.74 (3H, m), 7.77-7.92 (3H, m), 7.97-8.09 (2H, m), 11.22 (1H, s).<br>ESI-MS (m/z): 532 (M + H)⁺ |

TABLE 27-continued

| Ex. No. | Strc | Physical data |
| --- | --- | --- |
| 18-8 | | $^1$H-NMR (DMSO-$d_6$) δ ppm:<br>3.78 (3H, s), 3.84 (3H, s), 4.45 (2H, s), 6.65 (1H, dd, J = 2.3, 8.5 Hz), 6.88 (1H, d, J = 2.3 Hz), 7.23-7.89 (13H, m), 11.20 (1H, s), 11.50-12.60 (1H, br).<br>ESI-MS (m/z): 528 (M + H)$^+$ |
| 18-9 | | $^1$H-NMR (DMSO-$d_6$) δ ppm:<br>1.29 (3H, t, J = 7.3 Hz), 2.39 (3H, s), 3.54 (2H, q, J = 7.3 Hz), 4.49 (2H, s), 6.79-6.87 (1H, m), 7.12-7.18 (1H, m), 7.29-7.37 (1H, m), 7.45 (1H, d, J = 8.3 Hz), 7.59 (1H, dd, J = 1.4, 5.1 Hz), 7.66 (1H, dd, J = 3.0, 5.1 Hz), 7.82-7.94 (3H, m), 11.16 (1H, s), 11.32-11.64 (1H, br).<br>ESI-MS (m/z): 440 (M + H)$^+$ |
| 18-10 | | $^1$H-NMR (DMSO-$d_6$) δ ppm:<br>1.35 (6H, d, J = 7.0 Hz), 2.39 (3H, s), 3.73-3.86 (1H, m), 4.50 (2H, s), 6.79-6.86 (1H, m), 7.12-7.18 (1H, m), 7.35 (1H, dd, J = 2.5, 6.3 Hz), 7.47 (1H, d, J = 8.0 Hz), 7.59 (1H, dd, J = 1.4, 5.1 Hz), 7.66 (1H, dd, J = 2.8, 5.1 Hz), 7.81-7.95 (3H, m), 11.16 (1H, s), 11.30-11.54 (1H, br).<br>ESI-MS (m/z): 454 (M + H)$^+$ |
| 18-11 | | $^1$H-NMR (DMSO-$d_6$) δ ppm:<br>3.86 (3H, s), 4.42 (2H, s), 7.02 (1H, d, J = 7.5 Hz), 7.25-7.41 (3H, m), 7.42-7.55 (2H, m), 7.58-7.89 (7H, m), 8.00-8.11 (2H, m), 11.32 (1H, s), 11.70-12.40 (1H, br).<br>ESI-MS (m/z): 516 (M + H)$^+$ |

TABLE 28

| Ex. No. | Strc | Physical data |
| --- | --- | --- |
| 18-12 | | $^1$H-NMR (DMSO-$d_6$) δ ppm:<br>1.05-1.29 (4H, m), 1.38 (9H, s), 3.07-3.17 (1H, m), 3.73 (3H, s), 4.43 (2H, s), 6.55 (1H, dd, J = 2.3, 8.5 Hz), 6.84 (1H, d, J = 2.3 Hz), 7.13-7.22 (2H, m), 7.81-7.90 (2H, m), 10.46 (1H, s), 11.10-11.80 (1H, br).<br>ESI-MS (m/z): 442 (M + H)$^+$ |

TABLE 28-continued

| Ex. No. | Strc | Physical data |
|---|---|---|
| 18-13 | (structure) | $^1$H-NMR (DMSO-d$_6$) δ ppm:<br>1.37 (9H, s), 3.74 (3H, s), 4.47 (2H, s), 6.56 (1H, dd, J = 2.3, 8.7 Hz), 6.84 (1H, d, J = 2.3 Hz), 7.13-7.23 (2H, m), 7.40-7.50 (2H, m), 7.72-7.82 (2H, m), 7.87 (1H, t, J = 7.8 Hz), 7.99-8.07 (1H, m), 10.48 (1H, s).<br>ESI-MS (m/z): 496 (M + H)$^+$ |
| 18-14 | (structure) | $^1$H-NMR (DMSO-d$_6$) δ ppm:<br>1.37 (9H, s), 2.60 (3H, s), 3.74 (3H, s), 4.45 (2H, s), 6.56 (1H, dd, J = 2.3, 8.5 Hz), 6.84 (1H, d, J = 2.3 Hz), 7.10-7.25 (2H, m), 7.35-7.53 (2H, m), 7.53-7.65 (1H, m), 7.67-7.74 (1H, m), 7.74-7.85 (1H, m), 8.02-8.11 (1H, m), 10.45 (1H, s).<br>ESI-MS (m/z): 492 (M + H)$^+$ |

Reference Example 154

Tert-Butyl 6-methoxy-3-(6-methoxycarbonylpyridin-2-ylmethyl)-2-phenyl-1H-indole-1-carboxylate To a suspension of methyl 6-(6-methoxy-2-phenyl-1H-indol-3-ylmethyl)pyridine-2-carboxylate (0.5 g) in acetonitrile (5 mL) were added a solution of di-tert-butyl dicarbonate (440 mg) in acetonitrile (1 mL) and 4-dimethylaminopyridine (5 mg) at room temperature, and the mixture was stirred for 3 hours. The reaction mixture was concentrated under reduced pressure. The residue was purified by silica gel column chromatography (eluting solvent: ethyl acetate-hexane) to obtain the title compound (629 mg). $^1$H-NMR (CDCl$_3$) δ ppm: 1.23 (9H, s), 3.89 (3H, s), 4.01 (3H, s), 4.19 (2H, s), 6.82 (1H, dd, J=2.3, 8.6 Hz), 7.08-7.14 (1H, m), 7.23 (1H, d, J=8.6 Hz), 7.29-7.42 (5H, m), 7.61 (1H, t, J=7.8 Hz), 7.86 (1H, d, J=2.3 Hz), 7.90-7.95 (1H, m).

Reference Example 155

Tert-Butyl 3-(6-hydroxymethylpyridin-2-ylmethyl)-6-methoxy-2-phenyl-1H-indole-1-carboxylate To a solution of tert-butyl 6-methoxy-3-(6-methoxycarbonylpyridin-2-ylmethyl)-2-phenyl-1H-indole-1-carboxylate (628 mg) in methanol/tetrahydrofuran (6 mL/6 mL) was added sodium borohydride (251 mg) under ice-cooling. The mixture was stirred under ice-cooling for 2 hours. To the reaction mixture was added a saturated aqueous ammonium chloride solution carefully, followed by extraction with ethyl acetate. The organic layer was washed with water and saturated brine successively, dried over anhydrous magnesium sulfate, and then concentrated under reduced pressure to obtain the title compound (593 mg). $^1$H-NMR (CDCl$_3$) δ ppm: 1.23 (9H, s), 3.89 (3H, s), 3.95-4.01 (1H, m), 4.05 (2H, s), 4.65-4.72 (2H, m), 6.81-6.92 (2H, m), 6.94-7.00 (1H, m), 7.27-7.44 (6H, m), 7.44-7.52 (1H, m), 7.86 (1H, d, J=2.5 Hz).

Reference Example 156

Tert-Butyl 3-(6-formylpyridin-2-ylmethyl)-6-methoxy-2-phenyl-1H-indole-1-carboxylate To a solution of tert-butyl 3-(6-hydroxymethylpyridin-2-ylmethyl)-6-methoxy-2-phenyl-1H-indole-1-carboxylate (600 mg) in dichloromethane (6 mL) was added Dess-Martin periodinane (744 mg), and the mixture was stirred at room temperature for 2 hours. To the reaction mixture was added 1 mol/L aqueous sodium thiosulfate solution, followed by stirring for 5 minutes. The mixture was extracted with dichloromethane. The organic layer was washed with a saturated aqueous sodium hydrogen carbonate solution and saturated brine successively, dried over anhydrous sodium sulfate, and then concentrated under reduced pressure. The residue was purified by silica gel column chromatography (eluting solvent: ethyl acetate-hexane) to obtain the title compound (486 mg). $^1$H-NMR (CDCl$_3$) δ ppm: 1.23 (9H, s), 3.89 (3H, s), 4.15 (2H, s), 6.84 (1H, dd, J=2.3, 8.7 Hz), 7.15-7.21 (1H, m), 7.28-7.44 (6H, m), 7.61-7.69 (1H, m), 7.72-7.77 (1H, m), 7.86 (1H, d, J=2.3 Hz), 10.02-10.05 (1H, m).

Reference Example 157

Tert-Butyl 3-[6-((E)-2-cyanovinyl)pyridin-2-ylmethyl]-6-methoxy-2-phenyl-1H-indole-1-carboxylate To a solution of diethyl cyanomethylphosphonate (0.173 mL) in dimethylsulfoxide (6 mL) was added potassium tert-butoxide (127 mg) at room temperature, and the mixture was stirred for 30 minutes. Then a solution of tert-butyl 3-(6-formylpyridin-2-ylmethyl)-6-methoxy-2-phenyl-1H-indole-1-carboxylate (385 mg) in dimethylsulfoxide (3 mL) was added dropwise at room temperature, and the mixture was stirred overnight. To the reaction mixture were added water and saturated brine, followed by extraction with ethyl acetate. The aqueous layer was extracted with ethyl acetate. The combined organic layers were washed with water and saturated brine successively, dried over anhydrous magnesium sulfate, and then concentrated under reduced pressure. The residue was purified by silica gel column chromatography (eluting solvent: ethyl acetate-hexane) to obtain the title compound (192 mg). ¹H-NMR (CDCl₃) δ ppm: 1.23 (9H, s), 3.89 (3H, s), 4.04 (2H, s), 6.55 (1H, d, J=15.8 Hz), 6.82-6.90 (1H, m), 6.96-7.03 (1H, m), 7.04-7.12 (1H, m), 7.23-7.46 (7H, m), 7.48-7.57 (1H, m), 7.82-7.90 (1H, m).

Reference Example 158

(E)-3-[6-(6-Methoxy-2-phenyl-1H-indol-3-ylmethyl)pyridin-2-yl]acrylonitrile

To a solution of tert-butyl 3-[6-((E)-2-cyanovinyl)pyridin-2-ylmethyl]-6-methoxy-2-phenyl-1H-indole-1-carboxylate (100 mg) in acetonitrile/dichloromethane (1 mL/1 mL) was added trifluoroacetic acid (1 mL) under ice-cooling, and the mixture was stirred at room temperature overnight. To the reaction mixture were added ethyl acetate and a saturated aqueous sodium hydrogen carbonate solution. The organic layer was separated, washed with saturated brine, dried over anhydrous magnesium sulfate, and then concentrated under reduced pressure. The residue was purified by silica gel column chromatography (eluting solvent: ethyl acetate-hexane) to obtain the title compound (68.7 mg). ¹H-NMR (CDCl₃) δ ppm: 3.86 (3H, s), 4.40 (2H, s), 6.60 (1H, d, J=16.1 Hz), 6.76 (1H, dd, J=2.1, 8.7 Hz), 6.91 (1H, d, J=2.1 Hz), 7.07-7.16 (2H, m), 7.32-7.49 (5H, m), 7.50-7.63 (3H, m), 8.05 (1H, br s).

Reference Example 159

Tert-Butyl {5-chloro-4-methoxy-2-[2-(1-methylcyclopropyl)-2-oxoethyl]phenyl}carbamate In the same method as in Reference Example 131-1 using the corresponding starting material and reaction agents, the title compound was synthesized. ¹H-NMR (CDCl₃) δ ppm: 0.84-0.90 (2H, m), 1.35-1.45 (5H, m), 1.50 (9H, s), 3.64 (2H, s), 3.86 (3H, s), 6.63 (1H, s), 7.15-7.55 (1H, br), 7.59-7.80 (1H, br s).

Reference Example 160

Tert-Butyl {5-chloro-2-[1-(6-cyanopyridin-2-ylmethyl)-2-(1-methylcyclopropyl)-2-oxoethyl]-4-methoxyphenyl}carbamate In the same method as in Reference Example 150-1 using the corresponding starting material and reaction agents, the title compound was synthesized. ¹H-NMR (CDCl₃) δ ppm: 0.66-0.75 (2H, m), 1.21-1.31 (5H, m), 1.54 (9H, s), 3.25 (1H, dd, J=8.0, 16.0 Hz), 3.55 (1H, dd, J=6.6, 16.0 Hz), 3.82 (3H, s), 4.82-4.90 (1H, m), 6.65 (1H, s), 7.23-7.30 (1H, m), 7.34-7.58 (2H, m), 7.61-7.72 (2H, m).

Reference Example 161

6-[6-Chloro-5-methoxy-2-(1-methylcyclopropyl)-1H-indol-3-ylmethyl]pyridine-2-carbonitrile In the same method as in Reference Example 153-1 using the corresponding starting material and reaction agents, the title compound was synthesized. ¹H-NMR (CDCl₃) δ ppm: 0.73-0.80 (2H, m), 0.84-0.91 (2H, m), 1.35 (3H, s), 3.84 (3H, s), 4.39 (2H, s), 6.87 (1H, s), 7.15-7.22 (1H, m), 7.32 (1H, s), 7.44-7.55 (1H, m), 7.59-7.67 (1H, m), 7.77-7.95 (1H, br).

Reference Example 162

6-[6-Chloro-5-methoxy-2-(1-methylcyclopropyl)-1H-indol-3-ylmethyl]-pyridine-2-carboxamidoxime In the same method as in Reference Example 118-1 using the corresponding starting material and reaction agents, the title compound was synthesized. ¹H-NMR (DMSO-d₆) δ ppm: 0.69-0.76 (2H, m), 0.82-0.89 (2H, m), 1.30 (3H, s), 3.73 (3H, s), 4.27 (2H, s), 5.82 (2H, br s), 7.08 (1H, s), 7.12 (1H, dd, J=2.3, 6.3 Hz), 7.24 (1H, s), 7.60-7.69 (2H, m), 9.85 (1H, s), 10.84 (1H, s).

Reference Example 163

1-(4-Methyl-3-nitrophenyl)ethan-1-ol

To a solution of 1-(4-methyl-3-nitrophenyl)ethan-1-one (2.00 g) in ethanol/tetrahydrofuran (15 mL/7.5 mL) was added sodium borohydride (211 mg), and the mixture was stirred at room temperature for 10 minutes. To the reaction mixture were added 0.5 mol/L hydrochloric acid and water, followed by extraction with ethyl acetate. The organic layer was washed with a saturated aqueous sodium hydrogen carbonate solution and saturated brine successively, dried over anhydrous magnesium sulfate, and then concentrated under reduced pressure to obtain the title compound (1.96 g). ¹H-NMR (CDCl₃) δ ppm: 1.52 (3H, d, J=6.5 Hz), 1.84-1.95 (1H, m), 2.59 (3H, s), 4.91-5.02 (1H, m), 7.32 (1H, d, J=7.9 Hz), 7.52 (1H, dd, J=1.8, 7.9 Hz), 7.99 (1H, d, J=1.8 Hz).

Reference Example 164

1-(3-Amino-4-methylphenyl)ethan-1-ol

To a solution of 1-(4-methyl-3-nitrophenyl)ethan-1-ol (1.96 g) in ethyl acetate (55 mL) was added 10% palladium on carbon (56.5% water included, 901 mg), and the mixture was stirred at room temperature for 7 hours under a hydrogen atmosphere. The reaction mixture was filtered through celite (registered trademark) pad. The filtrate was concentrated under reduced pressure to obtain the title compound (1.60 g). ¹H-NMR (CDCl₃) δ ppm: 1.47 (3H, d, J=6.4 Hz), 1.73 (1H, br s), 2.16 (3H, s), 3.63 (2H, br s), 4.80 (1H, q, J=6.4 Hz), 6.66-6.75 (2H, m), 7.02 (1H, d, J=7.3 Hz).

Reference Example 165

Tert-Butyl [5-(1-hydroxyethyl)-2-methylphenyl]carbamate

A mixture of 1-(3-amino-4-methylphenyl)ethan-1-ol (1.60 g), di-tert-butyl dicarbonate (2.53 g) and tetrahydrofuran (21.2 mL) was heated under reflux for 26 hours. The reaction mixture was left to be cooled and concentrated under reduced pressure. The residue was purified by silica gel column chromatography (eluting solvent: ethyl acetate-hexane) to obtain the title compound (2.40 g). ¹H-NMR (CDCl₃) δ ppm: 1.49 (3H, d, J=6.5 Hz), 1.53 (9H, s), 1.85 (1H, d, J=3.8 Hz), 2.23 (3H, s), 4.80-4.94 (1H, m), 6.27 (1H, br s), 6.99-7.07 (1H, m), 7.13 (1H, d, J=7.8 Hz), 7.83 (1H, br s).

Reference Example 166

Tert-Butyl (5-ethyl-2-methylphenyl)carbamate

To a solution of tert-butyl [5-(1-hydroxyethyl)-2-methylphenyl]carbamate (2.39 g) in ethyl acetate (47.5 mL) was added 10% palladium on carbon (56.5% water included, 1.10 g), and the mixture was stirred at room temperature for 6 hours under a hydrogen atmosphere. The reaction mixture was filtered through celite (registered trademark) pad. The filtrate was concentrated under reduced pressure to obtain the title compound (2.23 g). $^1$H-NMR (DMSO-d$_6$) δ ppm: 1.14 (3H, t, J=7.5 Hz), 1.45 (9H, s), 2.13 (3H, s), 2.53 (2H, q, J=7.5 Hz), 6.82-6.90 (1H, m), 7.05 (1H, d, J=7.8 Hz), 7.11-7.18 (1H, m), 8.42 (1H, s).

Reference Example 167

Tert-Butyl {5-ethyl-2-[2-(1-methylcyclopropyl)-2-oxoethyl]phenyl}carbamate

In the same method as in Reference Example 131-1 using the corresponding starting material and reaction agents, the title compound was synthesized. $^1$H-NMR (CDCl$_3$) δ ppm: 0.80-0.89 (2H, m), 1.22 (3H, t, J=7.6 Hz), 1.36-1.49 (5H, m), 1.52 (9H, s), 2.62 (2H, q, J=7.6 Hz), 3.58 (2H, s), 6.86 (1H, dd, J=1.8, 7.8 Hz), 6.99 (1H, d, J=7.8 Hz), 7.63 (1H, br s), 7.70-8.20 (1H, br).

Reference Example 168

Tert-Butyl {2-[1-(6-cyanopyridin-2-ylmethyl)-2-(1-methylcyclopropyl)-2-oxoethyl]-5-ethylphenyl}carbamate In the same method as in Reference Example 150-1 using the corresponding starting material and reaction agents, the title compound was synthesized. $^1$H-NMR (CDCl$_3$) δ ppm: 0.59-0.75 (2H, m), 1.10-1.35 (8H, m), 1.56 (9H, s), 2.60 (2H, q, J=7.5 Hz), 3.21 (1H, dd, J=7.8, 15.8 Hz), 3.57 (1H, dd, J=6.8, 15.8 Hz), 4.72-4.84 (1H, m), 6.82-6.92 (1H, m), 6.98 (1H, d, J=8.0 Hz), 7.20-7.26 (1H, m), 7.46-7.60 (2H, m), 7.64 (1H, t, J=7.8 Hz), 7.72 (1H, br s).

Reference Example 169

6-[6-Ethyl-2-(1-methylcyclopropyl)-1H-indol-3-ylmethyl]pyridine-2-carbonitrile

In the same method as in Reference Example 153-1 using the corresponding starting material and reaction agents, the title compound was synthesized. $^1$H-NMR (CDCl$_3$) δ ppm: 0.70-0.78 (2H, m), 0.81-0.89 (2H, m), 1.26 (3H, t, J=7.6 Hz), 1.33 (3H, s), 2.72 (2H, q, J=7.6 Hz), 4.41 (2H, s), 6.86-6.93 (1H, m), 7.11-7.15 (1H, m), 7.16-7.23 (2H, m), 7.46-7.52 (1H, m), 7.58 (1H, t, J=7.8 Hz), 7.89 (1H, br s).

Reference Example 170

6-[6-Ethyl-2-(1-methylcyclopropyl)-1H-indol-3-ylmethyl]-pyridine-2-carboxamidoxime In the same method as in Reference Example 118-1 using the corresponding starting material and reaction agents, the title compound was synthesized. $^1$H-NMR (CDCl$_3$) δ ppm: 0.68-0.76 (2H, m), 0.84-0.92 (2H, m), 1.26 (3H, t, J=7.6 Hz), 1.34 (3H, s), 2.72 (2H, q, J=7.6 Hz), 4.37 (2H, s), 5.49-5.89 (2H, m), 6.60-6.86 (1H, br), 6.88 (1H, dd, J=1.5, 8.0 Hz), 6.99-7.06 (1H, m), 7.10-7.14 (1H, m), 7.24-7.30 (1H, m), 7.49 (1H, t, J=7.8 Hz), 7.65-7.72 (1H, m), 7.84 (1H, br s).

Reference Example 171

2,2,2-Trifluoro-N-(5-methoxy-2-methylphenyl)acetamide

To a solution of 5-methoxy-2-methylaniline (5 g) in dichloromethane (70 mL) was added trifluoroacetic anhydride (15.3 g) under ice-cooling, and the mixture was stirred at room temperature for 3 hours. To the reaction mixture were added water and sodium hydrogen carbonate, followed by extraction with dichloromethane. The organic layer was washed with saturated brine, dried over anhydrous magnesium sulfate, and then concentrated under reduced pressure to obtain the title compound (8.16 g). $^1$H-NMR (CDCl$_3$) δ ppm: 2.23 (3H, s), 3.80 (3H, s), 6.75 (1H, dd, J=2.6, 8.5 Hz), 7.13 (1H, d, J=8.5 Hz), 7.50 (1H, d, J=2.6 Hz), 7.50-7.90 (1H, br).

Reference Example 172

N-(4-Chloro-5-methoxy-2-methylphenyl)-2,2,2-trifluoroacetamide

To a solution of 2,2,2-Trifluoro-N-(5-methoxy-2-methylphenyl)acetamide (8.16 g) in chloroform (35 mL) was added sulfuryl chloride (3.12 mL) under ice-cooling, and the mixture was stirred overnight. To the reaction mixture was added water, followed by extraction with ethyl acetate. The organic layer was washed with water and saturated brine successively, dried over anhydrous magnesium sulfate, and then concentrated under reduced pressure. To the residue was added hexane, and the mixture was stirred at room temperature for 1 hour. The precipitate was collected by filtration, washed with hexane, and then dried under reduced pressure to obtain the title compound (7.02 g). $^1$H-NMR (CDCl$_3$) δ ppm: 2.23 (3H, s), 3.90 (3H, s), 7.24 (1H, s), 7.59 (1H, s), 7.60-7.82 (1H, br).

Reference Example 173

4-Chloro-5-methoxy-2-methylaniline

To a suspension of N-(4-chloro-5-methoxy-2-methylphenyl)-2,2,2-trifluoroacetamide (7.02 g) in ethanol (50 mL) was added 2 mol/L aqueous sodium hydroxide solution at room temperature, and the mixture was stirred at external temperature of 80° C. for 30 minutes. The reaction mixture was left to be cooled and concentrated under reduced pressure. To the residue was added water, and the mixture was stirred for 1 hour. The precipitate was collected by filtration, washed with water, and then dried under reduced pressure to obtain the title compound (4.15 g). $^1$H-NMR (CDCl$_3$) δ ppm: 2.08 (3H, s), 3.40-3.82 (2H, br), 3.83 (3H, s), 6.29 (1H, s), 6.99-7.04 (1H, m).

Reference Example 174

Tert-Butyl (4-chloro-5-methoxy-2-methylphenyl)carbamate

In the same method as in Reference Example 14 using the corresponding starting material and reaction agents, the title compound was synthesized. $^1$H-NMR (CDCl$_3$) δ ppm: 1.53 (9H, s), 2.16 (3H, s), 3.91 (3H, s), 6.27 (1H, br s), 7.07-7.15 (1H, m), 7.69 (1H, br s).

Reference Example 175

Tert-Butyl {4-chloro-5-methoxy-2-[2-(1-methylcyclopropyl)-2-oxoethyl]phenyl}carbamate In the same method as in Reference Example 131-1 using the corresponding starting material and reaction agents, the title compound was synthesized. $^1$H-NMR (CDCl$_3$) δ ppm: 0.84-0.92 (2H, m), 1.34-1.43 (5H, m), 1.52 (9H, s), 3.52 (2H, s), 3.91 (3H, s), 7.06 (1H, s), 7.58 (1H, br s), 7.95-8.31 (1H, br).

Reference Example 176

Tert-Butyl {4-chloro-2-[1-(6-cyanopyridin-2-ylmethyl)-2-(1-methylcyclopropyl)-2-oxoethyl]-5-methoxyphenyl}carbamate In the same method as in Reference Example 150-1 using the corresponding starting material and reaction agents, the title compound was synthesized. $^1$H-NMR (CDCl$_3$) δ ppm: 0.65-0.75 (2H, m), 1.21-1.33 (5H, m), 1.57 (9H, s), 3.23 (1H, dd, J=8.6, 16.1 Hz), 3.54 (1H, dd, J=6.3, 16.1 Hz), 3.89 (3H, s), 4.74 (1H, dd, J=6.3, 8.6 Hz), 7.07 (1H, s), 7.24-7.30 (1H, m), 7.46 (1H, br s), 7.50-7.57 (1H, m), 7.68 (1H, t, J=7.8 Hz), 8.00 (1H, br s).

Reference Example 177

6-[5-Chloro-6-methoxy-2-(1-methylcyclopropyl)-1H-indol-3-ylmethyl]pyridine-2-carbonitrile In the same method as in Reference Example 153-1 using the corresponding starting material and reaction agents, the title compound was synthesized. $^1$H-NMR (CDCl$_3$) δ ppm: 0.71-0.78 (2H, m), 0.82-0.89 (2H, m), 1.33 (3H, s), 3.90 (3H, s), 4.35 (2H, s), 6.87 (1H, s), 7.13-7.20 (1H, m), 7.27 (1H, s), 7.48-7.55 (1H, m), 7.63 (1H, t, J=7.8 Hz), 7.90 (1H, br s).

Reference Example 178

6-[5-Chloro-6-methoxy-2-(1-methylcyclopropyl)-1H-indol-3-ylmethyl]-pyridine-2-carboxamidoxime In the same method as in Reference Example 118-1 using the corresponding starting material and reaction agents, the title compound was synthesized.
$^1$H-NMR (DMSO-d$_6$) δ ppm: 0.69-0.76 (2H, m), 0.83-0.90 (2H, m), 1.31 (3H, s), 3.81 (3H, s), 4.23 (2H, s), 5.78 (2H, br s), 6.90 (1H, s), 7.09 (1H, dd, J=2.3, 6.3 Hz), 7.34 (1H, s), 7.61-7.70 (2H, m), 9.86 (1H, s), 10.89 (1H, s).

Reference Example 179

Tert-Butyl 6-methoxy-2-pyrimidin-5-yl-1H-indole-1-carboxylate

Sodium carbonate (364 mg) was dissolved in water (3.44 mL). 1,2-Dimethoxyethane (13.7 mL), 5-bromopyrimidine (273 mg), [1-(tert-butoxycarbonyl)-6-methoxy-1H-indol-2-yl]boronic acid (500 mg) and tetrakis(triphenylphosphine)palladium(0) (99.2 mg) were added thereto, and the mixture was stirred at 100° C. for 1 hour under microwave irradiation. The reaction mixture was left to be cooled. To the reaction mixture was added a mixed solution of water and saturated brine (each 10 mL), followed by extraction with ethyl acetate. The organic layer was dried over anhydrous sodium sulfate, and then concentrated under reduced pressure. The residue was purified by silica gel column chromatography (eluting solvent: ethyl acetate-hexane) to obtain the title compound (305 mg). $^1$H-NMR (CDCl$_3$) δ ppm: 1.41 (9H, s), 3.91 (3H, s), 6.60-6.64 (1H, m), 6.94 (1H, dd, J=2.3, 8.7 Hz), 7.47 (1H, d, J=8.7 Hz), 7.83 (1H, d, J=2.3 Hz), 8.78 (2H, s), 9.17 (1H, s).

Reference Example 180

6-Methoxy-2-pyrimidin-5-yl-1H-indole tert-Butyl 6-methoxy-2-pyrimidin-5-yl-1H-indole-1-carboxylate (295 mg) in tetrahydrofuran (2.27 mL) was added tetrabutylammonium fluoride (about 1.0 mol/L tetrahydrofuran solution, 3.63 mL) at room temperature, and the mixture was heated under reflux for 30 hours. The reaction mixture was left to be cooled, diluted with ethyl acetate, and then washed with saturated brine. The organic layer was dried over anhydrous sodium sulfate and concentrated under reduced pressure. The residue was purified by silica gel column chromatography (eluting solvent: ethyl acetate-hexane) to obtain the title compound (186 mg). $^1$H-NMR (CDCl$_3$) δ ppm: 3.88 (3H, s), 6.84 (1H, dd, J=2.3, 8.8 Hz), 6.88-6.95 (2H, m), 7.54 (1H, d, J=8.8 Hz), 8.20-8.52 (1H, br), 8.99 (2H, s), 9.11 (1H, s). ESI-MS (m/z): 226 (M+H)$^+$

Reference Example 181

Methyl 6-[hydroxy(6-methoxy-2-pyrimidin-5-yl-1H-indol-3-yl)methyl]pyridine-2-carboxylate To a suspension of 6-methoxy-2-pyrimidin-5-yl-1H-indole (779 mg) and methyl 6-formylpyridine-2-carboxylate (628 mg) in dichloromethane (17.3 mL) was added 1,8-diazabicyclo[5,4,0]-7-undecene (0.052 mL), and the mixture was stirred at 30° C. for 76 hours. The reaction mixture was purified by aminopropylated silica gel column chromatography (eluting solvent: methanol-ethyl acetate) to obtain the title compound (829 mg). $^1$H-NMR (DMSO-d$_6$) δ ppm: 3.75 (3H, s), 3.82 (3H, s), 5.99 (1H, d, J=3.5 Hz), 6.16 (1H, d, J=3.5 Hz), 6.61 (1H, dd, J=2.3, 8.8 Hz), 6.84 (1H, d, J=2.3 Hz), 7.49 (1H, d, J=8.8 Hz), 7.86-7.92 (1H, m), 8.06 (1H, t, J=7.8 Hz), 8.18-8.26 (1H, m), 9.23 (1H, s), 9.55 (2H, s), 11.40 (1H, br s).

Reference Example 182

Methyl 6-(6-methoxy-2-pyrimidin-5-yl-1H-indol-3-ylmethyl)pyridine-2-carboxylate

To a suspension of methyl 6-[hydroxyl(6-methoxy-2-pyrimidin-5-yl-1H-indol-3-yl)methyl]pyridine-2-carboxylate (828 mg) in dichloromethane (21.2 mL) was added triethylsilane (1.35 mL) under ice-cooling. Then trifluoroacetic acid (0.649 mL) was added dropwise thereto, and the mixture was stirred under ice-cooling for 30 minutes and then at room temperature for 1 hour. Triethylsilane (1.35 mL) and trifluoroacetic acid (0.649 mL) were added thereto, and the mixture was stirred at room temperature for additional 5 hours. The reaction mixture was diluted with ethyl acetate and washed with a saturated aqueous sodium hydrogen carbonate solution. The organic layer was washed with saturated brine, dried over anhydrous magnesium sulfate and then concentrated under reduced pressure. The residue was purified by silica gel column chromatography (eluting solvent: methanol-ethyl acetate) to obtain the title compound (468 mg). $^1$H-NMR (CDCl₃) δ ppm: 3.86 (3H, s), 4.03 (3H, s), 4.48 (2H, s), 6.80 (1H, dd, J=2.3, 8.8 Hz), 6.92 (1H, d, J=2.3 Hz), 7.23-7.28 (1H, m), 7.37 (1H, d, J=8.8 Hz), 7.64-7.71 (1H, m), 7.94-8.00 (1H, m), 8.16 (1H, br s), 9.04 (2H, s), 9.17 (1H, s). ESI-MS (m/z): 375 (M+H)⁺

Reference Example 183

6-(6-Methoxy-2-pyrimidin-5-yl-1H-indol-3-ylmethyl)pyridine-2-carboxamide

A mixture of methyl 6-(6-methoxy-2-pyrimidin-5-yl-1H-indol-3-ylmethyl)pyridine-2-carboxylate (466 mg), a solution of ammonia in methanol (about 7 mol/L, 18.6 mL) and tetrahydrofuran (6.2 mL) was stirred at room temperature for 48 hours. The precipitate was collected by filtration, washed with methanol, and then dried under reduced pressure to obtain the title compound (370 mg). $^1$H-NMR (DMSO-d₆) δ ppm: 3.79 (3H, s), 4.44 (2H, s), 6.70 (1H, dd, J=2.3, 8.5 Hz), 6.89 (1H, d, J=2.3 Hz), 7.34-7.41 (1H, m), 7.51 (1H, d, J=8.5 Hz), 7.63-7.77 (2H, m), 7.79-7.86 (2H, m), 9.13 (1H, s), 9.14 (2H, s), 11.45 (1H, s).

Reference Example 184

6-(6-Methoxy-2-pyrimidin-5-yl-1H-indol-3-ylmethyl)pyridine-2-carbonitrile

To a suspension of 6-(6-methoxy-2-pyrimidin-5-yl-1H-indol-3-ylmethyl)pyridine-2-carboxamide (351 mg) in N,N-dimethylformamide (9.8 mL) was added phosphoryl chloride (0.133 mL) under ice-cooling, and the mixture was stirred under ice-cooling for 3 hours. To the reaction mixture were added a saturated aqueous sodium hydrogen carbonate and water, followed by extraction with ethyl acetate. The organic layer was washed with water and saturated brine successively, dried over anhydrous sodium sulfate, and then concentrated under reduced pressure. The residue was purified by aminopropylated silica gel column chromatography (eluting solvent: methanol-ethyl acetate) to obtain the title compound (326 mg). $^1$H-NMR (CDCl₃) δ ppm: 3.87 (3H, s), 4.40 (2H, s), 6.81 (1H, dd, J=2.3, 8.5 Hz), 6.90-6.95 (1H, m), 7.30-7.39 (2H, m), 7.50-7.57 (1H, m), 7.64-7.72 (1H, m), 8.20 (1H, br s), 9.00 (2H, s), 9.20 (1H, s).

Reference Example 185

2-Bromo-1-(1-methylcyclopropyl)ethan-1-one

To a stirred solution of 1-(1-methylcyclopropyl)ethan-1-one (1.10 g) in methanol (10 mL) was added dropwise bromine (0.609 mL) under ice-cooling, and the mixture was stirred at room temperature for 70 minutes. To the reaction mixture was added water, followed by extraction with ethyl acetate. The organic layer was dried over anhydrous magnesium sulfate and concentrated under reduced pressure to obtain the title compound (1.98 g). $^1$H-NMR (CDCl₃) δ ppm: 0.81-0.89 (2H, m), 1.30-1.39 (2H, m), 1.46 (3H, s), 4.02 (2H, s).

Reference Example 186

6-Methoxy-5-methyl-2-(1-methylcyclopropyl)-1H-indole

A solution of 3-methoxy-4-methylaniline (2.26 g) in ethanol (7 mL) was heated under reflux while stirring. To the solution was added slowly a solution of 2-bromo-1-(1-methylcyclopropyl)ethan-1-one (885 mg) in ethanol (3 mL), and this mixture was heated under reflux for 3 hours while stirring. The reaction mixture was left to be cooled. To the reaction mixture was added 1 mol/L hydrochloric acid, followed by extraction with ethyl acetate. The organic layer was washed with 1 mol/L hydrochloric acid, a saturated aqueous sodium hydrogen carbonate solution and saturated brine successively, dried over anhydrous sodium sulfate, and then concentrated under reduced pressure. The residue was purified by silica gel column chromatography (eluting solvent: ethyl acetate-hexane) to obtain the title compound (588 mg). $^1$H-NMR (CDCl₃) δ ppm: 0.71-0.79 (2H, m), 0.87-0.95 (2H, m), 1.46 (3H, s), 2.27 (3H, s), 3.83 (3H, s), 6.03-6.08 (1H, m), 6.75 (1H, s), 7.22 (1H, s), 7.46-7.90 (1H, br).

Reference Example 187

Methyl 6-[6-methoxy-5-methyl-2-(1-methylcyclopropyl)-1H-indol-3-ylmethyl]pyridine-2-carboxylate To a solution of 6-methoxy-5-methyl-2-(1-methylcyclopropyl)-1H-indole (586 mg) and methyl 6-formylpyridine-2-carboxylate (450 mg) in dichloromethane (13.6 mL) was added triethylsilane (1.30 mL) under ice-cooling. Trifluoroacetic acid (0.313 mL) was added dropwise thereto, and the mixture was stirred under ice-cooling for 30 minutes and then at room temperature for 3 hours. The reaction mixture was diluted with ethyl acetate and washed with a saturated aqueous sodium hydrogen carbonate solution. The organic layer was washed with saturated brine, dried over anhydrous sodium sulfate, and then concentrated under reduced pressure. The residue was suspended in methanol. The precipitate was collected by filtration, washed with methanol, and then dried under reduced pressure at 40° C. to obtain the title compound (688 mg). $^1$H-NMR (CDCl₃) δ ppm: 0.66-0.72 (2H, m), 0.80-0.86 (2H, m), 1.31 (3H, s), 2.19 (3H, s), 3.84 (3H, s), 4.05 (3H, s), 4.48 (2H, s), 6.78 (1H, s), 7.00 (1H, s), 7.04-7.10 (1H, m), 7.59 (1H, t, J=7.8 Hz), 7.79 (1H, br s), 7.91-7.97 (1H, m). ESI-MS (m/z): 365 (M+H)⁺

Reference Example 188

6-[6-methoxy-5-methyl-2-(1-methylcyclopropyl)-1H-indol-3-ylmethyl]pyridine-2-carboxamide In the same method as in Reference Example 88 using the corresponding starting material and reaction agents, the title compound was synthesized. $^1$H-NMR (CDCl₃) δ ppm: 0.67-0.74 (2H, m), 0.82-0.89 (2H, m), 1.32 (3H, s), 2.22 (3H, s), 3.84 (3H, s), 4.34 (2H, s), 5.38-5.70 (1H, br), 6.77 (1H, s), 7.08 (1H, s), 7.14-7.21 (1H, m), 7.65 (1H, t, J=7.8 Hz), 7.78 (1H, br s), 7.82-8.10 (2H, m).

Reference Example 189

6-[6-Methoxy-5-methyl-2-(1-methylcyclopropyl)-1H-indol-3-ylmethyl]pyridine-2-carbonitrile In the same method as in Reference Example 87 using the corresponding starting material and reaction agents, the title compound was synthesized. $^1$H-NMR (CDCl$_3$) δ ppm: 0.67-0.76 (2H, m), 0.79-0.87 (2H, m), 1.31 (3H, s), 2.22 (3H, s), 3.84 (3H, s), 4.38 (2H, s), 6.77 (1H, s), 7.01 (1H, s), 7.14-7.21 (1H, m), 7.46-7.53 (1H, m), 7.54-7.63 (1H, m), 7.70-7.92 (1H, br).

Example 19

6-Methoxy-2-phenyl-3-{6-[(E)-2-(1H-tetrazol-5-yl)vinyl]pyridine-2-ylmethyl}-1H-indole

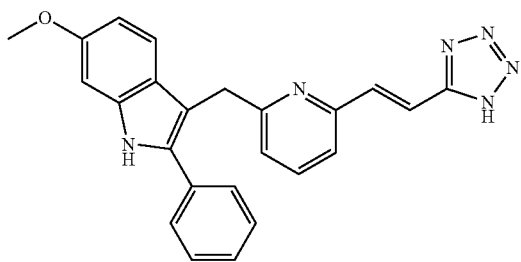 [SMILES: COc1ccc2c(Cc3cccc(/C=C/c4nnn[nH]4)n3)c(-c3ccccc3)[nH]c2c1]

To a mixture of (E)-3-[6-(6-methoxy-2-phenyl-1H-indol-3-ylmethyl)pyridin-2-yl]acrylonitrile (67 mg), isopropyl alcohol (1.5 mL) and water (0.5 mL) were added sodium azide (59.6 mg) and zinc bromide (51.6 mg), and the mixture was heated under reflux for 32 hours. Then isopropyl alcohol (1.5 mL) and water (0.5 mL) were added thereto, followed by heating under reflux for 62 hours. The reaction mixture was left to be cooled, diluted with 1 mol/L hydrochloric acid, and then stirred for 5 minutes. To the mixture was added water, followed by extraction with ethyl acetate. The organic layer was washed with water, dried over anhydrous magnesium sulfate, and then concentrated under reduced pressure. The residue was purified by silica gel column chromatography (eluting solvent: ethyl acetate-hexane) to obtain the title compound (25.8 mg). $^1$H-NMR (DMSO-d$_6$) δ ppm: 3.77 (3H, s), 4.34 (2H, s), 6.65 (1H, dd, J=2.3, 8.5 Hz), 6.87 (1H, d, J=2.3 Hz), 7.16-7.23 (1H, m), 7.32-7.43 (2H, m), 7.46-7.54 (3H, m), 7.65-7.85 (5H, m), 11.16 (1H, s). ESI-MS (m/z): 409 (M+H)$^+$

Examples 20-1 to 20-4

In the same method as in Example 5-1 using the corresponding starting material, the compounds shown in Table 29 were synthesized.

Examples 21-1 to 21-2

In the same method as in Example 7-1 using the corresponding starting material, the compounds shown in Table 30 were synthesized.

Example 22

3-{6-[6-Ethyl-2-(1-methylcyclopropyl)-1H-indol-3-ylmethyl]pyridine-2-yl}-4,5-dihydro-1,2,4-oxadiazole-5-thione

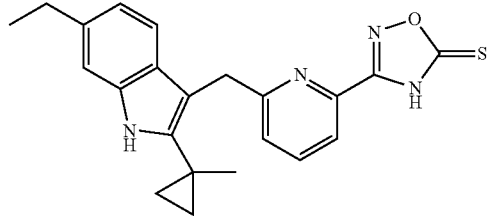 [SMILES: CCc1ccc2c(Cc3cccc(-c4noc(=S)[nH]4)n3)c(C3(C)CC3)[nH]c2c1]

In the same method as in Example 9 using the corresponding starting material, the title compound was synthesized. $^1$H-NMR (DMSO-d$_6$) δ ppm: 0.67-0.75 (2H, m), 0.83-0.91 (2H, m), 1.17 (3H, t, J=7.5 Hz), 1.33 (3H, s), 2.62 (2H, q, J=7.5 Hz), 4.27 (2H, s), 6.67-6.78 (1H, m), 6.96-7.09 (2H, m), 7.16 (1H, d, J=8.0 Hz), 7.64-7.74 (2H, m), 10.72 (1H, s). ESI-MS (m/z): 391 (M+H)$^+$

Example 23

6-Methoxy-2-pyrimidin-5-yl-3-[6-(1H-tetrazol-5-yl)pyridin-2-ylmethyl]-1H-indole

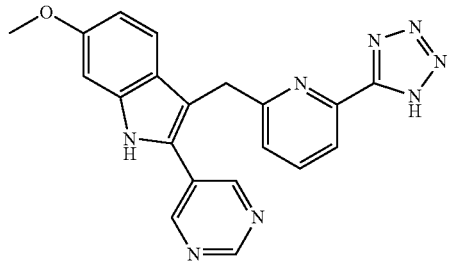 [SMILES: COc1ccc2c(Cc3cccc(-c4nnn[nH]4)n3)c(-c3cncnc3)[nH]c2c1]

A mixture of 6-(6-methoxy-2-pyrimidin-5-yl-1H-indol-3-ylmethyl)pyridine-2-carbonitrile (100 mg), sodium azide (95.2 mg), zinc bromide (82.5 mg), isopropyl alcohol (1.76 mL) and water (1.17 mL) was heated under reflux for 21 hours while stirring. The reaction mixture was left to be cooled. To the reaction mixture were added 1 mol/L hydrochloric acid and dichloromethane. The insoluble material was collected by filtration, washed with 1 mol/L hydrochloric acid and water successively, and then dried under reduced pressure at 50° C. to obtain the title compound (104 mg). $^1$H-NMR (DMSO-d$_6$) δ ppm: 3.79 (3H, s), 4.48 (2H, s), 6.69 (1H, dd, J=2.1, 8.7 Hz), 6.91 (1H, d, J=2.1 Hz), 7.25-7.35 (1H, m), 7.43 (1H, d, J=8.7 Hz), 7.90 (1H, t, J=7.8 Hz), 7.98-8.05 (1H, m), 9.00-9.20 (3H, m), 11.49 (1H, s). ESI-MS (m/z): 385 (M+H)$^+$

TABLE 29

| Ex. No. | Strc | Physical data |
|---|---|---|
| 20-1 | (structure) | ¹H-NMR (DMSO-d₆) δ ppm:<br>0.68-0.77 (2H, m), 0.81-0.89 (2H, m), 1.30 (3H, s), 3.66 (3H, s), 4.38 (2H, s), 7.03-7.13 (2H, m), 7.26 (1H, s), 7.85 (1H, t, J = 7.8 Hz), 7.95-8.02 (1H, m), 10.91 (1H, s).<br>ESI-MS (m/z): 395 (M + H)⁺ |
| 20-2 | (structure) | ¹H-NMR (DMSO-d₆) δ ppm:<br>0.68-0.76 (2H, m), 0.81-0.89 (2H, m), 1.17 (3H, t, J = 7.5 Hz), 1.31 (3H, s), 2.62 (2H, q, J = 7.5 Hz), 4.39 (2H, s), 6.70-6.76 (1H, m), 7.04-7.11 (2H, m), 7.16 (1H, d, J = 8.0 Hz), 7.85 (1H, t, J = 7.8 Hz), 7.97-8.04 (1H, m), 10.79 (1H, s).<br>ESI-MS (m/z): 359 (M + H)⁺ |
| 20-3 | (structure) | ¹H-NMR (DMSO-d₆) δ ppm:<br>0.67-0.75 (2H, m), 0.81-0.89 (2H, m), 1.29 (3H, s), 3.81 (3H, s), 4.35 (2H, s), 6.92 (1H, s), 7.02-7.09 (1H, m), 7.34 (1H, s), 7.84 (1H, t, J = 7.8 Hz), 7.95-8.02 (1H, m), 10.96 (1H, s).<br>ESI-MS (m/z): 395 (M + H)⁺ |
| 20-4 | (structure) | ¹H-NMR (DMSO-d₆) δ ppm:<br>0.64-0.73 (2H, m), 0.77-0.85 (2H, m), 1.28 (3H, s), 2.10 (3H, s), 3.76 (3H, s), 4.36 (2H, s), 6.76 (1H, s), 7.00-7.10 (2H, m), 7.86 (1H, t, J = 7.8 Hz), 7.96-8.05 (1H, m), 10.65 (1H, s).<br>ESI-MS (m/z): 375 (M + H)⁺ |

TABLE 30

| Ex. No. | Strc | Physical data |
|---|---|---|
| 21-1 | (structure) | ¹H-NMR (DMSO-d₆) δ ppm:<br>0.68-0.77 (2H, m), 0.80-0.88 (2H, m), 1.29 (3H, s), 3.71 (3H, s), 4.35 (2H, s), 7.05 (1H, s), 7.15-7.22 (1H, m), 7.26 (1H, s), 7.73-7.90 (2H, m), 10.91 (1H, s), 13.09 (1H, br s).<br>ESI-MS (m/z): 411 (M + H)⁺ |

TABLE 30-continued

| Ex. No. | Strc | Physical data |
|---|---|---|
| 21-2 | [structure: chloro-methoxy-indole with 1-methylcyclopropyl substituent, linked via CH2 to pyridine bearing a 1,3,4-oxadiazol-2(3H)-one] | $^1$H-NMR (DMSO-$d_6$) δ ppm: 0.67-0.75 (2H, m), 0.79-0.88 (2H, m), 1.29 (3H, s), 3.81 (3H, s), 4.31 (2H, s), 6.91 (1H, s), 7.10-7.18 (1H, m), 7.34 (1H, s), 7.74-7.80 (1H, m), 7.85 (1H, t, J = 7.8 Hz), 10.96 (1H, s), 13.06 (1H, br s). ESI-MS (m/z): 411 (M + H)$^+$ |

Test Example 1

Test for Confirmation of EP$_1$ Receptor Antagonism (1) Preparation of Rat EP$_1$ Expression Vector Using Rat Kidney BD Marathon-Ready cDNA (Nippon Becton Dickinson Company, Ltd.) as a template, a forward primer shown in (SEQ ID NO:1), and a reverse primer shown in (SEQ ID NO:2), a first run of PCR was carried out using KOD-Plus-Ver 2.0 (Toyobo Co., Ltd.). Further, using this amplification product as a template, a forward primer shown in (SEQ ID NO:3), and a reverse primer shown in (SEQ ID NO:4), a second run of PCR was carried out in the same manner. The amplification product obtained by the second run of PCR was incorporated into a vector (pcDNA3.1 D/V5-His-TOPO (registered trademark), Invitrogen Japan K. K.). By a conventional method, the vector containing this amplification product was introduced to E. coli (One Shot TOP 10 Competent Cells, Invitrogen Corporation) to transform. This transformed E. coli was cultured in an LB agar medium for one day. After the culture, colonies were selected and cultured in an LB liquid medium containing 50 μg/mL of ampicillin. After the culture, the vector was purified using a QIAprep Spin Miniprep Kit (Qiagen K. K.). The base sequence of the insertion site of this vector (SEQ ID NO:5) was compared with the rat EP$_1$ base sequence (Ptger1) registered as Accession No. NM_013100 in publicly-known database (NCBI), and as a result, they all matched except for a single base. Further, the amino acid sequence translated by the base sequence completely matched the amino acid sequence of the rat EP$_1$ receptor registered as an NCBI Accession No. NP_037232. Therefore, it was confirmed that the cloned gene sequence was a base sequence of the rat EP$_1$ receptor and the obtained amino acid sequence was that of the rat EP$_1$ receptor. The pcDNA3.1 D/V5-His-TOPO (registered trademark) to which the nucleic acid shown in (SEQ ID NO:5) had been inserted was taken as a rat EP$_1$-expressing vector.

(2) Preparation of Rat EP$_1$ Receptor-Expressing Cells (2-1) COS-1 Cell Culture COS-1 cells (Dainippon Sumitomo Pharma Co., Ltd.) were cultured until they reached confluence in an incubator at 37° C. under a 5% CO$_2$ gas condition, using a D-MEM liquid medium (high glucose and L-glutamine contained, Invitrogen Corporation) to which a penicillin-streptomycin solution (Invitrogen Corporation, final concentration: 100 U/mL as benzylpenicillin; 100 μg/mL as streptomycin) as an antibiotic, MEM nonessential amino acids (Invitrogen Corporation, final concentration: 0.1 mM), and fetal calf serum (Sanko Junyaku Co., Ltd., final concentration: 10%) were added.

(2-2) COS-1 Cell Subculture

The cells that had reached confluence were stripped with 0.05% trypsin/0.53 mM EDTA 4Na (Invitrogen Japan K. K.) and resuspended in the liquid medium. The resuspended cells were diluted and cultured in the liquid medium at a spread ratio from 1:4 to 1:8.

(2-3) Preparation of Cells for Introduction of Rat EP$_1$-Expressing Vector

The cells that had reached confluence were stripped with 0.05% trypsin/0.53 mM EDTA.4Na, and resuspended in a D-MEM liquid medium (high glucose and L-glutamine contained, Invitrogen Corporation) to which an MEM nonessential amino acid (final concentration: 0.1 mM) and fetal calf serum (final concentration: 10%) were added. In each well of a Poly D-lysine-coated 96-well microplate (BD BioCoat (registered trademark), Nippon Becton Dickinson Company, Ltd.), this resuspended cell suspension culture was prepared to be 5×10$^4$ cells/well in 100 μL of the liquid medium, and 100 μL of the cell suspension was seeded on each well. After seeding, the cells were cultured in an incubator at 37° C. under a 5% CO$_2$ gas condition. At a point when the cells for introduction of a rat EP$_1$-expressing vector were adhered (about 2 hours after seeding), introduction of the rat EP$_1$-expressing vector was carried out in the following order.

(2-4) Introduction of Rat EP$_1$-Expressing Vector

For introduction of the rat EP$_1$-expressing vector, Lipofectamine 2000 (Invitrogen Japan K. K.) was used. The rat EP$_1$-expressing vector was diluted with OPTI-MEM (registered trademark) I Reduced-Serum Medium (Invitrogen Japan K. K.) to 200 ng/25 μL/well, and at the same time, Lipofectamine 2000 (Invitrogen Japan K. K.) was also diluted with OPTI-MEM (registered trademark) I Reduced-Serum Medium (Invitrogen Japan K. K.) to 0.5 μL/25 μL/well, followed by incubation at room temperature for 5 minutes. After the incubation for 5 minutes, in order to form a complex of the rat EP$_1$-expressing vector/Lipofectamine 2000, the diluted rat EP$_1$-expressing vector and the diluted Lipofectamine 2000 were mixed and incubated at room temperature for 30 minutes. After the incubation for 30 minutes, the complex of the rat EP$_1$-expressing vector/Lipofectamine 2000 was distributed to the cells for introduction of the rat EP$_1$-expressing vector at 50 μL/well. The cells to which the complex of the rat EP$_1$-expressing vector/Lipofectamine 2000 had been distributed were cultured in an incubator at 37° C. for 20 hours under a 5% CO$_2$ gas condition. After the culture for 20 hours, the cells were used for measurement of an intracellular calcium concentration as rat EP$_1$ receptor-expressing cells.

(3) Study on Inhibitory Effect on Increase in Intracellular Calcium Concentration Using the rat EP$_1$ receptor-expressing cells, the inhibitory effect of each test compound on the increased intracellular calcium concentration induced by prostaglandin $E_2$ was studied in the method as shown below.

A 10 mM solution of each test compound in dimethyl sulfoxide was diluted with an assay buffer (20 mM HEPES/Hank's Balanced Salt Solution (HBSS), pH 7.2).

The rat $EP_1$ receptor-expressing cells were washed with the assay buffer. 100 μL of a fluorescent calcium indicator (Calcium kit II, Fluo 4 (Dojindo Laboratories): prepared by the protocol of the same product, Invitrogen Japan K. K., 2.5 mM probenecid contained) was added to each well, followed by incubation in an incubator at 37° C. for 60 minutes. Then, the intracellular calcium concentration was measured immediately.

The intracellular calcium concentration was measured as a fluorescence signal using FDSS (registered trademark) 7000 (manufactured by Hamamatsu Photonics K. K.). 50 μL of each test compound (final concentrations: 1 nM to 10 μM) was added to each well after 20 seconds from initiating the reading of the fluorescence signal, and the fluorescence signal was measured for 60 seconds. Then, 50 μL of a prostaglandin $E_2$ buffer solution were added to each well (final concentration 10 nM) and the fluorescence signal was measured for 60 seconds.

In the method above, as a fluorescence signal obtained by the addition of the prostaglandin $E_2$ with the addition of the assay buffer instead of the test compound was taken as 100% and a signal obtained without the addition of any of the test compound and the prostaglandin $E_2$ was taken as 0%, the concentration of the test compound showing 50% inhibition from the concentration-response curve was taken as an $IC_{50}$ value. As the values of the $EP_1$ receptor antagonism, the obtained $IC_{50}$ values of each test compound were shown in Tables 31 and 32 below.

TABLE 31

| Ex. No. | $IC_{50}$ (nM) |
|---|---|
| 1 | 99 |
| 2-1 | 27 |
| 2-2 | 29 |
| 3-1 | 33 |
| 3-3 | 30 |
| 3-4 | 39 |
| 3-5 | 55 |
| 3-6 | 18 |
| 3-7 | 33 |
| 3-9 | 25 |
| 3-10 | 47 |
| 3-11 | 17 |
| 3-12 | 27 |
| 3-13 | 27 |
| 3-14 | 88 |
| 3-15 | 27 |
| 3-20 | 68 |
| 3-21 | 86 |
| 3-23 | 58 |
| 3-24 | 58 |
| 3-25 | 78 |
| 3-30 | 43 |
| 3-31 | 47 |
| 3-32 | 51 |
| 3-33 | 66 |
| 3-34 | 40 |
| 3-35 | 46 |
| 5-1 | 61 |
| 5-2 | 4.7 |
| 5-3 | 15 |
| 5-4 | 12 |
| 5-5 | 19 |
| 5-6 | 45 |
| 5-7 | 20 |
| 5-8 | 12 |

TABLE 31-continued

| Ex. No. | $IC_{50}$ (nM) |
|---|---|
| 5-9 | 22 |
| 5-10 | 13 |
| 5-11 | 5.7 |
| 5-12 | 26 |
| 5-13 | 30 |
| 7-1 | 26 |
| 9 | 50 |
| 10 | 26 |

TABLE 32

| Ex. No. | $IC_{50}$ (nM) |
|---|---|
| 12-1 | 23 |
| 12-2 | 43 |
| 12-5 | 46 |
| 12-6 | 40 |
| 12-7 | 28 |
| 12-9 | 34 |
| 12-11 | 37 |
| 12-13 | 26 |
| 12-14 | 39 |
| 16-1 | 54 |
| 16-2 | 48 |
| 16-3 | 24 |
| 16-5 | 46 |
| 16-6 | 36 |
| 17-3 | 20 |
| 17-4 | 27 |
| 17-5 | 23 |
| 17-6 | 31 |
| 17-7 | 30 |
| 17-8 | 7.3 |
| 17-9 | 10 |
| 17-10 | 22 |
| 17-11 | 11 |
| 17-12 | 14 |
| 17-13 | 28 |
| 17-14 | 24 |
| 18-3 | 41 |
| 18-4 | 35 |
| 18-5 | 32 |
| 18-6 | 28 |
| 18-9 | 23 |
| 18-10 | 26 |
| 18-11 | 27 |
| 18-13 | 40 |
| 19 | 34 |
| 20-1 | 27 |
| 20-2 | 15 |
| 20-3 | 27 |
| 20-4 | 14 |
| 23 | 11 |

As shown in Tables 31 and 32, it is apparent that the compounds of the present invention exhibit potent $EP_1$ receptor antagonism.

Test Example 2

Inhibitory Effect of Compound on Sulprostone-Induced Bladder Contraction

Female SD rats were used. Under urethane anesthesia (1.25 g/kg, administered subcutaneously), a tracheal cannula (Size 8, HIBIKI) and a femoral vein cannula for administration (23 G needle-equipped PESO) were inserted thereinto. The bladder cannula (PESO) was inserted from the bladder apex. The bladder cannula was connected to a three-way stopcock, and then, one was connected to a pressure transducer and the other was connected to a syringe filled with saline. Saline was injected to the bladder at an injection rate of 3.6 mL/hour and the bladder contraction pressure was recorded at the time of injection with a recorder (RECTI-HORITZ-8K, NEC Corporation). After 10 minutes from stabilization of the bladder contraction pressure during urination, sulprostone was administered subcutaneously (0.3 mg/kg). Then, at the time point when the bladder contraction pressure became constant, a test agent was administered intravenously (1.0 mg/kg). An average bladder contraction pressure during the 10 minute period before administration of sulprostone was taken as a baseline (0%). Further, an average bladder contraction pressure during the 10 minute period directly before administration of the test agent was taken as a maximum bladder contraction pressure (100%). The average bladder contraction pressures were measured during 5 minutes before and after at 15 minutes and 60 minutes from administration of the test agent. The ratio of this measured value to the maximum bladder contraction pressure was calculated by the following equation and taken as an average bladder contraction rate after administration of the test agent:

(Average Bladder Contraction Rate after Administration of Test Agent (%))=[(Average Bladder Contraction Pressure after Administration of Test Agent)/(Maximum Bladder Contraction Pressure)]×100   EQUATION 1

In addition, the difference between the maximum bladder contraction rate (100%) and the average bladder contraction rate (%) after administration of the test agent was calculated by the following equation and taken as a bladder contraction inhibition rate of the test agent:

(Bladder Contraction Inhibition Rate)=100%−(Average Bladder Contraction Rate after Administration of Test Agent (%))   EQUATION 2

The results were shown in Tables 33 and 34.

TABLE 33

| Ex. No. | Bladder Contraction Inhibition Rate | |
|---|---|---|
| | 15 minutes | 60 minutes |
| 2-1 | 68.3 | 84.0 |
| 2-2 | 90.0 | 70.4 |
| 3-1 | 77.3 | 78.2 |
| 3-9 | 76.4 | 78.9 |
| 3-35 | 45.9 | 45.1 |
| 5-1 | 82.8 | 91.6 |

TABLE 33-continued

| Ex. No. | Bladder Contraction Inhibition Rate | |
|---|---|---|
| | 15 minutes | 60 minutes |
| 5-2 | 88.2 | 76.2 |
| 5-3 | 78.2 | 75.8 |
| 5-7 | 74.8 | 71.0 |
| 5-11 | 99.0 | 99.8 |
| 7-1 | 66.3 | 83.0 |

TABLE 34

| Ex. No. | Bladder Contraction Inhibition Rate | |
|---|---|---|
| | 15 minutes | 60 minutes |
| 3-6 | 67.5 | 63.6 |
| 10 | 82.9 | 90.7 |
| 12-11 | 74.9 | 46.7 |
| 12-13 | 72.9 | 96.0 |
| 12-14 | 80.5 | 59.1 |
| 17-11 | 92.8 | 100.9 |
| 17-12 | 81.9 | 74.7 |
| 20-3 | 71.7 | 50.0 |

From the results above, it was found that the compounds of the present invention had potent and sustained inhibition of the bladder contraction even when administered in vivo.

The compound of the present invention has a potent $EP_1$ receptor antagonism, and therefore, it is useful as an agent for treating or preventing diseases or symptoms caused by activation of an $EP_1$ receptor due to a stimulant action of $PGE_2$. In particular, it is useful as an agent for treating or preventing lower urinary tract symptoms (LUTS), particularly overactive bladder syndrome (OABs).

SEQ ID NO:1 is a sequence of a forward primer (5' primer) used for amplification of DNA of SEQ ID NO:5.

SEQ ID NO:2 is a sequence of a reverse primer (3' primer) used for amplification of DNA of SEQ ID NO:5.

SEQ ID NO:3 is a sequence of a forward primer (5' primer) used for amplification of DNA of SEQ ID NO:5.

SEQ ID NO:4 is a sequence of a reverse primer (3' primer) used for amplification of DNA of SEQ ID NO:5.

SEQ ID NO:5 is a DNA sequence for expressing a rat EP1 receptor which is amplified using the primers of SEQ ID NO:1, SEQ ID NO:2, SEQ ID NO:3, and SEQ ID NO:4.

What is claimed is:

1. A compound represented by the general formula (I) or a pharmaceutically acceptable salt thereof:

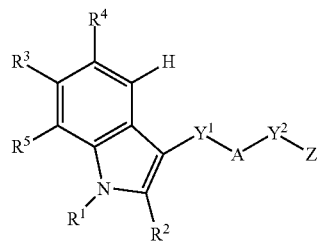

wherein

A represents a group selected from the group consisting of the following a) to h):

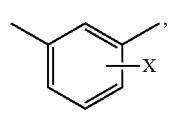
a)

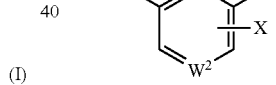
b)

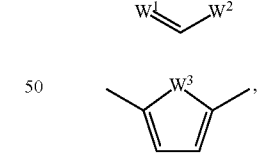
c)

d)

e)

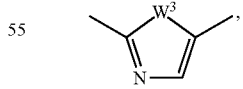
f)

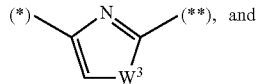
g)

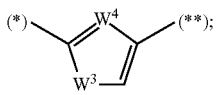

one of $W^1$ and $W^2$ represents a nitrogen atom and the other represents =CH— or a nitrogen atom;
$W^3$ represents an oxygen atom or a sulfur atom;
$W^4$ represents =CH— or a nitrogen atom;
X represents a hydrogen atom or a halogen atom;
$Y^1$ represents a $C_{1-6}$ alkylene group or a halo-$C_{1-6}$ alkylene group;
$Y^2$ represents a single bond, a $C_{1-6}$ alkylene group, a $C_{1-6}$ oxyalkylene group, or a $C_{2-4}$ alkenylene group;
$R^1$ represents a hydrogen atom or a $C_{1-6}$ alkyl group;
$R^2$ represents a group selected from the group consisting of the following i) to m):
i) a branched $C_{3-6}$ alkyl group,
j) a $C_{3-6}$ cycloalkyl group, in which the ring is unsubstituted or substituted with one $C_{1-6}$ alkyl group,
k) a phenyl group, in which the ring is unsubstituted or substituted with one to five groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group,
k) a 6-membered aromatic heterocyclic group, in which the ring is unsubstituted or substituted with one to four groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group, and
m) a 5-membered aromatic heterocyclic group, in which the ring is unsubstituted or substituted with one to three groups independently selected from the group consisting of the following: a halogen atom, a $C_{1-6}$ alkyl group, a halo-$C_{1-6}$ alkyl group, a hydroxy-$C_{1-6}$ alkyl group, a $C_{1-6}$ alkoxy group, and a cyano group;
$R^3$ represents a halogen atom, a $C_{1-6}$ alkyl group, a halo-$C_{1-6}$ alkyl group, a hydroxy-$C_{1-6}$ alkyl group, a $C_{1-6}$ alkoxy group, a halo-$C_{1-6}$ alkoxy group, a $C_{1-6}$ alkylsulfanyl group, a $C_{1-6}$ alkylsulfinyl group, a $C_{1-6}$ alkylsulfonyl group, a $C_{3-6}$ cycloalkyl group, a cyano group, an amino group, or a nitro group;
$R^4$ represents a hydrogen atom, a halogen atom, a $C_{1-6}$ alkyl group, or a $C_{1-6}$ alkoxy group;
$R^5$ represents a hydrogen atom, a halogen atom, a $C_{1-6}$ alkyl group, or a $C_{1-6}$ alkoxy group;
Z represents a group selected from the group consisting of the following n) to s):
n) —C(=O)—NHSO$_2$R$^6$,
o) —C(=O)—NHOH,
p) —C(=O)—NHCN,
q) —NH—C(=O)—R$^7$,
r) an acidic 5-membered hetero ring group, and
s) a 6-membered ring group substituted with a phenolic hydroxy group; and
$R^6$ and $R^7$ independently represent a group selected from the group consisting of the following t) to w):
t) a $C_{1-6}$ alkyl group,
u) a halo-$C_{1-6}$ alkyl group,
v) a $C_{3-6}$ cycloalkyl group, and
w) a phenyl group, in which the ring is unsubstituted or substituted with one to five groups independently selected from the group consisting of the following: a halogen atom, a $C_{1-6}$ alkyl group, a halo-$C_{1-6}$ alkyl group, and a $C_{1-6}$ alkoxy group (with the proviso that the bonds with (*) represent binding to $Y^1$; and the bonds with (**) represent binding to $Y^2$)].

2. The compound as claimed in claim 1 or a pharmaceutically acceptable salt thereof, wherein A represents a group selected from the group consisting of the following a), b), d), and h):

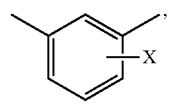

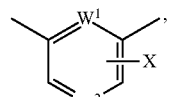

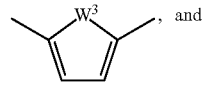

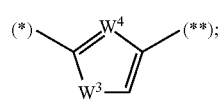

$Y^1$ represents a $C_{1-6}$ alkylene group;
$Y^2$ represents a single bond; and
$R^5$ represents a hydrogen atom (with the proviso that the bond with (*) represents binding to $Y^1$; and the bond with (**) represents binding to $Y^2$).

3. The compound as claimed in claim 2 or a pharmaceutically acceptable salt thereof, wherein $R^2$ is a group selected from the group consisting of the following j), x), y) and z):
j) a $C_{3-6}$ cycloalkyl group, in which the ring is unsubstituted or substituted with one $C_{1-6}$ alkyl group,
x) a phenyl group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group,
y) a 6-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group, and
z) a 5-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group.

4. The compound as claimed in claim 3 or a pharmaceutically acceptable salt thereof, wherein $R^2$ is a phenyl group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group.

5. The compound as claimed in claim 3 or a pharmaceutically acceptable salt thereof, wherein $R^2$ is a 5-membered aromatic heterocyclic group, in which the ring is unsubstituted or substituted with one group selected from the group consisting of the following: a halogen atom, a $C_{1-6}$ alkyl group, a halo-$C_{1-6}$ alkyl group, and a $C_{1-6}$ alkoxy group.

6. The compound as claimed in claim 2 or a pharmaceutically acceptable salt thereof, wherein $R^2$ is a branched $C_{3-6}$ alkyl group.

7. The compound as claimed in claim 2 or a pharmaceutically acceptable salt thereof, wherein:
Z is —C(=O)—NHSO$_2$R$^6$ or an acidic 5-membered hetero ring group; and
R$^6$ is a group selected from the group consisting of the following t) to w):
t) a $C_{1-6}$ alkyl group,
u) a halo-$C_{1-6}$ alkyl group,
v) a $C_{3-6}$ cycloalkyl group, and
w) a phenyl group, in which the ring is unsubstituted or substituted with one to three groups independently selected from the group consisting of the following: a halogen atom, a $C_{1-6}$ alkyl group, a halo-$C_{1-6}$ alkyl group, and a $C_{1-6}$ alkoxy group.

8. The compound as claimed in claim 7 or a pharmaceutically acceptable salt thereof, wherein Z is —C(=O)—NHSO$_2$R$^6$.

9. The compound as claimed in claim 3 or a pharmaceutically acceptable salt thereof, wherein $R^2$ is a $C_{3-6}$ cycloalkyl group, in which the ring is substituted with one $C_{1-6}$ alkyl group.

10. The compound as claimed in claim 9 or a pharmaceutically acceptable salt thereof, wherein Z is an acidic 5-membered hetero ring group.

11. The compound as claimed in claim 10 or a pharmaceutically acceptable salt thereof, wherein the acidic 5-membered hetero ring group is a group selected from Group D consisting of

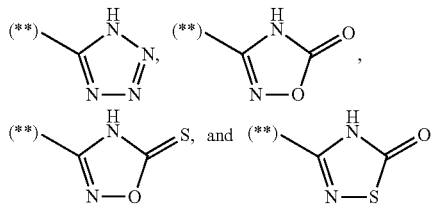

with the proviso that the bonds with (**) represent bonding to Y$^2$ of the compound represented by the general formula (I).

12. The compound as claimed in claim 1, which is selected from the following group, or a pharmaceutically acceptable salt thereof:
N-methanesulfonyl-6-(6-methoxy-2-phenyl-1H-indol-3-ylmethyl)pyridine-2-carboxamide,
6-(6-cyclopropyl-2-phenyl-1H-indol-3-ylmethyl)-N-methanesulfonylpyridine-2-carboxamide,
N-methanesulfonyl-6-(6-methyl-2-phenyl-1H-indol-3-ylmethyl)pyridine-2-carboxamide,
6-(5-fluoro-6-methoxy-2-phenyl-1H-indol-3-ylmethyl)-N-methanesulfonylpyridine-2-carboxamide,
N-ethanesulfonyl-6-(6-methoxy-2-thiophen-3-yl-1H-indol-3-ylmethyl)pyridine-2-carboxamide,
6-cyclopropyl-2-phenyl-3-[6-(1H-tetrazol-5-yl)pyridin-2-ylmethyl]-1H-indole,
6-methoxy-2-phenyl-3-[6-(1H-tetrazol-5-yl)pyridin-2-ylmethyl]-1H-indole,
6-methyl-2-phenyl-3-[6-(1H-tetrazol-5-yl)pyridin-2-ylmethyl]-1H-indole,
2-furan-3-yl-6-methoxy-3-[6-(1H-tetrazol-5-yl)pyridin-2-ylmethyl]-1H-indole,
3-[6-(6-methoxy-2-phenyl-1H-indol-3-ylmethyl)pyridin-2-yl]-4,5-dihydro-1,2,4-oxadiazol-5-one,
2-tert-butyl-6-methoxy-3-[6-(1H-tetrazol-5-yl)pyridin-2-ylmethyl]-1H-indole,
6-methoxy-2-(1-methylcyclopropyl)-3-[6-(1H-tetrazol-5-yl)pyridin-2-ylmethyl]-1H-indole,
6-methyl-2-(1-methylcyclopropyl)-3-[6-(1H-tetrazol-5-yl)pyridin-2-ylmethyl]-1H-indole,
6-cyclopropyl-2-(1-methylcyclopropyl)-3-[6-(1H-tetrazol-5-yl)pyridin-2-ylmethyl]-1H-indole,
6-chloro-2-(1-methylcyclopropyl)-3-[6-(1H-tetrazol-5-yl)pyridin-2-ylmethyl]-1H-indole,
6-chloro-5-methoxy-2-(1-methylcyclopropyl)-3-[6-(1H-tetrazol-5-yl)pyridin-2-ylmethyl]-1H-indole,
6-ethyl-2-(1-methylcyclopropyl)-3-[6-(1H-tetrazol-5-yl)pyridin-2-ylmethyl]-1H-indole,
5-chloro-6-methoxy-2-(1-methylcyclopropyl)-3-[6-(1H-tetrazol-5-yl)pyridin-2-ylmethyl]-1H-indole, and
6-methoxy-5-methyl-2-(1-methylcyclopropyl)-3-[6-(1H-tetrazol-5-yl)pyridin-2-ylmethyl]-1H-indole.

13. A pharmaceutical composition comprising the compound as claimed in claim 1 or a pharmaceutically acceptable salt thereof.

14. The pharmaceutical composition as claimed in claim 13, comprising a combination of at least one agent selected from the group consisting of the following: an anticholinergic agent, an $\alpha_1$ antagonist, a β agonist, a 5α-reductase inhibitor, a PDE inhibitor, an acetylcholine esterase inhibitor, an antiandrogen, a progesterone-based hormone, an LH-RH analog, a neurokinin inhibitor, an anti-diuretic, a calcium channel blocker, a direct smooth muscle agonist, a tricyclic antidepressant, a potassium channel modulator, a sodium channel blocker, an H$_1$ blocker, a serotonin reuptake inhibitor, a norepinephrine reuptake inhibitor, a dopamine reuptake inhibitor, a GABA agonist, a TRPV1 modulator, an endothelin antagonist, a 5-HT$_{1A}$ antagonist, an $\alpha_1$ agonist, an opioid agonist, a P$_2$X antagonist, a COX inhibitor, a σ agonist, and a muscarinic agonist.

15. An EP$_1$ receptor antagonist comprising the compound as claimed in claim 1 or a pharmaceutically acceptable salt thereof.

16. An agent for treating lower urinary tract symptoms, comprising the compound as claimed in claim 1 or a pharmaceutically acceptable salt thereof.

17. A method for treating lower urinary tract symptoms, comprising administering an effective amount of the compound as claimed in claim 1 or a pharmaceutically acceptable salt thereof.

* * * * *

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial
<220> FEATURE:
<223> OTHER INFORMATION: 5' primer

<400> SEQUENCE: 1
ttggccactg atatgagc                                             18

<210> SEQ ID NO 2
<211> LENGTH: 18
<212> TYPE: DNA
<213> ORGANISM: Artificial
<220> FEATURE:
<223> OTHER INFORMATION: 3' primer
```

```
<400> SEQUENCE: 2
gctttgggca cattcaca                                                    18

<210> SEQ ID NO 3
<211> LENGTH: 20
<212> TYPE: DNA
<213> ORGANISM: Artificial
<220> FEATURE:
<223> OTHER INFORMATION: 5' primer

<400> SEQUENCE: 3
caccactgat atgagcccct                                                  20

<210> SEQ ID NO 4
<211> LENGTH: 19
<212> TYPE: DNA
<213> ORGANISM: Artificial
<220> FEATURE:
<223> OTHER INFORMATION: 3' primer

<400> SEQUENCE: 4
gcctagcttt gggcacatt                                                   19

<210> SEQ ID NO 5
<211> LENGTH: 2414
<212> TYPE: DNA
<213> ORGANISM: Rattus norvegicus

<400> SEQUENCE: 5
aacgccaata gggactttcc attgacgtca atgggtggag tatttacggt aaactgccca        60
cttggcagta catcaagtgt atcatatgcc aagtacgccc cctattgacg tcaatgacgg       120
taaatggccc gcctggcatt atgcccagta catgacctta tgggactttc ctacttggca       180
gtacatctac gtattagtca tcgctattac catggtgatg cggttttggc agtacatcaa       240
tgggcgtgga tagcggtttg actcacgggg atttccaagt ctccacccca ttgacgtcaa       300
tgggagtttg ttttggcacc aaaatcaacg ggactttcca aaatgtcgta acaactccgc       360
cccattgacg caaatgggcg gtaggcgtgt acggtgggag gtctatataa gcagagctct       420
ctggctaact agagaaccca ctgcttactg gcttatcgaa attaatacga ctcactatag       480
ggagacccaa gctggctagt taagcttggt accgagctcg gatccagtac ccttcaccac       540
tgatatgagc ccctacgggc ttaacctgag cctagtggat gaggcaacaa cgtgtgtaac       600
acccagggtc cccaatacat ctgtggtgct gccaacaggc ggtaacggca catcaccagc       660
gctgcctatc ttctccatga cgctgggtgc tgtgtccaac gtgctggcgc tggcgctgct       720 gcccaggtt gcaggcagac tgcggcgccg ccgctcgact gccaccttcc tgttgttcgt       780
cgccagcctg cttgccatcg acctagcagg ccatgtgatc ccgggcgcct tggtgcttcg       840
cctgtatact gcaggacgtg cgcccgctgg cggggcctgt catttcctgg gcggctgtat       900
ggtcttcttt ggcctgtgcc cacttttgct tggctgtggc atggccgtgg agcgctgcgt       960
gggtgtcacg cagccgctga tccacgcggc gcgcgtgtcc gtagcccgcg cacgcctggc      1020
actagccctg ctggccgcca tggctttggc agtggcgctg ctgccactag tgcacgtggg      1080
tcactacgag ctacagtacc ctggcacttg gtgtttcatt agccttgggc ctcctggagg      1140
ttggcgccag gcgttgcttg cgggcctctt cgccggcctt ggcctggctg cgtcccttgc      1200
cgcactagtg tgtaatacgc tcagcggcct ggcgctcctt cgtgcccgct ggaggcggcg      1260
```

```
tcgctctcga cgtttccgag agaacgcagg tcccgatgat cgccggcgct gggggtcccg   1320
tggactccgc ttggcctccg cctcgtctgc gtcatccatc acttcaacca cagctgccct   1380
ccgcagctct cggggaggcg gctccgcgcg cagggttcac gcacacgacg tggaaatggt   1440
gggccagctc gtgggcatca tggtggtttc gtgcatctgc tggagccccc tgctggtatt   1500
ggtggtgttg gccatcgggg gctggaactc taactccctg cagcggccgc tctttctggc   1560
tgtacgcctc gcgtcgtgga accagatcct ggacccatgg gtgtacatcc tgctgcgcca   1620
ggctatgctg cgccaacttc ttcgcctcct acccctgagg gttagtgcca agggtggtcc   1680
aacggagctg agcctaacca agagtgcctg ggaggccagt tcactgcgta gctcccggca   1740
cagtggcttc agccacttgt gaatgtgccc aaagctaggc aagggtcaag acaattctgc   1800
agatatccag cacagtggcg gccgctcgag tctagagggc ccgcggttcg aaggtaagcc   1860
tatccctaac cctctcctcg gtctcgattc tacgcgtacc ggtcatcatc accatcacca   1920
ttgagtttaa acccgctgat cagcctcgac tgtgccttct agttgccagc catctgttgt   1980
ttgcccctcc cccgtgcctt ccttgaccct ggaaggtgcc actccactg tcctttccta    2040
ataaaatgag gaaattgcat cgcattgtct gagtaggtgt cattctattc tggggggtgg   2100
ggtggggcag gacagcaagg gggaggattg ggaagacaat agcaggcatg ctggggatgc   2160
ggtgggctct atggcttctg aggcggaaag aaccagctgg ggctctaggg ggtatcccca   2220
cgcgccctgt agcggcgcat taagcgcggc gggtgtggtg gttacgcgca gcgtgaccgc   2280
tacacttgcc agcgccctag cgcccgctcc tttcgctttc ttcccttcct ttctcgccac   2340
gttcgccggc tttccccgtc aagctctaaa tcgggggctc cctttagggt tccgatttag   2400
tgctttacgg cacc                                                    2414
```